US010172350B2

(12) United States Patent
Mosrin et al.

(10) Patent No.: US 10,172,350 B2
(45) Date of Patent: Jan. 8, 2019

(54) SUBSTITUTED 5-HYDROXY-2-PHENYL-3-HETEROARYL PENTANENITRILE DERIVATIVES, METHOD FOR THE PRODUCTION THEREOF AND USE THEREOF AS HERBICIDES AND/OR PLANT GROWTH REGULATORS

(71) Applicant: Bayer CropScience Aktiengesellschaft, Monheim am Rhein (DE)

(72) Inventors: Marc Mosrin, Cologne (DE); Harald Jakobi, Frankfurt (DE); Hansjoerg Dietrich, Liederbach (DE); Elmar Gatzweiler, Bad Nauheim (DE); Christopher Hugh Rosinger, Hofheim (DE); Dirk Schmutzler, Hattersheim (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/516,738

(22) PCT Filed: Oct. 5, 2015

(86) PCT No.: PCT/EP2015/072886
§ 371 (c)(1),
(2) Date: Apr. 4, 2017

(87) PCT Pub. No.: WO2016/055393
PCT Pub. Date: Apr. 14, 2016

(65) Prior Publication Data
US 2017/0290330 A1  Oct. 12, 2017

(30) Foreign Application Priority Data

Oct. 8, 2014  (EP) ..................................... 14188056

(51) Int. Cl.
| | | |
|---|---|---|
| C07D 213/61 | (2006.01) |
| A01N 43/40 | (2006.01) |
| A01N 33/02 | (2006.01) |
| A01N 43/10 | (2006.01) |
| A01N 43/60 | (2006.01) |
| A01N 43/78 | (2006.01) |
| C07D 333/28 | (2006.01) |
| C07D 241/16 | (2006.01) |
| C07D 277/32 | (2006.01) |
| A01N 43/76 | (2006.01) |
| A01N 25/14 | (2006.01) |
| A01N 43/00 | (2006.01) |
| C07C 211/01 | (2006.01) |
| C07C 269/00 | (2006.01) |
| C07C 291/08 | (2006.01) |
| C07D 211/80 | (2006.01) |

(52) U.S. Cl.
CPC ............. *A01N 33/02* (2013.01); *A01N 25/14* (2013.01); *A01N 43/00* (2013.01); *A01N 43/10* (2013.01); *A01N 43/40* (2013.01); *A01N 43/60* (2013.01); *A01N 43/76* (2013.01); *A01N 43/78* (2013.01); *C07C 211/01* (2013.01); *C07C 269/00* (2013.01); *C07C 291/08* (2013.01); *C07D 211/80* (2013.01); *C07D 213/61* (2013.01); *C07D 241/16* (2013.01); *C07D 277/32* (2013.01); *C07D 333/28* (2013.01)

(58) Field of Classification Search
None
See application file for complete search history.

(56) References Cited

U.S. PATENT DOCUMENTS

| 4,224,052 | A | 9/1980 | Szucs |
| 9,049,863 | B2 | 6/2015 | Jakobi et al. |
| 9,084,425 | B2 | 7/2015 | Mosrin et al. |
| 9,161,537 | B2 | 10/2015 | Jakobi et al. |
| 2014/0087945 | A1 | 3/2014 | Jakobi et al. |
| 2014/0194291 | A1 | 7/2014 | Jakobi et al. |
| 2014/0235446 | A1 | 8/2014 | Mosrin et al. |
| 2014/0364315 | A1 | 12/2014 | Jakobi et al. |

(Continued)

FOREIGN PATENT DOCUMENTS

| EP | 0005341 A2 | 11/1979 |
| EP | 0266725 A1 | 5/1988 |

(Continued)

OTHER PUBLICATIONS

Koyanagi et al, Bioisosterism in Agrochemicals, Chapter 2, pp. 15-24, cited by Baker et al, Synthesis and Chemistry of Agrochemicals IV, ACS Symposium Series, American Chemical Society, May 5 (Year: 1995).*

(Continued)

*Primary Examiner* — Zinna Northington Davis
(74) *Attorney, Agent, or Firm* — McBee Moore Woodward & Vanik IP, LLC

(57) ABSTRACT

Primarily, the present invention relates to compounds of the formula (I) defined below and to their use as herbicides, in particular for controlling broad-leaved weeds and/or weed grasses in crops of useful plants and/or as plant growth regulators for influencing the growth of crops of useful plants. The present invention also relates to herbicidal or plant growth-regulating compositions comprising one or more compounds of the formula (I). Moreover, the present invention relates to processes for preparing the compounds of the formula (I).

17 Claims, No Drawings

(56) References Cited

U.S. PATENT DOCUMENTS

2015/0327546 A1   11/2015   Jakobi et al.
2016/0113277 A1    4/2016   Mosrin et al.

FOREIGN PATENT DOCUMENTS

| | | |
|---|---|---|
| EP | 0270830 A1 | 6/1988 |
| WO | 2011003775 A2 | 1/2011 |
| WO | 2011003776 A2 | 1/2011 |
| WO | 2011042378 A1 | 4/2011 |
| WO | 2011073143 A1 | 6/2011 |
| WO | 2011098417 A1 | 8/2011 |
| WO | 2012126764 A1 | 9/2012 |
| WO | 2012126765 A1 | 9/2012 |
| WO | 2013010882 A2 | 1/2013 |
| WO | 2013092500 A1 | 6/2013 |
| WO | 2014095879 A1 | 6/2014 |
| WO | 2014195253 A1 | 12/2014 |

OTHER PUBLICATIONS

PCT International Search Report for PCT/EP2015/072886, dated Nov. 20, 2015.

* cited by examiner

SUBSTITUTED 5-HYDROXY-2-PHENYL-3-HETEROARYL PENTANENITRILE DERIVATIVES, METHOD FOR THE PRODUCTION THEREOF AND USE THEREOF AS HERBICIDES AND/OR PLANT GROWTH REGULATORS

CROSS-REFERENCE TO RELATED APPLICATIONS

This application is a National Stage entry of International Application No. PCT/EP2015/072886, filed Oct. 5, 2015, which claims priority to European Patent Application No. 14188056.7, filed Oct. 8, 2014.

BACKGROUND

Field

Primarily, the present invention relates to compounds of the formula (I) defined below and to their use as herbicides, in particular for controlling broad-leaved weeds and/or weed grasses in crops of useful plants and/or as plant growth regulators for influencing the growth of crops of useful plants. The present invention also relates to herbicidal or plant growth-regulating compositions comprising one or more compounds of the formula (I). Moreover, the present invention relates to processes for preparing the compounds of the formula (I).

Description of Related Art

In their application, crop protection agents known to date for the selective control of harmful plants in crops of useful plants or active ingredients for controlling unwanted vegetation sometimes have disadvantages, be it (a) that they have no or else insufficient herbicidal activity against particular harmful plants, (b) that the spectrum of harmful plants which can be controlled with an active ingredient is not wide enough, (c) that their selectivity in crops of useful plants is too low and/or (d) that they have a toxicologically unfavorable profile. Furthermore, some active ingredients which can be used as plant growth regulators for a number of useful plants cause unwanted reduced harvest yields in other useful plants or are not compatible with the crop plant, or only within a narrow application rate range. Some of the known active ingredients cannot be produced economically on an industrial scale owing to precursors and reagents which are difficult to obtain, or they have only insufficient chemical stabilities. In the case of other active ingredients, the activity is too highly dependent on environmental conditions, such as weather and soil conditions.

Inter alia, documents EP-A-0 005 341 (corresponding to U.S. Pat. No. 4,224,052), EP-A-0 266 725, EP-A-0 270 830, WO 2011/098417 A1, WO 2011/003775 A2, WO 2011/003776 A2, WO 2011/073143 A1, WO 2011/042378 A1, WO 2012/126764 A1, WO 2012/126765 A1, WO 2013/010882 A2, WO 2013/092500 A1 and WO 2014/095879 A1 disclose herbicidal cyanobutanoic acid derivatives.

EP-A-0 005 341 describes herbicidal esters and amides of 4-cyano-3,4-diphenylbutanoic acids which are optionally substituted at the phenyl radicals. According to EP-A-0 005 341, the threo isomers are generally suitable for the non-selective control of harmful plants, whereas the erythro/threo isomer mixtures are suitable for the selective control of harmful plants in some crops of useful plants. Moreover, EP-A-0 005 341 mentions that the 2 enantiomers belonging to the threo form have different activities, which was investigated in an exemplary manner on the different activities of the enantiomers of the enantiomer pair of 4-cyano-3,4-diphenylbutanoic acid unsubstituted in the phenyl radicals.

EP-A-0 266 725 discloses some erythro/threo isomer mixtures which can be used selectively for controlling weeds in rice crops.

EP-A-0 270 830 describes that threo isomers and erythro/threo isomer mixtures can be used as plant regulators, preventing the development of an infructescence in various harmful grasses.

WO 2011/003775 A2 discloses specific esters of 4-cyano-3,4-diphenylbutanoic acids which can be used as effective herbicides, preferably in crops of useful plants.

WO 2011/003776 A2, WO 2011/042378 A1, WO 2011/073143 A1, WO 2012/126764 A1 and WO 2012/126765 A1 disclose 4-cyano-3,4-diphenylbutanoic acids and esters which have specific substitutions at the phenyl radicals and can be used as effective herbicides, preferably also in crops of useful plants.

WO 2013/010882 describes 2,3-diphenylvaleronitrile derivatives and their use as herbicides and plant growth regulators.

WO 2013/092500 A1 describes substituted 4-cyano-3-phenyl-4-(pyridin-3-yl) butanoates, processes for their preparation and their use as herbicides and plant growth regulators.

WO 2014/095879 A1 describes substituted 4-cyano-3-(pyridyl)-4-phenylbutanoates and their use as herbicides and plant growth regulators.

The herbicidal activity of these known compounds, in particular at low application rates, and/or their compatibility with crop plants remain deserving of improvement.

For the reasons stated, there is still a need for potent herbicides and/or plant growth regulators for the selective use in crop plants or the use on non-crop land, where these active ingredients preferably should have further advantageous properties in application, for example with respect to their compatibility with crop plants.

SUMMARY

It is the primary object of the present invention to provide compounds having herbicidal activity (herbicides) which are highly effective against economically important harmful plants even at relatively low application rates and can be used selectively in crop plants, preferably with good activity for harmful plants, and at the same time preferably have good compatibility with crop plants. Preferably, these herbicidal compounds should be particularly effective and efficient against a broad spectrum of weed grasses and preferably also have good activity against a large number of weeds.

Surprisingly, it has now been found that this object is achieved by the compounds of the formula (I) defined below and their salts.

The present invention therefore relates to the compounds of the formula (I) and/or their salts,

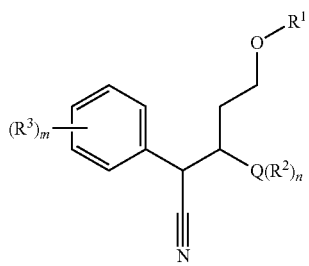

(I)

in which

Q represents a mono- or bicyclic heteroaromatic radical with in total 1 to 9 carbon ring atoms, where the heteroatom or heteroatoms in the heteroaromatic ring are selected from the group consisting of N, O, S, P, B, Si, and Se, $R^1$ represents hydrogen or a hydrolyzable radical, $(R^2)_n$ represent n substituents $R^2$, where $R^2$ (if n=1) or each of the substituents $R^2$ (if n is greater than 1) independently of one another represents halogen, cyano, nitro, $(C_1-C_8)$alkyl, $(C_1-C_8)$alkoxy, $(C_1-C_8)$alkylthio, $(C_1-C_8)$alkylsulfinyl, $(C_1-C_8)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri[$(C_1-C_4)$alkyl]silyl or tri[$(C_1-C_4)$alkyl]silyl $(C_1-C_4)$alkyl, or in each case two $R^2$ directly adjacent on the heteroaromatic radical Q are together a group of the formula —$Z^1$-$A^{*1}$—$Z^2$—, in which A* represents an alkylene group having 1 to 4 carbon atoms which is optionally substituted by one or more radicals selected from the group consisting of halogen, $(C_1-C_4)$alkyl, $(C_1-C_4)$haloalkyl, $(C_1-C_4)$alkoxy and $(C_1-C_4)$haloalkoxy, $Z^1$ represents a direct bond, O or S and $Z^2$ represents a direct bond, O or S, where the group —$Z^1$-$A^*$—$Z^2$— together with the atoms of the heteroaromatic radical Q bonded to this group Q form a 5- or 6-membered ring (i.e. a ring with 5 or 6 ring atoms), and $(R^3)_m$ represents m substituents $R^3$, where $R^3$ (if m=1) or each of the substituents $R^3$ (if m is greater than 1) independently of one another represents halogen, cyano, nitro, $(C_1-C_8)$alkyl, $(C_1-C_8)$alkoxy, $(C_1-C_8)$alkylthio, $(C_1-C_8)$alkylsulfinyl, $(C_1-C_8)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri[$(C_1-C_4)$alkyl]silyl, tri-[$(C_1-C_4)$alkyl]silyl-$(C_1-C_4)$alkyl or —NR*R**, where R* and R**, independently of one another and independently of any other radicals —NR*R** present, are in each case selected from the group consisting of H, $(C_1-C_8)$alkyl, $(C_2-C_8)$alkenyl, $(C_2-C_8)$alkynyl, $(C_1-C_4)$alkoxy-$(C_1-C_4)$alkyl, $(C_1-C_6)$alkanoyl, [$(C_1-C_4)$haloalkyl]carbonyl, [$(C_1-C_4)$alkoxy]carbonyl, [$(C_1-C_4)$haloalkoxy]carbonyl, $(C_3-C_6)$cycloalkyl, $(C_3-C_6)$cycloalkyl$(C_1-C_4)$alkyl, $(C_3-C_6)$cycloalkenyl, $(C_3-C_6)$cycloalkenyl-$(C_1-C_4)$alkyl, phenyl and phenyl-$(C_1-C_4)$alkyl, where each of the specified radicals $(C_3-C_6)$cycloalkyl, $(C_3-C_6)$cycloalkyl-$(C_1-C_4)$alkyl, $(C_3-C_6)$cycloalkenyl, $(C_3-C_6)$cycloalkenyl-$(C_1-C_4)$alkyl, phenyl and phenyl-$(C_1-C_4)$alkyl is substituted in the cycle optionally by one or more identical or different radicals $R^{bb}$, where $R^{bb}$ in each case represents halogen, $(C_1-C_4)$alkyl, $(C_1-C_4)$haloalkyl, $(C_1-C_4)$alkoxy or $(C_1-C_4)$haloalkoxy and, in the case of $(C_3-C_6)$cycloalkyl, $(C_3-C_6)$cycloalkyl-$(C_1-C_4)$alkyl, $(C_3-C_6)$cycloalkenyl, $(C_3-C_6)$cycloalkenyl-$(C_1-C_4)$alkyl, $R^{bb}$ may additionally represent oxo, or NR*R represents a 3- to 8-membered heterocycle which, in addition to this nitrogen atom, optionally contains one or two further ring heteroatoms selected from the group consisting of N, O and S and which is unsubstituted or substituted by one or more radicals selected from the group consisting of $(C_1-C_4)$-alkyl, $(C_1-C_4)$-haloalkyl and oxo, or where in each case two groups $R^3$ directly adjacent on the ring together represent a group of the formula —$Z^3$-$A^{}$-$Z^4$—, in which A represents an alkylene group having 1 to 4 carbon atoms which is optionally substituted by one or more radicals selected from the group consisting of halogen, $(C_1-C_4)$alkyl, $(C_1-C_4)$haloalkyl, $(C_1-C_4)$alkoxy and $(C_1-C_4)$haloalkoxy, $Z^3$ represents a direct bond, O or S and $Z^4$ represents a direct bond, O or S, where the group —$Z^3$-$A^{}$—$Z^4$ together with the carbon atoms, bonded to this group, of the phenyl ring form a 5- or 6-membered ring, n represents 0, or an integer in the range from 1 to 5, preferably 0, 1, 2 or 3, and m represents 0, 1, 2, 3, 4 or 5, preferably 0, 1, 2 or 3.

DETAILED DESCRIPTION OF A PREFERRED EMBODIMENT

The compounds of the formula (I) according to the invention and/or their salts have excellent herbicidal activity against a broad spectrum of economically important mono- and dicotyledonous annual harmful plants. The compounds according to the invention also have good control over perennial harmful plants which are difficult to control and produce shoots from rhizomes, root stocks or other perennial organs.

The compounds of the formula (I) according to the invention and/or their salts, for example compared to the compounds described in WO 2012/126765 A1, generally have more potent action at the same dosage, for example against weed grasses. Furthermore, the compounds according to the invention have a broader spectrum of activity against weeds, i.e. the compounds according to the invention and/or their salts can be used to control effectively a relatively large number of different weeds.

The compounds of the formula (I) according to the invention and/or their salts have proven to be very effective in controlling harmful plants such as *Alopecurus myosuroides, Avena fatua, Cyperus esculentus, Echinochloa crus-galli, Lolium multiflorum, Setaria viridis, Abutilon theophrasti, Amaranthus retroflexus, Polygonum convolvulus* (=*Fallopia convolvulus*), *Stellaria media, Viola tricolor*, and *Veronica persica*, where the preferred and particularly preferred compounds according to the invention exhibited in the biological tests an 80% to 100% herbicidal action against one, several or all of the specified harmful plants, and in so doing simultaneously more acceptable and mostly very slight damage to the useful plant.

In addition, the compounds of the formula (I) according to the invention and/or their salts show particularly good activity in the pre-emergence method, in particular against weed grasses. The pre-emergence activity of the compounds according to the invention is generally better than the pre-emergence activity of the compounds described in WO 2012/126765 A1.

Furthermore, it has been found that the compounds of the formula (I) according to the invention and/or their salts show this better pre-emergence action particularly selectively in certain crops, in particular in oilseed rape, soya beans, cotton and cereals (and here in particular in maize, barley, wheat, rye, oats, triticale, millet varieties, rice).

In general, the compounds of the formula (I) according to the invention also have a considerably broader activity spectrum.

In the formula (I), the formula "$(R^2)_n$" means n radicals $R^2$ which are attached as substituents at the heteroaromatic radical Q, where the radicals $R^2$ in the case of n greater than 1 may be identical or different and have the meaning mentioned in each case in more detail. In the case n=0, the heteroaromatic radical Q is not substituted by substituents $R^2$.

In the formula (I), the formula "$(R^3)_m$" means m radicals $R^3$ which are attached as substituents at the phenyl ring in question, where the radicals $R^3$ in the case of n greater than 1 may be identical or different and have the meaning mentioned in each case in more detail. In the case n=0, the phenyl ring in question is not substituted by substituents $R^3$, i.e. all ring carbon atoms of the phenyl ring in positions 2 to 6 are attached to a hydrogen atom.

In the case of $R^1$=H or in the case of suitable acidic substituents, the compounds of the formula (I) are able to form salts by reaction with bases where the acidic hydrogen is replaced by an agriculturally suitable cation.

By addition of a suitable inorganic or organic acid onto a basic group, such as, for example, amino or alkylamino, the compounds of the formula (I) are able to form salts. Suitable acidic groups present, such as, for example, carboxylic acid groups, are able to form inner salts with groups which for their part can be protonated, such as amino groups.

The compounds of the formula (I) may preferably be present in the form of agriculturally usable salts, where the type of salt is otherwise generally immaterial. In general, suitable salts are the salts of those cations or the acid addition salts of those acids whose cations and anions, respectively, have no adverse effect on the herbicidal activity of the compounds of the formula (I).

Suitable cations are in particular ions of the alkali metals, here preferably lithium, sodium or potassium, of the alkaline earth metals, here preferably calcium or magnesium, and of the transition metals, here preferably manganese, copper, zinc or iron. The cation used may also be ammonium ($NH_4^+$) or substituted ammonium, where one to four hydrogen atoms may be replaced here by $(C_1-C_4)$alkyl, hydroxy-$(C_1-C_4)$alkyl, $(C_1-C_4)$alkoxy-$(C_1-C_4)$alkyl, hydroxy $(C_1-C_4)$ alkoxy-$(C_1-C_4)$alkyl, phenyl or benzyl, preferred ammonium ions are ammonium, dimethylammonium, diisopropylammonium, tetramethylammonium, tetrabutylammonium, 2-(2-hydroxyeth-1-oxy)eth-1-ylammonium, di(2-hydroxyeth-1-yl)ammonium, trimethylbenzylammonium. Also suitable are phosphonium ions, sulfonium ions, preferably tri-$(C_1-C_4)$alkylsulfonium, in particular trimethylsulfonium, or sulfoxonium ions, preferably tri$(C_1-C_4)$ alkylsulfoxonium, in particular trimethylsulfoxonium.

Anions of suitable acid addition salts are preferably chloride, bromide, fluoride, hydrogensulfate, sulfate, dihydrogenphosphate, hydrogenphosphate, nitrate, bicarbonate, carbonate, hexafluorosilicate, hexafluorophosphate, benzoate and also the anions of $(C_1-C_4)$alkanoic acids, here in turn preferably formate, acetate, propionate, butyrate or trifluoroacetate.

In formula (I) and in all subsequent formulae, chemical radicals are referred to by names which are collective terms for the enumeration of individual group members or specifically refer to individual chemical radicals. Here, terms are used which are familiar to the person skilled in the art or have the meanings defined below.

A hydrolyzable radical (see definition of $R^1$) is a radical which can be hydrolyzed under the application conditions, for example a radical which can be hydrolyzed even in the spray liquor or in particular under the physiological conditions in plants, where a compound of the formula (I) where $R^1$ is not hydrogen is hydrolyzed to the corresponding compound of the formula (I) where $R^1$=H (hydrogen). Expressly, the definition of the hydrolyzable radicals also includes the radicals where $R^1$=hydrocarbon radical or heterocyclyl radical, the two last-mentioned radicals being unsubstituted or substituted, even if some of them are hydrolyzable comparatively slowly.

A hydrocarbon radical is an aliphatic, cycloaliphatic or aromatic monocyclic or, in the case of an optionally substituted hydrocarbon radical, also a bicyclic or polycyclic organic radical based on the elements carbon and hydrogen, including, for example, the radicals alkyl, alkenyl, alkynyl, cycloalkyl, cycloalkenyl, aryl, phenyl, naphthyl, indanyl, indenyl, etc. This applies correspondingly to hydrocarbon radicals in composite meanings, such as hydrocarbonoxy radicals or other hydrocarbon radicals attached via heteroatom groups.

Unless defined in more detail, the hydrocarbon radicals preferably have 1 to 20 carbon atoms, more preferably 1 to 16 carbon atoms, in particular 1 to 12 carbon atoms.

The hydrocarbon radicals, also in the special radicals alkyl, alkoxy, haloalkyl, haloalkoxy, alkylamino and alkylthio, and also the corresponding unsaturated and/or substituted radicals may in each case be straight-chain or branched in the carbon skeleton.

The expression "$(C_1-C_4)$alkyl" is shorthand for alkyl having from 1 to 4 carbon atoms, i.e. encompasses the radicals methyl, ethyl, 1-propyl, 2-propyl, 1-butyl, 2-butyl, 2-methylpropyl or tert-butyl. General alkyl radicals having a larger specified range of carbon atoms, for example "$(C_1-C_6)$alkyl", correspondingly also encompass straight-chain or branched alkyl radicals having a greater number of carbon atoms, i.e. in this example also the alkyl radicals having 5 and 6 carbon atoms.

Unless stated specifically or differently, preference is given to the lower carbon skeletons, for example having from 1 to 6 carbon atoms, or having from 2 to 6 carbon atoms in the case of unsaturated groups, in the case of the hydrocarbon radicals such as alkyl, alkenyl and alkynyl radicals, including in composite radicals. Alkyl radicals, including in the combined definitions such as alkoxy, haloalkyl, etc., are, for example, methyl, ethyl, n- or i-propyl, n-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals; alkenyl is, for example, vinyl, allyl, 1-methyl-2-propenyl, 2-methyl-2-propenyl, 2-butenyl, pentenyl, 2-methylpentenyl or hexenyl group, preferably allyl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl.

Alkenyl also includes in particular straight-chain or branched hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl.

Alkynyl is, for example, propargyl, but-2-yn-1-yl, but-3-yn-1-yl, 1-methylbut-3-yn-1-yl. Alkynyl also includes, in particular, straight-chain or branched hydrocarbon radicals having more than one triple bond or else having one or more triple bonds and one or more double bonds, for example 1,3-butatrienyl or 3-penten-1-yn-1-yl.

A 3- to 9-membered carbocyclic ring is $(C_3-C_9)$cycloalkyl or $(C_5-C_9)$cycloalkenyl.

$(C_3-C_9)$Cycloalkyl is a carbocyclic saturated ring system having preferably 3-9 carbon atoms, for example cyclopropyl, cyclobutyl, cyclopentyl, cyclohexyl, cycloheptyl, cyclooctyl or cyclononyl. In the case of substituted cycloalkyl, cyclic systems with substituents are included, where the substituents may also be bonded by a double bond on the cycloalkyl radical, for example an alkylidene group such as methylidene.

$(C_5-C_9)$Cycloalkenyl is a carbocyclic, nonaromatic, partially unsaturated ring system having 5-9 carbon atoms, for example 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl. In the case of substituted cycloalkenyl, the explanations for substituted cycloalkyl apply correspondingly.

Alkylidene, for example also in the form of $(C_1-C_{10})$ alkylidene, is the radical of a straight-chain or branched alkane which is bonded via a double bond, the position of the bonding site not being fixed. In the case of a branched alkane, the only positions possible are, of course, those in which two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

"Halogen" preferably refers to the group consisting of fluorine, chlorine, bromine and iodine. Haloalkyl, -alkenyl and -alkynyl are alkyl, alkenyl and alkynyl, respectively, which are partially or fully substituted by identical or different halogen atoms, preferably from the group consisting of fluorine, chlorine and bromine, in particular from the group consisting of fluorine and chlorine, for example monohaloalkyl, perhaloalkyl, $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

Aryl is a mono-, bi- or polycyclic aromatic system, for example phenyl, naphthyl, tetrahydronaphthyl, indenyl, indanyl, pentalenyl, fluorenyl and the like, preferably phenyl.

Optionally substituted aryl also includes polycyclic systems, such as tetrahydronaphthyl, indenyl, indanyl, fluorenyl, biphenylyl, where the point of attachment is at the aromatic system.

A heterocyclic radical (heterocyclyl) comprises at least one heterocyclic ring (=carbocyclic ring in which at least one carbon atom is replaced by a heteroatom, preferably by a heteroatom from the group consisting of N, O, S, P, B, Si, Se), which is saturated, unsaturated or heteroaromatic and may be unsubstituted or substituted, where the point of attachment is located at a ring atom. Unless defined otherwise it preferably contains one or more, in particular 1, 2 or 3, heteroatoms in the heterocyclic ring, preferably from the group consisting of N, O, and S; it is preferably an aliphatic heterocyclyl radical having 3 to 7 ring atoms or a heteroaromatic radical having 5 or 6 ring atoms. The heterocyclic radical may, for example, be a heteroaromatic radical or ring (heteroaryl), such as, for example, a monocyclic, bicyclic or polycyclic aromatic system in which at least 1 ring contains one or more heteroatoms.

If the heterocyclyl radical or the heterocyclic ring is optionally substituted, it may be fused to other carbocyclic or heterocyclic rings. Preference is given to benzo-fused heterocyclic or heteroaromatic rings.

Optionally substituted heterocyclyl also includes polycyclic systems, such as, for example, 8-aza-bicyclo[3.2.1] octanyl or 1-aza-bicyclo[2.2.1]heptyl. Optionally substituted heterocyclyl also includes spirocyclic systems, such as, for example, 1-oxa-5-aza-spiro[2.3]hexyl.

Preferably it is a radical of a heteroaromatic ring with a heteroatom from the group consisting of N, O, and S, for example the radical of a five- or six-membered ring such as pyridyl, pyrrolyl, thienyl or furyl; with further preference it is a radical of a corresponding heteroaromatic ring having 2, 3 or 4 heteroatoms, such as pyrimidinyl, pyridazinyl, pyrazinyl, triazinyl, tetrazinyl, thiazolyl, thiadiazolyl, oxazolyl, isoxazolyl, pyrazolyl, imidazolyl or triazolyl or tetrazolyl.

Here, preference is given to a radical of a heteroaromatic five- or six-membered ring having 1 to 4 heteroatoms, such as, for example, 1,2,3-triazolyl, 1,2,4-triazolyl, tetrazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, tetrazolyl, 1,2,3-triazinyl, 1,2,4-triazinyl, 1,3,5-triazinyl, 1,2,3,4-tetrazinyl, 1,2,3,5-tetrazinyl, 1,2,4,5-tetrazinyl, thiazolyl, isothiazolyl, oxazolyl, isoxazolyl, pyrazolyl, imidazolyl.

More preference is given here to heteroaromatic radicals of five-membered heterocycles having 3 nitrogen atoms such as 1,2,3-triazol-1-yl, 1,2,3-triazol-4-yl, 1,2,3-triazol-5-yl, 1,2,5-triazol-1-yl, 1,2,5-triazol-3-yl, 1,3,4-triazol-1-yl, 1,3,4-triazol-2-yl, 1,2,4-triazol-3-yl, 1,2,4-triazol-5-yl; more preference is also given to heteroaromatic radicals of six-membered heterocycles having 3 nitrogen atoms such as 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl; more preference is also given to heteroaromatic radicals of five-membered heterocycles having two nitrogen atoms and one oxygen atom such as 1,2,4-oxadiazol-3-yl; 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl; more preference is also given to heteroaromatic radicals of five-membered heterocycles having two nitrogen atoms and one sulfur atom such as 1,2,4-thiadiazol-3-yl, 1,2,4-thiadiazol-5-yl, 1,3,4-thiadiazol-2-yl, 1,2,3-thiadiazol-4-yl, 1,2,3-thiadiazol-5-yl, 1,2,5-thiadiazol-3-yl; more preference is also given to heteroaromatic radicals of five-membered heterocycles having four nitrogen atoms such as 1,2,3,4-tetrazol-1-yl, 1,2,3,4-tetrazol-5-yl, 1,2,3,5-tetrazol-1-yl, 1,2,3,5-tetrazol-4-yl, 2H-1,2,3,4-tetrazol-5-yl, 1H-1,2,3,4-tetrazol-5-yl, more preference is also given to heteroaromatic radicals of six-membered heterocycles such as 1,2,4,5-tetrazin-3-yl; more preference is also given to heteroaromatic radicals of five-membered heterocycles having three nitrogen atoms and one oxygen or sulfur atom such as 1,2,3,4-oxatriazol-5-yl; 1,2,3,5-oxatriazol-4-yl; 1,2,3,4-thiatriazol-5-yl; 1,2,3,5-thiatriazol-4-yl; more preference is also given to heteroaromatic radicals of six-membered heterocycles such as, for example, 1,2,4,6-thiatriazin-1-yl; 1,2,4,6-thiatriazin-3-yl; 1,2,4,6-thiatriazin-5-yl.

Furthermore preferably, the heterocyclic radical or ring is a partially or fully hydrogenated heterocyclic radical having one heteroatom from the group of N, O and S, for example oxiranyl, oxetanyl, oxolanyl (=tetrahydrofuryl), oxanyl, pyrrolinyl, pyrrolidyl or piperidyl.

It is also preferably a partially or fully hydrogenated heterocyclic radical having 2 heteroatoms from the group of N, O and S, for example piperazinyl, dioxolanyl, oxazolinyl, isoxazolinyl, oxazolidinyl, isoxazolidinyl and morpholinyl. Suitable substituents for a substituted heterocyclic radical are the substituents specified later on below, and additionally also oxo. The oxo group may also occur on the ring heteroatoms which are able to exist in different oxidation states, as in the case of N and S, for example.

Preferred examples of heterocyclyl are a heterocyclic radical having from 3 to 6 ring atoms from the group of pyridyl, thienyl, furyl, pyrrolyl, oxiranyl, 2-oxetanyl, 3-oxetanyl, oxolanyl (=tetrahydrofuryl), pyrrolidyl, piperidyl, especially oxiranyl, 2-oxetanyl, 3-oxetanyl or oxolanyl, or is a heterocyclic radical having two or three heteroatoms, for example pyrimidinyl, pyridazinyl, pyrazinyl, triazinyl, thiazolyl, thiadiazolyl, oxazolyl, isoxazolyl, pyrazolyl, triazolyl, piperazinyl, dioxolanyl, oxazolinyl, isoxazolinyl, oxazolidinyl, isoxazolidinyl or morpholinyl.

Preferred heterocyclic radicals are also benzo-fused heteroaromatic rings, for example benzofuryl, benzisofuryl, benzothiophenyl, benzisothiophenyl, isobenzothiophenyl, indolyl, isoindolyl, indazolyl, benzimidazolyl, benzotriazolyl, benzoxazolyl, 1,2-benzisoxazolyl, 2,1-benzisoxazolyl, benzothiazolyl, 1,2-benzisothiazolyl, 2,1-benzisothiazolyl, 1,2,3-benzoxadiazolyl, 2,1,3-benzoxadiazolyl, 1,2,3-benzothiadiazolyl, 2,1,3-benzothiadiazolyl, quinolyl (quinolinyl), isoquinolyl (isoquinolinyl), quinnolinyl, phthalazinyl, quinazolinyl, quinoxalinyl, naphthyridinyl, benzotriazinyl, purinyl, pteridinyl, indolizinyl, benzo-1,3-dioxylyl, 4H-benzo-1,3-dioxinyl and 4H-benzo-1,4-dioxinyl, and, where possible, N-oxides and salts thereof.

When a base structure is substituted "by one or more radicals" from a list of radicals (=group) or a generically defined group of radicals, this in each case includes simultaneous substitution by a plurality of identical and/or structurally different radicals.

Substituted radicals, such as a substituted alkyl, alkenyl, alkynyl, cycloalkyl, aryl, phenyl, benzyl, heterocyclyl and heteroaryl radical, are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, alkylsulfonyl and, in the case of cyclic radicals, also alkyl, haloalkyl, alkylthioalkyl, alkoxyalkyl, optionally substituted mono- and dialkylaminoalkyl and hydroxyalkyl; in the term "substituted radicals", such as substituted alkyl, etc., substituents include, in addition to the saturated hydrocarbon-containing radicals mentioned, corresponding unsaturated aliphatic and aromatic radicals, such as optionally substituted alkenyl, alkynyl, alkenyloxy, alkynyloxy, phenyl and phenoxy, etc. In the case of substituted cyclic radicals having aliphatic moieties in the ring, cyclic systems with those substituents which are bonded on the ring by a double bond are also included, for example substituted by an alkylidene group such as methylidene or ethylidene.

The term "radicals from the group consisting of" followed by a group (list of the substituents) is, wherever used, synonymous with "radicals selected from the group consisting of" (list of the substituents).

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Here, preferred substituents for the substituent levels are amino, hydroxyl, halogen, nitro, cyano, mercapto, carboxyl, carbonamide, $SF_5$, aminosulfonyl, alkyl, cycloalkyl, alkenyl, cycloalkenyl, alkynyl, monoalkylamino, dialkylamino, N-alkanoylamino, alkoxy, alkenyloxy, alkynyloxy, cycloalkoxy, cycloalkenyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, cycloalkylthio, alkenylthio, cycloalkenylthio, alkynylthio, alkylsulfinyl, alkylsulfonyl, monoalkylaminosulfonyl, dialkylaminosulfonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino and benzylamino.

Two substituents together may also form a saturated or unsaturated hydrocarbon bridge or a corresponding bridge in which carbon atoms, CH groups or $CH_2$ groups are replaced by heteroatoms, thus forming a fused-on or fused cycle. Here, with preference benzo-fused systems based on the base structure are formed.

Optionally substituted phenyl is preferably unsubstituted phenyl or phenyl which is substituted by one or more radicals from the group consisting of halogen, cyano, ($C_1$-$C_4$)-alkyl, ($C_1$-$C_4$)-haloalkyl, ($C_1$-$C_4$)-alkoxy-($C_1$-$C_4$)alkyl, ($C_1$-$C_4$)-alkoxy, ($C_1$-$C_4$)-haloalkoxy, ($C_1$-$C_4$)-alkoxy-($C_1$-$C_4$)-alkoxy, ($C_1$-$C_4$)-alkylthio and nitro, in particular phenyl which is optionally substituted by one or more radicals from the group consisting of halogen, ($C_1$-$C_4$)-alkyl, ($C_1$-$C_4$)-haloalkyl and ($C_1$-$C_4$)-alkoxy.

In the case of substituents having carbon atoms, preference is given to those having 1 to 6 carbon atoms, preferably to those having 1 to 4 carbon atoms, especially to those having 1 or 2 carbon atoms. Preference is generally given to substituents from the group of halogen, for example fluorine and chlorine, ($C_1$-$C_4$)alkyl, preferably methyl or ethyl, ($C_1$-$C_4$)haloalkyl, preferably trifluoromethyl, ($C_1$-$C_4$)alkoxy, preferably methoxy or ethoxy, ($C_1$-$C_4$)haloalkoxy, nitro and cyano. Particular preference is given here to the substituents methyl, methoxy, fluorine and chlorine.

Substituted amino, such as mono- or disubstituted amino, is a radical from the group of the substituted amino radicals which are N-substituted, for example, by one or two identical or different radicals from the group of alkyl, alkoxy, acyl and aryl; preferably mono- and dialkylamino, mono- and diarylamino, acylamino, N-alkyl-N-arylamino, N-alkyl-N-acylamino and N-heterocycles; preference is given to alkyl radicals having from 1 to 4 carbon atoms; aryl is preferably phenyl or substituted phenyl; acyl is as defined below, preferably ($C_1$-$C_4$)alkanoyl. The same applies to substituted hydroxylamino or hydrazino.

Acyl is a radical of an organic acid which arises in a formal sense by removal of a hydroxyl group on the acid function, and the organic radical in the acid may also be bonded to the acid function via a heteroatom. Examples of acyl are the radicals of a carboxylic acid and radicals of acids derived therefrom, such as those of thiocarboxylic acid, optionally N-substituted iminocarboxylic acids or the radical of carbonic monoesters, N-substituted carbamic acid, sulfonic acids, sulfinic acids, N-substituted sulfonamide acids, phosphonic acids or phosphinic acids.

Acyl is, for example, formyl, alkylcarbonyl, here preferably [($C_1$-$C_4$)-alkyl]carbonyl, phenylcarbonyl, alkyloxycarbonyl, phenyloxycarbonyl, benzyloxycarbonyl, alkylsulfonyl, alkylsulfinyl, N-alkyl-1-iminoalkyl and other radicals of organic acids. The radicals may each for their part be substituted in the alkyl or phenyl moiety, for example in the alkyl moiety by one or more radicals from the group of halogen, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example formyl, alkylcarbonyl such as acetyl or [($C_1$-$C_4$alkyl]carbonyl, phenylcarbonyl, alkylsulfonyl, alkylsulfinyl and other radicals of organic acids.

In a preferred embodiment, acyl is an alkanoyl radical having 1 to 8 carbon atoms, preferably 1 to 6 carbon atoms, particularly preferably 1 to 4 carbon atoms. Here, ($C_1$-$C_4$) alkanoyl is the radical of an alkanoic acid having 1 to 6 carbon atoms formed after removal of the OH group of the acid group, i.e. formyl, acetyl, n-propionyl, isopropionyl, n-, iso-, sec- or tert-butanoyl, n-, iso-, sec- or tert-pentanoyl, n-, iso- or sec-hexanoyl.

The "yl position" of a radical denotes the carbon atom having the free bond.

In the context of the present text, compounds of the formula (I) according to the invention and/or salts thereof are in short also referred to as "compounds (I)".

The invention also provides all stereoisomers which are encompassed by formula (I) and mixtures thereof. Compounds of the formula (I) contain two or more asymmetric carbon atoms, and may also contain double bonds, the stereochemistry of which is not stated separately in the general formula (I). The possible stereoisomers defined by their specific three-dimensional shape, such as enantiomers, diastereomers, Z- and E-isomers, are all encompassed by the formula (I) and can be obtained from mixtures of the stereoisomers by customary methods or else prepared by stereoselective reactions in combination with the use of stereochemically pure starting materials.

The compounds of the formula (I) according to the invention include all stereoisomers which can occur on the basis of the centers of asymmetry or double bonds in the molecule whose configuration is not designated specifically in the respective structural formula or which are not specified explicitly, and mixtures thereof, including the racemic mixtures and the mixtures enriched partly with particular stereoisomers.

The invention also provides all tautomers of the compounds of the formula (I) which may result from a hydrogen atom shift (for example keto-enol tautomers). The compound of the formula (I) also includes the tautomers, even if formally the formula (I) correctly describes only one of the respective tautomers which are in equilibrium with one another or which can be converted into one another.

The compounds of the formula (I) also include all physical forms in which they may be present as a pure substance or, if appropriate, as a mixture with other substances, in particular also polymorphic crystal forms of the compounds of the formula (I) and salts thereof and solvent adducts (for example hydrates).

Primarily for reasons of higher herbicidal activity, better selectivity and/or better producibility, compounds of the abovementioned formula (I) according to the invention or their salts or their use according to the invention are of particular interest in which individual radicals have one of the preferred meanings already specified or specified below, or in particular those in which one or more of the preferred meanings already specified or specified below occur in combination.

Irrespective of the respective other radicals from the group consisting of $R^1$, $(R^2)_n$ and $(R^3)_m$ and the subdefinitions corresponding to the general radicals, and preferably in combination with preferred definitions of one or more of these radicals, compounds according to the invention with the preferred meanings listed below of the radicals in question are of particular interest.

According to the invention, preference is given to compounds of the formula (I) and/or their salts, characterized in that Q represents a mono- or bicyclic heteroaromatic radical having in total 2 to 9 carbon ring atoms, where the heteroaromatic radical Q contains 1, 2, 3 or 4 heteroatoms in the heteroaromatic ring and the heteroatom or the heteroatoms are selected from the group consisting of N, O, and S.

According to the invention, preference is given to compounds of the formula (I) and/or their salts, characterized in that According to the invention, further preference is given to compounds of the formula (I) and/or their salts, characterized in that Q represents a mono- or bicyclic heteroaromatic radical selected from the group consisting of pyrimidinyl, pyridinyl, pyridazinyl, pyrazinyl, thienyl, furyl, oxazolyl, thiazolyl, imidazolyl, pyrazolyl, triazinyl, quinolyl, isoquinolyl, cinnolinyl-, quinazolinyl, quinoxalinyl, pteridinyl, indolyl and phthalazinyl.

Preferably, Q is a mono- or bicyclic heteroaromatic radical having in total 3 to 9 carbon ring atoms, where at least one of the heteroatoms present in the heteroaromatic ring is N or S, where further preferably at least one of the heteroatoms present in the heteroaromatic ring is N.

Here, in turn preferably Q is a heteroaromatic 5- or 6-membered ring (i.e. a heteroaromatic ring with 5 or 6 ring atoms), in which preferably all heteroatoms present in the heteroaromatic ring are N.

According to the invention, particular preference is given to compounds of the formula (I) and/or their salts, in which Q is pyridyl, corresponding to the formulae (I-1), (I-2) and (I-3) defined below:

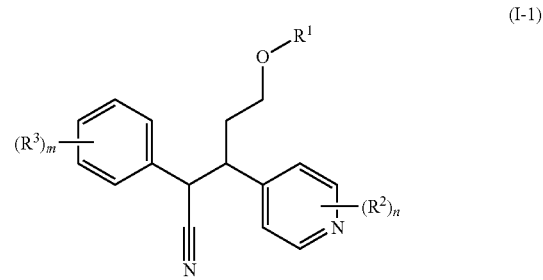

(I-1)

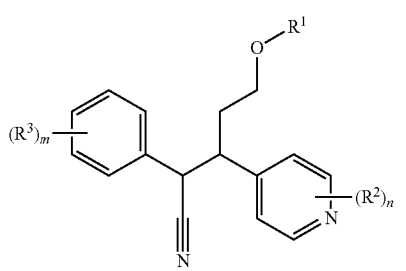

(I-2)

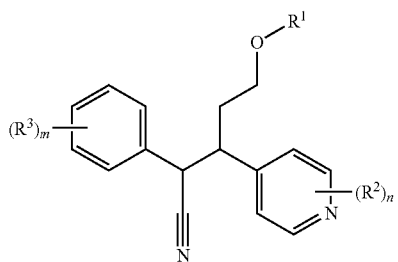

(I-3)

where $R^1$, $R^2$, $R^3$, m and n in each case have the meaning defined above or below.

Particularly preferred compounds of the formula (I) according to the invention correspond to the above-defined formula (I-2), i.e. a meaning of Q particularly preferred according to the invention is 3-pyridyl.

Preference is given to compounds of the formula (I) according to the invention or salts thereof in which $R^1$ represents hydrogen or a hydrolyzable radical having a total of up to 30 carbon atoms, preferably a hydrolyzable radical having a total of 1 to 24 carbon atoms, preferably having a total of 1 to 20 carbon atoms, more preferably having a total of 1 to 16 carbon atoms, particularly preferably having a total of 1 to 12 carbon atoms.

Further preference is given to compounds of the formula (I) or salts thereof in which $R^1$ represents hydrogen or a hydrolyzable radical having in total 1 to 24 carbon atoms, where $R^1$ represents an optionally substituted hydrocarbon radical or an optionally substituted heterocyclyl radical, or represents a radical of the formula $SiR^a R^b R^c$, or $-NR^a R^b$, where each of the radicals $R^a$ and $R^b$ independently of the other represents hydrogen or an optionally substituted hydrocarbon radical and $R^c$ independently represents an optionally substituted hydrocarbon radical, or $-NR^a R^b$ represents a 3- to 9-membered heterocycle which, in addition to this nitrogen atom, may contain one or two further ring heteroatoms from the group consisting of N, O and S and which is substituted or unsubstituted, or represents a radical of the formula $-C(=O)-R^e$ or $-P(=O)(R^f)_2$, where $R^e$ and both radicals $R^f$ in each case independently of one another are selected from the group consisting of hydrogen, OH, unsubstituted or substituted $(C_1-C_8)$alkyl, unsubstituted or substituted $(C_1-C_4)$haloalkyl, unsubstituted or substituted $(C_2-C_8)$alkenyl, unsubstituted or substituted $(C_2-C_8)$alkynyl, unsubstituted or substituted $(C_1-C_6)$alkoxy, unsubstituted or substituted $(C_1-C_6)$alkoxy-$(C_1-C_8)$alkyl, unsubstituted or substituted $(C_1-C_4)$haloalkoxy, unsubstituted or substituted $(C_1-C_4)$haloalkoxy-$(C_1-C_8)$alkyl, unsubstituted or substituted $(C_3-C_8)$alkenyloxy, unsubstituted or substituted $(C_3-C_8)$alkenyloxy-$(C_1-C_8)$alkyl, unsubstituted or substituted $(C_3-C_8)$alkynyloxy, unsubstituted or substituted $(C_3-C_8)$alkynyloxy-$(C_1-C_8)$alkyl, unsubstituted or substituted $-NR^*R^{**}$, where $R^*$ and $R^{**}$ are as defined above, unsubstituted or substituted tri-[$(C_1-C_4)$alkyl]silyl, unsubstituted or substituted tri-[$(C_1-C_4)$alkyl]silyl-$(C_1-C_8)$alkyl, unsubstituted or substituted $(C_3-C_6)$cycloalkyl, unsubstituted or substituted $(C_3-C_6)$cycloalkyl-$(C_1-C_8)$alkyl, unsubstituted or substituted $(C_5-C_6)$cycloalkenyl, unsubstituted or substituted $(C_5-C_6)$cycloalkenyl-$(C_1-C_8)$alkyl, unsubstituted or substituted $(C_5-C_6)$cycloalkynyl, unsubstituted or substituted $(C_5-C_6)$cycloalkynyl-$(C_1-C_8)$alkyl, unsubstituted or substituted phenyl, unsubstituted or substituted phenyl-$(C_1-C_8)$alkyl, unsubstituted or substituted phenoxy, unsubstituted or substituted phenoxy-$(C_1-C_8)$alkyl, unsubstituted or substituted phenylamino, unsubstituted or substituted phenylamino$(C_1-C_8)$alkyl, unsubstituted or substituted Het, unsubstituted or substituted Het-$(C_1-C_6)$alkyl and unsubstituted or substituted Het-O—$(C_1-C_6)$alkyl, where Het in each case represents a saturated, partially unsaturated or heteroaromatic monocyclic heterocyclyl radical having 3 to 9 ring atoms or a 9- or 10-membered bicyclic heterocycle in each case containing 1, 2, 3 or 4 heteroatoms selected from the group consisting of O, N and S, where each of the specified substituted radicals is substituted in the acyclic moiety by one or more identical or different radicals $R^A$ and/or where each of the specified substituted radicals is substituted in the cyclic moiety by one or more identical or different radicals $R^B$, where $R^A$ represents halogen, cyano, hydroxy or $(C_1-C_6)$alkoxy, and $R^B$ independently of any further radicals $R^B$ present is selected from the group consisting of halogen, cyano, hydroxy, oxo, nitro, $(C_1-C_8)$alkyl, $(C_1-C_6)$haloalkyl, cyano-$(C_1-C_6)$alkyl, hydroxy-$(C_1-C_6)$alkyl, nitro-$(C_1-C_6)$alkyl, $(C_2-C_8)$alkenyl, $(C_2-C_8)$haloalkenyl, $(C_2-C_8)$alkynyl, $(C_2-C_8)$haloalkynyl, $(C_1-C_8)$alkoxy, $(C_2-C_8)$alkenyloxy, $(C_2-C_8)$alkinyloxy, $(C_1-C_8)$haloalkoxy, $(C_1-C_6)$alkoxy-$(C_1-C_6)$alkyl, $(C_1-C_6)$alkoxy-$(C_1-C_4)$alkoxy, $(C_1-C_6)$haloalkoxy-$(C_1-C_4)$alkyl, $(C_1-C_6)$haloalkoxy-$(C_1-C_4)$alkoxy, $(C_1-C_8)$alkylthio, $(C_2-C_6)$alkenylthio, $(C_2-C_6)$alkynylthio, $(C_1-C_8)$alkylsulfinyl, $(C_1-C_6)$haloalkylsulfinyl, $(C_1-C_8)$alkylsulfonyl, $(C_1-C_6)$haloalkylsulfonyl, $R^{aa}—C(=O)—$, $R^{aa}—C(=O)—(C_1-C_6)$alkyl, $—NR^*R^{**}$, tri-[$(C_1-C_4)$alkyl]silyl, tri-[$(C_1-C_4)$alkyl]silyl-$(C_1-C_6)$alkyl, $(C_3-C_8)$cycloalkyl, $(C_3-C_8)$cycloalkoxy, $(C_3-C_8)$cycloalkyl-$(C_1-C_8)$alkyl, $(C_3-C_8)$cycloalkyl-$(C_1-C_8)$alkoxy, phenyl, phenyl-$(C_1-C_8)$alkyl, phenoxy, phenoxy-$(C_1-C_8)$alkyl, phenylamino, phenylamino-$(C_1-C_8)$alkyl or a 5- or 6-membered monocyclic or 9- or 10-membered bicyclic heterocycle containing 1, 2, 3 or 4 heteroatoms selected from the group consisting of O, N and S, where each of these specified radicals can be substituted in the cyclic moiety by one or more identical or different $R^{bb}$, where $R^{aa}$ in each case independently of one another represent hydrogen, OH, $(C_1-C_8)$alkyl, $(C_1-C_6)$haloalkyl, $(C_2-C_8)$alkenyl, $(C_2-C_8)$alkynyl, $(C_1-C_8)$alkoxy, $(C_1-C_6)$ alkoxy-$(C_1$-$C_6)$alkyl, $(C_1$-$C_6)$alkoxy-$(C_1$-$C_6)$alkyloxy, $(C_1$-$C_6)$haloalkoxy, $(C_1$-$C_6)$haloalkoxy-$(C_1$-$C_6)$alkyl, $(C_1$-$C_6)$haloalkoxy-$(C_1$-$C_6)$alkoxy, $(C_3$-$C_8)$alkenyloxy, $(C_3$-$C_8)$alkenyloxy-$(C_1$-$C_6)$alkyl, $(C_3$-$C_8)$alkenyloxy-$(C_1$-$C_6)$alkoxy, $(C_3$-$C_8)$alkynyloxy, $(C_3$-$C_8)$alkynyloxy-$(C_1$-$C_6)$alkyl, $(C_3$-$C_8)$alkynyloxy-$(C_1$-$C_6)$alkoxy, —NR*R**, tri-[$(C_1$-$C_4)$alkyl]silyl, tri-[$(C_1$-$C_4)$alkyl]silyl-$(C_1$-$C_6)$alkyl, tri-[$(C_1$-$C_4)$alkyl]silyl-$(C_1$-$C_6)$alkoxy, $(C_3$-$C_8)$cycloalkyl, $(C_3$-$C_8)$cycloalkoxy, $(C_3$-$C_8)$cycloalkyl-$(C_1$-$C_8)$alkyl, $(C_3$-$C_8)$cycloalkyl-$(C_1$-$C_8)$alkoxy, $(C_5$-$C_8)$cycloalkenyl, $(C_5$-$C_8)$cycloalkenyl-$(C_1$-$C_6)$alkyl, $(C_5$-$C_8)$cycloalkenyloxy, $(C_5$-$C_8)$cycloalkynyl, $(C_5$-$C_8)$cycloalkynyl-$(C_1$-$C_6)$alkyl, $(C_5$-$C_8)$cycloalkynyl-$(C_1$-$C_6)$alkoxy, phenyl, phenyl-$(C_1$-$C_8)$alkyl, phenyl-$(C_1$-$C_8)$alkoxy, phenoxy, phenoxy-$(C_1$-$C_8)$alkyl, phenoxy-$(C_1$-$C_8)$alkoxy, phenylamino, phenylamino-$(C_1$-$C_8)$alkyl, phenylamino-$(C_1$-$C_8)$alkoxy or a 5- or 6-membered monocyclic or 9- or 10-membered bicyclic heterocycle containing 1, 2, 3 or 4 heteroatoms and optionally bonded via an alkylene group or an alkoxy group is selected from the group consisting of O, N and S, where each of the radicals $R^{aa}$ encompassing a cycle is optionally substituted in the cyclic moiety by one or more identical or different radicals $R^{bb}$, and where R*, R**, —NR*R** and $R^{bb}$ have the meaning given above.

Further preference is given to compounds of the formula (I) or salts thereof in which $R^1$ represents hydrogen, unsubstituted $(C_1$-$C_{18})$alkyl, unsubstituted $(C_2$-$C_{18})$alkenyl, unsubstituted $(C_2$-$C_{18})$alkynyl, substituted $(C_1$-$C_{18})$alkyl, substituted $(C_2$-$C_{18})$alkenyl or substituted $(C_2$-$C_{18})$alkynyl, where in the case of substituted $(C_1$-$C_{18})$alkyl, substituted $(C_2$-$C_{18})$alkenyl and substituted $(C_2$-$C_{18})$alkynyl the substituent(s) is/are each independently of one another selected from groups (a)-(e) below:

(a) halogen, cyano, thio, nitro, hydroxy, carboxy, $(C_1$-$C_8)$alkoxy, $(C_2$-$C_8)$alkenyloxy, $(C_2$-$C_8)$alkynyloxy, $(C_1$-$C_8)$haloalkoxy, $(C_1$-$C_4)$alkoxy-$(C_1$-$C_4)$alkoxy, $(C_1$-$C_8)$alkylthio, $(C_2$-$C_8)$alkenylthio, $(C_2$-$C_8)$alkynylthio, $(C_1$-$C_8)$haloalkylthio, $(C_2$-$C_8)$haloalkenylthio, $(C_2$-$C_8)$haloalkinylthio, $(C_1$-$C_8)$alkylsulfinyl, $(C_2$-$C_8)$alkenylsulfinyl, $(C_2$-$C_8)$alkynylsulfinyl, $(C_1$-$C_8)$haloalkylsulfinyl, $(C_2$-$C_8)$haloalkenylsulfinyl, $(C_2$-$C_8)$haloalkinylsulfinyl, $(C_1$-$C_8)$alkylsulfonyl, $(C_2$-$C_8)$alkenylsulfonyl, $(C_2$-$C_8)$alkynylsulfonyl, $(C_1$-$C_8)$haloalkylsulfonyl, $(C_2$-$C_8)$haloalkenylsulfonyl, $(C_2$-$C_8)$haloalkynylsulfonyl, —NR*R**, where R*, R** and —NR*R** each have the meaning given above, (b) $(C_3$-$C_8)$cycloalkyl, $(C_5$-$C_8)$cycloalkenyl, $(C_5$-$C_8)$cycloalkinyl, $(C_3$-$C_8)$cycloalkyl-$(C_1$-$C_6)$alkoxy, $(C_3$-$C_8)$cycloalkyl-$(C_1$-$C_6)$alkyl-$S(O)_p$—, $(C_5$-$C_8)$cycloalkenyl-$(C_1$-$C_6)$alkoxy, $(C_5$-$C_8)$cycloalkenyl-$(C_1$-$C_6)$alkyl-$S(O)_p$—, $(C_5$-$C_8)$cycloalkynyl-$(C_1$-$C_6)$alkoxy, $(C_5$-$C_8)$cycloalkynyl-$(C_1$-$C_6)$alkyl-$S(O)_p$—, $(C_3$-$C_8)$cycloalkoxy, $(C_3$-$C_8)$cycloalkyl-$S(O)_p$—, $(C_5$-$C_8)$cycloalkenyloxy, $(C_5$-$C_8)$cycloalkenyl-$S(O)_p$—, $(C_5$-$C_8)$cycloalkynyloxy, $(C_5$-$C_8)$cycloalkynyl-$S(O)_p$—, $(C_3$-$C_8)$cycloalkoxy-$(C_1$-$C_6)$alkoxy, $(C_3$-$C_8)$cycloalkoxy-$(C_1$-$C_6)$alkyl-$S(O)_p$—, phenyl, phenyl$(C_1$-$C_6)$alkoxy, phenoxy, phenyl-$S(O)_p$—, phenyl-$(C_1$-$C_6)$alkyl-$S(O)_p$—, phenoxy-$(C_1$-$C_6)$alkoxy, phenoxy-$(C_1$-$C_6)$alkyl-$S(O)_p$—, a radical $Het^1$, $Het^1$-$S(O)_p$—, $Het^1$-$(C_1$-$C_6)$alkoxy, $Het^1$-O—, $Het^1$-O—$(C_1$-$C_6)$alkoxy, where the radical $Het^1$ has the meaning given above, and where each of the last-mentioned radicals of the group (b) in the acyclic moiety is unsubstituted or substituted by one or more identical or different radicals selected from the group consisting of halogen, cyano, hydroxy and $(C_1$-$C_6)$alkoxy, and/or in the cyclic moiety is unsubstituted or substituted by one or more identical or different radicals $R^B$, where $R^B$ has the meaning given above, and the index p is in each case 0, 1 or 2, (c) —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$), where R*, R** and —NR*R** each have the meaning given above and $R^C$ and $R^D$ are as defined below, (d) —Si$R'_3$, —O—Si$R'_3$, $(R')_3$Si—$(C_1$-$C_6)$alkoxy, —CO—O—N$R'_2$, —O—N=C$R'_2$, —N=C$R'_2$, —O—N$R'_2$, —CH(OR')$_2$ and —O—(CH$_2)_q$—CH(OR')$_2$, in which each of the radicals R' is independently selected from the group consisting of H, $(C_1$-$C_4)$alkyl or phenyl which is unsubstituted or substituted by one or more radicals from the group consisting of halogen, $(C_1$-$C_4)$alkyl, $(C_1$-$C_4)$alkoxy, $(C_1$-$C_4)$haloalkyl, $(C_1$-$C_4)$haloalkoxy and nitro or substituted at two adjacent positions by a $(C_2$-$C_6)$alkylene bridge, and the index q is an integer from 0 to 6, and (e) R"O—CHR'"CH(OR")—$(C_1$-$C_6)$alkoxy,
in which each of the radicals R" independently of the others represents H or $(C_1$-$C_4)$alkyl or together the radicals represent a $(C_1$-$C_6)$alkylene group and R'" represents H or $(C_1$-$C_4)$alkyl, or $R^1$ $(C_3$-$C_9)$cycloalkyl, $(C_5$-$C_9)$cycloalkenyl, $(C_5$-$C_9)$cycloalkynyl or phenyl,
where each of these radicals is unsubstituted or substituted by one or more radicals from the group consisting of the radicals of subgroups (a')-(e') below:

(a') halogen, cyano, thio, nitro, hydroxy, carboxy, $(C_1$-$C_8)$alkyl, $(C_1$-$C_8)$haloalkyl, $(C_1$-$C_4)$alkoxy-$(C_1$-$C_4)$alkyl, $(C_2$-$C_8)$alkenyl, $(C_2$-$C_8)$haloalkenyl, $(C_2$-$C_8)$alkynyl, $(C_2$-$C_8)$haloalkynyl, $(C_1$-$C_8)$alkoxy, $(C_2$-$C_8)$alkenyloxy, $(C_2$-$C_8)$alkynyloxy, $(C_1$-$C_8)$haloalkoxy, $(C_1$-$C_4)$alkoxy-$(C_1$-$C_4)$alkoxy, $(C_1$-$C_8)$alkylthio, $(C_2$-$C_8)$alkenylthio, $(C_2$-$C_8)$alkynylthio and —NR*R**,
where R*, R**, —NR*R**, and $R^{bb}$ in each case have the meaning given above, (b') radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$), where R*, R**, —NR*R** and $R^{bb}$ have the meaning given above and $R^C$ and $R^D$ have the meaning defined below, (c') radicals of the formulae —SiR'$_3$, —O—SiR'$_3$, (R')$_3$Si—(C$_1$-C$_6$)alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals $R^1$ independently of the others represents H, (C$_1$-C$_4$)-alkyl or phenyl which is unsubstituted or substituted by one or more radicals from the group consisting of halogen, (C$_1$-C$_4$)alkyl, (C$_1$-C$_4$)alkoxy, (C$_1$-C$_4$)haloalkyl, (C$_1$-C$_4$)haloalkoxy and nitro or is substituted at two adjacent positions by a (C$_2$-C$_6$)alkylene bridge, and q represents an integer from 0 to 6, and (d') radicals of the formula R"O—CHR'"CH(OR")—(C$_1$-C$_6$)alkoxy, in which each of the radicals R" independently of the others represents H or (C$_1$-C$_4$)alkyl or together the radicals represent a (C$_1$-C$_6$)alkylene group and R'" represents H or (C$_1$-C$_4$)alkyl, and (e') a radical of the formula Het$^1$ which is unsubstituted or substituted by one or more identical or different radicals $R^B$, where $R^B$ has the meaning given above, or $R^1$ represents a polycyclic radical based on (C$_3$-C$_9$)cycloalkyl, (C$_5$-C$_9$)cycloalkenyl, (C$_5$-C$_9$)cycloalkynyl or phenyl, where the base ring is fused with a carbocyclic or heterocyclic ring, preferably a 5- or 6-membered ring having 0, 1, 2 or 3 ring heteroatoms from the group consisting of N, O and S, preferably benzo-fused, and where the base ring or the polycyclic system is unsubstituted or substituted by one or more identical or different radicals $R^B$, where $R^B$ has the meaning given above, is preferably unsubstituted or substituted by one or more radicals selected from the group consisting of halogen, cyano, nitro, hydroxy, carboxy, (C$_1$-C$_6$)alkyl, (C$_1$-C$_6$)haloalkyl, (C$_1$-C$_4$)alkoxy-(C$_1$-C$_4$)alkyl, (C$_2$-C$_6$)alkenyl, (C$_2$-C$_6$)haloalkenyl, (C$_2$-C$_6$)alkynyl, (C$_2$-C$_6$)haloalkynyl, (C$_1$-C$_6$)alkoxy, (C$_2$-C$_6$)alkenyloxy, (C$_2$-C$_6$)alkynyloxy, (C$_1$-C$_6$)haloalkoxy, (C$_1$-C$_4$)alkoxy-(C$_1$-C$_4$)alkoxy, (C$_1$-C$_6$)alkylthio, (C$_2$-C$_6$)alkenylthio, (C$_2$-C$_6$)alkynylthio, (C$_3$-C$_6$)cycloalkyl, (C$_3$-C$_6$)cycloalkoxy, [(C$_1$-C$_8$)alkoxy]carbonyl, [(C$_1$-C$_6$)haloalkoxy]carbonyl and oxo, or $R^1$ is a heterocyclic radical Het$^1$, which is unsubstituted in the ring or in the polycyclic system or is substituted by one or more identical or different radicals $R^B$, where $R^B$ has the meaning given above, preferably is unsubstituted or substituted by one or more radicals from the group halogen, cyano, thio, nitro, hydroxy, carboxy, (C$_1$-C$_6$)alkyl, (C$_1$-C$_6$)haloalkyl, (C$_1$-C$_4$)alkoxy-(C$_1$-C$_4$)alkyl, (C$_2$-C$_6$)alkenyl, (C$_2$-C$_6$)haloalkenyl, (C$_2$-C$_6$)alkynyl, (C$_2$-C$_6$)haloalkynyl, (C$_1$-C$_6$)alkoxy, (C$_2$-C$_6$)alkenyloxy, (C$_2$-C$_6$)alkynyloxy, (C$_1$-C$_6$)haloalkoxy, (C$_1$-C$_4$)alkoxy-(C$_1$-C$_4$)alkoxy, (C$_1$-C$_6$)alkylthio, (C$_2$-C$_6$)alkenylthio, (C$_2$-C$_6$)alkynylthio, (C$_3$-C$_6$)cycloalkyl, (C$_3$-C$_6$)cycloalkoxy, [(C$_1$-C$_8$)alkoxy]carbonyl, [(C$_1$-C$_6$)haloalkoxy]carbonyl and oxo, where Het$^1$ in each case independently of the others is a saturated, partially unsaturated or heteroaromatic monocyclic heterocyclyl radical having 3 to 9 ring atoms, preferably having 5 or 6 ring atoms, or a 9- or 10-membered bicyclic heterocycle containing 1, 2, 3 or 4 heteroatoms selected from the group consisting of O, N and S, preferably a 5- or 6-membered heterocycle having 1 to 3 ring heteroatoms from the group consisting of N, O and S which is optionally also fused to a carbocyclic or heterocyclic ring, preferably a carbocyclic ring having 3 to 6 carbon atoms or a heterocyclic ring having 5 or 6 ring atoms and 1 to 3 ring heteroatoms from the group consisting of N, O and S, preferably optionally benzo-fused, $R^A$ has the meaning given above, $R^B$ has the meaning given above, and where $R^B$ preferably represents a radical selected from the group consisting of halogen, cyano, hydroxy, oxo, nitro, (C$_1$-C$_6$)alkyl, (C$_1$-C$_4$)haloalkyl, cyano-(C$_1$-C$_4$)alkyl, hydroxy-(C$_1$-C$_4$)alkyl, nitro-(C$_1$-C$_4$)alkyl, (C$_2$-C$_6$)alkenyl, (C$_2$-C$_6$)haloalkenyl, (C$_2$-C$_6$)alkynyl, (C$_2$-C$_6$)haloalkynyl, (C$_1$-C$_6$)alkoxy, (C$_2$-C$_6$)alkenyloxy, (C$_2$-C$_6$)alkynyloxy, (C$_1$-C$_6$)haloalkoxy, (C$_1$-C$_4$)alkoxy-(C$_1$-C$_4$)alkyl, (C$_1$-C$_4$)alkoxy-(C$_1$-C$_4$)alkoxy, (C$_1$-C$_4$)haloalkoxy-(C$_1$-C$_4$)alkyl, (C$_1$-C$_4$)haloalkoxy-(C$_1$-C$_4$)alkoxy, (C$_1$-C$_6$)alkylthio, (C$_2$-C$_6$)alkenylthio, (C$_2$-C$_6$)alkynylthio, (C$_1$-C$_6$)alkylsulfinyl, (C$_1$-C$_6$)haloalkylsulfinyl, (C$_1$-C$_6$)alkylsulfonyl, (C$_1$-C$_6$)haloalkylsulfonyl, a radical of the formula $R^{aa}$—C(=O)— or $R^{aa}$—C(=O)—(C$_1$-C$_6$)alkyl, where $R^{aa}$ has the meaning given above, —NR*R**, where R*, R**, —NR*R**, and $R^{bb}$ in each case have the meaning given above, tri-[(C$_1$-C$_4$)alkyl]silyl, tri-[(C$_1$-C$_4$)alkyl]silyl-(C$_1$-C$_6$)alkyl, (C$_3$-C$_6$)cycloalkyl, (C$_3$-C$_6$)cycloalkoxy, (C$_3$-C$_6$)cycloalkyl-(C$_1$-C$_4$)alkyl, (C$_3$-C$_6$)cycloalkyl-(C$_1$-C$_8$)alkoxy, phenyl, phenyl-(C$_1$-C$_6$)alkyl, phenoxy, phenoxy-(C$_1$-C$_6$)alkyl, phenylamino, phenylamino-(C$_1$-C$_6$)alkyl, or a 5- or 6-membered monocyclic or 9- or 10-membered bicyclic heterocycle containing 1, 2, 3 or 4 heteroatoms selected from the group consisting of O, N and S, where each of the radicals $R^B$ in the cyclic moiety is optionally substituted by one or more identical or different radicals $R^{bb}$, where $R^B$ and $R^{bb}$ in each case have the meaning given above, $R^C$ and $R^D$ each independently of one another (and also independently of radicals $R^C$, $R^D$ in other groups) represent a radical selected from the group consisting of:

(i) hydrogen, unsubstituted (C$_1$-C$_8$)alkyl, unsubstituted (C$_2$-C$_8$)alkenyl, unsubstituted (C$_2$-C$_8$)alkynyl, substituted (C$_1$-C$_8$)alkyl, substituted (C$_2$-C$_8$)alkenyl, and substituted (C$_2$-C$_8$)alkynyl, where each of these substituted radicals is substituted by one or more radicals from the group halogen, cyano, nitro, hydroxy, (C$_1$-C$_6$)alkoxy, (C$_2$-C$_6$)alkenyloxy, (C$_2$-C$_6$)alkynyloxy, (C$_1$-C$_8$)haloalkoxy, (C$_1$-C$_4$)alkoxy-(C$_1$-C$_4$)alkoxy, (C$_1$-C$_8$)alkylthio, (C$_1$-C$_8$)haloalkylthio, (C$_1$-C$_8$)alkylsulfinyl, (C$_1$-C$_8$)haloalkylsulfinyl, (C$_1$-C$_8$)alkylsulfonyl, (C$_1$-C$_8$)haloalkylsulfonyl and tri-[(C$_1$-C$_4$)alkyl]silyl, and (ii) (C$_3$-C$_8$)cycloalkyl, (C$_5$-C$_8$)cycloalkenyl, (C$_5$-C$_8$)cycloalkynyl, phenyl, (C$_3$-C$_8$)cycloalkyl-(C$_1$-C$_6$)alkyl, (C$_5$-C$_8$)cycloalkenyl-(C$_1$-C$_6$)alkyl, (C$_5$-C$_8$)cycloalkynyl-(C$_1$-C$_6$)alkyl, phenyl-(C$_1$-C$_6$)alkyl, (C$_3$-C$_8$)cycloalkyloxy-(C$_1$-C$_6$)alkyl, (C$_3$-C$_8$)cycloalkyl-S(O)$_p$—(C$_1$-C$_6$)alkyl, (C$_5$-C$_8$)cycloalkenyloxy-(C$_1$-

$C_6$)alkyl, ($C_5$-$C_8$)cycloalkynyloxy-($C_1$-$C_6$)alkyl, phenoxy-($C_1$-$C_6$)alkyl, phenyl-S(O)$_p$—($C_1$-$C_6$)alkyl, ($C_3$-$C_8$)cycloalkylamino-($C_1$-$C_6$)alkyl, ($C_5$-$C_8$)cycloalkenylamino-($C_1$-$C_6$)alkyl, ($C_5$-$C_8$)cycloalkynylamino-($C_1$-$C_6$)alkyl, phenylamino-($C_1$-$C_6$)alkyl, Het$^1$, Het$^1$-($C_1$-$C_6$)alkyl, Het$^1$-O—($C_1$-$C_6$)alkyl or Het$^1$-S(O)$_p$—($C_1$-$C_6$)alkyl, where Het$^1$ has the meaning given above, and where each of these radicals is unsubstituted in the acyclic moiety or substituted by one or more identical or different radicals $R^A$ and in the cyclic moiety is unsubstituted or substituted by one or more identical or different radicals $R^B$ and p in each case represents 0, 1 or 2, where $R^A$ and $R^B$ in each case have the meaning given above, $R^{aa}$ has the meaning given above, and where $R^{aa}$ preferably independently is a radical selected from the group consisting of hydrogen, OH, ($C_1$-$C_6$)alkyl, ($C_1$-$C_4$)haloalkyl, ($C_2$-$C_6$)alkenyl, ($C_2$-$C_6$)alkynyl, ($C_1$-$C_6$)alkoxy, ($C_1$-$C_6$)alkoxy-($C_1$-$C_6$)alkyl, ($C_1$-$C_6$)alkoxy-($C_1$-$C_6$)alkyloxy, ($C_1$-$C_4$)haloalkoxy, ($C_1$-$C_4$)haloalkoxy-($C_1$-$C_6$)alkyl, ($C_1$-$C_4$)haloalkoxy-($C_1$-$C_6$)alkoxy, ($C_3$-$C_6$)alkenyloxy, ($C_3$-$C_6$)alkenyloxy-($C_1$-$C_6$)alkyl, ($C_3$-$C_6$)alkenyloxy-($C_1$-$C_6$)alkoxy, ($C_3$-$C_6$)alkynyloxy, ($C_3$-$C_6$)alkynyloxy-($C_1$-$C_6$)alkyl, ($C_3$-$C_6$)alkynyloxy-($C_1$-$C_6$)alkoxy, —NR*R**, where R* and R** are as defined above, tri[($C_1$-$C_4$)alkyl]silyl, tri[($C_1$-$C_4$)alkyl]silyl-($C_1$-$C_6$)alkyl, tri[($C_1$-$C_4$)alkyl]silyl-($C_1$-$C_6$)alkoxy, ($C_3$-$C_6$)cycloalkyl, ($C_3$-$C_6$)cycloalkoxy, ($C_3$-$C_6$)cycloalkyl-($C_1$-$C_8$)alkyl, ($C_3$-$C_6$)cycloalkyl-($C_1$-$C_8$)alkoxy, ($C_5$-$C_6$)cycloalkenyl, ($C_5$-$C_6$)cycloalkenyl-($C_1$-$C_6$)alkyl, ($C_5$-$C_6$)cycloalkenyloxy, ($C_5$-$C_6$)cycloalkynyl, ($C_5$-$C_6$)cycloalkynyl-($C_1$-$C_6$)alkyl, ($C_5$-$C_6$)cycloalkynyl-($C_1$-$C_6$)alkoxy, phenyl, phenyl-($C_1$-$C_6$)alkyl, phenyl-($C_1$-$C_6$)alkoxy, phenoxy, phenoxy-($C_1$-$C_6$)alkyl, phenoxy-($C_1$-$C_6$)alkoxy, phenylthio, phenyl-S(O)$_p$—($C_1$-$C_6$)alkyl, phenyl-S(O)$_p$—($C_1$-$C_6$)alkoxy, where p in each case independently of one another is 0, 1 or 2, phenylamino, phenylamino-($C_1$-$C_6$)alkyl, phenylamino-($C_1$-$C_6$)alkoxy or a 5- or 6-membered monocyclic or 9- or 10-membered bicyclic heterocycle optionally bonded via an alkylene group or an alkoxy group, containing 1, 2, 3 or 4 heteroatoms selected from the group consisting of O, N and S, where each of the specified cyclic radicals $R^{aa}$ in the cyclic moiety is optionally substituted by one or more identical or different radicals selected from the group consisting of halogen, ($C_1$-$C_4$)alkyl, ($C_1$-$C_4$)haloalkyl, ($C_1$-$C_4$)alkoxy and ($C_1$-$C_4$)haloalkoxy.

For reasons of stronger herbicidal activity, better selectivity and better or easier handling, inter alia, compounds of the formula (I) according to the invention and/or salts thereof in which $R^1$=H (hydrogen), preferably compounds of the formula (Ia) defined below, are particularly preferable in the context of the present invention.

Particular preference is likewise given to compounds of the formula (I) according to the invention and/or salts thereof which, under application conditions, comparatively easily lead to a compound of the formula (I) where $R^1$=H, for example by degradation or hydrolysis.

In this case, the actual structure of group $R^1$ is not critical, where—as mentioned—preferably under the application conditions—for example by (enzymatic) degradation, cleavage or hydrolysis—at least to some extent a compound of the formula (I) where $R^1$=H, corresponding to a compound of the formula (Ia) defined below, is formed.

In the context of what was discussed above, in a preferred aspect $R^1$ represents hydrogen or a group selected from the group consisting of —C(=O)—$R^C$, —C(=O)—O—$R^C$, —C(=O)—S—$R^C$, —C(=S)—S—$R^C$ and —C(=O)—NR*R**, particularly preferably hydrogen or a group —C(=O)—$R^C$, where $R^C$, R* and R** each have the meaning defined above, preferably each have one of the meanings given above as being preferred.

Especially preferably, $R^1$ represents hydrogen or a group selected from the group consisting of —C(=O)—$R^C$ and —C(=O)—O—$R^C$, here in turn particularly preferably hydrogen or —C(=O)—$R^C$, where $R^C$ preferably comprises a total of 1 to 16 carbon atoms, with preference a total of 1 to 12 carbon atoms.

Particularly preferably, $R^C$ in each case particularly preferably represents a radical selected from the group consisting of:

(i) hydrogen, unsubstituted ($C_1$-$C_8$)alkyl, unsubstituted ($C_2$-$C_8$)alkenyl, unsubstituted ($C_2$-$C_8$)alkynyl, substituted ($C_1$-$C_8$)alkyl, substituted ($C_2$-$C_8$)alkenyl, and substituted ($C_2$-$C_8$)alkynyl, where each of these substituted radicals is substituted by one or more radicals from the group halogen, cyano, hydroxy, ($C_1$-$C_4$)alkoxy, ($C_2$-$C_6$)alkenyloxy, ($C_1$-$C_4$)haloalkoxy, ($C_1$-$C_4$)alkoxy-($C_1$-$C_4$)alkoxy, ($C_1$-$C_6$)alkylthio, ($C_1$-$C_6$)haloalkylthio, ($C_1$-$C_6$)alkylsulfinyl, ($C_1$-$C_6$)alkylsulfonyl, ($C_1$-$C_8$)haloalkylsulfonyl and tri [($C_1$-$C_4$)alkyl]silyl, and (ii) ($C_3$-$C_8$)cycloalkyl, ($C_5$-$C_8$)cycloalkenyl, phenyl, phenyl-($C_1$-$C_6$)alkyl, ($C_3$-$C_8$)cycloalkyloxy-($C_1$-$C_6$)alkyl, phenoxy-($C_1$-$C_6$)alkyl, Het$^1$, Het$^1$-($C_1$-$C_6$)alkyl, Het$^1$-O—($C_1$-$C_6$)alkyl, where Het$^1$ has the meaning mentioned above and where each of these radicals in the acyclic moiety is unsubstituted or substituted by one or more identical or different radicals $R^A$ and in the cyclic moiety is unsubstituted or substituted by one or more identical or different radicals $R^B$, where $R^A$ and $R^B$ in each case have the meaning given above, where in turn preferably $R^A$ and $R^B$ have the following meaning:

$R^A$ independently of any other radicals $R^A$ present is selected from the group consisting of halogen, cyano, hydroxy and ($C_1$-$C_4$)alkoxy, and $R^B$ independently of any other radicals $R^B$ present is selected from the group consisting of halogen, cyano, hydroxy, nitro, ($C_1$-$C_6$)alkyl, ($C_1$-$C_6$)haloalkyl, cyano-($C_1$-$C_6$)alkyl, hydroxy-($C_1$-$C_6$)alkyl, ($C_2$-$C_8$)alkenyl, ($C_2$-$C_8$)haloalkenyl, ($C_2$-$C_6$)alkynyl, ($C_2$-$C_6$)haloalkynyl, ($C_1$-$C_6$)alkoxy, ($C_2$-$C_6$)alkenyloxy, ($C_1$-$C_6$)haloalkoxy, ($C_1$-$C_6$)alkoxy-($C_1$-$C_4$)alkyl, ($C_1$-$C_4$)alkoxy-($C_1$-$C_4$)alkoxy, ($C_1$-$C_4$)haloalkoxy-($C_1$-$C_4$)alkyl, ($C_1$-$C_4$)haloalkoxy-($C_1$-$C_4$)alkoxy, ($C_1$-$C_6$)alkylthio, ($C_2$-$C_6$)alkenylthio, ($C_1$-$C_6$)alkylsulfinyl, ($C_1$-$C_6$)haloalkylsulfinyl, ($C_1$-$C_6$)alkylsulfonyl, and ($C_1$-$C_6$)haloalkylsulfonyl, where $R^C$ preferably comprises a total of 1 to 16 carbon atoms, with preference a total of 1 to 12 carbon atoms.

In formula (I), especially preferably $R^1$ represents hydrogen, —C(=O)—O—$R^C$ or —C(=O)—$R^C$, where the group $R^C$ is in each case selected from the group consisting of:

(i) unsubstituted ($C_1$-$C_6$)alkyl, unsubstituted ($C_2$-$C_6$)alkenyl, unsubstituted ($C_2$-$C_6$)alkynyl, substituted ($C_1$-$C_6$)alkyl, substituted ($C_2$-$C_6$)alkenyl and substituted ($C_2$-$C_6$)alkynyl, where each of these substituted radicals is substituted by one or more radicals from the group consisting of methyl, hydroxy, fluorine and chlorine, (ii) $(C_3-C_6)$cycloalkyl, $(C_3-C_6)$cycloalkyloxy-$(C_1-C_4)$alkyl, phenyl, where each of these radicals in the cyclic moiety is unsubstituted or substituted by one or more identical or different radicals $R^B$, where $R^B$ independently of any other radicals $R^B$ present is selected from the group consisting of halogen (here preferably fluorine, chlorine, bromine), cyano, nitro and $(C_1-C_4)$alkyl (here in turn preferably methyl), where $R^C$ preferably comprises a total of 1 to 12 carbon atoms, with preference a total of 1 to 10 carbon atoms.

In formula (I), $R^1$ especially preferably represents hydrogen or a group selected from the group consisting of: acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl, 2-nitrobenzoyl, 2-fluoroacetyl, 2-chloroacetyl, 2-bromoacetyl, 2,2-dichloroacetyl, 2-methoxyacetyl, 2,6-difluorobenzoyl, C(O)C(=O)OMe and C(O)CH$_2$C(O)OMe.

Preferred compounds according to the invention are, therefore, compounds of the formula (I), in which $R^1$ has the meaning given in Table U1 below (see Example Section).

In formula (I), $R^1$ especially preferably represents hydrogen or a group selected from the group consisting of:

acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl and 2-nitrobenzoyl.

Further preference is given to compounds of the formula (I) according to the invention or salts thereof in which $(R^2)_n$ represents n substituents $R^2$,
where $R_2$ (if n=1) or each of the substituents $R^2$ (if n is greater than 1) independently of the others represents halogen, cyano, nitro, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri[$(C_1-C_4)$alkyl]silyl or tri[$(C_1-C_4)$alkyl]silyl-$(C_1-C_4)$alkyl,
and/or
$(R^3)_m$ represents m substituents $R^3$,
where $R^3$ (if m=1) or each of the substituents $R^3$ (if m is greater than 1) independently of the others represents halogen, cyano, nitro, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, NR*R**, tri[$(C_1-C_4)$alkyl]silyl or tri[$(C_1-C_4)$alkyl]silyl$(C_1-C_4)$alkyl,
or where in each case two groups $R^3$ directly adjacent on the ring together represent a group of the formula —$Z^3$-A**—$Z^4$, in which
A** represents an alkylene group having 1 to 4 carbon atoms which is optionally substituted by one or more radicals from the group consisting of halogen, $(C_1-C_4)$alkyl, $(C_1-C_4)$haloalkyl, $(C_1-C_4)$alkoxy and $(C_1-C_4)$haloalkoxy,
$Z^3$ represents a direct bond, O or S and
$Z^4$ represents a direct bond, O or S,
where the group —$Z^3$-A**—$Z^4$ together with the carbon atoms, attached to the group, of the phenyl ring form a fused-on 5- or 6-membered ring, R*, R** each independently of one another or together with the nitrogen atom have the meaning given above,
n, m in each case independently of one another are 0, 1, 2, 3, 4 or 5, preferably 0, 1, 2 or 3, in particular 0, 1 or 2, where in addition preferably
$R^1$ is hydrogen or a group selected from the group consisting of:
acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl, 2-nitrobenzoyl, 2-fluoroacetyl, 2-chloroacetyl, 2-bromoacetyl, 2,2-dichloroacetyl, 2-methoxyacetyl, 2,6-difluorobenzoyl, C(O)C(=O)OMe and C(O)CH$_2$C(O)OMe.

Further preference is given to compounds of the formula (I) according to the invention or salts thereof or of the formula (Ia) defined below or salts thereof, in which
$(R^2)_n$ represents n substituents $R^2$,
where, in the case that n=1, the substituent $R^2$ or, in the case that n is greater than 1, each of the substituents $R^2$ independently of the others represents
halogen, cyano, nitro, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, $(C_1-C_4)$haloalkyl, $(C_2-C_4)$haloalkenyl, $(C_1-C_4)$haloalkoxy, $(C_1-C_4)$haloalkylthio, $(C_1-C_4)$haloalkylsulfinyl, $(C_1-C_4)$haloalkylsulfonyl, $(C_2-C_4)$alkenyl, $(C_2-C_4)$alkynyl, tri[$(C_1-C_4)$alkyl]silyl or tri[$(C_1-C_4)$alkyl]silyl $(C_1-C_4)$alkyl and
n represents 0, 1, 2, 3 or 4, preferably 0, 1, 2 or 3, in particular 0, 1 or 2,
and/or
$(R^3)_m$ represents m substituents $R^3$,
where in the case that m=1, the substituent $R^3$ or, in the case that m is greater than 1, each of the substituents $R^3$ independently of one another represents halogen, cyano, nitro, $(C_1-C_4)$alkyl, $(C_1-C_4)$alkoxy, $(C_1-C_4)$alkylthio, $(C_1-C_4)$alkylsulfinyl, $(C_1-C_4)$alkylsulfonyl, $(C_1-C_4)$haloalkyl, $(C_2-C_4)$haloalkenyl, $(C_1-C_4)$haloalkoxy, $(C_1-C_4)$haloalkylthio, $(C_1-C_4)$haloalkylsulfinyl, $(C_1-C_4)$haloalkylsulfonyl, $(C_2-C_6)$alkenyl, $(C_2-C_6)$alkynyl or tri-[$(C_1-C_4)$alkyl]silyl-$Z^b$—, where $Z^b$= is a covalent bond or $(C_1-C_4)$alkylene, or
in each case two groups $R^3$ directly adjacent to one another at the ring together represent a group of the formula —$Z^3$-A**-Z
where
A** represents an alkylene group which is optionally substituted by one or more radicals from the group halogen, $(C_1-C_4)$alkyl, $(C_1-C_4)$haloalkyl, $(C_1-C_4)$alkoxy and $(C_1-C_4)$haloalkoxy,
$Z^3$ represents O or S and
$Z^4$ represents O or S, where the group —$Z^3$-A**—$Z^4$ together with the carbon atoms, attached to the group, of the phenyl ring form a fused-on 5- or 6-membered ring,
m represents 0, 1, 2, 3, 4 or 5, preferably 0, 1, 2, 3 or 4, in particular 0, 1, 2 or 3.

Further preference is given to compounds of the formula (I) according to the invention or salts thereof or of the formula (Ia) defined below or salts thereof, in which $(R^2)_n$ represents n substituents $R^2$, where, in the case that n=1, the substituent $R^2$ or, in the case that n is greater than 1, each of the substituents $R^2$ independently of one another represents fluorine, chlorine, bromine, iodine, cyano, nitro, methyl, ethyl, methoxy, methylthio, methylsulfinyl, methylsulfonyl, trifluoromethyl, trifluoromethoxy, trifluoroalkylthio, trifluoromethylsulfinyl or trifluoromethylsulfonyl, and $(R^3)_m$ represents m substituents $R^3$, where, in the case that m=1, the substituent radical $R^3$ or, in the case that m is greater than 1, each of the substituents $R^3$ independently of one another represents fluorine, chlorine, bromine, iodine, cyano, nitro, methyl, methoxy, (here preferably 2-methoxy, 3-methoxy), methylthio, methylsulfinyl, methylsulfonyl, trifluoromethyl, trifluoromethoxy, trifluoroalkylthio, trifluoromethylsulfinyl or trifluoromethylsulfonyl, and m represents 0, 1, 2, 3 or 4, preferably 0, 1, 2 or 3, and
n represents 0, 1, 2 or 3, preferably 0, 1 or 2,
and also preferably $R^1$ is hydrogen or a group selected from the group consisting of: acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl and 2-nitrobenzoyl.

Particular preference is given to compounds of the formula (I) according to the invention or salts thereof or of the formula (Ia) defined below or salts thereof, in which $(R^2)_n$ represents n substituents $R^2$, where, in the case that n=1, the substituent $R^2$ or, in the case that n is greater than 1, each of the substituents $R^2$ independently of the others is fluorine, chlorine, bromine, iodine, cyano, nitro, methyl, ethyl, or methoxy.

Particular preference is given to compounds of the formula (I) according to the invention or salts thereof or of the formula (Ia) defined below or salts thereof, in which $(R^3)_m$ represents m substituents $R^3$, 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-CF$_3$, 3-CF$_3$, 4-CF$_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfinyl, 2-methylsulfonyl, 3-methylsulfonyl, 4-methylsulfonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-NO$_2$-3-F), (4-OMe-3-F), (3-Br-4-F), (3-CN-4-F), (3-NO$_2$-4-F), (3-CN-4-Cl), (3-NO$_2$-4-Cl), (5-CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-F$_2$-4-Cl).

Preferred compounds according to the invention are compounds of the formula (Ia) shown below, (corresponding to compounds of the formula (I) in which the radical $R^1$=hydrogen), their salts and their esters

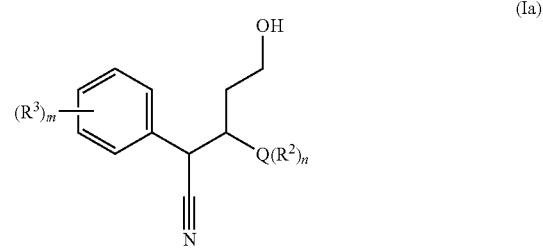

(Ia)

in which Q, $R^2$, $R^3$, m and n in each case have the meanings given above and below, with preference the meanings stated as preferred, preferably the meanings stated as preferred, particularly preferably the meanings stated as preferred, and especially (preferably) the meanings stated as especially (preferred).

In a preferred embodiment of the present invention, m+n>0, i.e. preferably at least one of the radicals $R^2$ and $R^3$ does not represent hydrogen.

Preference according to the invention is given to compounds of the formula (I) or (Ia) or salts thereof in which n>0.

Preference according to the invention is likewise given to compounds of the formula (I) or (Ia) or salts thereof in which m>0.

In a preferred embodiment of the present invention, m+n>1, i.e. preferably at least two radicals $R^2$, at least two radicals $R^3$ or at least one radical $R^2$ and at least one radical $R^3$ do not represent hydrogen.

In preferred compounds of the formula (I) or (Ia) according to the invention or salts thereof, the sum of m+n=2, 3, 4 or 5.

In particularly preferred compounds of the formula (I) or (Ia) according to the invention, n is greater than or equal to 1 and one or more radicals $R^2$ represent halogen, preferably halogen selected from the group consisting of F, Cl and Br.

In particularly preferred compounds of the formula (I) or (Ia) according to the invention, m is greater than or equal to 1 and one or more radicals $R^3$ represent halogen, preferably halogen from the group consisting of F, Cl and Br.

Particularly preferred compounds of the formula (Ia) according to the invention correspond to the above-defined formula (I-2), in which $R^1$=hydrogen.

Particular preference is likewise given to compounds of the formula (I) according to the invention or salts thereof in which $(R^2)_n$ represents n substituents $R^2$, where, in the case that n=1, the substituent $R^2$ or, in the case that n is greater than 1, each of the substituents $R^2$ independently of the others is fluorine, chlorine, bromine, iodine, cyano, nitro, methyl, ethyl, or methoxy, $(R^3)_m$ represents m substituents $R^3$, where, in the case that m=1, the substituent radical $R^3$ or, in the case that m is greater than 1, each of the substituents $R^3$ independently of the others is 2-bromo, 3-bromo, 4-bromo, 2-chloro, 3-chloro, 4-chloro, 2-fluoro, 3-fluoro, 4-fluoro, 2-cyano, 3-cyano, 4-cyano, 2-methyl, 3-methyl, 4-methyl, 2-ethyl, 3-ethyl, 4-ethyl, 2-CF$_3$, 3-CF$_3$, 4-CF$_3$, 2-methoxy, 3-methoxy, 4-methoxy, 2-ethoxy, 3-ethoxy, 4-ethoxy, 2-methylthio, 3-methylthio, 4-methylthio, 2-methylsulfinyl, 3-methylsulfinyl, 4-methylsulfinyl, 2-methylsulfonyl, 3-methylsulfonyl, 4-methylsulfonyl, 2-nitro, 3-nitro, 4-nitro, 2,3-dimethyl, 2,4-dimethyl, 2,5-dimethyl, 2,6-dimethyl, 3,4-dimethyl, 3,5-dimethyl, 2,3-difluoro, 2,4-difluoro, 2,5-difluoro, 2,6-difluoro, 3,4-difluoro, 3,5-difluoro, 2,3-dichloro, 2,4-dichloro, 2,5-dichloro, 2,6-dichloro, 3,4-dichloro, 3,5-dichloro, 2,5-dicyano, 2,6-dicyano, (2-Cl-3-F), (2-Cl-4-F), (2-Cl-5-F), (2-Cl-6-F), (3-Cl-2-F), (3-Cl-4-F), (3-Cl-5-F), (3-Cl-6-F), (4-Cl-2-F), (4-Cl-3-F), (4-Br-2-F), (4-Br-3-F), (4-CN-3-F), (4-NO$_2$-3-F), (4-OMe-3-F), (3-Br-4-F), (3-CN-4-F), (3-NO$_2$-4-F), (3-CN-4-Cl), (3-NO$_2$-4-Cl), (S—CN-2-F), 2,3,4-trifluoro, 2,3,5-trifluoro, 2,3,6-trifluoro, 2,4,6-trifluoro, 3,4,5-trifluoro, 2,3,4-trichloro, 2,3,5-trichloro, 2,3,6-trichloro, 2,4,6-trichloro, 3,4,5-trichloro or (2,6-F$_2$-4-Cl), $R^1$ is hydrogen or a group selected from the group consisting of: acetyl, propanoyl, butanoyl, pentanoyl, hexanoyl, 2-methylpropanoyl (=isopropanoyl), 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl (=pivaloyl), 3,3-dimethylbutanoyl and 2-nitrobenzoyl, m is 0, 1, 2 or 3, and
n is 0, 1 or 2,
where preferably the sum of m+n=2, 3, 4, or 5.

Preferred compounds according to the invention are compounds of the formula (I) or (Ia), in which Q(R$^2$)$_n$ has the meaning given in Table 1 below.

Preferred compounds according to the invention are compounds of the formula (I) or (Ia), in which (R$^3$)$_n$ has the meaning given in Table 1 below.

Preferred compounds according to the invention are compounds of the formula (I) or of the formula (Ia) as defined in Table 1 below.

Table 1 below gives preferred meanings of Q(R$^2$)$_n$ and (R$^3$)$_m$. The abbreviations and annotations used herein are explained in the Example Section.

TABLE 1

Preferred meanings of Q(R$^2$)$_n$ and (R$^3$)$_m$ in compounds of the formula (I) or of the formula (Ia) according to the invention:

| No. | Q(R$^2$)$_n$ | (R$^3$)$_m$ |
| --- | --- | --- |
| 1 | 6-fluoropyridin-2-yl | H |
| 2 | 6-fluoropyridin-2-yl | 2-F |
| 3 | 6-fluoropyridin-2-yl | 3-F |
| 4 | 6-fluoropyridin-2-yl | 4-F |
| 5 | 6-fluoropyridin-2-yl | 3-Cl |
| 6 | 6-fluoropyridin-2-yl | 4-Cl |
| 7 | 6-fluoropyridin-2-yl | 3-Br |
| 8 | 6-fluoropyridin-2-yl | 4-Br |
| 9 | 6-fluoropyridin-2-yl | 3-I |
| 10 | 6-fluoropyridin-2-yl | 3-CN |
| 11 | 6-fluoropyridin-2-yl | 4-CN |
| 12 | 6-fluoropyridin-2-yl | 3-NO$_2$ |
| 13 | 6-fluoropyridin-2-yl | 3-Me |
| 14 | 6-fluoropyridin-2-yl | 4-Me |
| 15 | 6-fluoropyridin-2-yl | 2,3-F$_2$ |
| 16 | 6-fluoropyridin-2-yl | 2,4-F$_2$ |

TABLE 1-continued

Preferred meanings of Q(R$^2$)$_n$ and (R$^3$)$_m$ in compounds of the formula (I) or of the formula (Ia) according to the invention:

| No. | Q(R$^2$)$_n$ | (R$^3$)$_m$ |
| --- | --- | --- |
| 17 | 6-fluoropyridin-2-yl | 2,5-F$_2$ |
| 18 | 6-fluoropyridin-2-yl | 2,6-F$_2$ |
| 19 | 6-fluoropyridin-2-yl | 3,4-F$_2$ |
| 20 | 6-fluoropyridin-2-yl | 3,5-F$_2$ |
| 21 | 6-fluoropyridin-2-yl | 3,4,5-F$_3$ |
| 22 | 6-fluoropyridin-2-yl | 3-F, 4-Cl |
| 23 | 6-fluoropyridin-2-yl | 3-F, 4-Br |
| 24 | 6-fluoropyridin-2-yl | 3-CN, 4-F |
| 25 | 6-fluoropyridin-2-yl | 3-Br, 4-F |
| 26 | 6-fluoropyridin-2-yl | 3-Cl, 4-F |
| 27 | 6-fluoropyridin-2-yl | 3,4-Cl$_2$ |
| 28 | 5-fluoropyridin-2-yl | H |
| 29 | 5-fluoropyridin-2-yl | 2-F |
| 30 | 5-fluoropyridin-2-yl | 3-F |
| 31 | 5-fluoropyridin-2-yl | 4-F |
| 32 | 5-fluoropyridin-2-yl | 3-Cl |
| 33 | 5-fluoropyridin-2-yl | 4-Cl |
| 34 | 5-fluoropyridin-2-yl | 3-Br |
| 35 | 5-fluoropyridin-2-yl | 4-Br |
| 36 | 5-fluoropyridin-2-yl | 3-I |
| 37 | 5-fluoropyridin-2-yl | 3-CN |
| 38 | 5-fluoropyridin-2-yl | 4-CN |
| 39 | 5-fluoropyridin-2-yl | 3-NO$_2$ |
| 40 | 5-fluoropyridin-2-yl | 3-Me |
| 41 | 5-fluoropyridin-2-yl | 4-Me |
| 42 | 5-fluoropyridin-2-yl | 2,3-F$_2$ |
| 43 | 5-fluoropyridin-2-yl | 2,4-F$_2$ |
| 44 | 5-fluoropyridin-2-yl | 2,5-F$_2$ |
| 45 | 5-fluoropyridin-2-yl | 2,6-F$_2$ |
| 46 | 5-fluoropyridin-2-yl | 3,4-F$_2$ |
| 47 | 5-fluoropyridin-2-yl | 3,5-F$_2$ |
| 48 | 5-fluoropyridin-2-yl | 3,4,5-F$_3$ |
| 49 | 5-fluoropyridin-2-yl | 3-F, 4-Cl |
| 50 | 5-fluoropyridin-2-yl | 3-F, 4-Br |
| 51 | 5-fluoropyridin-2-yl | 3-CN, 4-F |
| 52 | 5-fluoropyridin-2-yl | 3-Br, 4-F |
| 53 | 5-fluoropyridin-2-yl | 3-Cl, 4-F |
| 54 | 5-fluoropyridin-2-yl | 3,4-Cl$_2$ |
| 55 | 4-fluoropyridin-2-yl | H |
| 56 | 4-fluoropyridin-2-yl | 2-F |
| 57 | 4-fluoropyridin-2-yl | 3-F |
| 58 | 4-fluoropyridin-2-yl | 4-F |
| 59 | 4-fluoropyridin-2-yl | 3-Cl |
| 60 | 4-fluoropyridin-2-yl | 4-Cl |
| 61 | 4-fluoropyridin-2-yl | 3-Br |
| 62 | 4-fluoropyridin-2-yl | 4-Br |
| 63 | 4-fluoropyridin-2-yl | 3-I |
| 64 | 4-fluoropyridin-2-yl | 3-CN |
| 65 | 4-fluoropyridin-2-yl | 4-CN |
| 66 | 4-fluoropyridin-2-yl | 3-NO$_2$ |
| 67 | 4-fluoropyridin-2-yl | 3-Me |
| 68 | 4-fluoropyridin-2-yl | 4-Me |
| 69 | 4-fluoropyridin-2-yl | 2,3-F$_2$ |
| 70 | 4-fluoropyridin-2-yl | 2,4-F$_2$ |
| 71 | 4-fluoropyridin-2-yl | 2,5-F$_2$ |
| 72 | 4-fluoropyridin-2-yl | 2,6-F$_2$ |
| 73 | 4-fluoropyridin-2-yl | 3,4-F$_2$ |
| 74 | 4-fluoropyridin-2-yl | 3,5-F$_2$ |
| 75 | 4-fluoropyridin-2-yl | 3,4,5-F$_3$ |
| 76 | 4-fluoropyridin-2-yl | 3-F, 4-Cl |
| 77 | 4-fluoropyridin-2-yl | 3-F, 4-Br |
| 78 | 4-fluoropyridin-2-yl | 3-CN, 4-F |
| 79 | 4-fluoropyridin-2-yl | 3-Br, 4-F |
| 80 | 4-fluoropyridin-2-yl | 3-Cl, 4-F |
| 81 | 4-fluoropyridin-2-yl | 3,4-Cl$_2$ |
| 82 | 3-fluoropyridin-2-yl | H |
| 83 | 3-fluoropyridin-2-yl | 2-F |
| 84 | 3-fluoropyridin-2-yl | 3-F |
| 85 | 3-fluoropyridin-2-yl | 4-F |
| 86 | 3-fluoropyridin-2-yl | 3-Cl |
| 87 | 3-fluoropyridin-2-yl | 4-Cl |
| 88 | 3-fluoropyridin-2-yl | 3-Br |
| 89 | 3-fluoropyridin-2-yl | 4-Br |
| 90 | 3-fluoropyridin-2-yl | 3-I |
| 91 | 3-fluoropyridin-2-yl | 3-CN |

TABLE 1-continued

Preferred meanings of $Q(R^2)_n$ and $(R^3)_m$ in compounds of the formula (I) or of the formula (Ia) according to the invention:

| No. | $Q(R^2)_n$ | $(R^3)_m$ |
|---|---|---|
| 92 | 3-fluoropyridin-2-yl | 4-CN |
| 93 | 3-fluoropyridin-2-yl | 3-NO$_2$ |
| 94 | 3-fluoropyridin-2-yl | 3-Me |
| 95 | 3-fluoropyridin-2-yl | 4-Me |
| 96 | 3-fluoropyridin-2-yl | 2,3-F$_2$ |
| 97 | 3-fluoropyridin-2-yl | 2,4-F$_2$ |
| 98 | 3-fluoropyridin-2-yl | 2,5-F$_2$ |
| 99 | 3-fluoropyridin-2-yl | 2,6-F$_2$ |
| 100 | 3-fluoropyridin-2-yl | 3,4-F$_2$ |
| 101 | 3-fluoropyridin-2-yl | 3,5-F$_2$ |
| 102 | 3-fluoropyridin-2-yl | 3,4,5-F$_3$ |
| 103 | 3-fluoropyridin-2-yl | 3-F, 4-Cl |
| 104 | 3-fluoropyridin-2-yl | 3-F, 4-Br |
| 105 | 3-fluoropyridin-2-yl | 3-CN, 4-F |
| 106 | 3-fluoropyridin-2-yl | 3-Br, 4-F |
| 107 | 3-fluoropyridin-2-yl | 3-Cl, 4-F |
| 108 | 3-fluoropyridin-2-yl | 3,4-Cl$_2$ |
| 109 | 6-chloropyridin-2-yl | H |
| 110 | 6-chloropyridin-2-yl | 2-F |
| 111 | 6-chloropyridin-2-yl | 3-F |
| 112 | 6-chloropyridin-2-yl | 4-F |
| 113 | 6-chloropyridin-2-yl | 3-Cl |
| 114 | 6-chloropyridin-2-yl | 4-Cl |
| 115 | 6-chloropyridin-2-yl | 3-Br |
| 116 | 6-chloropyridin-2-yl | 4-Br |
| 117 | 6-chloropyridin-2-yl | 3-I |
| 118 | 6-chloropyridin-2-yl | 3-CN |
| 119 | 6-chloropyridin-2-yl | 4-CN |
| 120 | 6-chloropyridin-2-yl | 3-NO$_2$ |
| 121 | 6-chloropyridin-2-yl | 3-Me |
| 122 | 6-chloropyridin-2-yl | 4-Me |
| 123 | 6-chloropyridin-2-yl | 2,3-F$_2$ |
| 124 | 6-chloropyridin-2-yl | 2,4-F$_2$ |
| 125 | 6-chloropyridin-2-yl | 2,5-F$_2$ |
| 126 | 6-chloropyridin-2-yl | 2,6-F$_2$ |
| 127 | 6-chloropyridin-2-yl | 3,4-F$_2$ |
| 128 | 6-chloropyridin-2-yl | 3,5-F$_2$ |
| 129 | 6-chloropyridin-2-yl | 3,4,5-F$_3$ |
| 130 | 6-chloropyridin-2-yl | 3-F, 4-Cl |
| 131 | 6-chloropyridin-2-yl | 3-F, 4-Br |
| 132 | 6-chloropyridin-2-yl | 3-CN, 4-F |
| 133 | 6-chloropyridin-2-yl | 3-Br, 4-F |
| 134 | 6-chloropyridin-2-yl | 3-Cl, 4-F |
| 135 | 6-chloropyridin-2-yl | 3,4-Cl$_2$ |
| 136 | 5-chloropyridin-2-yl | H |
| 137 | 5-chloropyridin-2-yl | 2-F |
| 138 | 5-chloropyridin-2-yl | 3-F |
| 139 | 5-chloropyridin-2-yl | 4-F |
| 140 | 5-chloropyridin-2-yl | 3-Cl |
| 141 | 5-chloropyridin-2-yl | 4-Cl |
| 142 | 5-chloropyridin-2-yl | 3-Br |
| 143 | 5-chloropyridin-2-yl | 4-Br |
| 144 | 5-chloropyridin-2-yl | 3-I |
| 145 | 5-chloropyridin-2-yl | 3-CN |
| 146 | 5-chloropyridin-2-yl | 4-CN |
| 147 | 5-chloropyridin-2-yl | 3-NO$_2$ |
| 148 | 5-chloropyridin-2-yl | 3-Me |
| 149 | 5-chloropyridin-2-yl | 4-Me |
| 150 | 5-chloropyridin-2-yl | 2,3-F$_2$ |
| 151 | 5-chloropyridin-2-yl | 2,4-F$_2$ |
| 152 | 5-chloropyridin-2-yl | 2,5-F$_2$ |
| 153 | 5-chloropyridin-2-yl | 2,6-F$_2$ |
| 154 | 5-chloropyridin-2-yl | 3,4-F$_2$ |
| 155 | 5-chloropyridin-2-yl | 3,5-F$_2$ |
| 156 | 5-chloropyridin-2-yl | 3,4,5-F$_3$ |
| 157 | 5-chloropyridin-2-yl | 3-F, 4-Cl |
| 158 | 5-chloropyridin-2-yl | 3-F, 4-Br |
| 159 | 5-chloropyridin-2-yl | 3-CN, 4-F |
| 160 | 5-chloropyridin-2-yl | 3-Br, 4-F |
| 161 | 5-chloropyridin-2-yl | 3-Cl, 4-F |
| 162 | 5-chloropyridin-2-yl | 3,4-Cl$_2$ |
| 163 | 4-chloropyridin-2-yl | H |
| 164 | 4-chloropyridin-2-yl | 2-F |
| 165 | 4-chloropyridin-2-yl | 3-F |
| 166 | 4-chloropyridin-2-yl | 4-F |
| 167 | 4-chloropyridin-2-yl | 3-Cl |
| 168 | 4-chloropyridin-2-yl | 4-Cl |
| 169 | 4-chloropyridin-2-yl | 3-Br |
| 170 | 4-chloropyridin-2-yl | 4-Br |
| 171 | 4-chloropyridin-2-yl | 3-I |
| 172 | 4-chloropyridin-2-yl | 3-CN |
| 173 | 4-chloropyridin-2-yl | 4-CN |
| 174 | 4-chloropyridin-2-yl | 3-NO$_2$ |
| 175 | 4-chloropyridin-2-yl | 3-Me |
| 176 | 4-chloropyridin-2-yl | 4-Me |
| 177 | 4-chloropyridin-2-yl | 2,3-F$_2$ |
| 178 | 4-chloropyridin-2-yl | 2,4-F$_2$ |
| 179 | 4-chloropyridin-2-yl | 2,5-F$_2$ |
| 180 | 4-chloropyridin-2-yl | 2,6-F$_2$ |
| 181 | 4-chloropyridin-2-yl | 3,4-F$_2$ |
| 182 | 4-chloropyridin-2-yl | 3,5-F$_2$ |
| 183 | 4-chloropyridin-2-yl | 3,4,5-F$_3$ |
| 184 | 4-chloropyridin-2-yl | 3-F, 4-Cl |
| 185 | 4-chloropyridin-2-yl | 3-F, 4-Br |
| 186 | 4-chloropyridin-2-yl | 3-CN, 4-F |
| 187 | 4-chloropyridin-2-yl | 3-Br, 4-F |
| 188 | 4-chloropyridin-2-yl | 3-Cl, 4-F |
| 189 | 4-chloropyridin-2-yl | 3,4-Cl$_2$ |
| 190 | 3-chloropyridin-2-yl | H |
| 191 | 3-chloropyridin-2-yl | 2-F |
| 192 | 3-chloropyridin-2-yl | 3-F |
| 193 | 3-chloropyridin-2-yl | 4-F |
| 194 | 3-chloropyridin-2-yl | 3-Cl |
| 195 | 3-chloropyridin-2-yl | 4-Cl |
| 196 | 3-chloropyridin-2-yl | 3-Br |
| 197 | 3-chloropyridin-2-yl | 4-Br |
| 198 | 3-chloropyridin-2-yl | 3-I |
| 199 | 3-chloropyridin-2-yl | 3-CN |
| 200 | 3-chloropyridin-2-yl | 4-CN |
| 201 | 3-chloropyridin-2-yl | 3-NO$_2$ |
| 202 | 3-chloropyridin-2-yl | 3-Me |
| 203 | 3-chloropyridin-2-yl | 4-Me |
| 204 | 3-chloropyridin-2-yl | 2,3-F$_2$ |
| 205 | 3-chloropyridin-2-yl | 2,4-F$_2$ |
| 206 | 3-chloropyridin-2-yl | 2,5-F$_2$ |
| 207 | 3-chloropyridin-2-yl | 2,6-F$_2$ |
| 208 | 3-chloropyridin-2-yl | 3,4-F$_2$ |
| 209 | 3-chloropyridin-2-yl | 3,5-F$_2$ |
| 210 | 3-chloropyridin-2-yl | 3,4,5-F$_3$ |
| 211 | 3-chloropyridin-2-yl | 3-F, 4-Cl |
| 212 | 3-chloropyridin-2-yl | 3-F, 4-Br |
| 213 | 3-chloropyridin-2-yl | 3-CN, 4-F |
| 214 | 3-chloropyridin-2-yl | 3-Br, 4-F |
| 215 | 3-chloropyridin-2-yl | 3-Cl, 4-F |
| 216 | 3-chloropyridin-2-yl | 3,4-Cl$_2$ |
| 217 | 2-fluoropyridin-3-yl | H |
| 218 | 2-fluoropyridin-3-yl | 2-F |
| 219 | 2-fluoropyridin-3-yl | 3-F |
| 220 | 2-fluoropyridin-3-yl | 4-F |
| 221 | 2-fluoropyridin-3-yl | 3-Cl |
| 222 | 2-fluoropyridin-3-yl | 4-Cl |
| 223 | 2-fluoropyridin-3-yl | 3-Br |
| 224 | 2-fluoropyridin-3-yl | 4-Br |
| 225 | 2-fluoropyridin-3-yl | 3-I |
| 226 | 2-fluoropyridin-3-yl | 3-CN |
| 227 | 2-fluoropyridin-3-yl | 4-CN |
| 228 | 2-fluoropyridin-3-yl | 3-NO$_2$ |
| 229 | 2-fluoropyridin-3-yl | 3-Me |
| 230 | 2-fluoropyridin-3-yl | 4-Me |
| 231 | 2-fluoropyridin-3-yl | 2,3-F$_2$ |
| 232 | 2-fluoropyridin-3-yl | 2,4-F$_2$ |
| 233 | 2-fluoropyridin-3-yl | 2,5-F$_2$ |
| 234 | 2-fluoropyridin-3-yl | 2,6-F$_2$ |
| 235 | 2-fluoropyridin-3-yl | 3,4-F$_2$ |
| 236 | 2-fluoropyridin-3-yl | 3,5-F$_2$ |
| 237 | 2-fluoropyridin-3-yl | 3,4,5-F$_3$ |
| 238 | 2-fluoropyridin-3-yl | 3-F, 4-Cl |
| 239 | 2-fluoropyridin-3-yl | 3-F, 4-Br |
| 240 | 2-fluoropyridin-3-yl | 3-CN, 4-F |
| 241 | 2-fluoropyridin-3-yl | 3-Br, 4-F |

TABLE 1-continued

Preferred meanings of $Q(R^2)_n$ and $(R^3)_m$ in compounds of the formula (I) or of the formula (Ia) according to the invention:

| No. | $Q(R^2)_n$ | $(R^3)_m$ |
|---|---|---|
| 242 | 2-fluoropyridin-3-yl | 3-Cl, 4-F |
| 243 | 2-fluoropyridin-3-yl | 3,4-Cl$_2$ |
| 244 | 6-fluoropyridin-3-yl | H |
| 245 | 6-fluoropyridin-3-yl | 2-F |
| 246 | 6-fluoropyridin-3-yl | 3-F |
| 247 | 6-fluoropyridin-3-yl | 4-F |
| 248 | 6-fluoropyridin-3-yl | 3-Cl |
| 249 | 6-fluoropyridin-3-yl | 4-Cl |
| 250 | 6-fluoropyridin-3-yl | 3-Br |
| 251 | 6-fluoropyridin-3-yl | 4-Br |
| 252 | 6-fluoropyridin-3-yl | 3-I |
| 253 | 6-fluoropyridin-3-yl | 3-CN |
| 254 | 6-fluoropyridin-3-yl | 4-CN |
| 255 | 6-fluoropyridin-3-yl | 3-NO$_2$ |
| 256 | 6-fluoropyridin-3-yl | 3-Me |
| 257 | 6-fluoropyridin-3-yl | 4-Me |
| 258 | 6-fluoropyridin-3-yl | 2,3-F$_2$ |
| 259 | 6-fluoropyridin-3-yl | 2,4-F$_2$ |
| 260 | 6-fluoropyridin-3-yl | 2,5-F$_2$ |
| 261 | 6-fluoropyridin-3-yl | 2,6-F$_2$ |
| 262 | 6-fluoropyridin-3-yl | 3,4-F$_2$ |
| 263 | 6-fluoropyridin-3-yl | 3,5-F$_2$ |
| 264 | 6-fluoropyridin-3-yl | 3,4,5-F$_3$ |
| 265 | 6-fluoropyridin-3-yl | 3-F, 4-Cl |
| 266 | 6-fluoropyridin-3-yl | 3-F, 4-Br |
| 267 | 6-fluoropyridin-3-yl | 3-CN, 4-F |
| 268 | 6-fluoropyridin-3-yl | 3-Br, 4-F |
| 269 | 6-fluoropyridin-3-yl | 3-Cl, 4-F |
| 270 | 6-fluoropyridin-3-yl | 3,4-Cl$_2$ |
| 271 | 5-fluoropyridin-3-yl | H |
| 272 | 5-fluoropyridin-3-yl | 2-F |
| 273 | 5-fluoropyridin-3-yl | 3-F |
| 274 | 5-fluoropyridin-3-yl | 4-F |
| 275 | 5-fluoropyridin-3-yl | 3-Cl |
| 276 | 5-fluoropyridin-3-yl | 4-Cl |
| 277 | 5-fluoropyridin-3-yl | 3-Br |
| 278 | 5-fluoropyridin-3-yl | 4-Br |
| 279 | 5-fluoropyridin-3-yl | 3-I |
| 280 | 5-fluoropyridin-3-yl | 3-CN |
| 281 | 5-fluoropyridin-3-yl | 4-CN |
| 282 | 5-fluoropyridin-3-yl | 3-NO$_2$ |
| 283 | 5-fluoropyridin-3-yl | 3-Me |
| 284 | 5-fluoropyridin-3-yl | 4-Me |
| 285 | 5-fluoropyridin-3-yl | 2,3-F$_2$ |
| 286 | 5-fluoropyridin-3-yl | 2,4-F$_2$ |
| 287 | 5-fluoropyridin-3-yl | 2,5-F$_2$ |
| 288 | 5-fluoropyridin-3-yl | 2,6-F$_2$ |
| 289 | 5-fluoropyridin-3-yl | 3,4-F$_2$ |
| 290 | 5-fluoropyridin-3-yl | 3,5-F$_2$ |
| 291 | 5-fluoropyridin-3-yl | 3,4,5-F$_3$ |
| 292 | 5-fluoropyridin-3-yl | 3-F, 4-Cl |
| 293 | 5-fluoropyridin-3-yl | 3-F, 4-Br |
| 294 | 5-fluoropyridin-3-yl | 3-CN, 4-F |
| 295 | 5-fluoropyridin-3-yl | 3-Br, 4-F |
| 296 | 5-fluoropyridin-3-yl | 3-Cl, 4-F |
| 297 | 5-fluoropyridin-3-yl | 3,4-Cl$_2$ |
| 298 | 4-fluoropyridin-3-yl | H |
| 299 | 4-fluoropyridin-3-yl | 2-F |
| 300 | 4-fluoropyridin-3-yl | 3-F |
| 301 | 4-fluoropyridin-3-yl | 4-F |
| 302 | 4-fluoropyridin-3-yl | 3-Cl |
| 303 | 4-fluoropyridin-3-yl | 4-Cl |
| 304 | 4-fluoropyridin-3-yl | 3-Br |
| 305 | 4-fluoropyridin-3-yl | 4-Br |
| 306 | 4-fluoropyridin-3-yl | 3-I |
| 307 | 4-fluoropyridin-3-yl | 3-CN |
| 308 | 4-fluoropyridin-3-yl | 4-CN |
| 309 | 4-fluoropyridin-3-yl | 3-NO$_2$ |
| 310 | 4-fluoropyridin-3-yl | 3-Me |
| 311 | 4-fluoropyridin-3-yl | 4-Me |
| 312 | 4-fluoropyridin-3-yl | 2,3-F$_2$ |
| 313 | 4-fluoropyridin-3-yl | 2,4-F$_2$ |
| 314 | 4-fluoropyridin-3-yl | 2,5-F$_2$ |
| 315 | 4-fluoropyridin-3-yl | 2,6-F$_2$ |
| 316 | 4-fluoropyridin-3-yl | 3,4-F$_2$ |
| 317 | 4-fluoropyridin-3-yl | 3,5-F$_2$ |
| 318 | 4-fluoropyridin-3-yl | 3,4,5-F$_3$ |
| 319 | 4-fluoropyridin-3-yl | 3-F, 4-Cl |
| 320 | 4-fluoropyridin-3-yl | 3-F, 4-Br |
| 321 | 4-fluoropyridin-3-yl | 3-CN, 4-F |
| 322 | 4-fluoropyridin-3-yl | 3-Br, 4-F |
| 323 | 4-fluoropyridin-3-yl | 3-Cl, 4-F |
| 324 | 4-fluoropyridin-3-yl | 3,4-Cl$_2$ |
| 325 | 2-chloropyridin-3-yl | H |
| 326 | 2-chloropyridin-3-yl | 2-F |
| 327 | 2-chloropyridin-3-yl | 3-F |
| 328 | 2-chloropyridin-3-yl | 4-F |
| 329 | 2-chloropyridin-3-yl | 3-Cl |
| 330 | 2-chloropyridin-3-yl | 4-Cl |
| 331 | 2-chloropyridin-3-yl | 3-Br |
| 332 | 2-chloropyridin-3-yl | 4-Br |
| 333 | 2-chloropyridin-3-yl | 3-I |
| 334 | 2-chloropyridin-3-yl | 3-CN |
| 335 | 2-chloropyridin-3-yl | 4-CN |
| 336 | 2-chloropyridin-3-yl | 3-NO$_2$ |
| 337 | 2-chloropyridin-3-yl | 3-Me |
| 338 | 2-chloropyridin-3-yl | 4-Me |
| 339 | 2-chloropyridin-3-yl | 2,3-F$_2$ |
| 340 | 2-chloropyridin-3-yl | 2,4-F$_2$ |
| 341 | 2-chloropyridin-3-yl | 2,5-F$_2$ |
| 342 | 2-chloropyridin-3-yl | 2,6-F$_2$ |
| 343 | 2-chloropyridin-3-yl | 3,4-F$_2$ |
| 344 | 2-chloropyridin-3-yl | 3,5-F$_2$ |
| 345 | 2-chloropyridin-3-yl | 3,4,5-F$_3$ |
| 346 | 2-chloropyridin-3-yl | 3-F, 4-Cl |
| 347 | 2-chloropyridin-3-yl | 3-F, 4-Br |
| 348 | 2-chloropyridin-3-yl | 3-CN, 4-F |
| 349 | 2-chloropyridin-3-yl | 3-Br, 4-F |
| 350 | 2-chloropyridin-3-yl | 3-Cl, 4-F |
| 351 | 2-chloropyridin-3-yl | 3,4-Cl$_2$ |
| 352 | 6-chloropyridin-3-yl | H |
| 353 | 6-chloropyridin-3-yl | 2-F |
| 354 | 6-chloropyridin-3-yl | 3-F |
| 355 | 6-chloropyridin-3-yl | 4-F |
| 356 | 6-chloropyridin-3-yl | 3-Cl |
| 357 | 6-chloropyridin-3-yl | 4-Cl |
| 358 | 6-chloropyridin-3-yl | 3-Br |
| 359 | 6-chloropyridin-3-yl | 4-Br |
| 360 | 6-chloropyridin-3-yl | 3-I |
| 361 | 6-chloropyridin-3-yl | 3-CN |
| 362 | 6-chloropyridin-3-yl | 4-CN |
| 363 | 6-chloropyridin-3-yl | 3-NO$_2$ |
| 364 | 6-chloropyridin-3-yl | 3-Me |
| 365 | 6-chloropyridin-3-yl | 4-Me |
| 366 | 6-chloropyridin-3-yl | 2,3-F$_2$ |
| 367 | 6-chloropyridin-3-yl | 2,4-F$_2$ |
| 368 | 6-chloropyridin-3-yl | 2,5-F$_2$ |
| 369 | 6-chloropyridin-3-yl | 2,6-F$_2$ |
| 370 | 6-chloropyridin-3-yl | 3,4-F$_2$ |
| 371 | 6-chloropyridin-3-yl | 3,5-F$_2$ |
| 372 | 6-chloropyridin-3-yl | 3,4,5-F$_3$ |
| 373 | 6-chloropyridin-3-yl | 3-F, 4-Cl |
| 374 | 6-chloropyridin-3-yl | 3-F, 4-Br |
| 375 | 6-chloropyridin-3-yl | 3-CN, 4-F |
| 376 | 6-chloropyridin-3-yl | 3-Br, 4-F |
| 377 | 6-chloropyridin-3-yl | 3-Cl, 4-F |
| 378 | 6-chloropyridin-3-yl | 3,4-Cl$_2$ |
| 379 | 5-chloropyridin-3-yl | H |
| 380 | 5-chloropyridin-3-yl | 2-F |
| 381 | 5-chloropyridin-3-yl | 3-F |
| 382 | 5-chloropyridin-3-yl | 4-F |
| 383 | 5-chloropyridin-3-yl | 3-Cl |
| 384 | 5-chloropyridin-3-yl | 4-Cl |
| 385 | 5-chloropyridin-3-yl | 3-Br |
| 386 | 5-chloropyridin-3-yl | 4-Br |
| 387 | 5-chloropyridin-3-yl | 3-I |
| 388 | 5-chloropyridin-3-yl | 3-CN |
| 389 | 5-chloropyridin-3-yl | 4-CN |
| 390 | 5-chloropyridin-3-yl | 3-NO$_2$ |
| 391 | 5-chloropyridin-3-yl | 3-Me |

TABLE 1-continued

Preferred meanings of Q(R$^2$)$_n$ and (R$^3$)$_m$ in compounds of the formula (I) or of the formula (Ia) according to the invention:

| No. | Q(R$^2$)$_n$ | (R$^3$)$_m$ |
|---|---|---|
| 392 | 5-chloropyridin-3-yl | 4-Me |
| 393 | 5-chloropyridin-3-yl | 2,3-F$_2$ |
| 394 | 5-chloropyridin-3-yl | 2,4-F$_2$ |
| 395 | 5-chloropyridin-3-yl | 2,5-F$_2$ |
| 396 | 5-chloropyridin-3-yl | 2,6-F$_2$ |
| 397 | 5-chloropyridin-3-yl | 3,4-F$_2$ |
| 398 | 5-chloropyridin-3-yl | 3,5-F$_2$ |
| 399 | 5-chloropyridin-3-yl | 3,4,5-F$_3$ |
| 400 | 5-chloropyridin-3-yl | 3-F, 4-Cl |
| 401 | 5-chloropyridin-3-yl | 3-F, 4-Br |
| 402 | 5-chloropyridin-3-yl | 3-CN, 4-F |
| 403 | 5-chloropyridin-3-yl | 3-Br, 4-F |
| 404 | 5-chloropyridin-3-yl | 3-Cl, 4-F |
| 405 | 5-chloropyridin-3-yl | 3,4-Cl$_2$ |
| 406 | 4-chloropyridin-3-yl | H |
| 407 | 4-chloropyridin-3-yl | 2-F |
| 408 | 4-chloropyridin-3-yl | 3-F |
| 409 | 4-chloropyridin-3-yl | 4-F |
| 410 | 4-chloropyridin-3-yl | 3-Cl |
| 411 | 4-chloropyridin-3-yl | 4-Cl |
| 412 | 4-chloropyridin-3-yl | 3-Br |
| 413 | 4-chloropyridin-3-yl | 4-Br |
| 414 | 4-chloropyridin-3-yl | 3-I |
| 415 | 4-chloropyridin-3-yl | 3-CN |
| 416 | 4-chloropyridin-3-yl | 4-CN |
| 417 | 4-chloropyridin-3-yl | 3-NO$_2$ |
| 418 | 4-chloropyridin-3-yl | 3-Me |
| 419 | 4-chloropyridin-3-yl | 4-Me |
| 420 | 4-chloropyridin-3-yl | 2,3-F$_2$ |
| 421 | 4-chloropyridin-3-yl | 2,4-F$_2$ |
| 422 | 4-chloropyridin-3-yl | 2,5-F$_2$ |
| 423 | 4-chloropyridin-3-yl | 2,6-F$_2$ |
| 424 | 4-chloropyridin-3-yl | 3,4-F$_2$ |
| 425 | 4-chloropyridin-3-yl | 3,5-F$_2$ |
| 426 | 4-chloropyridin-3-yl | 3,4,5-F$_3$ |
| 427 | 4-chloropyridin-3-yl | 3-F, 4-Cl |
| 428 | 4-chloropyridin-3-yl | 3-F, 4-Br |
| 429 | 4-chloropyridin-3-yl | 3-CN, 4-F |
| 430 | 4-chloropyridin-3-yl | 3-Br, 4-F |
| 431 | 4-chloropyridin-3-yl | 3-Cl, 4-F |
| 432 | 4-chloropyridin-3-yl | 3,4-Cl$_2$ |
| 433 | 3-fluoropyridin-4-yl | H |
| 434 | 3-fluoropyridin-4-yl | 2-F |
| 435 | 3-fluoropyridin-4-yl | 3-F |
| 436 | 3-fluoropyridin-4-yl | 4-F |
| 437 | 3-fluoropyridin-4-yl | 3-Cl |
| 438 | 3-fluoropyridin-4-yl | 4-Cl |
| 439 | 3-fluoropyridin-4-yl | 3-Br |
| 440 | 3-fluoropyridin-4-yl | 4-Br |
| 441 | 3-fluoropyridin-4-yl | 3-I |
| 442 | 3-fluoropyridin-4-yl | 3-CN |
| 443 | 3-fluoropyridin-4-yl | 4-CN |
| 444 | 3-fluoropyridin-4-yl | 3-NO$_2$ |
| 445 | 3-fluoropyridin-4-yl | 3-Me |
| 446 | 3-fluoropyridin-4-yl | 4-Me |
| 447 | 3-fluoropyridin-4-yl | 2,3-F$_2$ |
| 448 | 3-fluoropyridin-4-yl | 2,4-F$_2$ |
| 449 | 3-fluoropyridin-4-yl | 2,5-F$_2$ |
| 450 | 3-fluoropyridin-4-yl | 2,6-F$_2$ |
| 451 | 3-fluoropyridin-4-yl | 3,4-F$_2$ |
| 452 | 3-fluoropyridin-4-yl | 3,5-F$_2$ |
| 453 | 3-fluoropyridin-4-yl | 3,4,5-F$_3$ |
| 454 | 3-fluoropyridin-4-yl | 3-F, 4-Cl |
| 455 | 3-fluoropyridin-4-yl | 3-F, 4-Br |
| 456 | 3-fluoropyridin-4-yl | 3-CN, 4-F |
| 457 | 3-fluoropyridin-4-yl | 3-Br, 4-F |
| 458 | 3-fluoropyridin-4-yl | 3-Cl, 4-F |
| 459 | 3-fluoropyridin-4-yl | 3,4-Cl$_2$ |
| 460 | 2-fluoropyridin-4-yl | H |
| 461 | 2-fluoropyridin-4-yl | 2-F |
| 462 | 2-fluoropyridin-4-yl | 3-F |
| 463 | 2-fluoropyridin-4-yl | 4-F |
| 464 | 2-fluoropyridin-4-yl | 3-Cl |
| 465 | 2-fluoropyridin-4-yl | 4-Cl |
| 466 | 2-fluoropyridin-4-yl | 3-Br |
| 467 | 2-fluoropyridin-4-yl | 4-Br |
| 468 | 2-fluoropyridin-4-yl | 3-I |
| 469 | 2-fluoropyridin-4-yl | 3-CN |
| 470 | 2-fluoropyridin-4-yl | 4-CN |
| 471 | 2-fluoropyridin-4-yl | 3-NO$_2$ |
| 472 | 2-fluoropyridin-4-yl | 3-Me |
| 473 | 2-fluoropyridin-4-yl | 4-Me |
| 474 | 2-fluoropyridin-4-yl | 2,3-F$_2$ |
| 475 | 2-fluoropyridin-4-yl | 2,4-F$_2$ |
| 476 | 2-fluoropyridin-4-yl | 2,5-F$_2$ |
| 477 | 2-fluoropyridin-4-yl | 2,6-F$_2$ |
| 478 | 2-fluoropyridin-4-yl | 3,4-F$_2$ |
| 479 | 2-fluoropyridin-4-yl | 3,5-F$_2$ |
| 480 | 2-fluoropyridin-4-yl | 3,4,5-F$_3$ |
| 481 | 2-fluoropyridin-4-yl | 3-F, 4-Cl |
| 482 | 2-fluoropyridin-4-yl | 3-F, 4-Br |
| 483 | 2-fluoropyridin-4-yl | 3-CN, 4-F |
| 484 | 2-fluoropyridin-4-yl | 3-Br, 4-F |
| 485 | 2-fluoropyridin-4-yl | 3-Cl, 4-F |
| 486 | 2-fluoropyridin-4-yl | 3,4-Cl$_2$ |
| 487 | 3-chloropyridin-4-yl | H |
| 488 | 3-chloropyridin-4-yl | 2-F |
| 489 | 3-chloropyridin-4-yl | 3-F |
| 490 | 3-chloropyridin-4-yl | 4-F |
| 491 | 3-chloropyridin-4-yl | 3-Cl |
| 492 | 3-chloropyridin-4-yl | 4-Cl |
| 493 | 3-chloropyridin-4-yl | 3-Br |
| 494 | 3-chloropyridin-4-yl | 4-Br |
| 495 | 3-chloropyridin-4-yl | 3-I |
| 496 | 3-chloropyridin-4-yl | 3-CN |
| 497 | 3-chloropyridin-4-yl | 4-CN |
| 498 | 3-chloropyridin-4-yl | 3-NO$_2$ |
| 499 | 3-chloropyridin-4-yl | 3-Me |
| 500 | 3-chloropyridin-4-yl | 4-Me |
| 501 | 3-chloropyridin-4-yl | 2,3-F$_2$ |
| 502 | 3-chloropyridin-4-yl | 2,4-F$_2$ |
| 503 | 3-chloropyridin-4-yl | 2,5-F$_2$ |
| 504 | 3-chloropyridin-4-yl | 2,6-F$_2$ |
| 505 | 3-chloropyridin-4-yl | 3,4-F$_2$ |
| 506 | 3-chloropyridin-4-yl | 3,5-F$_2$ |
| 507 | 3-chloropyridin-4-yl | 3,4,5-F$_3$ |
| 508 | 3-chloropyridin-4-yl | 3-F, 4-Cl |
| 509 | 3-chloropyridin-4-yl | 3-F, 4-Br |
| 510 | 3-chloropyridin-4-yl | 3-CN, 4-F |
| 511 | 3-chloropyridin-4-yl | 3-Br, 4-F |
| 512 | 3-chloropyridin-4-yl | 3-Cl, 4-F |
| 513 | 3-chloropyridin-4-yl | 3,4-Cl$_2$ |
| 514 | 2-chloropyridin-4-yl | H |
| 515 | 2-chloropyridin-4-yl | 2-F |
| 516 | 2-chloropyridin-4-yl | 3-F |
| 517 | 2-chloropyridin-4-yl | 4-F |
| 518 | 2-chloropyridin-4-yl | 3-Cl |
| 519 | 2-chloropyridin-4-yl | 4-Cl |
| 520 | 2-chloropyridin-4-yl | 3-Br |
| 521 | 2-chloropyridin-4-yl | 4-Br |
| 522 | 2-chloropyridin-4-yl | 3-I |
| 523 | 2-chloropyridin-4-yl | 3-CN |
| 524 | 2-chloropyridin-4-yl | 4-CN |
| 525 | 2-chloropyridin-4-yl | 3-NO$_2$ |
| 526 | 2-chloropyridin-4-yl | 3-Me |
| 527 | 2-chloropyridin-4-yl | 4-Me |
| 528 | 2-chloropyridin-4-yl | 2,3-F$_2$ |
| 529 | 2-chloropyridin-4-yl | 2,4-F$_2$ |
| 530 | 2-chloropyridin-4-yl | 2,5-F$_2$ |
| 531 | 2-chloropyridin-4-yl | 2,6-F$_2$ |
| 532 | 2-chloropyridin-4-yl | 3,4-F$_2$ |
| 533 | 2-chloropyridin-4-yl | 3,5-F$_2$ |
| 534 | 2-chloropyridin-4-yl | 3,4,5-F$_3$ |
| 535 | 2-chloropyridin-4-yl | 3-F, 4-Cl |
| 536 | 2-chloropyridin-4-yl | 3-F, 4-Br |
| 537 | 2-chloropyridin-4-yl | 3-CN, 4-F |
| 538 | 2-chloropyridin-4-yl | 3-Br, 4-F |
| 539 | 2-chloropyridin-4-yl | 3-Cl, 4-F |
| 540 | 2-chloropyridin-4-yl | 3,4-Cl$_2$ |
| 541 | 2,3-difluoropyridin-4-yl | H |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 542 | 2,3-difluoropyridin-4-yl | 2-F |
| 543 | 2,3-difluoropyridin-4-yl | 3-F |
| 544 | 2,3-difluoropyridin-4-yl | 4-F |
| 545 | 2,3-difluoropyridin-4-yl | 3-Cl |
| 546 | 2,3-difluoropyridin-4-yl | 4-Cl |
| 547 | 2,3-difluoropyridin-4-yl | 3-Br |
| 548 | 2,3-difluoropyridin-4-yl | 4-Br |
| 549 | 2,3-difluoropyridin-4-yl | 3-I |
| 550 | 2,3-difluoropyridin-4-yl | 3-CN |
| 551 | 2,3-difluoropyridin-4-yl | 4-CN |
| 552 | 2,3-difluoropyridin-4-yl | 3-NO₂ |
| 553 | 2,3-difluoropyridin-4-yl | 3-Me |
| 554 | 2,3-difluoropyridin-4-yl | 4-Me |
| 555 | 2,3-difluoropyridin-4-yl | 2,3-F₂ |
| 556 | 2,3-difluoropyridin-4-yl | 2,4-F₂ |
| 557 | 2,3-difluoropyridin-4-yl | 2,5-F₂ |
| 558 | 2,3-difluoropyridin-4-yl | 2,6-F₂ |
| 559 | 2,3-difluoropyridin-4-yl | 3,4-F₂ |
| 560 | 2,3-difluoropyridin-4-yl | 3,5-F₂ |
| 561 | 2,3-difluoropyridin-4-yl | 3,4,5-F₃ |
| 562 | 2,3-difluoropyridin-4-yl | 3-F, 4-Cl |
| 563 | 2,3-difluoropyridin-4-yl | 3-F, 4-Br |
| 564 | 2,3-difluoropyridin-4-yl | 3-CN, 4-F |
| 565 | 2,3-difluoropyridin-4-yl | 3-Br, 4-F |
| 566 | 2,3-difluoropyridin-4-yl | 3-Cl, 4-F |
| 567 | 2,3-difluoropyridin-4-yl | 3,4-Cl₂ |
| 568 | 2,5-difluoropyridin-4-yl | H |
| 569 | 2,5-difluoropyridin-4-yl | 2-F |
| 570 | 2,5-difluoropyridin-4-yl | 3-F |
| 571 | 2,5-difluoropyridin-4-yl | 4-F |
| 572 | 2,5-difluoropyridin-4-yl | 3-Cl |
| 573 | 2,5-difluoropyridin-4-yl | 4-Cl |
| 574 | 2,5-difluoropyridin-4-yl | 3-Br |
| 575 | 2,5-difluoropyridin-4-yl | 4-Br |
| 576 | 2,5-difluoropyridin-4-yl | 3-I |
| 577 | 2,5-difluoropyridin-4-yl | 3-CN |
| 578 | 2,5-difluoropyridin-4-yl | 4-CN |
| 579 | 2,5-difluoropyridin-4-yl | 3-NO₂ |
| 580 | 2,5-difluoropyridin-4-yl | 3-Me |
| 581 | 2,5-difluoropyridin-4-yl | 4-Me |
| 582 | 2,5-difluoropyridin-4-yl | 2,3-F₂ |
| 583 | 2,5-difluoropyridin-4-yl | 2,4-F₂ |
| 584 | 2,5-difluoropyridin-4-yl | 2,5-F₂ |
| 585 | 2,5-difluoropyridin-4-yl | 2,6-F₂ |
| 586 | 2,5-difluoropyridin-4-yl | 3,4-F₂ |
| 587 | 2,5-difluoropyridin-4-yl | 3,5-F₂ |
| 588 | 2,5-difluoropyridin-4-yl | 3,4,5-F₃ |
| 589 | 2,5-difluoropyridin-4-yl | 3-F, 4-Cl |
| 590 | 2,5-difluoropyridin-4-yl | 3-F, 4-Br |
| 591 | 2,5-difluoropyridin-4-yl | 3-CN, 4-F |
| 592 | 2,5-difluoropyridin-4-yl | 3-Br, 4-F |
| 593 | 2,5-difluoropyridin-4-yl | 3-Cl, 4-F |
| 594 | 2,5-difluoropyridin-4-yl | 3,4-Cl₂ |
| 595 | 3,5-difluoropyridin-4-yl | H |
| 596 | 3,5-difluoropyridin-4-yl | 2-F |
| 597 | 3,5-difluoropyridin-4-yl | 3-F |
| 598 | 3,5-difluoropyridin-4-yl | 4-F |
| 599 | 3,5-difluoropyridin-4-yl | 3-Cl |
| 600 | 3,5-difluoropyridin-4-yl | 4-Cl |
| 601 | 3,5-difluoropyridin-4-yl | 3-Br |
| 602 | 3,5-difluoropyridin-4-yl | 4-Br |
| 603 | 3,5-difluoropyridin-4-yl | 3-I |
| 604 | 3,5-difluoropyridin-4-yl | 3-CN |
| 605 | 3,5-difluoropyridin-4-yl | 4-CN |
| 606 | 3,5-difluoropyridin-4-yl | 3-NO₂ |
| 607 | 3,5-difluoropyridin-4-yl | 3-Me |
| 608 | 3,5-difluoropyridin-4-yl | 4-Me |
| 609 | 3,5-difluoropyridin-4-yl | 2,3-F₂ |
| 610 | 3,5-difluoropyridin-4-yl | 2,4-F₂ |
| 611 | 3,5-difluoropyridin-4-yl | 2,5-F₂ |
| 612 | 3,5-difluoropyridin-4-yl | 2,6-F₂ |
| 613 | 3,5-difluoropyridin-4-yl | 3,4-F₂ |
| 614 | 3,5-difluoropyridin-4-yl | 3,5-F₂ |
| 615 | 3,5-difluoropyridin-4-yl | 3,4,5-F₃ |
| 616 | 3,5-difluoropyridin-4-yl | 3-F, 4-Cl |
| 617 | 3,5-difluoropyridin-4-yl | 3-F, 4-Br |
| 618 | 3,5-difluoropyridin-4-yl | 3-CN, 4-F |
| 619 | 3,5-difluoropyridin-4-yl | 3-Br, 4-F |
| 620 | 3,5-difluoropyridin-4-yl | 3-Cl, 4-F |
| 621 | 3,5-difluoropyridin-4-yl | 3,4-Cl₂ |
| 622 | 2,4-difluoropyridin-3-yl | H |
| 623 | 2,4-difluoropyridin-3-yl | 2-F |
| 624 | 2,4-difluoropyridin-3-yl | 3-F |
| 625 | 2,4-difluoropyridin-3-yl | 4-F |
| 626 | 2,4-difluoropyridin-3-yl | 3-Cl |
| 627 | 2,4-difluoropyridin-3-yl | 4-Cl |
| 628 | 2,4-difluoropyridin-3-yl | 3-Br |
| 629 | 2,4-difluoropyridin-3-yl | 4-Br |
| 630 | 2,4-difluoropyridin-3-yl | 3-I |
| 631 | 2,4-difluoropyridin-3-yl | 3-CN |
| 632 | 2,4-difluoropyridin-3-yl | 4-CN |
| 633 | 2,4-difluoropyridin-3-yl | 3-NO₂ |
| 634 | 2,4-difluoropyridin-3-yl | 3-Me |
| 635 | 2,4-difluoropyridin-3-yl | 4-Me |
| 636 | 2,4-difluoropyridin-3-yl | 2,3-F₂ |
| 637 | 2,4-difluoropyridin-3-yl | 2,4-F₂ |
| 638 | 2,4-difluoropyridin-3-yl | 2,5-F₂ |
| 639 | 2,4-difluoropyridin-3-yl | 2,6-F₂ |
| 640 | 2,4-difluoropyridin-3-yl | 3,4-F₂ |
| 641 | 2,4-difluoropyridin-3-yl | 3,5-F₂ |
| 642 | 2,4-difluoropyridin-3-yl | 3,4,5-F₃ |
| 643 | 2,4-difluoropyridin-3-yl | 3-F, 4-Cl |
| 644 | 2,4-difluoropyridin-3-yl | 3-F, 4-Br |
| 645 | 2,4-difluoropyridin-3-yl | 3-CN, 4-F |
| 646 | 2,4-difluoropyridin-3-yl | 3-Br, 4-F |
| 647 | 2,4-difluoropyridin-3-yl | 3-Cl, 4-F |
| 648 | 2,4-difluoropyridin-3-yl | 3,4-Cl₂ |
| 649 | 2,5-difluoropyridin-3-yl | H |
| 650 | 2,5-difluoropyridin-3-yl | 2-F |
| 651 | 2,5-difluoropyridin-3-yl | 3-F |
| 652 | 2,5-difluoropyridin-3-yl | 4-F |
| 653 | 2,5-difluoropyridin-3-yl | 3-Cl |
| 654 | 2,5-difluoropyridin-3-yl | 4-Cl |
| 655 | 2,5-difluoropyridin-3-yl | 3-Br |
| 656 | 2,5-difluoropyridin-3-yl | 4-Br |
| 657 | 2,5-difluoropyridin-3-yl | 3-I |
| 658 | 2,5-difluoropyridin-3-yl | 3-CN |
| 659 | 2,5-difluoropyridin-3-yl | 4-CN |
| 660 | 2,5-difluoropyridin-3-yl | 3-NO₂ |
| 661 | 2,5-difluoropyridin-3-yl | 3-Me |
| 662 | 2,5-difluoropyridin-3-yl | 4-Me |
| 663 | 2,5-difluoropyridin-3-yl | 2,3-F₂ |
| 664 | 2,5-difluoropyridin-3-yl | 2,4-F₂ |
| 665 | 2,5-difluoropyridin-3-yl | 2,5-F₂ |
| 666 | 2,5-difluoropyridin-3-yl | 2,6-F₂ |
| 667 | 2,5-difluoropyridin-3-yl | 3,4-F₂ |
| 668 | 2,5-difluoropyridin-3-yl | 3,5-F₂ |
| 669 | 2,5-difluoropyridin-3-yl | 3,4,5-F₃ |
| 670 | 2,5-difluoropyridin-3-yl | 3-F, 4-Cl |
| 671 | 2,5-difluoropyridin-3-yl | 3-F, 4-Br |
| 672 | 2,5-difluoropyridin-3-yl | 3-CN, 4-F |
| 673 | 2,5-difluoropyridin-3-yl | 3-Br, 4-F |
| 674 | 2,5-difluoropyridin-3-yl | 3-Cl, 4-F |
| 675 | 2,5-difluoropyridin-3-yl | 3,4-Cl₂ |
| 676 | 2,6-difluoropyridin-3-yl | H |
| 677 | 2,6-difluoropyridin-3-yl | 2-F |
| 678 | 2,6-difluoropyridin-3-yl | 3-F |
| 679 | 2,6-difluoropyridin-3-yl | 4-F |
| 680 | 2,6-difluoropyridin-3-yl | 3-Cl |
| 681 | 2,6-difluoropyridin-3-yl | 4-Cl |
| 682 | 2,6-difluoropyridin-3-yl | 3-Br |
| 683 | 2,6-difluoropyridin-3-yl | 4-Br |
| 684 | 2,6-difluoropyridin-3-yl | 3-I |
| 685 | 2,6-difluoropyridin-3-yl | 3-CN |
| 686 | 2,6-difluoropyridin-3-yl | 4-CN |
| 687 | 2,6-difluoropyridin-3-yl | 3-NO₂ |
| 688 | 2,6-difluoropyridin-3-yl | 3-Me |
| 689 | 2,6-difluoropyridin-3-yl | 4-Me |
| 690 | 2,6-difluoropyridin-3-yl | 2,3-F₂ |
| 691 | 2,6-difluoropyridin-3-yl | 2,4-F₂ |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 692 | 2,6-difluoropyridin-3-yl | 2,5-F₂ |
| 693 | 2,6-difluoropyridin-3-yl | 2,6-F₂ |
| 694 | 2,6-difluoropyridin-3-yl | 3,4-F₂ |
| 695 | 2,6-difluoropyridin-3-yl | 3,5-F₂ |
| 696 | 2,6-difluoropyridin-3-yl | 3,4,5-F₃ |
| 697 | 2,6-difluoropyridin-3-yl | 3-F, 4-Cl |
| 698 | 2,6-difluoropyridin-3-yl | 3-F, 4-Br |
| 699 | 2,6-difluoropyridin-3-yl | 3-CN, 4-F |
| 700 | 2,6-difluoropyridin-3-yl | 3-Br, 4-F |
| 701 | 2,6-difluoropyridin-3-yl | 3-Cl, 4-F |
| 702 | 2,6-difluoropyridin-3-yl | 3,4-Cl₂ |
| 703 | 5,6-difluoropyridin-3-yl | H |
| 704 | 5,6-difluoropyridin-3-yl | 2-F |
| 705 | 5,6-difluoropyridin-3-yl | 3-F |
| 706 | 5,6-difluoropyridin-3-yl | 4-F |
| 707 | 5,6-difluoropyridin-3-yl | 3-Cl |
| 708 | 5,6-difluoropyridin-3-yl | 4-Cl |
| 709 | 5,6-difluoropyridin-3-yl | 3-Br |
| 710 | 5,6-difluoropyridin-3-yl | 4-Br |
| 711 | 5,6-difluoropyridin-3-yl | 3-I |
| 712 | 5,6-difluoropyridin-3-yl | 3-CN |
| 713 | 5,6-difluoropyridin-3-yl | 4-CN |
| 714 | 5,6-difluoropyridin-3-yl | 3-NO₂ |
| 715 | 5,6-difluoropyridin-3-yl | 3-Me |
| 716 | 5,6-difluoropyridin-3-yl | 4-Me |
| 717 | 5,6-difluoropyridin-3-yl | 2,3-F₂ |
| 718 | 5,6-difluoropyridin-3-yl | 2,4-F₂ |
| 719 | 5,6-difluoropyridin-3-yl | 2,5-F₂ |
| 720 | 5,6-difluoropyridin-3-yl | 2,6-F₂ |
| 721 | 5,6-difluoropyridin-3-yl | 3,4-F₂ |
| 722 | 5,6-difluoropyridin-3-yl | 3,5-F₂ |
| 723 | 5,6-difluoropyridin-3-yl | 3,4,5-F₃ |
| 724 | 5,6-difluoropyridin-3-yl | 3-F, 4-Cl |
| 725 | 5,6-difluoropyridin-3-yl | 3-F, 4-Br |
| 726 | 5,6-difluoropyridin-3-yl | 3-CN, 4-F |
| 727 | 5,6-difluoropyridin-3-yl | 3-Br, 4-F |
| 728 | 5,6-difluoropyridin-3-yl | 3-Cl, 4-F |
| 729 | 5,6-difluoropyridin-3-yl | 3,4-Cl₂ |
| 730 | 4,5-difluoropyridin-3-yl | H |
| 731 | 4,5-difluoropyridin-3-yl | 2-F |
| 732 | 4,5-difluoropyridin-3-yl | 3-F |
| 733 | 4,5-difluoropyridin-3-yl | 4-F |
| 734 | 4,5-difluoropyridin-3-yl | 3-Cl |
| 735 | 4,5-difluoropyridin-3-yl | 4-Cl |
| 736 | 4,5-difluoropyridin-3-yl | 3-Br |
| 737 | 4,5-difluoropyridin-3-yl | 4-Br |
| 738 | 4,5-difluoropyridin-3-yl | 3-I |
| 739 | 4,5-difluoropyridin-3-yl | 3-CN |
| 740 | 4,5-difluoropyridin-3-yl | 4-CN |
| 741 | 4,5-difluoropyridin-3-yl | 3-NO₂ |
| 742 | 4,5-difluoropyridin-3-yl | 3-Me |
| 743 | 4,5-difluoropyridin-3-yl | 4-Me |
| 744 | 4,5-difluoropyridin-3-yl | 2,3-F₂ |
| 745 | 4,5-difluoropyridin-3-yl | 2,4-F₂ |
| 746 | 4,5-difluoropyridin-3-yl | 2,5-F₂ |
| 747 | 4,5-difluoropyridin-3-yl | 2,6-F₂ |
| 748 | 4,5-difluoropyridin-3-yl | 3,4-F₂ |
| 749 | 4,5-difluoropyridin-3-yl | 3,5-F₂ |
| 750 | 4,5-difluoropyridin-3-yl | 3,4,5-F₃ |
| 751 | 4,5-difluoropyridin-3-yl | 3-F, 4-Cl |
| 752 | 4,5-difluoropyridin-3-yl | 3-F, 4-Br |
| 753 | 4,5-difluoropyridin-3-yl | 3-CN, 4-F |
| 754 | 4,5-difluoropyridin-3-yl | 3-Br, 4-F |
| 755 | 4,5-difluoropyridin-3-yl | 3-Cl, 4-F |
| 756 | 4,5-difluoropyridin-3-yl | 3,4-Cl₂ |
| 757 | 4,6-difluoropyridin-3-yl | H |
| 758 | 4,6-difluoropyridin-3-yl | 2-F |
| 759 | 4,6-difluoropyridin-3-yl | 3-F |
| 760 | 4,6-difluoropyridin-3-yl | 4-F |
| 761 | 4,6-difluoropyridin-3-yl | 3-Cl |
| 762 | 4,6-difluoropyridin-3-yl | 4-Cl |
| 763 | 4,6-difluoropyridin-3-yl | 3-Br |
| 764 | 4,6-difluoropyridin-3-yl | 4-Br |
| 765 | 4,6-difluoropyridin-3-yl | 3-I |
| 766 | 4,6-difluoropyridin-3-yl | 3-CN |
| 767 | 4,6-difluoropyridin-3-yl | 4-CN |
| 768 | 4,6-difluoropyridin-3-yl | 3-NO₂ |
| 769 | 4,6-difluoropyridin-3-yl | 3-Me |
| 770 | 4,6-difluoropyridin-3-yl | 4-Me |
| 771 | 4,6-difluoropyridin-3-yl | 2,3-F₂ |
| 772 | 4,6-difluoropyridin-3-yl | 2,4-F₂ |
| 773 | 4,6-difluoropyridin-3-yl | 2,5-F₂ |
| 774 | 4,6-difluoropyridin-3-yl | 2,6-F₂ |
| 775 | 4,6-difluoropyridin-3-yl | 3,4-F₂ |
| 776 | 4,6-difluoropyridin-3-yl | 3,5-F₂ |
| 777 | 4,6-difluoropyridin-3-yl | 3,4,5-F₃ |
| 778 | 4,6-difluoropyridin-3-yl | 3-F, 4-Cl |
| 779 | 4,6-difluoropyridin-3-yl | 3-F, 4-Br |
| 780 | 4,6-difluoropyridin-3-yl | 3-CN, 4-F |
| 781 | 4,6-difluoropyridin-3-yl | 3-Br, 4-F |
| 782 | 4,6-difluoropyridin-3-yl | 3-Cl, 4-F |
| 783 | 4,6-difluoropyridin-3-yl | 3,4-Cl₂ |
| 784 | 3,5-difluoropyridin-2-yl | H |
| 785 | 3,5-difluoropyridin-2-yl | 2-F |
| 786 | 3,5-difluoropyridin-2-yl | 3-F |
| 787 | 3,5-difluoropyridin-2-yl | 4-F |
| 788 | 3,5-difluoropyridin-2-yl | 3-Cl |
| 789 | 3,5-difluoropyridin-2-yl | 4-Cl |
| 790 | 3,5-difluoropyridin-2-yl | 3-Br |
| 791 | 3,5-difluoropyridin-2-yl | 4-Br |
| 792 | 3,5-difluoropyridin-2-yl | 3-I |
| 793 | 3,5-difluoropyridin-2-yl | 3-CN |
| 794 | 3,5-difluoropyridin-2-yl | 4-CN |
| 795 | 3,5-difluoropyridin-2-yl | 3-NO₂ |
| 796 | 3,5-difluoropyridin-2-yl | 3-Me |
| 797 | 3,5-difluoropyridin-2-yl | 4-Me |
| 798 | 3,5-difluoropyridin-2-yl | 2,3-F₂ |
| 799 | 3,5-difluoropyridin-2-yl | 2,4-F₂ |
| 800 | 3,5-difluoropyridin-2-yl | 2,5-F₂ |
| 801 | 3,5-difluoropyridin-2-yl | 2,6-F₂ |
| 802 | 3,5-difluoropyridin-2-yl | 3,4-F₂ |
| 803 | 3,5-difluoropyridin-2-yl | 3,5-F₂ |
| 804 | 3,5-difluoropyridin-2-yl | 3,4,5-F₃ |
| 805 | 3,5-difluoropyridin-2-yl | 3-F, 4-Cl |
| 806 | 3,5-difluoropyridin-2-yl | 3-F, 4-Br |
| 807 | 3,5-difluoropyridin-2-yl | 3-CN, 4-F |
| 808 | 3,5-difluoropyridin-2-yl | 3-Br, 4-F |
| 809 | 3,5-difluoropyridin-2-yl | 3-Cl, 4-F |
| 810 | 3,5-difluoropyridin-2-yl | 3,4-Cl₂ |
| 811 | 3,6-difluoropyridin-2-yl | H |
| 812 | 3,6-difluoropyridin-2-yl | 2-F |
| 813 | 3,6-difluoropyridin-2-yl | 3-F |
| 814 | 3,6-difluoropyridin-2-yl | 4-F |
| 815 | 3,6-difluoropyridin-2-yl | 3-Cl |
| 816 | 3,6-difluoropyridin-2-yl | 4-Cl |
| 817 | 3,6-difluoropyridin-2-yl | 3-Br |
| 818 | 3,6-difluoropyridin-2-yl | 4-Br |
| 819 | 3,6-difluoropyridin-2-yl | 3-I |
| 820 | 3,6-difluoropyridin-2-yl | 3-CN |
| 821 | 3,6-difluoropyridin-2-yl | 4-CN |
| 822 | 3,6-difluoropyridin-2-yl | 3-NO₂ |
| 823 | 3,6-difluoropyridin-2-yl | 3-Me |
| 824 | 3,6-difluoropyridin-2-yl | 4-Me |
| 825 | 3,6-difluoropyridin-2-yl | 2,3-F₂ |
| 826 | 3,6-difluoropyridin-2-yl | 2,4-F₂ |
| 827 | 3,6-difluoropyridin-2-yl | 2,5-F₂ |
| 828 | 3,6-difluoropyridin-2-yl | 2,6-F₂ |
| 829 | 3,6-difluoropyridin-2-yl | 3,4-F₂ |
| 830 | 3,6-difluoropyridin-2-yl | 3,5-F₂ |
| 831 | 3,6-difluoropyridin-2-yl | 3,4,5-F₃ |
| 832 | 3,6-difluoropyridin-2-yl | 3-F, 4-Cl |
| 833 | 3,6-difluoropyridin-2-yl | 3-F, 4-Br |
| 834 | 3,6-difluoropyridin-2-yl | 3-CN, 4-F |
| 835 | 3,6-difluoropyridin-2-yl | 3-Br, 4-F |
| 836 | 3,6-difluoropyridin-2-yl | 3-Cl, 4-F |
| 837 | 3,6-difluoropyridin-2-yl | 3,4-Cl₂ |
| 838 | 4,6-difluoropyridin-2-yl | H |
| 839 | 4,6-difluoropyridin-2-yl | 2-F |
| 840 | 4,6-difluoropyridin-2-yl | 3-F |
| 841 | 4,6-difluoropyridin-2-yl | 4-F |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 842 | 4,6-difluoropyridin-2-yl | 3-Cl |
| 843 | 4,6-difluoropyridin-2-yl | 4-Cl |
| 844 | 4,6-difluoropyridin-2-yl | 3-Br |
| 845 | 4,6-difluoropyridin-2-yl | 4-Br |
| 846 | 4,6-difluoropyridin-2-yl | 3-I |
| 847 | 4,6-difluoropyridin-2-yl | 3-CN |
| 848 | 4,6-difluoropyridin-2-yl | 4-CN |
| 849 | 4,6-difluoropyridin-2-yl | 3-NO₂ |
| 850 | 4,6-difluoropyridin-2-yl | 3-Me |
| 851 | 4,6-difluoropyridin-2-yl | 4-Me |
| 852 | 4,6-difluoropyridin-2-yl | 2,3-F₂ |
| 853 | 4,6-difluoropyridin-2-yl | 2,4-F₂ |
| 854 | 4,6-difluoropyridin-2-yl | 2,5-F₂ |
| 855 | 4,6-difluoropyridin-2-yl | 2,6-F₂ |
| 856 | 4,6-difluoropyridin-2-yl | 3,4-F₂ |
| 857 | 4,6-difluoropyridin-2-yl | 3,5-F₂ |
| 858 | 4,6-difluoropyridin-2-yl | 3,4,5-F₃ |
| 859 | 4,6-difluoropyridin-2-yl | 3-F, 4-Cl |
| 860 | 4,6-difluoropyridin-2-yl | 3-F, 4-Br |
| 861 | 4,6-difluoropyridin-2-yl | 3-CN, 4-F |
| 862 | 4,6-difluoropyridin-2-yl | 3-Br, 4-F |
| 863 | 4,6-difluoropyridin-2-yl | 3-Cl, 4-F |
| 864 | 4,6-difluoropyridin-2-yl | 3,4-Cl₂ |
| 865 | 5,6-difluoropyridin-2-yl | H |
| 866 | 5,6-difluoropyridin-2-yl | 2-F |
| 867 | 5,6-difluoropyridin-2-yl | 3-F |
| 868 | 5,6-difluoropyridin-2-yl | 4-F |
| 869 | 5,6-difluoropyridin-2-yl | 3-Cl |
| 870 | 5,6-difluoropyridin-2-yl | 4-Cl |
| 871 | 5,6-difluoropyridin-2-yl | 3-Br |
| 872 | 5,6-difluoropyridin-2-yl | 4-Br |
| 873 | 5,6-difluoropyridin-2-yl | 3-I |
| 874 | 5,6-difluoropyridin-2-yl | 3-CN |
| 875 | 5,6-difluoropyridin-2-yl | 4-CN |
| 876 | 5,6-difluoropyridin-2-yl | 3-NO₂ |
| 877 | 5,6-difluoropyridin-2-yl | 3-Me |
| 878 | 5,6-difluoropyridin-2-yl | 4-Me |
| 879 | 5,6-difluoropyridin-2-yl | 2,3-F₂ |
| 880 | 5,6-difluoropyridin-2-yl | 2,4-F₂ |
| 881 | 5,6-difluoropyridin-2-yl | 2,5-F₂ |
| 882 | 5,6-difluoropyridin-2-yl | 2,6-F₂ |
| 883 | 5,6-difluoropyridin-2-yl | 3,4-F₂ |
| 884 | 5,6-difluoropyridin-2-yl | 3,5-F₂ |
| 885 | 5,6-difluoropyridin-2-yl | 3,4,5-F₃ |
| 886 | 5,6-difluoropyridin-2-yl | 3-F, 4-Cl |
| 887 | 5,6-difluoropyridin-2-yl | 3-F, 4-Br |
| 888 | 5,6-difluoropyridin-2-yl | 3-CN, 4-F |
| 889 | 5,6-difluoropyridin-2-yl | 3-Br, 4-F |
| 890 | 5,6-difluoropyridin-2-yl | 3-Cl, 4-F |
| 891 | 5,6-difluoropyridin-2-yl | 3,4-Cl₂ |
| 892 | 4,5-difluoropyridin-2-yl | H |
| 893 | 4,5-difluoropyridin-2-yl | 2-F |
| 894 | 4,5-difluoropyridin-2-yl | 3-F |
| 895 | 4,5-difluoropyridin-2-yl | 4-F |
| 896 | 4,5-difluoropyridin-2-yl | 3-Cl |
| 897 | 4,5-difluoropyridin-2-yl | 4-Cl |
| 898 | 4,5-difluoropyridin-2-yl | 3-Br |
| 899 | 4,5-difluoropyridin-2-yl | 4-Br |
| 900 | 4,5-difluoropyridin-2-yl | 3-I |
| 901 | 4,5-difluoropyridin-2-yl | 3-CN |
| 902 | 4,5-difluoropyridin-2-yl | 4-CN |
| 903 | 4,5-difluoropyridin-2-yl | 3-NO₂ |
| 904 | 4,5-difluoropyridin-2-yl | 3-Me |
| 905 | 4,5-difluoropyridin-2-yl | 4-Me |
| 906 | 4,5-difluoropyridin-2-yl | 2,3-F₂ |
| 907 | 4,5-difluoropyridin-2-yl | 2,4-F₂ |
| 908 | 4,5-difluoropyridin-2-yl | 2,5-F₂ |
| 909 | 4,5-difluoropyridin-2-yl | 2,6-F₂ |
| 910 | 4,5-difluoropyridin-2-yl | 3,4-F₂ |
| 911 | 4,5-difluoropyridin-2-yl | 3,5-F₂ |
| 912 | 4,5-difluoropyridin-2-yl | 3,4,5-F₃ |
| 913 | 4,5-difluoropyridin-2-yl | 3-F, 4-Cl |
| 914 | 4,5-difluoropyridin-2-yl | 3-F, 4-Br |
| 915 | 4,5-difluoropyridin-2-yl | 3-CN, 4-F |
| 916 | 4,5-difluoropyridin-2-yl | 3-Br, 4-F |
| 917 | 4,5-difluoropyridin-2-yl | 3-Cl, 4-F |
| 918 | 4,5-difluoropyridin-2-yl | 3,4-Cl₂ |
| 919 | 6-methoxypyridin-2-yl | H |
| 920 | 6-methoxypyridin-2-yl | 2-F |
| 921 | 6-methoxypyridin-2-yl | 3-F |
| 922 | 6-methoxypyridin-2-yl | 4-F |
| 923 | 6-methoxypyridin-2-yl | 3-Cl |
| 924 | 6-methoxypyridin-2-yl | 4-Cl |
| 925 | 6-methoxypyridin-2-yl | 3-Br |
| 926 | 6-methoxypyridin-2-yl | 4-Br |
| 927 | 6-methoxypyridin-2-yl | 3-I |
| 928 | 6-methoxypyridin-2-yl | 3-CN |
| 929 | 6-methoxypyridin-2-yl | 4-CN |
| 930 | 6-methoxypyridin-2-yl | 3-NO₂ |
| 931 | 6-methoxypyridin-2-yl | 3-Me |
| 932 | 6-methoxypyridin-2-yl | 4-Me |
| 933 | 6-methoxypyridin-2-yl | 2,3-F₂ |
| 934 | 6-methoxypyridin-2-yl | 2,4-F₂ |
| 935 | 6-methoxypyridin-2-yl | 2,5-F₂ |
| 936 | 6-methoxypyridin-2-yl | 2,6-F₂ |
| 937 | 6-methoxypyridin-2-yl | 3,4-F₂ |
| 938 | 6-methoxypyridin-2-yl | 3,5-F₂ |
| 939 | 6-methoxypyridin-2-yl | 3,4,5-F₃ |
| 940 | 6-methoxypyridin-2-yl | 3-F, 4-Cl |
| 941 | 6-methoxypyridin-2-yl | 3-F, 4-Br |
| 942 | 6-methoxypyridin-2-yl | 3-CN, 4-F |
| 943 | 6-methoxypyridin-2-yl | 3-Br, 4-F |
| 944 | 6-methoxypyridin-2-yl | 3-Cl, 4-F |
| 945 | 6-methoxypyridin-2-yl | 3,4-Cl₂ |
| 946 | 5-methoxypyridin-2-yl | H |
| 947 | 5-methoxypyridin-2-yl | 2-F |
| 948 | 5-methoxypyridin-2-yl | 3-F |
| 949 | 5-methoxypyridin-2-yl | 4-F |
| 950 | 5-methoxypyridin-2-yl | 3-Cl |
| 951 | 5-methoxypyridin-2-yl | 4-Cl |
| 952 | 5-methoxypyridin-2-yl | 3-Br |
| 953 | 5-methoxypyridin-2-yl | 4-Br |
| 954 | 5-methoxypyridin-2-yl | 3-I |
| 955 | 5-methoxypyridin-2-yl | 3-CN |
| 956 | 5-methoxypyridin-2-yl | 4-CN |
| 957 | 5-methoxypyridin-2-yl | 3-NO₂ |
| 958 | 5-methoxypyridin-2-yl | 3-Me |
| 959 | 5-methoxypyridin-2-yl | 4-Me |
| 960 | 5-methoxypyridin-2-yl | 2,3-F₂ |
| 961 | 5-methoxypyridin-2-yl | 2,4-F₂ |
| 962 | 5-methoxypyridin-2-yl | 2,5-F₂ |
| 963 | 5-methoxypyridin-2-yl | 2,6-F₂ |
| 964 | 5-methoxypyridin-2-yl | 3,4-F₂ |
| 965 | 5-methoxypyridin-2-yl | 3,5-F₂ |
| 966 | 5-methoxypyridin-2-yl | 3,4,5-F₃ |
| 967 | 5-methoxypyridin-2-yl | 3-F, 4-Cl |
| 968 | 5-methoxypyridin-2-yl | 3-F, 4-Br |
| 969 | 5-methoxypyridin-2-yl | 3-CN, 4-F |
| 970 | 5-methoxypyridin-2-yl | 3-Br, 4-F |
| 971 | 5-methoxypyridin-2-yl | 3-Cl, 4-F |
| 972 | 5-methoxypyridin-2-yl | 3,4-Cl₂ |
| 973 | 4-methoxypyridin-2-yl | H |
| 974 | 4-methoxypyridin-2-yl | 2-F |
| 975 | 4-methoxypyridin-2-yl | 3-F |
| 976 | 4-methoxypyridin-2-yl | 4-F |
| 977 | 4-methoxypyridin-2-yl | 3-Cl |
| 978 | 4-methoxypyridin-2-yl | 4-Cl |
| 979 | 4-methoxypyridin-2-yl | 3-Br |
| 980 | 4-methoxypyridin-2-yl | 4-Br |
| 981 | 4-methoxypyridin-2-yl | 3-I |
| 982 | 4-methoxypyridin-2-yl | 3-CN |
| 983 | 4-methoxypyridin-2-yl | 4-CN |
| 984 | 4-methoxypyridin-2-yl | 3-NO₂ |
| 985 | 4-methoxypyridin-2-yl | 3-Me |
| 986 | 4-methoxypyridin-2-yl | 4-Me |
| 987 | 4-methoxypyridin-2-yl | 2,3-F₂ |
| 988 | 4-methoxypyridin-2-yl | 2,4-F₂ |
| 989 | 4-methoxypyridin-2-yl | 2,5-F₂ |
| 990 | 4-methoxypyridin-2-yl | 2,6-F₂ |
| 991 | 4-methoxypyridin-2-yl | 3,4-F₂ |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 992 | 4-methoxypyridin-2-yl | 3,5-F₂ |
| 993 | 4-methoxypyridin-2-yl | 3,4,5-F₃ |
| 994 | 4-methoxypyridin-2-yl | 3-F, 4-Cl |
| 995 | 4-methoxypyridin-2-yl | 3-F, 4-Br |
| 996 | 4-methoxypyridin-2-yl | 3-CN, 4-F |
| 997 | 4-methoxypyridin-2-yl | 3-Br, 4-F |
| 998 | 4-methoxypyridin-2-yl | 3-Cl, 4-F |
| 999 | 4-methoxypyridin-2-yl | 3,4-Cl₂ |
| 1000 | 3-methoxypyridin-2-yl | H |
| 1001 | 3-methoxypyridin-2-yl | 2-F |
| 1002 | 3-methoxypyridin-2-yl | 3-F |
| 1003 | 3-methoxypyridin-2-yl | 4-F |
| 1004 | 3-methoxypyridin-2-yl | 3-Cl |
| 1005 | 3-methoxypyridin-2-yl | 4-Cl |
| 1006 | 3-methoxypyridin-2-yl | 3-Br |
| 1007 | 3-methoxypyridin-2-yl | 4-Br |
| 1008 | 3-methoxypyridin-2-yl | 3-I |
| 1009 | 3-methoxypyridin-2-yl | 3-CN |
| 1010 | 3-methoxypyridin-2-yl | 4-CN |
| 1011 | 3-methoxypyridin-2-yl | 3-NO₂ |
| 1012 | 3-methoxypyridin-2-yl | 3-Me |
| 1013 | 3-methoxypyridin-2-yl | 4-Me |
| 1014 | 3-methoxypyridin-2-yl | 2,3-F₂ |
| 1015 | 3-methoxypyridin-2-yl | 2,4-F₂ |
| 1016 | 3-methoxypyridin-2-yl | 2,5-F₂ |
| 1017 | 3-methoxypyridin-2-yl | 2,6-F₂ |
| 1018 | 3-methoxypyridin-2-yl | 3,4-F₂ |
| 1019 | 3-methoxypyridin-2-yl | 3,5-F₂ |
| 1020 | 3-methoxypyridin-2-yl | 3,4,5-F₃ |
| 1021 | 3-methoxypyridin-2-yl | 3-F, 4-Cl |
| 1022 | 3-methoxypyridin-2-yl | 3-F, 4-Br |
| 1023 | 3-methoxypyridin-2-yl | 3-CN, 4-F |
| 1024 | 3-methoxypyridin-2-yl | 3-Br, 4-F |
| 1025 | 3-methoxypyridin-2-yl | 3-Cl, 4-F |
| 1026 | 3-methoxypyridin-2-yl | 3,4-Cl₂ |
| 1027 | 4-methoxypyridin-3-yl | H |
| 1028 | 4-methoxypyridin-3-yl | 2-F |
| 1029 | 4-methoxypyridin-3-yl | 3-F |
| 1030 | 4-methoxypyridin-3-yl | 4-F |
| 1031 | 4-methoxypyridin-3-yl | 3-Cl |
| 1032 | 4-methoxypyridin-3-yl | 4-Cl |
| 1033 | 4-methoxypyridin-3-yl | 3-Br |
| 1034 | 4-methoxypyridin-3-yl | 4-Br |
| 1035 | 4-methoxypyridin-3-yl | 3-I |
| 1036 | 4-methoxypyridin-3-yl | 3-CN |
| 1037 | 4-methoxypyridin-3-yl | 4-CN |
| 1038 | 4-methoxypyridin-3-yl | 3-NO₂ |
| 1039 | 4-methoxypyridin-3-yl | 3-Me |
| 1040 | 4-methoxypyridin-3-yl | 4-Me |
| 1041 | 4-methoxypyridin-3-yl | 2,3-F₂ |
| 1042 | 4-methoxypyridin-3-yl | 2,4-F₂ |
| 1043 | 4-methoxypyridin-3-yl | 2,5-F₂ |
| 1044 | 4-methoxypyridin-3-yl | 2,6-F₂ |
| 1045 | 4-methoxypyridin-3-yl | 3,4-F₂ |
| 1046 | 4-methoxypyridin-3-yl | 3,5-F₂ |
| 1047 | 4-methoxypyridin-3-yl | 3,4,5-F₃ |
| 1048 | 4-methoxypyridin-3-yl | 3-F, 4-Cl |
| 1049 | 4-methoxypyridin-3-yl | 3-F, 4-Br |
| 1050 | 4-methoxypyridin-3-yl | 3-CN, 4-F |
| 1051 | 4-methoxypyridin-3-yl | 3-Br, 4-F |
| 1052 | 4-methoxypyridin-3-yl | 3-Cl, 4-F |
| 1053 | 4-methoxypyridin-3-yl | 3,4-Cl₂ |
| 1054 | 5-methoxypyridin-3-yl | H |
| 1055 | 5-methoxypyridin-3-yl | 2-F |
| 1056 | 5-methoxypyridin-3-yl | 3-F |
| 1057 | 5-methoxypyridin-3-yl | 4-F |
| 1058 | 5-methoxypyridin-3-yl | 3-Cl |
| 1059 | 5-methoxypyridin-3-yl | 4-Cl |
| 1060 | 5-methoxypyridin-3-yl | 3-Br |
| 1061 | 5-methoxypyridin-3-yl | 4-Br |
| 1062 | 5-methoxypyridin-3-yl | 3-I |
| 1063 | 5-methoxypyridin-3-yl | 3-CN |
| 1064 | 5-methoxypyridin-3-yl | 4-CN |
| 1065 | 5-methoxypyridin-3-yl | 3-NO₂ |
| 1066 | 5-methoxypyridin-3-yl | 3-Me |
| 1067 | 5-methoxypyridin-3-yl | 4-Me |
| 1068 | 5-methoxypyridin-3-yl | 2,3-F₂ |
| 1069 | 5-methoxypyridin-3-yl | 2,4-F₂ |
| 1070 | 5-methoxypyridin-3-yl | 2,5-F₂ |
| 1071 | 5-methoxypyridin-3-yl | 2,6-F₂ |
| 1072 | 5-methoxypyridin-3-yl | 3,4-F₂ |
| 1073 | 5-methoxypyridin-3-yl | 3,5-F₂ |
| 1074 | 5-methoxypyridin-3-yl | 3,4,5-F₃ |
| 1075 | 5-methoxypyridin-3-yl | 3-F, 4-Cl |
| 1076 | 5-methoxypyridin-3-yl | 3-F, 4-Br |
| 1077 | 5-methoxypyridin-3-yl | 3-CN, 4-F |
| 1078 | 5-methoxypyridin-3-yl | 3-Br, 4-F |
| 1079 | 5-methoxypyridin-3-yl | 3-Cl, 4-F |
| 1080 | 5-methoxypyridin-3-yl | 3,4-Cl₂ |
| 1081 | 6-methoxypyridin-3-yl | H |
| 1082 | 6-methoxypyridin-3-yl | 2-F |
| 1083 | 6-methoxypyridin-3-yl | 3-F |
| 1084 | 6-methoxypyridin-3-yl | 4-F |
| 1085 | 6-methoxypyridin-3-yl | 3-Cl |
| 1086 | 6-methoxypyridin-3-yl | 4-Cl |
| 1087 | 6-methoxypyridin-3-yl | 3-Br |
| 1088 | 6-methoxypyridin-3-yl | 4-Br |
| 1089 | 6-methoxypyridin-3-yl | 3-I |
| 1090 | 6-methoxypyridin-3-yl | 3-CN |
| 1091 | 6-methoxypyridin-3-yl | 4-CN |
| 1092 | 6-methoxypyridin-3-yl | 3-NO₂ |
| 1093 | 6-methoxypyridin-3-yl | 3-Me |
| 1094 | 6-methoxypyridin-3-yl | 4-Me |
| 1095 | 6-methoxypyridin-3-yl | 2,3-F₂ |
| 1096 | 6-methoxypyridin-3-yl | 2,4-F₂ |
| 1097 | 6-methoxypyridin-3-yl | 2,5-F₂ |
| 1098 | 6-methoxypyridin-3-yl | 2,6-F₂ |
| 1099 | 6-methoxypyridin-3-yl | 3,4-F₂ |
| 1100 | 6-methoxypyridin-3-yl | 3,5-F₂ |
| 1101 | 6-methoxypyridin-3-yl | 3,4,5-F₃ |
| 1102 | 6-methoxypyridin-3-yl | 3-F, 4-Cl |
| 1103 | 6-methoxypyridin-3-yl | 3-F, 4-Br |
| 1104 | 6-methoxypyridin-3-yl | 3-CN, 4-F |
| 1105 | 6-methoxypyridin-3-yl | 3-Br, 4-F |
| 1106 | 6-methoxypyridin-3-yl | 3-Cl, 4-F |
| 1107 | 6-methoxypyridin-3-yl | 3,4-Cl₂ |
| 1108 | 2-methoxypyridin-3-yl | H |
| 1109 | 2-methoxypyridin-3-yl | 2-F |
| 1110 | 2-methoxypyridin-3-yl | 3-F |
| 1111 | 2-methoxypyridin-3-yl | 4-F |
| 1112 | 2-methoxypyridin-3-yl | 3-Cl |
| 1113 | 2-methoxypyridin-3-yl | 4-Cl |
| 1114 | 2-methoxypyridin-3-yl | 3-Br |
| 1115 | 2-methoxypyridin-3-yl | 4-Br |
| 1116 | 2-methoxypyridin-3-yl | 3-I |
| 1117 | 2-methoxypyridin-3-yl | 3-CN |
| 1118 | 2-methoxypyridin-3-yl | 4-CN |
| 1119 | 2-methoxypyridin-3-yl | 3-NO₂ |
| 1120 | 2-methoxypyridin-3-yl | 3-Me |
| 1121 | 2-methoxypyridin-3-yl | 4-Me |
| 1122 | 2-methoxypyridin-3-yl | 2,3-F₂ |
| 1123 | 2-methoxypyridin-3-yl | 2,4-F₂ |
| 1124 | 2-methoxypyridin-3-yl | 2,5-F₂ |
| 1125 | 2-methoxypyridin-3-yl | 2,6-F₂ |
| 1126 | 2-methoxypyridin-3-yl | 3,4-F₂ |
| 1127 | 2-methoxypyridin-3-yl | 3,5-F₂ |
| 1128 | 2-methoxypyridin-3-yl | 3,4,5-F₃ |
| 1129 | 2-methoxypyridin-3-yl | 3-F, 4-Cl |
| 1130 | 2-methoxypyridin-3-yl | 3-F, 4-Br |
| 1131 | 2-methoxypyridin-3-yl | 3-CN, 4-F |
| 1132 | 2-methoxypyridin-3-yl | 3-Br, 4-F |
| 1133 | 2-methoxypyridin-3-yl | 3-Cl, 4-F |
| 1134 | 2-methoxypyridin-3-yl | 3,4-Cl₂ |
| 1135 | 2-methoxypyridin-4-yl | H |
| 1136 | 2-methoxypyridin-4-yl | 2-F |
| 1137 | 2-methoxypyridin-4-yl | 3-F |
| 1138 | 2-methoxypyridin-4-yl | 4-F |
| 1139 | 2-methoxypyridin-4-yl | 3-Cl |
| 1140 | 2-methoxypyridin-4-yl | 4-Cl |
| 1141 | 2-methoxypyridin-4-yl | 3-Br |

TABLE 1-continued

Preferred meanings of $Q(R^2)_n$ and $(R^3)_m$ in compounds of the formula (I) or of the formula (Ia) according to the invention:

| No. | $Q(R^2)_n$ | $(R^3)_m$ |
|---|---|---|
| 1142 | 2-methoxypyridin-4-yl | 4-Br |
| 1143 | 2-methoxypyridin-4-yl | 3-I |
| 1144 | 2-methoxypyridin-4-yl | 3-CN |
| 1145 | 2-methoxypyridin-4-yl | 4-CN |
| 1146 | 2-methoxypyridin-4-yl | 3-NO$_2$ |
| 1147 | 2-methoxypyridin-4-yl | 3-Me |
| 1148 | 2-methoxypyridin-4-yl | 4-Me |
| 1149 | 2-methoxypyridin-4-yl | 2,3-F$_2$ |
| 1150 | 2-methoxypyridin-4-yl | 2,4-F$_2$ |
| 1151 | 2-methoxypyridin-4-yl | 2,5-F$_2$ |
| 1152 | 2-methoxypyridin-4-yl | 2,6-F$_2$ |
| 1153 | 2-methoxypyridin-4-yl | 3,4-F$_2$ |
| 1154 | 2-methoxypyridin-4-yl | 3,5-F$_2$ |
| 1155 | 2-methoxypyridin-4-yl | 3,4,5-F$_3$ |
| 1156 | 2-methoxypyridin-4-yl | 3-F, 4-Cl |
| 1157 | 2-methoxypyridin-4-yl | 3-F, 4-Br |
| 1158 | 2-methoxypyridin-4-yl | 3-CN, 4-F |
| 1159 | 2-methoxypyridin-4-yl | 3-Br, 4-F |
| 1160 | 2-methoxypyridin-4-yl | 3-Cl, 4-F |
| 1161 | 2-methoxypyridin-4-yl | 3,4-Cl$_2$ |
| 1162 | 3-methoxypyridin-4-yl | H |
| 1163 | 3-methoxypyridin-4-yl | 2-F |
| 1164 | 3-methoxypyridin-4-yl | 3-F |
| 1165 | 3-methoxypyridin-4-yl | 4-F |
| 1166 | 3-methoxypyridin-4-yl | 3-Cl |
| 1167 | 3-methoxypyridin-4-yl | 4-Cl |
| 1168 | 3-methoxypyridin-4-yl | 3-Br |
| 1169 | 3-methoxypyridin-4-yl | 4-Br |
| 1170 | 3-methoxypyridin-4-yl | 3-I |
| 1171 | 3-methoxypyridin-4-yl | 3-CN |
| 1172 | 3-methoxypyridin-4-yl | 4-CN |
| 1173 | 3-methoxypyridin-4-yl | 3-NO$_2$ |
| 1174 | 3-methoxypyridin-4-yl | 3-Me |
| 1175 | 3-methoxypyridin-4-yl | 4-Me |
| 1176 | 3-methoxypyridin-4-yl | 2,3-F$_2$ |
| 1177 | 3-methoxypyridin-4-yl | 2,4-F$_2$ |
| 1178 | 3-methoxypyridin-4-yl | 2,5-F$_2$ |
| 1179 | 3-methoxypyridin-4-yl | 2,6-F$_2$ |
| 1180 | 3-methoxypyridin-4-yl | 3,4-F$_2$ |
| 1181 | 3-methoxypyridin-4-yl | 3,5-F$_2$ |
| 1182 | 3-methoxypyridin-4-yl | 3,4,5-F$_3$ |
| 1183 | 3-methoxypyridin-4-yl | 3-F, 4-Cl |
| 1184 | 3-methoxypyridin-4-yl | 3-F, 4-Br |
| 1185 | 3-methoxypyridin-4-yl | 3-CN, 4-F |
| 1186 | 3-methoxypyridin-4-yl | 3-Br, 4-F |
| 1187 | 3-methoxypyridin-4-yl | 3-Cl, 4-F |
| 1188 | 3-methoxypyridin-4-yl | 3,4-Cl$_2$ |
| 1189 | 3,5-dichloropyrazin-2-yl | H |
| 1190 | 3,5-dichloropyrazin-2-yl | 2-F |
| 1191 | 3,5-dichloropyrazin-2-yl | 3-F |
| 1192 | 3,5-dichloropyrazin-2-yl | 4-F |
| 1193 | 3,5-dichloropyrazin-2-yl | 3-Cl |
| 1194 | 3,5-dichloropyrazin-2-yl | 4-Cl |
| 1195 | 3,5-dichloropyrazin-2-yl | 3-Br |
| 1196 | 3,5-dichloropyrazin-2-yl | 4-Br |
| 1197 | 3,5-dichloropyrazin-2-yl | 3-I |
| 1198 | 3,5-dichloropyrazin-2-yl | 3-CN |
| 1199 | 3,5-dichloropyrazin-2-yl | 4-CN |
| 1200 | 3,5-dichloropyrazin-2-yl | 3-NO$_2$ |
| 1201 | 3,5-dichloropyrazin-2-yl | 3-Me |
| 1202 | 3,5-dichloropyrazin-2-yl | 4-Me |
| 1203 | 3,5-dichloropyrazin-2-yl | 2,3-F$_2$ |
| 1204 | 3,5-dichloropyrazin-2-yl | 2,4-F2 |
| 1205 | 3,5-dichloropyrazin-2-yl | 2,5-F$_2$ |
| 1206 | 3,5-dichloropyrazin-2-yl | 2,6-F$_2$ |
| 1207 | 3,5-dichloropyrazin-2-yl | 3,4-F$_2$ |
| 1208 | 3,5-dichloropyrazin-2-yl | 3,5-F$_2$ |
| 1209 | 3,5-dichloropyrazin-2-yl | 3,4,5-F$_3$ |
| 1210 | 3,5-dichloropyrazin-2-yl | 3-F, 4-Cl |
| 1211 | 3,5-dichloropyrazin-2-yl | 3-F, 4-Br |
| 1212 | 3,5-dichloropyrazin-2-yl | 3-CN, 4-F |
| 1213 | 3,5-dichloropyrazin-2-yl | 3-Br, 4-F |
| 1214 | 3,5-dichloropyrazin-2-yl | 3-Cl, 4-F |
| 1215 | 3,5-dichloropyrazin-2-yl | 3,4-Cl$_2$ |
| 1216 | 3,6-dichloropyrazin-2-yl | H |
| 1217 | 3,6-dichloropyrazin-2-yl | 2-F |
| 1218 | 3,6-dichloropyrazin-2-yl | 3-F |
| 1219 | 3,6-dichloropyrazin-2-yl | 4-F |
| 1220 | 3,6-dichloropyrazin-2-yl | 3-Cl |
| 1221 | 3,6-dichloropyrazin-2-yl | 4-Cl |
| 1222 | 3,6-dichloropyrazin-2-yl | 3-Br |
| 1223 | 3,6-dichloropyrazin-2-yl | 4-Br |
| 1224 | 3,6-dichloropyrazin-2-yl | 3-I |
| 1225 | 3,6-dichloropyrazin-2-yl | 3-CN |
| 1226 | 3,6-dichloropyrazin-2-yl | 4-CN |
| 1227 | 3,6-dichloropyrazin-2-yl | 3-NO$_2$ |
| 1228 | 3,6-dichloropyrazin-2-yl | 3-Me |
| 1229 | 3,6-dichloropyrazin-2-yl | 4-Me |
| 1230 | 3,6-dichloropyrazin-2-yl | 2,3-F$_2$ |
| 1231 | 3,6-dichloropyrazin-2-yl | 2,4-F2 |
| 1232 | 3,6-dichloropyrazin-2-yl | 2,5-F$_2$ |
| 1233 | 3,6-dichloropyrazin-2-yl | 2,6-F$_2$ |
| 1234 | 3,6-dichloropyrazin-2-yl | 3,4-F$_2$ |
| 1235 | 3,6-dichloropyrazin-2-yl | 3,5-F$_2$ |
| 1236 | 3,6-dichloropyrazin-2-yl | 3,4,5-F$_3$ |
| 1237 | 3,6-dichloropyrazin-2-yl | 3-F, 4-Cl |
| 1238 | 3,6-dichloropyrazin-2-yl | 3-F, 4-Br |
| 1239 | 3,6-dichloropyrazin-2-yl | 3-CN, 4-F |
| 1240 | 3,6-dichloropyrazin-2-yl | 3-Br, 4-F |
| 1241 | 3,6-dichloropyrazin-2-yl | 3-Cl, 4-F |
| 1242 | 3,6-dichloropyrazin-2-yl | 3,4-Cl$_2$ |
| 1243 | 6-chloropyrazin-2-yl | H |
| 1244 | 6-chloropyrazin-2-yl | 2-F |
| 1245 | 6-chloropyrazin-2-yl | 3-F |
| 1246 | 6-chloropyrazin-2-yl | 4-F |
| 1247 | 6-chloropyrazin-2-yl | 3-Cl |
| 1248 | 6-chloropyrazin-2-yl | 4-Cl |
| 1249 | 6-chloropyrazin-2-yl | 3-Br |
| 1250 | 6-chloropyrazin-2-yl | 4-Br |
| 1251 | 6-chloropyrazin-2-yl | 3-I |
| 1252 | 6-chloropyrazin-2-yl | 3-CN |
| 1253 | 6-chloropyrazin-2-yl | 4-CN |
| 1254 | 6-chloropyrazin-2-yl | 3-NO$_2$ |
| 1255 | 6-chloropyrazin-2-yl | 3-Me |
| 1256 | 6-chloropyrazin-2-yl | 4-Me |
| 1257 | 6-chloropyrazin-2-yl | 2,3-F$_2$ |
| 1258 | 6-chloropyrazin-2-yl | 2,4-F2 |
| 1259 | 6-chloropyrazin-2-yl | 2,5-F$_2$ |
| 1260 | 6-chloropyrazin-2-yl | 2,6-F$_2$ |
| 1261 | 6-chloropyrazin-2-yl | 3,4-F$_2$ |
| 1262 | 6-chloropyrazin-2-yl | 3,5-F$_2$ |
| 1263 | 6-chloropyrazin-2-yl | 3,4,5-F$_3$ |
| 1264 | 6-chloropyrazin-2-yl | 3-F, 4-Cl |
| 1265 | 6-chloropyrazin-2-yl | 3-F, 4-Br |
| 1266 | 6-chloropyrazin-2-yl | 3-CN, 4-F |
| 1267 | 6-chloropyrazin-2-yl | 3-Br, 4-F |
| 1268 | 6-chloropyrazin-2-yl | 3-Cl, 4-F |
| 1269 | 6-chloropyrazin-2-yl | 3,4-Cl$_2$ |
| 1270 | 5-chloropyrazin-2-yl | H |
| 1271 | 5-chloropyrazin-2-yl | 2-F |
| 1272 | 5-chloropyrazin-2-yl | 3-F |
| 1273 | 5-chloropyrazin-2-yl | 4-F |
| 1274 | 5-chloropyrazin-2-yl | 3-Cl |
| 1275 | 5-chloropyrazin-2-yl | 4-Cl |
| 1276 | 5-chloropyrazin-2-yl | 3-Br |
| 1277 | 5-chloropyrazin-2-yl | 4-Br |
| 1278 | 5-chloropyrazin-2-yl | 3-I |
| 1279 | 5-chloropyrazin-2-yl | 3-CN |
| 1280 | 5-chloropyrazin-2-yl | 4-CN |
| 1281 | 5-chloropyrazin-2-yl | 3-NO$_2$ |
| 1282 | 5-chloropyrazin-2-yl | 3-Me |
| 1283 | 5-chloropyrazin-2-yl | 4-Me |
| 1284 | 5-chloropyrazin-2-yl | 2,3-F$_2$ |
| 1285 | 5-chloropyrazin-2-yl | 2,4-F2 |
| 1286 | 5-chloropyrazin-2-yl | 2,5-F$_2$ |
| 1287 | 5-chloropyrazin-2-yl | 2,6-F$_2$ |
| 1288 | 5-chloropyrazin-2-yl | 3,4-F$_2$ |
| 1289 | 5-chloropyrazin-2-yl | 3,5-F$_2$ |
| 1290 | 5-chloropyrazin-2-yl | 3,4,5-F$_3$ |
| 1291 | 5-chloropyrazin-2-yl | 3-F, 4-Cl |

TABLE 1-continued

Preferred meanings of $Q(R^2)_n$ and $(R^3)_m$ in compounds of the formula (I) or of the formula (Ia) according to the invention:

| No. | $Q(R^2)_n$ | $(R^3)_m$ |
|---|---|---|
| 1292 | 5-chloropyrazin-2-yl | 3-F, 4-Br |
| 1293 | 5-chloropyrazin-2-yl | 3-CN, 4-F |
| 1294 | 5-chloropyrazin-2-yl | 3-Br, 4-F |
| 1295 | 5-chloropyrazin-2-yl | 3-Cl, 4-F |
| 1296 | 5-chloropyrazin-2-yl | 3,4-Cl$_2$ |
| 1297 | 3-chloropyrazin-2-yl | H |
| 1298 | 3-chloropyrazin-2-yl | 2-F |
| 1299 | 3-chloropyrazin-2-yl | 3-F |
| 1300 | 3-chloropyrazin-2-yl | 4-F |
| 1301 | 3-chloropyrazin-2-yl | 3-Cl |
| 1302 | 3-chloropyrazin-2-yl | 4-Cl |
| 1303 | 3-chloropyrazin-2-yl | 3-Br |
| 1304 | 3-chloropyrazin-2-yl | 4-Br |
| 1305 | 3-chloropyrazin-2-yl | 3-I |
| 1306 | 3-chloropyrazin-2-yl | 3-CN |
| 1307 | 3-chloropyrazin-2-yl | 4-CN |
| 1308 | 3-chloropyrazin-2-yl | 3-NO$_2$ |
| 1309 | 3-chloropyrazin-2-yl | 3-Me |
| 1310 | 3-chloropyrazin-2-yl | 4-Me |
| 1311 | 3-chloropyrazin-2-yl | 2,3-F$_2$ |
| 1312 | 3-chloropyrazin-2-yl | 2,4-F2 |
| 1313 | 3-chloropyrazin-2-yl | 2,5-F$_2$ |
| 1314 | 3-chloropyrazin-2-yl | 2,6-F$_2$ |
| 1315 | 3-chloropyrazin-2-yl | 3,4-F$_2$ |
| 1316 | 3-chloropyrazin-2-yl | 3,5-F$_2$ |
| 1317 | 3-chloropyrazin-2-yl | 3,4,5-F$_3$ |
| 1318 | 3-chloropyrazin-2-yl | 3-F, 4-Cl |
| 1319 | 3-chloropyrazin-2-yl | 3-F, 4-Br |
| 1320 | 3-chloropyrazin-2-yl | 3-CN, 4-F |
| 1321 | 3-chloropyrazin-2-yl | 3-Br, 4-F |
| 1322 | 3-chloropyrazin-2-yl | 3-Cl, 4-F |
| 1323 | 3-chloropyrazin-2-yl | 3,4-Cl$_2$ |
| 1324 | 5-chloro-3-thienyl | H |
| 1325 | 5-chloro-3-thienyl | 2-F |
| 1326 | 5-chloro-3-thienyl | 3-F |
| 1327 | 5-chloro-3-thienyl | 4-F |
| 1328 | 5-chloro-3-thienyl | 3-Cl |
| 1329 | 5-chloro-3-thienyl | 4-Cl |
| 1330 | 5-chloro-3-thienyl | 3-Br |
| 1331 | 5-chloro-3-thienyl | 4-Br |
| 1332 | 5-chloro-3-thienyl | 3-I |
| 1333 | 5-chloro-3-thienyl | 3-CN |
| 1334 | 5-chloro-3-thienyl | 4-CN |
| 1335 | 5-chloro-3-thienyl | 3-NO$_2$ |
| 1336 | 5-chloro-3-thienyl | 3-Me |
| 1337 | 5-chloro-3-thienyl | 4-Me |
| 1338 | 5-chloro-3-thienyl | 2,3-F$_2$ |
| 1339 | 5-chloro-3-thienyl | 2,4-F2 |
| 1340 | 5-chloro-3-thienyl | 2,5-F$_2$ |
| 1341 | 5-chloro-3-thienyl | 2,6-F$_2$ |
| 1342 | 5-chloro-3-thienyl | 3,4-F$_2$ |
| 1343 | 5-chloro-3-thienyl | 3,5-F$_2$ |
| 1344 | 5-chloro-3-thienyl | 3,4,5-F$_3$ |
| 1345 | 5-chloro-3-thienyl | 3-F, 4-Cl |
| 1346 | 5-chloro-3-thienyl | 3-F, 4-Br |
| 1347 | 5-chloro-3-thienyl | 3-CN, 4-F |
| 1348 | 5-chloro-3-thienyl | 3-Br, 4-F |
| 1349 | 5-chloro-3-thienyl | 3-Cl, 4-F |
| 1350 | 5-chloro-3-thienyl | 3,4-Cl$_2$ |
| 1351 | 4-chloro-3-thienyl | H |
| 1352 | 4-chloro-3-thienyl | 2-F |
| 1353 | 4-chloro-3-thienyl | 3-F |
| 1354 | 4-chloro-3-thienyl | 4-F |
| 1355 | 4-chloro-3-thienyl | 3-Cl |
| 1356 | 4-chloro-3-thienyl | 4-Cl |
| 1357 | 4-chloro-3-thienyl | 3-Br |
| 1358 | 4-chloro-3-thienyl | 4-Br |
| 1359 | 4-chloro-3-thienyl | 3-I |
| 1360 | 4-chloro-3-thienyl | 3-CN |
| 1361 | 4-chloro-3-thienyl | 4-CN |
| 1362 | 4-chloro-3-thienyl | 3-NO$_2$ |
| 1363 | 4-chloro-3-thienyl | 3-Me |
| 1364 | 4-chloro-3-thienyl | 4-Me |
| 1365 | 4-chloro-3-thienyl | 2,3-F$_2$ |
| 1366 | 4-chloro-3-thienyl | 2,4-F2 |
| 1367 | 4-chloro-3-thienyl | 2,5-F$_2$ |
| 1368 | 4-chloro-3-thienyl | 2,6-F$_2$ |
| 1369 | 4-chloro-3-thienyl | 3,4-F$_2$ |
| 1370 | 4-chloro-3-thienyl | 3,5-F$_2$ |
| 1371 | 4-chloro-3-thienyl | 3,4,5-F$_3$ |
| 1372 | 4-chloro-3-thienyl | 3-F, 4-Cl |
| 1373 | 4-chloro-3-thienyl | 3-F, 4-Br |
| 1374 | 4-chloro-3-thienyl | 3-CN, 4-F |
| 1375 | 4-chloro-3-thienyl | 3-Br, 4-F |
| 1376 | 4-chloro-3-thienyl | 3-Cl, 4-F |
| 1377 | 4-chloro-3-thienyl | 3,4-Cl$_2$ |
| 1378 | 2-chloro-3-thienyl | H |
| 1379 | 2-chloro-3-thienyl | 2-F |
| 1380 | 2-chloro-3-thienyl | 3-F |
| 1381 | 2-chloro-3-thienyl | 4-F |
| 1382 | 2-chloro-3-thienyl | 3-Cl |
| 1383 | 2-chloro-3-thienyl | 4-Cl |
| 1384 | 2-chloro-3-thienyl | 3-Br |
| 1385 | 2-chloro-3-thienyl | 4-Br |
| 1386 | 2-chloro-3-thienyl | 3-I |
| 1387 | 2-chloro-3-thienyl | 3-CN |
| 1388 | 2-chloro-3-thienyl | 4-CN |
| 1389 | 2-chloro-3-thienyl | 3-NO$_2$ |
| 1390 | 2-chloro-3-thienyl | 3-Me |
| 1391 | 2-chloro-3-thienyl | 4-Me |
| 1392 | 2-chloro-3-thienyl | 2,3-F$_2$ |
| 1393 | 2-chloro-3-thienyl | 2,4-F2 |
| 1394 | 2-chloro-3-thienyl | 2,5-F$_2$ |
| 1395 | 2-chloro-3-thienyl | 2,6-F$_2$ |
| 1396 | 2-chloro-3-thienyl | 3,4-F$_2$ |
| 1397 | 2-chloro-3-thienyl | 3,5-F$_2$ |
| 1398 | 2-chloro-3-thienyl | 3,4,5-F$_3$ |
| 1399 | 2-chloro-3-thienyl | 3-F, 4-Cl |
| 1400 | 2-chloro-3-thienyl | 3-F, 4-Br |
| 1401 | 2-chloro-3-thienyl | 3-CN, 4-F |
| 1402 | 2-chloro-3-thienyl | 3-Br, 4-F |
| 1403 | 2-chloro-3-thienyl | 3-Cl, 4-F |
| 1404 | 2-chloro-3-thienyl | 3,4-Cl$_2$ |
| 1405 | 2,5-dichloro-3-thienyl | H |
| 1406 | 2,5-dichloro-3-thienyl | 2-F |
| 1407 | 2,5-dichloro-3-thienyl | 3-F |
| 1408 | 2,5-dichloro-3-thienyl | 4-F |
| 1409 | 2,5-dichloro-3-thienyl | 3-Cl |
| 1410 | 2,5-dichloro-3-thienyl | 4-Cl |
| 1411 | 2,5-dichloro-3-thienyl | 3-Br |
| 1412 | 2,5-dichloro-3-thienyl | 4-Br |
| 1413 | 2,5-dichloro-3-thienyl | 3-I |
| 1414 | 2,5-dichloro-3-thienyl | 3-CN |
| 1415 | 2,5-dichloro-3-thienyl | 4-CN |
| 1416 | 2,5-dichloro-3-thienyl | 3-NO$_2$ |
| 1417 | 2,5-dichloro-3-thienyl | 3-Me |
| 1418 | 2,5-dichloro-3-thienyl | 4-Me |
| 1419 | 2,5-dichloro-3-thienyl | 2,3-F$_2$ |
| 1420 | 2,5-dichloro-3-thienyl | 2,4-F2 |
| 1421 | 2,5-dichloro-3-thienyl | 2,5-F$_2$ |
| 1422 | 2,5-dichloro-3-thienyl | 2,6-F$_2$ |
| 1423 | 2,5-dichloro-3-thienyl | 3,4-F$_2$ |
| 1424 | 2,5-dichloro-3-thienyl | 3,5-F$_2$ |
| 1425 | 2,5-dichloro-3-thienyl | 3,4,5-F$_3$ |
| 1426 | 2,5-dichloro-3-thienyl | 3-F, 4-Cl |
| 1427 | 2,5-dichloro-3-thienyl | 3-F, 4-Br |
| 1428 | 2,5-dichloro-3-thienyl | 3-CN, 4-F |
| 1429 | 2,5-dichloro-3-thienyl | 3-Br, 4-F |
| 1430 | 2,5-dichloro-3-thienyl | 3-Cl, 4-F |
| 1431 | 2,5-dichloro-3-thienyl | 3,4-Cl$_2$ |
| 1432 | 5-chloro-2-thienyl | H |
| 1433 | 5-chloro-2-thienyl | 2-F |
| 1434 | 5-chloro-2-thienyl | 3-F |
| 1435 | 5-chloro-2-thienyl | 4-F |
| 1436 | 5-chloro-2-thienyl | 3-Cl |
| 1437 | 5-chloro-2-thienyl | 4-Cl |
| 1438 | 5-chloro-2-thienyl | 3-Br |
| 1439 | 5-chloro-2-thienyl | 4-Br |
| 1440 | 5-chloro-2-thienyl | 3-I |
| 1441 | 5-chloro-2-thienyl | 3-CN |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 1442 | 5-chloro-2-thienyl | 4-CN |
| 1443 | 5-chloro-2-thienyl | 3-NO₂ |
| 1444 | 5-chloro-2-thienyl | 3-Me |
| 1445 | 5-chloro-2-thienyl | 4-Me |
| 1446 | 5-chloro-2-thienyl | 2,3-F₂ |
| 1447 | 5-chloro-2-thienyl | 2,4-F2 |
| 1448 | 5-chloro-2-thienyl | 2,5-F₂ |
| 1449 | 5-chloro-2-thienyl | 2,6-F₂ |
| 1450 | 5-chloro-2-thienyl | 3,4-F₂ |
| 1451 | 5-chloro-2-thienyl | 3,5-F₂ |
| 1452 | 5-chloro-2-thienyl | 3,4,5-F₃ |
| 1453 | 5-chloro-2-thienyl | 3-F, 4-Cl |
| 1454 | 5-chloro-2-thienyl | 3-F, 4-Br |
| 1455 | 5-chloro-2-thienyl | 3-CN, 4-F |
| 1456 | 5-chloro-2-thienyl | 3-Br, 4-F |
| 1457 | 5-chloro-2-thienyl | 3-Cl, 4-F |
| 1458 | 5-chloro-2-thienyl | 3,4-Cl₂ |
| 1459 | 4-chloro-2-thienyl | H |
| 1460 | 4-chloro-2-thienyl | 2-F |
| 1461 | 4-chloro-2-thienyl | 3-F |
| 1462 | 4-chloro-2-thienyl | 4-F |
| 1463 | 4-chloro-2-thienyl | 3-Cl |
| 1464 | 4-chloro-2-thienyl | 4-Cl |
| 1465 | 4-chloro-2-thienyl | 3-Br |
| 1466 | 4-chloro-2-thienyl | 4-Br |
| 1467 | 4-chloro-2-thienyl | 3-I |
| 1468 | 4-chloro-2-thienyl | 3-CN |
| 1469 | 4-chloro-2-thienyl | 4-CN |
| 1470 | 4-chloro-2-thienyl | 3-NO₂ |
| 1471 | 4-chloro-2-thienyl | 3-Me |
| 1472 | 4-chloro-2-thienyl | 4-Me |
| 1473 | 4-chloro-2-thienyl | 2,3-F₂ |
| 1474 | 4-chloro-2-thienyl | 2,4-F2 |
| 1475 | 4-chloro-2-thienyl | 2,5-F₂ |
| 1476 | 4-chloro-2-thienyl | 2,6-F₂ |
| 1477 | 4-chloro-2-thienyl | 3,4-F₂ |
| 1478 | 4-chloro-2-thienyl | 3,5-F₂ |
| 1479 | 4-chloro-2-thienyl | 3,4,5-F₃ |
| 1480 | 4-chloro-2-thienyl | 3-F, 4-Cl |
| 1481 | 4-chloro-2-thienyl | 3-F, 4-Br |
| 1482 | 4-chloro-2-thienyl | 3-CN, 4-F |
| 1483 | 4-chloro-2-thienyl | 3-Br, 4-F |
| 1484 | 4-chloro-2-thienyl | 3-Cl, 4-F |
| 1485 | 4-chloro-2-thienyl | 3,4-Cl₂ |
| 1486 | 3-chloro-2-thienyl | H |
| 1487 | 3-chloro-2-thienyl | 2-F |
| 1488 | 3-chloro-2-thienyl | 3-F |
| 1489 | 3-chloro-2-thienyl | 4-F |
| 1490 | 3-chloro-2-thienyl | 3-Cl |
| 1491 | 3-chloro-2-thienyl | 4-Cl |
| 1492 | 3-chloro-2-thienyl | 3-Br |
| 1493 | 3-chloro-2-thienyl | 4-Br |
| 1494 | 3-chloro-2-thienyl | 3-I |
| 1495 | 3-chloro-2-thienyl | 3-CN |
| 1496 | 3-chloro-2-thienyl | 4-CN |
| 1497 | 3-chloro-2-thienyl | 3-NO₂ |
| 1498 | 3-chloro-2-thienyl | 3-Me |
| 1499 | 3-chloro-2-thienyl | 4-Me |
| 1500 | 3-chloro-2-thienyl | 2,3-F₂ |
| 1501 | 3-chloro-2-thienyl | 2,4-F2 |
| 1502 | 3-chloro-2-thienyl | 2,5-F₂ |
| 1503 | 3-chloro-2-thienyl | 2,6-F₂ |
| 1504 | 3-chloro-2-thienyl | 3,4-F₂ |
| 1505 | 3-chloro-2-thienyl | 3,5-F₂ |
| 1506 | 3-chloro-2-thienyl | 3,4,5-F₃ |
| 1507 | 3-chloro-2-thienyl | 3-F, 4-Cl |
| 1508 | 3-chloro-2-thienyl | 3-F, 4-Br |
| 1509 | 3-chloro-2-thienyl | 3-CN, 4-F |
| 1510 | 3-chloro-2-thienyl | 3-Br, 4-F |
| 1511 | 3-chloro-2-thienyl | 3-Cl, 4-F |
| 1512 | 3-chloro-2-thienyl | 3,4-Cl₂ |
| 1513 | 2-bromo-1,3-thiazol-5-yl | H |
| 1514 | 2-bromo-1,3-thiazol-5-yl | 2-F |
| 1515 | 2-bromo-1,3-thiazol-5-yl | 3-F |
| 1516 | 2-bromo-1,3-thiazol-5-yl | 4-F |
| 1517 | 2-bromo-1,3-thiazol-5-yl | 3-Cl |
| 1518 | 2-bromo-1,3-thiazol-5-yl | 4-Cl |
| 1519 | 2-bromo-1,3-thiazol-5-yl | 3-Br |
| 1520 | 2-bromo-1,3-thiazol-5-yl | 4-Br |
| 1521 | 2-bromo-1,3-thiazol-5-yl | 3-I |
| 1522 | 2-bromo-1,3-thiazol-5-yl | 3-CN |
| 1523 | 2-bromo-1,3-thiazol-5-yl | 4-CN |
| 1524 | 2-bromo-1,3-thiazol-5-yl | 3-NO₂ |
| 1525 | 2-bromo-1,3-thiazol-5-yl | 3-Me |
| 1526 | 2-bromo-1,3-thiazol-5-yl | 4-Me |
| 1527 | 2-bromo-1,3-thiazol-5-yl | 2,3-F₂ |
| 1528 | 2-bromo-1,3-thiazol-5-yl | 2,4-F2 |
| 1529 | 2-bromo-1,3-thiazol-5-yl | 2,5-F₂ |
| 1530 | 2-bromo-1,3-thiazol-5-yl | 2,6-F₂ |
| 1531 | 2-bromo-1,3-thiazol-5-yl | 3,4-F₂ |
| 1532 | 2-bromo-1,3-thiazol-5-yl | 3,5-F₂ |
| 1533 | 2-bromo-1,3-thiazol-5-yl | 3,4,5-F₃ |
| 1534 | 2-bromo-1,3-thiazol-5-yl | 3-F, 4-Cl |
| 1535 | 2-bromo-1,3-thiazol-5-yl | 3-F, 4-Br |
| 1536 | 2-bromo-1,3-thiazol-5-yl | 3-CN, 4-F |
| 1537 | 2-bromo-1,3-thiazol-5-yl | 3-Br, 4-F |
| 1538 | 2-bromo-1,3-thiazol-5-yl | 3-Cl, 4-F |
| 1539 | 2-bromo-1,3-thiazol-5-yl | 3,4-Cl₂ |
| 1540 | 2-chloro-1,3-thiazol-5-yl | H |
| 1541 | 2-chloro-1,3-thiazol-5-yl | 2-F |
| 1542 | 2-chloro-1,3-thiazol-5-yl | 3-F |
| 1543 | 2-chloro-1,3-thiazol-5-yl | 4-F |
| 1544 | 2-chloro-1,3-thiazol-5-yl | 3-Cl |
| 1545 | 2-chloro-1,3-thiazol-5-yl | 4-Cl |
| 1546 | 2-chloro-1,3-thiazol-5-yl | 3-Br |
| 1547 | 2-chloro-1,3-thiazol-5-yl | 4-Br |
| 1548 | 2-chloro-1,3-thiazol-5-yl | 3-I |
| 1549 | 2-chloro-1,3-thiazol-5-yl | 3-CN |
| 1550 | 2-chloro-1,3-thiazol-5-yl | 4-CN |
| 1551 | 2-chloro-1,3-thiazol-5-yl | 3-NO₂ |
| 1552 | 2-chloro-1,3-thiazol-5-yl | 3-Me |
| 1553 | 2-chloro-1,3-thiazol-5-yl | 4-Me |
| 1554 | 2-chloro-1,3-thiazol-5-yl | 2,3-F₂ |
| 1555 | 2-chloro-1,3-thiazol-5-yl | 2,4-F2 |
| 1556 | 2-chloro-1,3-thiazol-5-yl | 2,5-F₂ |
| 1557 | 2-chloro-1,3-thiazol-5-yl | 2,6-F₂ |
| 1558 | 2-chloro-1,3-thiazol-5-yl | 3,4-F₂ |
| 1559 | 2-chloro-1,3-thiazol-5-yl | 3,5-F₂ |
| 1560 | 2-chloro-1,3-thiazol-5-yl | 3,4,5-F₃ |
| 1561 | 2-chloro-1,3-thiazol-5-yl | 3-F, 4-Cl |
| 1562 | 2-chloro-1,3-thiazol-5-yl | 3-F, 4-Br |
| 1563 | 2-chloro-1,3-thiazol-5-yl | 3-CN, 4-F |
| 1564 | 2-chloro-1,3-thiazol-5-yl | 3-Br, 4-F |
| 1565 | 2-chloro-1,3-thiazol-5-yl | 3-Cl, 4-F |
| 1566 | 2-chloro-1,3-thiazol-5-yl | 3,4-Cl₂ |
| 1567 | 5-fluoro-3-thienyl | H |
| 1568 | 5-fluoro-3-thienyl | 2-F |
| 1569 | 5-fluoro-3-thienyl | 3-F |
| 1570 | 5-fluoro-3-thienyl | 4-F |
| 1571 | 5-fluoro-3-thienyl | 3-Cl |
| 1572 | 5-fluoro-3-thienyl | 4-Cl |
| 1573 | 5-fluoro-3-thienyl | 3-Br |
| 1574 | 5-fluoro-3-thienyl | 4-Br |
| 1575 | 5-fluoro-3-thienyl | 3-I |
| 1576 | 5-fluoro-3-thienyl | 3-CN |
| 1577 | 5-fluoro-3-thienyl | 4-CN |
| 1578 | 5-fluoro-3-thienyl | 3-NO₂ |
| 1579 | 5-fluoro-3-thienyl | 3-Me |
| 1580 | 5-fluoro-3-thienyl | 4-Me |
| 1581 | 5-fluoro-3-thienyl | 2,3-F₂ |
| 1582 | 5-fluoro-3-thienyl | 2,4-F2 |
| 1583 | 5-fluoro-3-thienyl | 2,5-F₂ |
| 1584 | 5-fluoro-3-thienyl | 2,6-F₂ |
| 1585 | 5-fluoro-3-thienyl | 3,4-F₂ |
| 1586 | 5-fluoro-3-thienyl | 3,5-F₂ |
| 1587 | 5-fluoro-3-thienyl | 3,4,5-F₃ |
| 1588 | 5-fluoro-3-thienyl | 3-F, 4-Cl |
| 1589 | 5-fluoro-3-thienyl | 3-F, 4-Br |
| 1590 | 5-fluoro-3-thienyl | 3-CN, 4-F |
| 1591 | 5-fluoro-3-thienyl | 3-Br, 4-F |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 1592 | 5-fluoro-3-thienyl | 3-Cl, 4-F |
| 1593 | 5-fluoro-3-thienyl | 3,4-Cl₂ |
| 1594 | 4-fluoro-3-thienyl | H |
| 1595 | 4-fluoro-3-thienyl | 2-F |
| 1596 | 4-fluoro-3-thienyl | 3-F |
| 1597 | 4-fluoro-3-thienyl | 4-F |
| 1598 | 4-fluoro-3-thienyl | 3-Cl |
| 1599 | 4-fluoro-3-thienyl | 4-Cl |
| 1600 | 4-fluoro-3-thienyl | 3-Br |
| 1601 | 4-fluoro-3-thienyl | 4-Br |
| 1602 | 4-fluoro-3-thienyl | 3-I |
| 1603 | 4-fluoro-3-thienyl | 3-CN |
| 1604 | 4-fluoro-3-thienyl | 4-CN |
| 1605 | 4-fluoro-3-thienyl | 3-NO₂ |
| 1606 | 4-fluoro-3-thienyl | 3-Me |
| 1607 | 4-fluoro-3-thienyl | 4-Me |
| 1608 | 4-fluoro-3-thienyl | 2,3-F₂ |
| 1609 | 4-fluoro-3-thienyl | 2,4-F2 |
| 1610 | 4-fluoro-3-thienyl | 2,5-F₂ |
| 1611 | 4-fluoro-3-thienyl | 2,6-F₂ |
| 1612 | 4-fluoro-3-thienyl | 3,4-F₂ |
| 1613 | 4-fluoro-3-thienyl | 3,5-F₂ |
| 1614 | 4-fluoro-3-thienyl | 3,4,5-F₃ |
| 1615 | 4-fluoro-3-thienyl | 3-F, 4-Cl |
| 1616 | 4-fluoro-3-thienyl | 3-F, 4-Br |
| 1617 | 4-fluoro-3-thienyl | 3-CN, 4-F |
| 1618 | 4-fluoro-3-thienyl | 3-Br, 4-F |
| 1619 | 4-fluoro-3-thienyl | 3-Cl, 4-F |
| 1620 | 4-fluoro-3-thienyl | 3,4-Cl₂ |
| 1621 | 2-fluoro-3-thienyl | H |
| 1622 | 2-fluoro-3-thienyl | 2-F |
| 1623 | 2-fluoro-3-thienyl | 3-F |
| 1624 | 2-fluoro-3-thienyl | 4-F |
| 1625 | 2-fluoro-3-thienyl | 3-Cl |
| 1626 | 2-fluoro-3-thienyl | 4-Cl |
| 1627 | 2-fluoro-3-thienyl | 3-Br |
| 1628 | 2-fluoro-3-thienyl | 4-Br |
| 1629 | 2-fluoro-3-thienyl | 3-I |
| 1630 | 2-fluoro-3-thienyl | 3-CN |
| 1631 | 2-fluoro-3-thienyl | 4-CN |
| 1632 | 2-fluoro-3-thienyl | 3-NO₂ |
| 1633 | 2-fluoro-3-thienyl | 3-Me |
| 1634 | 2-fluoro-3-thienyl | 4-Me |
| 1635 | 2-fluoro-3-thienyl | 2,3-F₂ |
| 1636 | 2-fluoro-3-thienyl | 2,4-F2 |
| 1637 | 2-fluoro-3-thienyl | 2,5-F₂ |
| 1638 | 2-fluoro-3-thienyl | 2,6-F₂ |
| 1639 | 2-fluoro-3-thienyl | 3,4-F₂ |
| 1640 | 2-fluoro-3-thienyl | 3,5-F₂ |
| 1641 | 2-fluoro-3-thienyl | 3,4,5-F₃ |
| 1642 | 2-fluoro-3-thienyl | 3-F, 4-Cl |
| 1643 | 2-fluoro-3-thienyl | 3-F, 4-Br |
| 1644 | 2-fluoro-3-thienyl | 3-CN, 4-F |
| 1645 | 2-fluoro-3-thienyl | 3-Br, 4-F |
| 1646 | 2-fluoro-3-thienyl | 3-Cl, 4-F |
| 1647 | 2-fluoro-3-thienyl | 3,4-Cl₂ |
| 1648 | 2,5-difluoro-3-thienyl | H |
| 1649 | 2,5-difluoro-3-thienyl | 2-F |
| 1650 | 2,5-difluoro-3-thienyl | 3-F |
| 1651 | 2,5-difluoro-3-thienyl | 4-F |
| 1652 | 2,5-difluoro-3-thienyl | 3-Cl |
| 1653 | 2,5-difluoro-3-thienyl | 4-Cl |
| 1654 | 2,5-difluoro-3-thienyl | 3-Br |
| 1655 | 2,5-difluoro-3-thienyl | 4-Br |
| 1656 | 2,5-difluoro-3-thienyl | 3-I |
| 1657 | 2,5-difluoro-3-thienyl | 3-CN |
| 1658 | 2,5-difluoro-3-thienyl | 4-CN |
| 1659 | 2,5-difluoro-3-thienyl | 3-NO₂ |
| 1660 | 2,5-difluoro-3-thienyl | 3-Me |
| 1661 | 2,5-difluoro-3-thienyl | 4-Me |
| 1662 | 2,5-difluoro-3-thienyl | 2,3-F₂ |
| 1663 | 2,5-difluoro-3-thienyl | 2,4-F2 |
| 1664 | 2,5-difluoro-3-thienyl | 2,5-F₂ |
| 1665 | 2,5-difluoro-3-thienyl | 2,6-F₂ |
| 1666 | 2,5-difluoro-3-thienyl | 3,4-F₂ |
| 1667 | 2,5-difluoro-3-thienyl | 3,5-F₂ |
| 1668 | 2,5-difluoro-3-thienyl | 3,4,5-F₃ |
| 1669 | 2,5-difluoro-3-thienyl | 3-F, 4-Cl |
| 1670 | 2,5-difluoro-3-thienyl | 3-F, 4-Br |
| 1671 | 2,5-difluoro-3-thienyl | 3-CN, 4-F |
| 1672 | 2,5-difluoro-3-thienyl | 3-Br, 4-F |
| 1673 | 2,5-difluoro-3-thienyl | 3-Cl, 4-F |
| 1674 | 2,5-difluoro-3-thienyl | 3,4-Cl₂ |
| 1675 | 5-fluoro-2-thienyl | H |
| 1676 | 5-fluoro-2-thienyl | 2-F |
| 1677 | 5-fluoro-2-thienyl | 3-F |
| 1678 | 5-fluoro-2-thienyl | 4-F |
| 1679 | 5-fluoro-2-thienyl | 3-Cl |
| 1680 | 5-fluoro-2-thienyl | 4-Cl |
| 1681 | 5-fluoro-2-thienyl | 3-Br |
| 1682 | 5-fluoro-2-thienyl | 4-Br |
| 1683 | 5-fluoro-2-thienyl | 3-I |
| 1684 | 5-fluoro-2-thienyl | 3-CN |
| 1685 | 5-fluoro-2-thienyl | 4-CN |
| 1686 | 5-fluoro-2-thienyl | 3-NO₂ |
| 1687 | 5-fluoro-2-thienyl | 3-Me |
| 1688 | 5-fluoro-2-thienyl | 4-Me |
| 1689 | 5-fluoro-2-thienyl | 2,3-F₂ |
| 1690 | 5-fluoro-2-thienyl | 2,4-F2 |
| 1691 | 5-fluoro-2-thienyl | 2,5-F₂ |
| 1692 | 5-fluoro-2-thienyl | 2,6-F₂ |
| 1693 | 5-fluoro-2-thienyl | 3,4-F₂ |
| 1694 | 5-fluoro-2-thienyl | 3,5-F₂ |
| 1695 | 5-fluoro-2-thienyl | 3,4,5-F₃ |
| 1696 | 5-fluoro-2-thienyl | 3-F, 4-Cl |
| 1697 | 5-fluoro-2-thienyl | 3-F, 4-Br |
| 1698 | 5-fluoro-2-thienyl | 3-CN, 4-F |
| 1699 | 5-fluoro-2-thienyl | 3-Br, 4-F |
| 1700 | 5-fluoro-2-thienyl | 3-Cl, 4-F |
| 1701 | 5-fluoro-2-thienyl | 3,4-Cl₂ |
| 1702 | 4-fluoro-2-thienyl | H |
| 1703 | 4-fluoro-2-thienyl | 2-F |
| 1704 | 4-fluoro-2-thienyl | 3-F |
| 1705 | 4-fluoro-2-thienyl | 4-F |
| 1706 | 4-fluoro-2-thienyl | 3-Cl |
| 1707 | 4-fluoro-2-thienyl | 4-Cl |
| 1708 | 4-fluoro-2-thienyl | 3-Br |
| 1709 | 4-fluoro-2-thienyl | 4-Br |
| 1710 | 4-fluoro-2-thienyl | 3-I |
| 1711 | 4-fluoro-2-thienyl | 3-CN |
| 1712 | 4-fluoro-2-thienyl | 4-CN |
| 1713 | 4-fluoro-2-thienyl | 3-NO₂ |
| 1714 | 4-fluoro-2-thienyl | 3-Me |
| 1715 | 4-fluoro-2-thienyl | 4-Me |
| 1716 | 4-fluoro-2-thienyl | 2,3-F₂ |
| 1717 | 4-fluoro-2-thienyl | 2,4-F2 |
| 1718 | 4-fluoro-2-thienyl | 2,5-F₂ |
| 1719 | 4-fluoro-2-thienyl | 2,6-F₂ |
| 1720 | 4-fluoro-2-thienyl | 3,4-F₂ |
| 1721 | 4-fluoro-2-thienyl | 3,5-F₂ |
| 1722 | 4-fluoro-2-thienyl | 3,4,5-F₃ |
| 1723 | 4-fluoro-2-thienyl | 3-F, 4-Cl |
| 1724 | 4-fluoro-2-thienyl | 3-F, 4-Br |
| 1725 | 4-fluoro-2-thienyl | 3-CN, 4-F |
| 1726 | 4-fluoro-2-thienyl | 3-Br, 4-F |
| 1727 | 4-fluoro-2-thienyl | 3-Cl, 4-F |
| 1728 | 4-fluoro-2-thienyl | 3,4-Cl₂ |
| 1729 | 3-fluoro-2-thienyl | H |
| 1730 | 3-fluoro-2-thienyl | 2-F |
| 1731 | 3-fluoro-2-thienyl | 3-F |
| 1732 | 3-fluoro-2-thienyl | 4-F |
| 1733 | 3-fluoro-2-thienyl | 3-Cl |
| 1734 | 3-fluoro-2-thienyl | 4-Cl |
| 1735 | 3-fluoro-2-thienyl | 3-Br |
| 1736 | 3-fluoro-2-thienyl | 4-Br |
| 1737 | 3-fluoro-2-thienyl | 3-I |
| 1738 | 3-fluoro-2-thienyl | 3-CN |
| 1739 | 3-fluoro-2-thienyl | 4-CN |
| 1740 | 3-fluoro-2-thienyl | 3-NO₂ |
| 1741 | 3-fluoro-2-thienyl | 3-Me |

TABLE 1-continued

Preferred meanings of Q(R²)ₙ and (R³)ₘ in compounds of the formula (I) or of the formula (Ia) according to the invention:

| No. | Q(R²)ₙ | (R³)ₘ |
|---|---|---|
| 1742 | 3-fluoro-2-thienyl | 4-Me |
| 1743 | 3-fluoro-2-thienyl | 2,3-F₂ |
| 1744 | 3-fluoro-2-thienyl | 2,4-F2 |
| 1745 | 3-fluoro-2-thienyl | 2,5-F₂ |
| 1746 | 3-fluoro-2-thienyl | 2,6-F₂ |
| 1747 | 3-fluoro-2-thienyl | 3,4-F₂ |
| 1748 | 3-fluoro-2-thienyl | 3,5-F₂ |
| 1749 | 3-fluoro-2-thienyl | 3,4,5-F₃ |
| 1750 | 3-fluoro-2-thienyl | 3-F, 4-Cl |
| 1751 | 3-fluoro-2-thienyl | 3-F, 4-Br |
| 1752 | 3-fluoro-2-thienyl | 3-CN, 4-F |
| 1753 | 3-fluoro-2-thienyl | 3-Br, 4-F |
| 1754 | 3-fluoro-2-thienyl | 3-Cl, 4-F |
| 1755 | 3-fluoro-2-thienyl | 3,4-Cl₂ |
| 1756 | 1,3-thiazol-5-yl | H |
| 1757 | 1,3-thiazol-5-yl | 2-F |
| 1758 | 1,3-thiazol-5-yl | 3-F |
| 1759 | 1,3-thiazol-5-yl | 4-F |
| 1760 | 1,3-thiazol-5-yl | 3-Cl |
| 1761 | 1,3-thiazol-5-yl | 4-Cl |
| 1762 | 1,3-thiazol-5-yl | 3-Br |
| 1763 | 1,3-thiazol-5-yl | 4-Br |
| 1764 | 1,3-thiazol-5-yl | 3-I |
| 1765 | 1,3-thiazol-5-yl | 3-CN |
| 1766 | 1,3-thiazol-5-yl | 4-CN |
| 1767 | 1,3-thiazol-5-yl | 3-NO₂ |
| 1768 | 1,3-thiazol-5-yl | 3-Me |
| 1769 | 1,3-thiazol-5-yl | 4-Me |
| 1770 | 1,3-thiazol-5-yl | 2,3-F₂ |
| 1771 | 1,3-thiazol-5-yl | 2,4-F2 |
| 1772 | 1,3-thiazol-5-yl | 2,5-F₂ |
| 1773 | 1,3-thiazol-5-yl | 2,6-F₂ |
| 1774 | 1,3-thiazol-5-yl | 3,4-F₂ |
| 1775 | 1,3-thiazol-5-yl | 3,5-F₂ |
| 1776 | 1,3-thiazol-5-yl | 3,4,5-F₃ |
| 1777 | 1,3-thiazol-5-yl | 3-F, 4-Cl |
| 1778 | 1,3-thiazol-5-yl | 3-F, 4-Br |
| 1779 | 1,3-thiazol-5-yl | 3-CN, 4-F |
| 1780 | 1,3-thiazol-5-yl | 3-Br, 4-F |
| 1781 | 1,3-thiazol-5-yl | 3-Cl, 4-F |
| 1782 | 1,3-thiazol-5-yl | 3,4-Cl₂ |
| 1783 | 1,3-oxazol-5-yl | H |
| 1784 | 1,3-oxazol-5-yl | 2-F |
| 1785 | 1,3-oxazol-5-yl | 3-F |
| 1786 | 1,3-oxazol-5-yl | 4-F |
| 1787 | 1,3-oxazol-5-yl | 3-Cl |
| 1788 | 1,3-oxazol-5-yl | 4-Cl |
| 1789 | 1,3-oxazol-5-yl | 3-Br |
| 1790 | 1,3-oxazol-5-yl | 4-Br |
| 1791 | 1,3-oxazol-5-yl | 3-I |
| 1792 | 1,3-oxazol-5-yl | 3-CN |
| 1793 | 1,3-oxazol-5-yl | 4-CN |
| 1794 | 1,3-oxazol-5-yl | 3-NO₂ |
| 1795 | 1,3-oxazol-5-yl | 3-Me |
| 1796 | 1,3-oxazol-5-yl | 4-Me |
| 1797 | 1,3-oxazol-5-yl | 2,3-F₂ |
| 1798 | 1,3-oxazol-5-yl | 2,4-F2 |
| 1799 | 1,3-oxazol-5-yl | 2,5-F₂ |
| 1800 | 1,3-oxazol-5-yl | 2,6-F₂ |
| 1801 | 1,3-oxazol-5-yl | 3,4-F₂ |
| 1802 | 1,3-oxazol-5-yl | 3,5-F₂ |
| 1803 | 1,3-oxazol-5-yl | 3,4,5-F₃ |
| 1804 | 1,3-oxazol-5-yl | 3-F, 4-Cl |
| 1805 | 1,3-oxazol-5-yl | 3-F, 4-Br |
| 1806 | 1,3-oxazol-5-yl | 3-CN, 4-F |
| 1807 | 1,3-oxazol-5-yl | 3-Br, 4-F |
| 1808 | 1,3-oxazol-5-yl | 3-Cl, 4-F |
| 1809 | 1,3-oxazol-5-yl | 3,4-Cl₂ |

Likewise preferred compounds of the formula (I) or (Ia) according to the invention are described in the Example section below.

For preferred compounds of the formula (I) or (Ia) according to the invention, m is greater than or equal to 1, preferably greater than or equal to 2, and the following applies:

one, more than one or all radicals $R^2$ are selected from the group consisting of F, Cl, Br, I, methyl and CN, and one, more than one or all radicals $R^3$ are selected from the group consisting of F, Cl, Br, methyl, methoxy, nitro and CN.

For preferred compounds of the formula (I) or (Ia) according to the invention, the following applies:

n is greater than or equal to 1, preferably greater than or equal to 2, m is greater than or equal to 1, preferably greater than or equal to 2, one, more than one or all radicals $R^2$ are selected from the group consisting of F, Cl, Br, I, methyl and CN, and one, more than one or all radicals $R^3$ are selected from the group consisting of F, Cl, Br, methyl, methoxy and CN.

Particular preference according to the invention is given to compounds of the formula (I) or (Ia) or salts thereof where the following applies:

n=1, 2 or 3, and at least one $R^2$ is selected, preferably all $R^2$ are selected, from the group consisting of fluorine, chlorine and bromine, and/or m=1, 2 or 3, and at least one $R^3$ is selected, preferably all $R^3$ are selected, from the group consisting of fluorine and chlorine.

Likewise preferred according to the invention are compounds of the formula (I) and/or salts thereof in which $(R^3)_m$ is 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F₂-4-Cl).

Likewise preferred according to the invention are compounds of the formula (Ia) and/or salts thereof in which $(R^3)_m$ is 3-chloro, 4-chloro, 2,3-dichloro, 2,4-dichloro, 2,5-dichloro, 2,6-dichloro, 3,4-dichloro, 3,5-dichloro, 2-fluoro, 3-fluoro, 4-fluoro, 2,3-difluoro, 2,4-difluoro, 2,5-difluoro, 2,6-difluoro, 3,4-difluoro, 3,5-difluoro, 2,3,6-trifluoro, 2,4,6-trifluoro, (3-Cl-2-F), (3-Cl-4-F), (3-Cl-5-F), (3-Cl-6-F), (4-Cl-2-F), (4-Cl-3-F) or (2,6-F₂-4-Cl).

Among the compounds according to the invention with the meanings given above, preference is given to those in which the structural element Q, $R^1$, $(R^2)_n$ and $(R^3)_m$ defined in each case as preferred, in each case as particularly preferred or in each case as especially preferred are realized in combination with one another.

The compounds of the formula (I) according to the invention can have (2,3)-erythro configuration, i.e. correspond to the compounds of the following formulae (I eryrthro-1) and (I eryrthro-2):

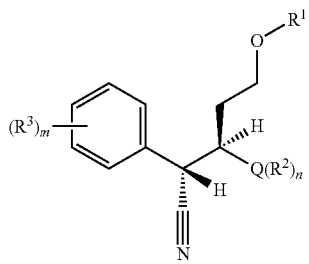
(I erythro-1)

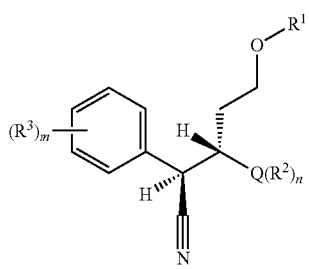
(I erythro-2)

Furthermore, it has been found that the compounds of the formula (I) according to the invention and/or their salts or (Ia) and/or their salts which are (2,3)-threo-configured have better herbicidal properties than the corresponding (2,3)-erythro-configured compounds. Accordingly, (2,3)-threo-configured compounds of the formulae (I) and (Ia) and their salts are preferred. The same applies accordingly to compositions according to the invention.

Accordingly, preference according to the invention is given to mixtures and compositions in which the molar ratio of a (2,3)-threo-configured compound of the formula (I) to the corresponding (2,3)-erythro-configured compound of the formula (I) is greater than 1, more preferably greater than 2, particularly preferably greater than 3 and especially preferably greater than 4.

Likewise, preference according to the invention is given to mixtures and compositions in which the weight ratio of the total amount of (2,3)-threo-configured compounds of the formulae (I) and (Ia) to the total amount of (2,3)-erythro-configured compounds of the formulae (I) and (Ia) is greater than 1, more preferably greater than 2, particularly preferably greater than 3 and especially preferably greater than 4.

Surprisingly, it has furthermore been found that optically active threo-configured compounds of the formula (I) and their salts have particularly good herbicidal activities and at the same time advantageous selectivities with respect to some useful plants.

Accordingly, in the context of the present invention preference is given to compounds of the formula (I) and their salts having a (2,3)-threo-configuration, i.e. compounds of the following formulae (I threo-1) and (I threo-2)

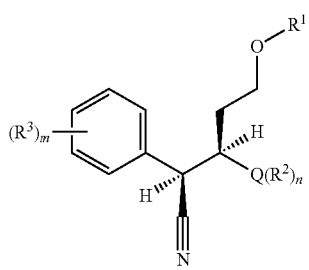
(I threo-1)

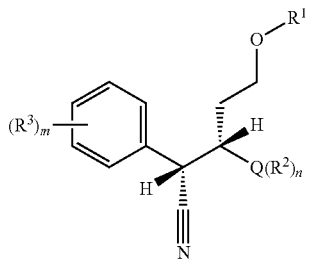
(I threo-2)

in which
$R^1$, $R^2$, $R^3$, n and m each have the meaning mentioned above, preferably one of the meanings given in each case as being preferred or particularly preferred.

In the context of the present invention preference is given to compounds of the formula (Ia) and their salts having a (2,3)-threo-configuration, i.e. compounds of the following formulae (Ia threo-1) and/or (Ia threo-2)

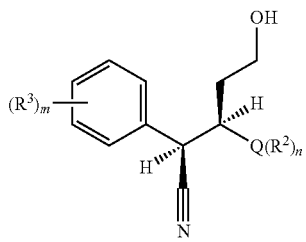
(Ia threo-1)

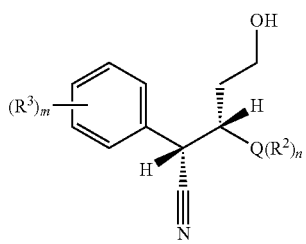
(Ia threo-2)

in which
$R^2$, $R^3$, n and m each have the meaning mentioned above, preferably one of the meanings given in each case as being preferred or particularly preferred or especially preferred.

The stereochemical configuration at the carbon atom in position 2 of the pentanonitrile derivative of the formulae (I) and (Ia) preferably has a stereochemical purity of from 60 to 100% (S), with preference from 70 to 100% (S), more preferably from 80 to 100% (S), especially preferably from 90 to 100% (S), and the stereochemical configuration at the carbon atom in position 3 of the pentanonitrile derivative preferably has a stereochemical purity of from 60 to 100% (S), with preference from 70 to 100% (S), more preferably from 80 to 100% (S), especially preferably from 90 to 100% (S), in each case based on the total amount of the threo-enantiomers in question.

The stereochemical configuration at the carbon atom in position 2 of the pentanonitrile derivative of the formulae (I) and (Ia) preferably has a stereochemical purity of from 60 to 100% (R), with preference from 70 to 100% (R), more preferably from 80 to 100% (R), especially preferably from 90 to 100% (R), and the stereochemical configuration at the carbon atom in position 3 of the pentanonitrile derivative preferably has a stereochemical purity of from 60 to 100% (R), with preference from 70 to 100% (R), more preferably from 80 to 100% (R), especially preferably from 90 to 100% (R), in each case based on the total amount of the threo-enantiomers in question.

By virtue of their even better property profile, in particular their even better herbicidal activity, special preference is given to the (2R,3R)-configured pentanonitrile derivatives of the formulae (I) and (Ia), preferably in the stereochemical purities stated above. As a consequence, compounds of the formulae (I threo-1) and (Ia threo-1) are particularly preferred in the context of the present invention. The absolute configuration of these (2R,3R)-configured pentanonitrile derivatives was assigned by X-ray structural analysis.

That stated above applies accordingly to mixtures according to the invention and compositions according to the invention.

The compounds of the formula (I) according to the invention can be prepared by various processes.

In the processes described below, in some cases solvents are employed. In this context, "inert solvents" refers in each case to solvents which are inert under the particular reaction conditions, but which do not have to be inert under any reaction conditions. In the processes below, the reactions described can alternatively also be carried out in a microwave reactor.

The compounds according to the invention can be prepared by methods known per se. Here, the starting material may, for example, be compounds of the formula (E). Compounds of the formula (E) are known from the prior art, for example from WO 2014/095879 A1. The scheme below shows, in an exemplary manner, how the compounds according to the invention can be prepared.

represents hydrogen or an organic radical, preferably a radical selected from the group of the radicals defined above for $R^1$.

With respect to "Step 1" of the above scheme:

Methods for the selective reduction of compounds of the formula (E) to give corresponding compounds of the formula (Ia) are known to the person skilled in the art from the prior art and described, for example, in European Journal of Organic Chemistry 2009, (11), 1806-1811 or in WO 2012/076513 A1. Preferably, the selective reduction in this case is carried out using borohydrides, with preference using borohydrides of alkali metal borohydrides, in particular of lithium borohydride, sodium borohydride or potassium borohydride, and in turn preferably in the presence of a lithium halide, preferably in the presence of lithium chloride. Here, this reduction can be carried out in a protic organic solvent such as, for example, ethanol (see, for example, WO 2011/014383), or an aprotic organic solvent such as, for example, tetrahydrofuran (THF), here preferably by heating under reflux.

With respect to "Step 2" of the above scheme:

The present optional further reaction (nucleophilic substitution) of the primary alcohol (Ia) obtained in "Step 1" with $R^1$—$X^1$ (where $X^1$ represents a leaving group) to give compounds of the formula (I) is known in principle to the person skilled in the art and described, for example, in Journal of Organic Chemistry 2011, 76(3), 811-819. Here, the nucleophilic substitution is preferably carried out in the presence of 4-(dimethylamino)pyridine. The reaction can also be carried out, for example, in an aprotic organic solvent such as tetrahydrofuran (THF) or dichloromethane, if appropriate at elevated temperature, for example by heating under reflux.

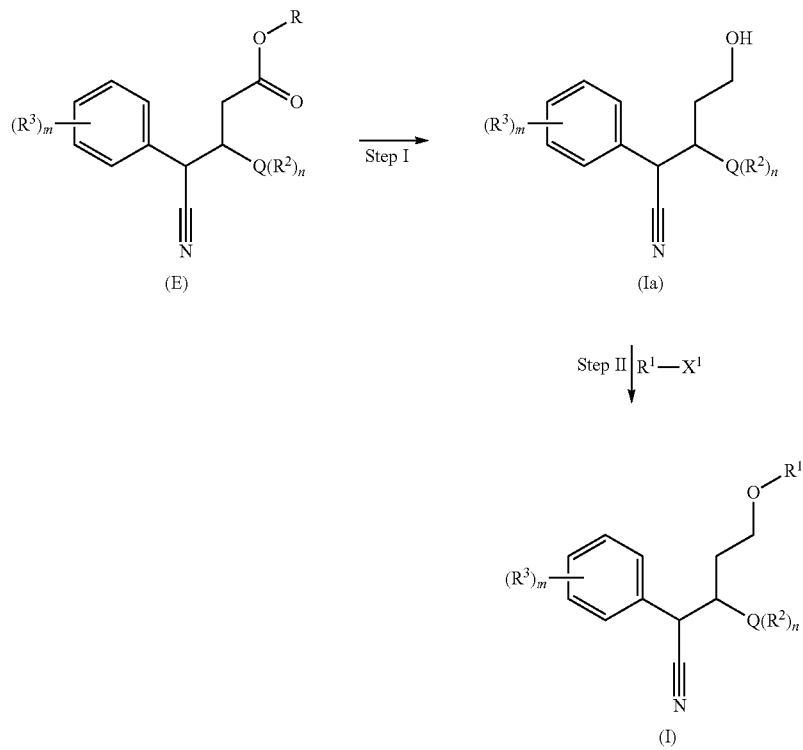

Here, $R^1$, $R^2$, $R^3$, n and m each have the (preferred or particularly preferred) meaning mentioned above, and R Accordingly, the present invention also relates to a process for preparing a compound of the formula (I) according to the invention and/or a salt thereof, characterized in that a compound of the formula (E)

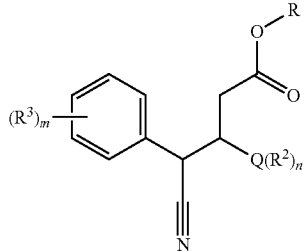

is converted by reduction into a compound of the formula (Ia)

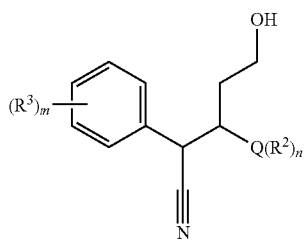

and the compound (Ia) is optionally reacted further to give a compound of the formula (I), provided $R^1$ does not represent hydrogen,
where
R represents hydrogen or an organic radical, preferably a radical selected from the group of the radicals defined above for $R^1$, with preference selected from one of the radicals characterized as being preferred, and
$R^2$, $R^3$, m and n each have the meaning defined above, and are preferably in each case selected from one of the groups of radicals characterized as being preferred.

The starting materials (E) used for preparing the compounds of the formula (Ia) or (I) are known from the literature cited or can be prepared analogously to the literature cited.

To prepare the compounds (Ia) or (I) according to the invention, it is also possible to use the corresponding diastereomer mixtures in the form of their racemic mixtures.

If stereochemically enriched compounds of the formula (E) mentioned above are used in the process according to the invention, it is possible to obtain the corresponding stereochemically enriched compounds of the formula (Ia) or (I).

Solvents suitable for this purpose are, for example, organic solvents such as:
aliphatic hydrocarbons such as pentane, hexane, cyclohexane or petroleum ether;
aromatic hydrocarbons such as toluene, o-, m- or p-xylene,
halogenated hydrocarbons such as methylene chloride, chloroform or chlorobenzene,
ethers, such as diethyl ether, diisopropyl ether, tert-butyl methyl ether, dioxane, anisole and tetrahydrofuran (THF),
nitriles such as acetonitrile or propionitrile,
ketones such as acetone, methyl ethyl ketone, diethyl ketone and tert-butyl methyl ketone,
dimethyl sulfoxide, dimethylformamide, dimethylacetamide, sulfolane, and also
mixtures of the stated organic solvents.

In individual cases, it is also appropriate to use inorganic solvents such as water or mixtures of organic solvents with water.

Suitable conditions and catalysts for the preparation of compounds of the formula (I) in which $R^1$ does not represent H from compounds of the formula (Ia), for example by esterification, are known to the person skilled in the art.

The conversion of compounds of the formula (Ia) into compounds of the formula (I) in which $R^1$ does not represent H can be carried out in the presence of a base, for example a base from the group of the inorganic bases such as the alkali metal and alkaline earth metal hydroxides, for example lithium hydroxide, sodium hydroxide, potassium hydroxide or calcium hydroxide, the alkali metal and alkaline earth metal oxides, for example lithium oxide, sodium oxide, calcium oxide or magnesium oxide, the alkali metal and alkaline earth metal hydrides, for example lithium hydride, sodium hydride, potassium hydride or calcium hydride, the alkali metal amides, for example lithium amide, sodium amide or potassium amide, the alkali metal and alkaline earth metal carbonates, for example lithium carbonate, potassium carbonate or calcium carbonate, the alkali metal bicarbonates, for example sodium bicarbonate, or the organometallic compounds such as, preferably, the alkali metal alkyls, for example methyllithium, butyllithium or phenyllithium, the alkylmagnesium halides, for example methylmagnesium chloride, or the alkali metal and alkaline earth metal alkoxides, for example sodium methoxide, sodium ethoxide, potassium ethoxide, potassium tert-butoxide or dimethoxymagnesium.

The bases used can also be organic bases, for example from the group of the tertiary aliphatic amines, for example trimethylamine, triethylamine, tributylamine, diisopropylethylamine or N-methylpiperidine, or the aromatic tertiary amines, for example pyridine or substituted pyridines such as collidine, lutidine or 4-dimethylaminopyridine, or the bicyclic amines such as 7-methyl-1,5,7-triazabicyclo[4.4.0]-dec-5-ene or 1,8-diazabicyclo[5.4.0]undec-7-ene (DBU).

Preferred bases are, for example, lithium hydroxide, potassium carbonate, potassium tert-butoxide, lithium bis(trimethylsilyl)amide, pyridines, substituted pyridines, 7-methyl-1,5,7-triazabicyclo[4.4.0]-dec-5-ene or DBU.

The amount of base may generally vary within wide limits. For example, it may be expedient to employ the base in catalytic amounts, in substoichiometric amounts, in equimolar amounts or in excess. A preferably liquid organic base may optionally also be used as solvent.

Suitable catalysts for the conversion of compounds of the formula (Ia) into compounds of the formula (I) in which $R^1$ is not H may also be acidic catalysts, for example from the group of the inorganic acids, for example Broensted acids, such as hydrofluoric acid, hydrochloric acid, hydrobromic acid, sulfuric acid or perchloric acid, or Lewis acids, such as boron trifluoride, aluminum trichloride, iron(III) chloride, tin(IV) chloride, titanium(IV) chloride, scandium(III) triflate or zinc(II) chloride, and also organic acids, for example formic acid, acetic acid, propionic acid, oxalic acid, toluenesulfonic acid, benzenesulfonic acid, camphorsulfonic acid, citric acid or trifluoroacetic acid.

The reaction mixtures obtained are worked up in a customary manner, for example by mixing with water, separating the phases and optionally chromatographic purification of the crude products. Some of the compounds are obtained in the form of colorless or slightly brownish viscous oils which are purified or freed from volatile components under reduced pressure and at moderately elevated temperature.

If the compounds are obtained as solids, the purification can also be carried out by recrystallization or digestion. If individual compounds (I) cannot be obtained in a satisfactory manner by the routes described above, they can be prepared by derivatization of other compounds (I) or (Ia).

Suitable isolation methods, purification methods and methods for separating stereoisomers of compounds of the formula (I) or (Ia) are methods generally known to the person skilled in the art from analogous cases, for example by physical processes such as crystallization, chromatographic methods, in particular column chromatography and HPLC (high pressure liquid chromatography), distillation, optionally under reduced pressure, extraction and other methods, any mixtures that remain can generally be separated by chromatographic separation, for example on chiral solid phases. Suitable for preparative amounts or on an industrial scale are processes such as crystallization, for example of diastereomeric salts which can be obtained from the diastereomer mixtures using optically active acids and, if appropriate, provided that acidic groups are present, using optically active bases.

Optically active acids which are suitable for optical resolution by crystallization of diastereomeric salts are, for example, camphorsulfonic acid, camphoric acid, bromocamphorsulfonic acid, quinic acid, tartaric acid, dibenzoyltartaric acid and other analogous acids; suitable optically active bases are, for example, quinine, cinchonine, quinidine, brucine, 1-(S)- or 1-(R)-phenylethylamine and other analogous bases.

The crystallizations are then in most cases carried out in aqueous, alcoholic or aqueous-organic solvents, where the diastereomer which is less soluble precipitates first, if appropriate after seeding. One enantiomer of the compound of the formula (I) is then liberated from the precipitated salt, or the other is liberated from the crystallizate, by acidification or using a base.

As an alternative to the optical resolution methods mentioned, enantioselective processes starting with stereochemically pure starting materials are in principle also suitable for preparing the (threo) enantiomers.

The following acids are generally suitable for preparing the acid addition salts of the compounds of the formula (I): hydrohalic acids, such as hydrochloric acid or hydrobromic acid, furthermore phosphoric acid, nitric acid, sulfuric acid, mono- or bifunctional carboxylic acids and hydroxycarboxylic acids, such as acetic acid, maleic acid, succinic acid, fumaric acid, tartaric acid, citric acid, salicylic acid, sorbic acid, or lactic acid, and also sulfonic acids, such as p-toluenesulfonic acid and 1,5-naphthalenedisulfonic acid. The acid addition compounds of the formula (I) can be obtained in a manner known per se by the customary methods for forming salts, for example by dissolving a compound of the formula (I) in a suitable organic solvent, such as, for example, methanol, acetone, methylene chloride or benzene, and adding the acid at temperatures of from 0 to 100° C., and they can be isolated in a known manner, for example by filtration, and, if appropriate, purified by washing with an inert organic solvent.

Base addition salts of the compounds of the formula (I) can be prepared, for example, in polar solvents such as, for example, water, methanol or acetone, at temperatures of from 0 to 100° C. Examples of bases which are suitable for the preparation of such salts are, for example, alkali metal carbonates, such as potassium carbonate, alkali metal hydroxides and alkaline earth metal hydroxides, for example NaOH or KOH, alkali metal hydrides and alkaline earth metal hydrides, for example NaH, alkali metal alkoxides and alkaline earth metal alkoxides, for example sodium methoxide or potassium tert-butoxide, or ammonia, ethanolamine or quaternary ammonium hydroxide.

A collection of compounds of the formula (I) can additionally be prepared in a parallel or combinatorial manner, it being possible for this to take place in a manual, partly automated or completely automated manner. In this connection, it is possible to automate the reaction procedure, the work-up or the purification of the products and/or intermediates.

For the parallelized reaction procedure and work-up it is possible to use a range of commercially available instruments, of the kind offered by, for example, the companies Stem Corporation, Woodrolfe Road, Tollesbury, Essex, CM9 8SE, England, or H+P Labortechnik GmbH, Bruckmannring 28, 85764 Oberschleißheim, Germany. For the parallelized purification of compounds (I) or of intermediates produced during the preparation, there are available, inter alia, chromatography apparatuses, for example from ISCO, Inc., 4700 Superior Street, Lincoln, Nebr. 68504, USA. The apparatuses listed allow a modular procedure in which the individual process steps are automated, but between the process steps manual operations have to be carried out. This can be circumvented by using partly or completely integrated automation systems in which the respective automation modules are operated, for example, by robots. Automation systems of this type can be acquired, for example, from Zymark Corporation, Zymark Center, Hopkinton, Mass. 01748, USA.

Besides the methods described, the preparation of compounds of the formula (I) can take place completely or partially by solid-phase-supported methods. For this purpose, individual intermediates or all intermediates in the synthesis or a synthesis adapted for the corresponding procedure are bonded to a synthesis resin. Solid-phase-supported synthesis methods are described extensively in the specialist literature, for example: Barry A. Bunin in "The Combinatorial Index", Verlag Academic Press, 1998.

The use of solid-phase-supported synthesis methods permits a number of protocols, which are known from the literature and which for their part may be performed manually or in an automated manner. For example, the so-called "tea bag method" (U.S. Pat. No. 4,631,211) in which products from IRORI, 11149 North Torrey Pines Road, La Jolla, Calif. 92037, USA, are employed, may be semiautomated. The automation of solid-phase-supported parallel syntheses is performed successfully, for example, by apparatuses from Argonaut Technologies, Inc., 887 Industrial Road, San Carlos, Calif. 94070, USA or MultiSynTech GmbH, Wullener Feld 4, 58454 Witten, Germany.

The preparation according to the processes described herein produces compounds of the formula (I) in the form of substance collections or libraries. Accordingly, the present invention also provides libraries of compounds of the formula (I) which comprise at least two compounds of the formula (I), and precursors thereof.

The present invention furthermore provides a method for controlling harmful plants and/or for regulating the growth of plants, characterized in that an effective amount of one or more compounds of the formula (I) and/or salts thereof, as defined above, of one or more compounds of the formula (Ia) and/or salts thereof, as defined above, or of a composition, as defined above, is applied to the (harmful) plants, seeds of (harmful) plants, the soil in which or on which the (harmful) plants grow or the area under cultivation.

The present invention also provides a method for controlling unwanted plants, preferably in crops of useful plants, characterized in that an effective amount
of one or more compounds of the formula (I) and/or salts thereof, as defined above,
of one or more compounds of the formula (Ia) and/or salts thereof, as defined above, or
of a composition according to the invention, as defined above,
is applied to unwanted plants (for example harmful plants such as mono- or dicotyledonous weeds or unwanted crop plants), the seed of the unwanted plants (i.e. plant seeds, for example grains, seeds or vegetative propagation organs such as tubers or shoot parts with buds), the soil in which or on which the unwanted plants grow (for example the soil of crop land or non-crop land) or the area under cultivation (i.e. the area on which the unwanted plants will grow).

The present invention furthermore also provides methods for regulating the growth of plants, preferably of useful plants, characterized in that an effective amount
of one or more compounds of the formula (I) and/or salts thereof, as defined above,
of one or more compounds of the formula (Ia) and/or salts thereof, as defined above, or
of a composition according to the invention, as defined above,
is applied to the plant, the seed of the plant (i.e. plant seed, for example grains, seeds or vegetative propagation organs such as tubers or shoot parts with buds), the soil in which or on which the plants grow (for example the soil of crop land or non-crop land) or the area under cultivation (i.e. the area on which the plants will grow).

In this context, the compounds according to the invention or the compositions according to the invention can be applied for example by pre-sowing (if appropriate also by incorporation into the soil), pre-emergence and/or post-emergence processes. Specific examples of some representatives of the monocotyledonous and dicotyledonous weed flora which can be controlled by the compounds of the invention are as follows, though there is no intention to restrict the enumeration to particular species.

In a method according to the invention for controlling harmful plants or for regulating the growth of plants, one or more compounds of the formula (I), (Ia) and/or salts thereof are preferably employed for controlling harmful plants or for regulating growth in crops of useful plants or ornamental plants, where in a preferred embodiment the useful plants or ornamental plants are transgenic plants.

The compounds of the formula (I) or (Ia) according to the invention and/or their salts are suitable for controlling the following genera of monocotyledonous and dicotyledonous harmful plants:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria* and *Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola* and *Xanthium.*

When the compounds according to the invention are applied to the soil surface before germination of the harmful plants (weed grasses and/or broad-leaved weeds) (pre-emergence method), either the seedlings of the weed grasses or broad-leaved weeds are prevented completely from emerging or they grow until they have reached the cotyledon stage, but then stop growing and eventually, after three to four weeks have elapsed, die completely.

If the active ingredients are applied post-emergence to the green parts of the plants, growth stops after the treatment, and the harmful plants remain at the growth stage at the time of application, or they die completely after a certain time, such that competition by the weeds, which is harmful to the crop plants, is thus eliminated very early and in a lasting manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, triticale, triticum, Zea*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamental plants.

In addition, the compounds according to the invention (depending on their particular structure and the application rate deployed) have outstanding growth-regulating properties in crop plants. They intervene in the plants' own metabolism with regulatory effect, and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active ingredients can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material.

It is preferred with a view to transgenic crops to use the compounds according to the invention and/or their salts in economically important transgenic crops of useful plants and ornamentals, for example of cereals such as wheat, barley, rye, oats, millet, rice and maize or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant growth regulatory properties, the active ingredients can also be used to control harmful plants in crops of genetically modified plants which are known or are yet to be developed. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further special properties may be tolerance or resistance to abiotic stressors, for example heat, cold, drought, salinity and ultraviolet radiation.

Preference is given to the use of the compounds of the formula (I) according to the invention or salts thereof in economically important transgenic crops of useful plants and ornamental plants, for example of cereals such as wheat, barley, rye, oats, triticale, millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods.

A large number of molecular-biological techniques by means of which novel transgenic plants with modified properties can be generated are known to the person skilled in the art. For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or against herbicides which inhibit essential plant enzymes, for example acetolactate synthases (ALS), EPSP synthases, glutamine synthases (GS) or hydroxyphenylpyruvate dioxygenases (HPPD), or against herbicides from the group of the sulfonylureas, glyphosate, glufosinate or benzoylisoxazoles and analogous active ingredients.

When the active ingredients of the invention are used in transgenic crops, not only do the effects toward harmful plants which are observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the formula (I) according to the invention and/or their salts as herbicides for controlling harmful plants in crops of useful plants or ornamentals, optionally in transgenic crop plants.

Preference is given to the use in cereals, here preferably maize, wheat, barley, rye, oats, millet or rice, by the pre- or post-emergence method.

Preference is also given to the use in soy beans by the pre- or post-emergence method.

The use according to the invention for the control of harmful plants or for growth regulation of plants also includes the case in which the active ingredient of the formula (I) or its salt is not formed from a precursor substance ("prodrug") until after application on the plant, in the plant or in the soil.

The invention also provides the use of one or more compounds of the formula (I) or salts thereof or of a composition according to the invention (as defined below) (in a method) for controlling harmful plants or for regulating the growth of plants which comprises applying an effective amount of one or more compounds of the formula (I) or salts thereof onto the plants (harmful plants, if appropriate together with the useful plants), plant seeds, the soil in which or on which the plants grow or the area under cultivation.

The invention also provides a herbicidal or plant growth-regulating composition, characterized in that the composition (a) comprises one or more compounds of the formula (I) and/or salts thereof as defined above, preferably one or more compounds of the formula (Ia) and/or salts thereof, in each case as defined above,
and
(b) one or more further substances selected from groups (i) and/or (ii):
  (i) one or more further agrochemically active substances, preferably selected from the group consisting of insecticides, acaricides, nematicides, further herbicides (i.e. those not corresponding to the formula (I) defined above), fungicides, safeners, fertilizers and/or further growth regulators,
  (ii) one or more formulation auxiliaries customary in crop protection.

A herbicidal or plant growth-regulating composition according to the invention comprises preferably one, two, three or more formulation auxiliaries (ii) customary in crop protection selected from the group consisting of surfactants, emulsifiers, dispersants, film-formers, thickeners, inorganic salts, dusting agents, carriers solid at 25° C. and 1013 mbar, preferably absorbant granulated inert materials, wetting agents, antioxidants, stabilizers, buffer substances, antifoam agents, water, organic solvents, preferably organic solvents miscible with water in any ratio at 25° C. and 1013 mbar.

The compounds (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the formula (I) and/or salts thereof.

The compounds of the formula (I) and/or salts thereof can be formulated in various ways according to which biological and/or physicochemical parameters are required. Possible formulations include, for example: Wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types and the formulation assistants, such as inert materials, surfactants, solvents and further additives, are known to the person skilled in the art and are described, for example, in: Watkins, "Handbook of Insecticide Dust Diluents and Carriers", 2nd ed., Darland Books, Caldwell N.J.; H. v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologic" [Chemical Technology], volume 7, C. Hanser Verlag Munich, 4th Ed. 1986.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active ingredients are finely ground, for example in customary apparatuses such as hammer mills, blower mills and air jet mills, and simultaneously or subsequently mixed with the formulation auxiliaries.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dustable powders are obtained by grinding the active ingredient with finely distributed solid substances, for example talc, natural clays such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be prepared either by spraying the active ingredient onto adsorptive granular inert material or by applying active ingredient concentrates to the surface of carriers, such as sand, kaolinites or granular inert material, by means of adhesives, for example polyvinyl alcohol, sodium polyacrylate or else mineral oils. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan, fluidized-bed, extruder and spray granules, see e.g. processes in "Spray Drying Handbook" 3rd Ed. 1979, G. Goodwin Ltd., London, J. E. Browning, "Agglomeration", Chemical and Engineering 1967, pages 147 ff, "Perry's Chemical Engineer's Handbook", 5th Ed., McGraw Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations, preferably herbicidal or plant growth-regulating compositions, of the present invention preferably comprise a total amount of from 0.1 to 99% by weight, preferably 0.5 to 95% by weight, particularly preferably 1 to 90% by weight, especially preferably 2 to 80% by weight, of active ingredients of the formula (I) and their salts.

In wettable powders, the active ingredient concentration is, for example, about 10% to 90% by weight, the remainder to 100% by weight consisting of customary formulation constituents. In emulsifiable concentrates, the active ingredient concentration may be about 1% to 90% and preferably 5% to 80% by weight. Formulations in the form of dusts comprise 1% to 30% by weight of active ingredient, preferably usually 5% to 20% by weight of active ingredient; sprayable solutions contain about 0.05% to 80% by weight, preferably 2% to 50% by weight of active ingredient. In the case of water-dispersible granules, the active ingredient content depends partially on whether the active compound is present in liquid or solid form and on which granulation auxiliaries, fillers, etc., are used. In the water-dispersible granules, the content of active ingredient is, for example, between 1% and 95% by weight, preferably between 10% and 80% by weight.

In addition, the active ingredient formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the formula (I) or salts thereof can be employed as such or in the form of their preparations (formulations) combined with other pesticidally active compounds, such as, for example, insecticides, acaricides, nematicides, herbicides, fungicides, safeners, fertilizers and/or growth regulators, for example as finished formulation or as tank mixes. The combination formulations can be prepared on the basis of the abovementioned formulations, while taking account of the physical properties and stabilities of the active ingredients to be combined.

Active ingredients which can be employed in combination with the compounds of formula (I) according to the invention in mixture formulations or in a tank mix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 16th edition, The British Crop Protection Council and the Royal Soc. of Chemistry, 2012 and literature cited therein.

Of particular interest is the selective control of harmful plants in crops of useful plants and ornamentals. Although the compounds (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds (I) according to the invention are of particular interest which comprise the compounds (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugarbeet, sugarcane, oilseed rape, cotton and soybeans, preferably cereals.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tank mix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The application rate of the compounds of the formula (I) and/or their salts is affected to a certain extent by external conditions such as temperature, humidity, etc. Here, the application rate may vary within wide limits. For the application as a herbicide for controlling harmful plants, the total amount of compounds of the formula (I) and their salts is preferably in the range from 0.001 to 10.0 kg/ha, with preference in the range from 0.005 to 5 kg/ha, more preferably in the range from 0.01 to 1.5 kg/ha, in particular in the range from 0.05 to 1 kg/ha. This applies both to application by the pre-emergence method and the post-emergence method, the pre-emergence treatment being preferred by virtue of the significantly higher activity.

When the compounds of the formula (I) and/or their salts are used as plant growth regulator, for example as culm stabilizer for crop plants like those mentioned above, preferably cereal plants, such as wheat, barley, rye, triticale, millet, rice or maize, the total application rate is preferably in the range of from 0.001 to 2 kg/ha, preferably in the range of from 0.005 to 1 kg/ha, in particular in the range of from 10 to 500 g/ha, very particularly in the range from 20 to 250 g/ha. This applies both to the pre-emergence and the post-emergence application.

The application as culm stabilizer may take place at various stages of the growth of the plants. Preferred is, for example, the application after the tillering phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

EXAMPLE SECTION

Abbreviations and Designations

The symbols ">" and "<" mean "greater than" and "smaller than", respectively. The symbol "≥" means "greater than or equal to", the symbol "≤" means "smaller than or equal to".

If, in the context of the description and the examples, the designations "R" and "S" are stated for the absolute configuration at a center of chirality of the stereoisomers of the formulae (I) and (Ia), this follows the RS nomenclature of the Cahn-Ingold-Prelog rules.

Abbreviations and designations used:
Ex.=Example number
H=hydrogen (atom)
Me=methyl
Et=ethyl
n-Pr=n-propyl
i-Pr=isopropyl
n-Bu=n-butyl
i-Bu=isobutyl
F, Cl, Br, I=fluorine, chlorine, bromine and iodine, respectively, in accordance with the conventional chemical atom symbols
MeO or OMe=methoxy
CN=cyano
$NO_2$=nitro The position of a substituent at a (phenyl) ring, for example in position 2 or position 3, is stated as a prefix to the symbol or the abbreviation of the radical, for example
2-Cl=2-chloro
2-Me=2-methyl
3-$NO_2$=3-nitro Numerations of the substituent positions for di- or trisubstituted substitution patterns are analogously stated as a prefix, for example
2,3,6-$F_3$ or 2,3,6-F3=2,3,6-trifluoro (e.g. as substitution at the phenyl ring)
2,3-$F_2$ or 2,3-F2=2,3-difluoro (e.g. as substitution at the phenyl ring)

Other abbreviations are to be understood analogously to the examples stated above.
"$(R^2)_n$"="H"=unsubstituted heteroaromatic radical Q (n=0)
"$(R^3)_m$"="H"=unsubstituted phenyl ring (m=0)

In addition, the customary chemical symbols and formulae apply, such as, for example, $CH_2$ for methylene or $CF_3$ for trifluoromethyl or OH for hydroxyl. Correspondingly, composite meanings are defined as composed of the abbreviations mentioned.

In an exemplary manner, some synthesis examples of compounds of the formula (I) are described below. In the examples, the amounts (including the percentages) refer to the weight, unless stated otherwise.

Synthesis Examples

1a) Preparation of methyl 4-(3-bromo-4-fluorophenyl)-4-cyano-3-(3,5-difluoropyridin-4-yl)butanoate Under protective gas (argon), 46 mg (0.41 mmol) of potassium tert-butoxide were added to 0.413 g (2.07 mmol) of methyl (2E)-3-(3,5-difluoropyridin-4-yl)acrylate and 0.443 g (2.07 mmol) of (3-bromo-4-fluorophenyl)acetonitrile in 21.0 ml of toluene and 1 ml of DMF, and the mixture was stirred at 60° C. for 5 h. After removal of the solvent under reduced pressure, the residue was taken up in ethyl acetate and washed twice with in each case 50 ml of water. The combined organic phases were dried over sodium sulfate and the solvent was removed under reduced pressure. Chromatography of the residue over silica gel (ethyl acetate/heptane=15:85) gave 0.501 g (58% of theory) of the diastereomeric methyl 4-(3-bromo-4-fluorophenyl)-4-cyano-3-(3,5-difluoropyridin-4-yl)butanoates 1b) Preparation of 2-(3-bromo-4-fluorophenyl)-3-(3,5-difluoropyridin-4-yl)-5-hydroxypentane-nitrile Under protective gas (argon), 0.480 g (1.16 mmol) of the methyl 4-(3-bromo-4-fluorophenyl)-4-cyano-3-(3,5-difluoropyridin-4-yl)butanoate obtained in step 1a) in 3 ml of THF were added to 0.125 g (2.32 mmol) of potassium borohydride and 0.049 g (1.16 mmol) of lithium chloride in 2 ml of THF, and the mixture was stirred at 70° C. for 5 h. After cooling to 0° C., water was added. The residue was then taken up in ethyl acetate and washed twice with in each case 50 ml of water. The combined organic phases were dried over sodium sulfate and the solvent was removed under reduced pressure. Chromatography of the residue over silica gel (ethyl acetate/heptane=15:85) gave 73 mg (16% of theory) of the diastereomeric 2-(3-bromo-4-fluorophenyl)-3-(3,5-difluoropyridin-4-yl)-5-hydroxypentanenitriles (erythro:threo=49:51, comparison of the doublet in $^1$H-NMR in $CDCl_3$ at 4.24 and 4.16 ppm).

1c) Preparation of methyl 4-cyano-4-(3,4-difluorophenyl)-3-(5-fluoropyridin-3-yl)butanoate Under protective gas (argon), 125 mg (1.11 mmol) of potassium tert-butoxide were added to 1.006 g (5.55 mmol) of methyl (2E)-3-(5-fluoropyridin-3-yl)acrylate and 0.850 g (5.55 mmol) of (3,4-difluorophenyl)acetonitrile in 45.0 ml of toluene and 2 ml of DMF, and the mixture was stirred at 60° C. for 5 h. After removal of the solvent under reduced pressure, the residue was taken up in ethyl acetate and washed twice with in each case 50 ml of water. The combined organic phases were dried over sodium sulfate and the solvent was removed under reduced pressure. Chromatography of the residue over silica gel (ethyl acetate/heptane=15:85) gave 1.050 g (57% of theory) of the diastereomeric methyl 4-cyano-4-(3,4-difluorophenyl)-3-(5-fluoropyridin-3-yl)butanoates.

1d) Preparation of 2-(3,4-difluorophenyl)-3-(5-fluoropyridin-3-yl)-5-hydroxypentanenitrile Under protective gas (argon), 1.050 g (3.14 mmol) of the methyl 4-cyano-4-(3,4-difluorophenyl)-3-(5-fluoropyridin-3-yl)butanoate obtained in step 1c) in 5 ml THF were added to 0.339 g (6.28 mmol) of potassium borohydride and 0.133 g (3.14 mmol) of lithium chloride in 10 ml of THF, and the mixture was stirred at 70° C. for 5 h. After cooling to 0° C., water was added. The residue was then taken up in ethyl acetate and washed twice with in each case 50 ml of water. The combined organic phases were dried over sodium sulfate and the solvent was removed under reduced pressure. Chromatography of the residue over silica gel (ethyl acetate/heptane=15:85) gave 330 mg (35% of theory) of the diastereomeric 2-(3,4-difluorophenyl)-3-(5-fluoropyridin-3-yl)-5-hydroxypentanenitriles (erythro:threo=59:41, comparison of the doublet in $^1$H-NMR in $CDCl_3$ at 4.29 and 4.04 ppm).

1e) Preparation of (2R,3R)-2-(3,4-difluorophenyl)-3-(5-fluoropyridin-3-yl)-5-hydroxypentanenitrile Preparative chromatography [(80 ml/min n-heptane/2-propanol (80:20)] of 100 mg of the diastereomer mixture obtained as above in step 1d) (dissolved in 4.0 ml of methanol) on a chiral stationary phase [Chiralpak IC, 20 μm, (250×50) mm column] gave 19 mg of (2R,3R)-2-(3,4-difluorophenyl)-3-(5-fluoropyridin-3-yl)-5-hydroxypentanenitrile which eluted as the penultimate of the four stereoisomers (retention time: 11.9 min). The absolute configuration of this compound was subsequently assigned by X-ray structure analysis.

1f) Preparation of 4-(3-bromo-4-fluorophenyl)-4-cyano-3-(3,5-difluoropyridin-4-yl)butyl chloroacetate Under protective gas (argon), 21 mg (0.18 mmol) of chloroacetyl chloride were added to 35 mg (0.09 mmol) of 2-(3-bromo-4-fluorophenyl)-3-(3,5-difluoropyridin-4-yl)-5-hydroxypentanenitrile (obtained in step 1b) above), 4-(dimethylamino)pyridine 7 mg (0.05 mmol) and 18 mg (0.18 mmol) of triethylamine in 3 ml of dichloromethane, and the mixture was stirred at 25° C. for 3 h. The residue was taken up in ethyl acetate and washed twice with in each case 50 ml of water. The combined organic phases were then dried over sodium sulfate and the solvent was removed under reduced pressure. Chromatography of the residue over silica gel (ethyl acetate/heptane=15:85) gave 17 mg (41% of theory) of the diastereomeric 4-(3-bromo-4-fluorophenyl)-4-cyano-3-(3,5-difluoropyridin-4-yl)butyl chloroacetates (erythro:threo=48:52, comparison of the singlets in $^1$H-NMR in CDCl$_3$ at 8.42 and 8.25 ppm).

Definition and Description of Preferred Compounds According to the Invention—Analytical and Physical Data Compounds of the formula (I) according to the invention having corresponding individual numbers (=example numbers) are listed below, where the respective compound name is composed of the compound number of the chemical formula (I) which refers to the same number as given in the respective line of the table, i.e. the structure combination of groups $Q(R^2)_n$ and $(R^3)_m$ is defined according to the corresponding consecutive entry number (hereinbelow "line number", without counting the header of table 1) of table 1.

In this manner, the respective chemical structure of a compound of the formula (I) according to the invention is defined unambiguously, which is demonstrated using the following examples:

The compound name "215a" identifies the compound of the formula (Ia) [corresponds to formula (I) in which $R^1$=H (=hydrogen)] in which $Q(R^2)_n$=3-chloropyridin-2-yl and $(R^3)_m$=3-Cl, 4-F according to line number 215 of table 1.

The compound name "296a" identifies the compound of the formula (Ia) [corresponds to formula (I) in which $R^1$=H (=hydrogen)] in which $Q(R^2)_n$=5-fluoropyridin-3-yl and $(R^3)_m$=3-Cl, 4-F according to line number 296 of table 1.

The compound name "599a" identifies the compound of the formula (Ia) [corresponds to formula (I) in which $R^1$=H (=hydrogen)] in which $Q(R^2)_n$=3,5-difluoropyridin-4-yl and $(R^3)_m$=3-Cl according to line number 599 of table 1.

The compound name "1295a" identifies the compound of the formula (Ia) [corresponds to formula (I) in which $R^1$=H (=hydrogen)] in which $Q(R^2)_n$=5-chloropyrazin-2-yl and $(R^3)_m$=3-Cl, 4-F according to line number 1295 of table 1.

The compound name "1477a" identifies the compound of the formula (Ia) [corresponds to formula (I) in which $R^1$=H (=hydrogen)] in which $Q(R^2)_n$=4-chloro-2-thienyl and $(R^3)_m$=3,4-F$_2$ according to line number 1477 of table 1.

Definitions of $R^1$ in preferred compounds of the formula (I) according to the invention are listed in table U1 below.

TABLE U1

| Formula | $R^1$ in formula (I) |
|---|---|
| (Ia) | H (hydrogen) |
| (Ibb) | acetyl |
| (Ibc) | propanoyl |
| (Ibd) | butanoyl |
| (Ibe) | 2-methylpropanoyl (= isopropanoyl) |
| (Ibf) | 2,2-difluoroacetyl |
| (Ibg) | 2,2,2-trifluoroacetyl |
| (Ibh) | C(O)OMe |
| (Ibi) | cyclopropanecarbonyl |
| (Ibj) | 1-methylcyclopropanecarbonyl |
| (Ibk) | acryl |
| (Ibl) | prop-2-ynoyl |
| (Ibm) | but-2-ynoyl |
| (Ibn) | 2-methylacryl |
| (Ibo) | benzoyl |
| (Ibp) | 4-chlorobenzoyl |
| (Ibq) | 3-chlorobenzoyl |
| (Ibr) | 2-chlorobenzoyl |
| (Ibs) | 4-fluorobenzoyl |
| (Ibt) | 3-fluorobenzoyl |
| (Ibu) | 2-fluorobenzoyl |
| (Ibv) | 2,2-dimethylpropanoyl (= pivaloyl) |
| (Ibw) | 3,3-dimethylbutanoyl |
| (Ibx) | pentanoyl |
| (Iby) | hexanoyl |
| (Ibz) | 2-nitrobenzoyl |
| (Ibaa) | 2-fluoroacetyl |
| (Ibab) | 2-chloroacetyl |
| (Ibac) | 2-bromoacetyl |
| (Ibad) | 2,2-dichloroacetyl |
| (Ibae) | 2-methoxyacetyl |
| (Ibaf) | 2,6-difluorobenzoyl |
| (Ibag) | C(O)C(O)OMe |
| (Ibah) | C(O)CH$_2$C(O)OMe |

Examples of compounds of the formulae (Ia) and (Ibb) to (Ibah) according to the invention are the compounds of the relevant formulae (Ia) and (Ibb) to (Ibah) according to table U1 above in which the structure combination of groups $Q(R^2)_n$ and $(R^3)_m$ is defined by a line number of table 1.

Thus, for example, the compound name "619bab" identifies the compound of the formula (I) in which $R^1$=2-chloroacetyl and $Q(R^2)_n$=3,5-difluoropyridin-4-yl and $(R^3)_m$=3-Br, 4-F according to line number 619 of table 1.

The compound name "599bae" identifies the compound of the formula (I) in which $R^1$=2-methoxy-acetyl and $Q(R^2)_n$=3,5-difluoropyridin-4-yl and $(R^3)_m$=3-Cl according to line number 599 of table 1.

These compounds may be present, for example, in the form of an erythro/threo mixture in a quantitative ratio of 70:30 to 30:70, for example in the form of a racemic erythro/threo mixture.

Information regarding the examples given in Tables 2a to 2d:

In Tables 2a to 2d below, the compounds according to the invention are assigned corresponding individual numbers (=example numbers), where the particular example number is composed of the compound number of the chemical formula (I), which refers to the same number as given in the respective line of the table, followed by the respective stereoisomeric form. The particular stereoisomeric form corresponds to the above-defined formulae (I threo-1), (I threo-2), (I erythro-1) and (I erythro-2), or mixtures of these stereoisomers.

The same applies to the assignment of racemic or optically active threo stereoisomers or erythro stereoisomers of the compounds according to the invention.

In this way, the stereoisomers are given the respective clearly defined chemical structure of a compound of the formula (I) according to the invention, which the following examples aim to illustrate:

The compound name "208a threo" identifies a mixture of the "threo" isomers of the compound of the formula (I), in which $R^1$=H (=hydrogen), and $Q(R^2)_n$=3-chloropyridin-2-yl and $(R^3)_m$=3,4-$F_2$ according to line number 208 from Table 1.

The compound name "532a erythro" identifies a mixture of the "erythro" isomers of the compound of the formula (I) in which $R^1$=H (=hydrogen), and $Q(R^2)_n$=2-chloropyridin-4-yl and $(R^3)_m$=3,4-$F_2$ according to line number 532 from Table 1.

The compound name "289a threo-2" identifies the "threo-2" isomers of the compound of the formula (I) [corresponding to formula (I threo-2)], in which $R^1$=H (=hydrogen), and $Q(R^2)_n$=5-fluoropyridin-3-yl and $(R^3)_m$=3,4-$F_2$ according to entry number 289 from Table 1.

The compound name "532a erythro-1" identifies the "erythro-1" isomers of the compound of the formula (I) [corresponding to formula (I erythro-1)], in which $R^1$=H (=hydrogen), and $Q(R^2)_n$=2-chloropyridin-4-yl and $(R^3)_m$=3,4-$F_2$ according to line number 532 from Table 1.

Tables 2a to 2d: Preferred Compounds of the Formulae (I threo-1), (I threo-2), (I erytro-1) and (I erytro-2) According to the Invention

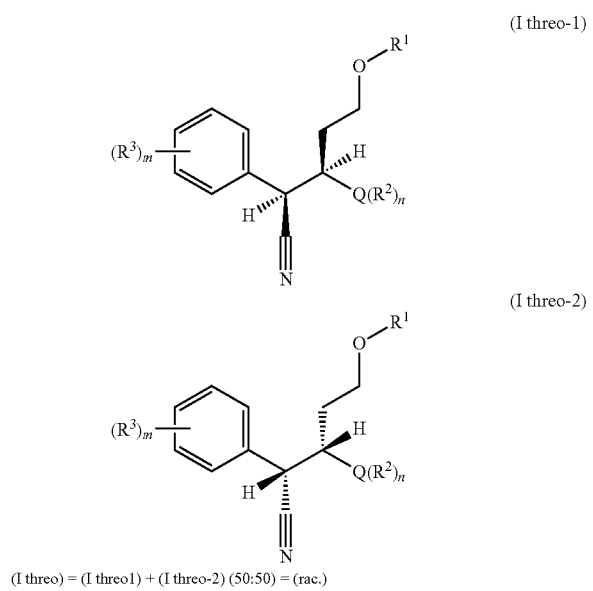

(I threo) = (I threo1) + (I threo-2) (50:50) = (rac.)

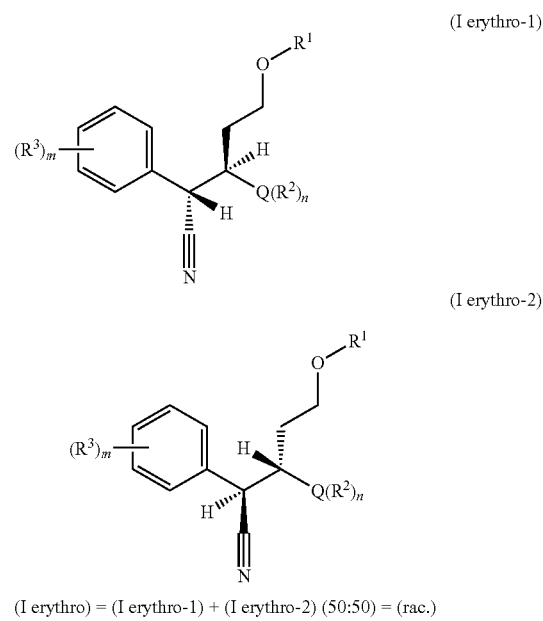

(I erythro) = (I erythro-1) + (I erythro-2) (50:50) = (rac.)

Table 2a: Preferred (I threo-1) Enantiomers

Table 2a describes the compounds of the formulae (1 threo-1) to (1809 threo-1), in which the structure combination of the groups $Q(R^2)_n$ and $(R^3)_m$ is defined according to a line number from Table 1, as explained in detail above, $R^1$ preferably being selected from Table U1 and preferably $R^1$=H (hydrogen).

Table 2b: Preferred (I threo-2) Enantiomers

Table 2b describes the compounds of the formulae (1 threo-2) to (1809 threo-2), in which the structure combination of the groups $Q(R^2)_n$ and $(R^3)_m$ is defined according to a line number from Table 1, as explained in detail above, $R^1$ preferably being selected from Table U1 and preferably $R^1$=H (hydrogen).

Table 2c: Preferred (I erythro-1) Enantiomers

Table 2c describes the compounds of the formulae (1 erythro-1) to (1809 erythro-1), in which the structure combination of the groups $Q(R^2)_n$ and $(R^3)_m$ is defined according to a line number from Table 1, as explained in detail above, $R^1$ preferably being selected from Table U1 and preferably $R^1$=H (hydrogen).

Table 2d: Preferred (I erythro-2) Enantiomers

Table 2d describes the compounds of the formulae (1 erythro-2) to (1809 erythro-2), in which the structure combination of the groups $Q(R^2)_n$ and $(R^3)_m$ is defined according to a line number from Table 1, as explained in detail above, $R^1$ preferably being selected from Table U1 and preferably $R^1$=H (hydrogen).

Physical Data of Some Compounds According to the Invention:

Test Methods:
1) NMR=$^1$H-NMR data (400 MHz, $CDCl_3$); characteristic chemical shifts [in ppm] are given for the respective example.
2) HPLC=High Performance Liquid Chromatography, column: Zorbax Eclipse, 50×3.0, C18 1.8 µm, mobile phase: water+0.06% formic acid/acrylonitrile+0.06% formic acid, gradient: 90:10, after 2 min 5:95; detector: DAD (210-400 nm); retention time (Rt) indicated for the example in question,
3) chiral HPLC=HPLC on a chiral column, column: Chiralpak IC, 250×4.6 mm, 5 µm DAIC 83325, detector wavelength: 210 nm; column temperature 25° C., mobile phase a: (n-heptane:2-propanol), (60:40), Chromasolv, flow rate: 1.0 ml/min
mobile phase b: (n-heptane:2-propanol), (70:30), Chromasolv, flow rate: 1.0 ml/min
mobile phase c: (n-heptane:2-propanol), (80:20), Chromasolv, flow rate: 1.0 ml/min
mobile phase d: (n-heptane:2-propanol), (90:10), Chromasolv, flow rate: 0.6 ml/min NMR Data of Selected Compounds According to the Invention $^1$H-NMR data ($CDCl_3$)—chemical shift of selected characteristic signals in ppm.

NMR Peak List Method

The ¹H-NMR data (also referred to below as 1H-NMR) of selected examples are noted in the form of 1H-NMR peak lists. For each signal peak, first the δ value in ppm and then the signal intensity in round brackets are listed. The pairs of δ value—signal intensity numbers for different signal peaks are listed with separation from one another by semicolons.

The peak list for one example therefore has the form:

$\delta_1$ (intensity$_1$); $\delta_2$ (intensity$_2$); ... ; $\delta_i$ (intensity$_i$); ... ; $\delta_a$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of 1H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the 1H-NMR peaks are similar to the classic 1H-NMR prints and thus usually comprise all peaks listed in classic NMR interpretations.

In addition, like classic 1H-NMR prints, they may show solvent signals, signals of stereoisomers of the target compounds, which are likewise part of the subject matter of the invention, and/or peaks of impurities.

When stating compound signals in the delta range of solvents and/or water, in our lists of 1H NMR peaks, the usual solvent peaks, for example peaks of DMSO in DMSO-$D_6$ and the peak of water are shown, which usually have on average a high intensity.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the relevant peak picking in classical 1H-NMR interpretation.

Further details of 1H NMR peak lists can be found in the Research Disclosure Database Number 564025.

---

Compound 215a: 1H-NMR (400.0 MHz. CDCl3): δ =

8.577(10.7); 8.573(11.0); 8.565(11.1); 8.562(10.9); 8.524(6.5); 8.520(6.7); 8.512(6.8); 8.509(6.5); 7.729(11.1); 7.725(11.2); 7.708(12.4); 7.705(11.8); 7.539(8.0); 7.535(7.9); 7.518(15.9); 7.515(8.7); 7.414(8.9); 7.409(9.8); 7.398(9.1); 7.392(9.5); 7.359(1.4); 7.292(2.8); 7.260(1373.1); 7.251(10.7); 7.245(7.0); 7.239(5.8); 7.235(7.8); 7.227(15.1); 7.224(8.3); 7.216(14.9); 7.210(5.7); 7.207(12.2); 7.196(13.8); 7.192(6.9); 7.181(6.4); 7.175(6.8); 7.166(13.1); 7.158(1.8); 7.145(21.2); 7.124(8.8); 7.115(9.4); 7.103(9.0); 7.094(8.5); 7.083(8.6); 7.046(2.6); 7.040(2.5); 7.035(2.9); 7.029(2.6); 7.025(4.6); 7.019(4.5); 7.013 (4.6); 7008(4.4); 6.996(8.2); 6.984(8.8); 6.963(12.5); 6.942(4.6); 6.914(1.0); 4.362(13.3); 4.357(9.1); 4.338(16.0); 44.332 (10.9); 4.163(2.9); 4.144(7.3); 4.133(5.4); 4.128(3.7); 4.120(10.4); 4.109(8.1); 4.103(2.9); 4.096(3.7); 4.085(3.6); 3.637(2.4); 3.623(4.6); 3.609(5.6); 3.596(6.3); 3.581(3.2); 3.524(3.3); 3.510(6.7); 3.496(7.6); 3.492(4.3); 3.482(10.3); 3.476(5.7); 3.468 (5.7); 3.458(3.7); 3.448(3.5); 3.430(2.6); 3.415(5.5); 3.401(6.5); 3.395(6.4); 3.387(3.9); 3.382(6.1); 3.374(3.9); 3.367(4.2); 3.354(3.6); 2.413(4.9); 2.398(7.4); 2.382(6.8); 2.379(8.4); 2.365(4.9); 2.110(1.9); 2.097(3.6); 2.087(2.2); 2.073(4.2); 2.062 (5.0); 2.052(2.8); 2.038(4.6); 2.025(2.2); 2.005(2.4); 1.882(2.8); 1.870(3.1); 1.866(3.3); 1.862(3.3); 1.855(3.1); 1.851(3.6); 1.847(4.9); 1.836(4.7); 1.832(2.8); 1.827(2.8); 1.821(2.6); 1.816(2.5); 1.801(2.0); 1.587(6.3); 0.157(2.0); 0.146(1.6); 0.008 (16.7); 0.000(516.3); −0.009(15.4); −0.050(1.6); −0.149(1.6)

---

Compound 1484a: 1H-NMR (400.0 MHz. CDCl3): δ =

8.003(1.8); 7.301(2.2); 7.295(2.4); 7.284(2.4); 7.279(2.3); 7.263(50.3); 7.220(4.5); 7.214(4.8); 7.203(4.6); 7.197(4.6); 7.131 (1.3); 7.110(6.2); 7.089(14.8); 7.083(2.2); 7.077(2.4); 7.068(7.4); 7.062(0.8); 7.056(0.6); 7.050(0.6); 7.019(3.1); 7.014 (3.1); 7.009(3.5); 7.000(6.4); 6.997(6.9); 6.992(2.2); 6.987(2.1); 6.981(2.0); 6.973(11.3); 6.969(11.7); 6.718(14.0); 6.717(14.2); 6.715(14.3); 4.190(6.7); 4.176(7.0); 4.010(3.4); 3.993(3.7); 3.813(1.8); 3.801(4.0); 3.787(3.7); 3.774(5.2); 3.761(2.5); 3.750 (0.9); 3.741(1.1); 3.736(1.1); 3.724(1.4); 3.714(1.3); 3.709(1.3); 3.699(1.1); 3.623(2.4); 3.612(2.7); 3.602(2.8); 3.596(2.2); 3.590(2.8); 3.585(2.2); 3.575(2.6); 3.564(2.9); 3.556(1.0); 3.546(3.2); 3.532(3.3); 3.522(2.5); 3.517(3.5); 3.508(3.8); 3.493 (3.1); 3.484(15.8); 3.479(1.4); 3.466(1.1); 3.454(1.0); 2.958(16.0); 2.880(13.6); 2.879(13.4); 2.279(0.5); 2.270(0.6); 2.264 (0.6); 2.255(1.1); 2.244(0.9); 2.240(0.6); 2.235(0.48); 2.230(0.9); 2.220(1.3); 2.211(0.7); 2.205(0.6); 2.196(0.6); 2.189(0.7); 2.176(1.2); 2.168(0.7); 2.163(0.9); 2.154(2.6); 2.141(3.5); 2.133(2.0); 2.127(1.8); 2.119(2.9); 2.114(1.8); 2.106(1.9); 2.102 (3.3); 2.090(3.1); 2.078(3.4); 2.066(2.6); 2.054(1.2); 2.042(1.2); 2.030(0.6); 2.018(0.6); 2.007(1.0); 1.996(0.7); 1.989(0.6); 1.983(0.7); 1.979(1.1); 1.972(0.9); 1.968(0.7); 1.954(0.5); 1.944(0.8); 1.496(6.6); 0.008(0.6); 0.000(19.0)

---

Compound 181a: 1H-NMR (400.0 MHz. CDCl3): δ =

8.523(3.7); 8.520(1.5); 8.517(1.6); 8.513(3.7); 8.481(5.3); 8.472(5.3); 7.263(50.0); 7.259(12.4); 7.200(1.1); 7.186(2.3); 7.180(1.4); 7.176(1.6); 7.170(2.8); 7.166(4.8); 7.162(5.3); 7.157(5.1); 7.154(4.); 7.147(1.2); 7.086(0.3); 7.063(1.6); 7.061 (1.3); 7.057(1.2); 7.046(2.2); 7.032(2.7); 7.016(2.6); 7.002(1.5); 6.990(1.4); 6.987(1.5); 6.978(1.5); 6.974(2.0); 6.969(1.5); 6.960 (1.4); 6.957(1.4); 6.930(6.1); 6.927(5.8); 6.866(1.9); 6.863(1.6); 6.859(1.5); 6.852(1.6); 4.381(4.8); 4.364(5.0); 4.317(3.8); 4.301(3.9); 3.684(1.3); 3.677(1.8); 3.675(1.8); 3.667(2.2); 3.658(2.1); 3.657(2.0); 3.649(1.5); 3.563(1.0); 3.554(1.7); 3.545 (2.1); 3.536(2.0); 3.527(1.2); 3.488(4.1); 3.458(1.0); 3.451(1.1); 3.442(2.0); 3.435(2.4); 3.426(1.3); 3.420(2.9); 3.415(2.5); 3.404(1.4); 3.398(1.3); 3.377(1.5); 3.370(1.7); 3.361(2.0); 3.359(1.8); 3.354(2.0); 3.352(1.8); 3.343(1.5); 3.336(1.4); 3.330 (1.2); 3.322(1.3); 3.315(1.4); 3.312(1.3); 3.307(1.4); 3.304(1.3); 3.297(1.2); 3.289(1.0); 2.403(0.6); 2.397(0.7); 2.393(0.7); 2.387(1.2); 2.380(1.3); 2.371(1.3); 2.364(1.6); 2.358(1.0); 2.354(0.9); 2.349(0.8); 2.261(0.9); 2.254(1.7); 2.246(1.0); 2.243 (1.0); 2.236(1.9); 2.230(1.6); 2.223(0.7); 2.220(0.7); 2.213(1.2); 2.205(0.6); 2.001(0.7); 1.994(1.2); 1.985(1.2); 1.977(1.7); 1.970(2.0); 1.962(1.7); 1.953(2.1); 1.945(1.7); 1.915(2.2); 1.833(0.9); 1.825(1.1); 1.817(1.2); 1.810(1.4); 1.801(1.4); 1.794(0.9); 1.787(0.8); 1.778(0.6); 0.005(0.6); 0.000(12.8); −0.006(0.5)

---

Compound 1515a: 1H-NMR (400.0 MHz. CDCl3): δ =

7.361(0.5); 7.351(0.7); 7.348(1.0); 7.338(2.5); 7.328(2.1); 7.324(3.6); 7.315(3.2); 7.311(2.1); 7.301(1.9); 7.291(4.1); 7.262 (50.0); 7.114(12.4); 7.092(0.4); 7.085(0.3); 7.072(0.5); 7.068(0.6); 7.058(1.0); 7.052(1.8); 7.047(1.8); 7.036(3.3); 7.033(4.1);

-continued 7.019(2.6); 7.010(0.8); 7.007(1.0); 6.995(0.48); 6.992(1.0); 6.969(3.8); 6.956(3.5); 6.930(2.2); 6.927(3.0); 6.914(2.2); 6.911 (2.9); 4.280(5.6); 4.271(5.7); 4.061(1.8); 4.050(1.9); 3.851(1.5); 3.843(3.0); 3.834(2.9); 3.825(3.5); 3.816(1.7); 3.761(0.6); 3.755(1.0); 3.749(1.1); 3.739(2.5); 3.730(3.8); 3.723(2.5); 3.714(2.9); 3.705(1.4); 3.640(1.7); 3.633(1.9); 3.625(2.1); 3.622 (1.9); 3.618(2.1); 3.615(1.8); 3.607(1.6); 3.600(1.5); 3.495(0.6); 3.490(2.8); 3.478(0.9); 3.471(0.9); 3.460(0.5); 3.453(0.5); 2.259(0.5); 2.252(0.6); 2.243(0.6); 2.236(0.6); 2.230(1.0); 2.221(1.4); 2.215(0.9); 2.212(0.9); 2.207(2.1); 2.198(2.3); 2.192 (1.3); 2.189(1.2); 2.183(1.7); 2.174(0.9); 2.110(1.0); 2.103(1.7); 2.095(1.9); 2.087(2.3); 2.079(2.1); 2.071(1.3); 2.064(1.1); 2.055(0.6); 1.939(0.5); 1.932(0.3); 1.928(0.3); 1.921(0.6); 1.916(0.6); 1.897(0.5); 1.556(7.6); 0.000(14.4); −0.006(0.5)

Compound 1461a: 1H-NMR (400.0 MHz. CDCl3): δ =

8.004(1.0); 7.343(1.1); 7.328(1.4); 7.324(3.8); 7.309(4.0); 7.304(5.0); 7.289(4.9); 7.284(3.1); 7.269(3.2); 7.261(50.1); 7.054 (0.9); 7.052(1.1); 7.047(1.1); 7.045(1.5); 7.043(1.9); 7.041(2.0); 7.036(2.1); 7.034(2.6); 7.031(2.5); 7.027(3.6); 7.024(4.7); 7.022(5.5); 7.020(4.4); 7.016(3.6); 7.013(3.8); 7.009(2.2); 7.004(3.9); 7.001(2.0); 6.999(2.0); 6.995(1.9); 6.992(2.1); 6.988 (6.3); 6.985(7.2); 6.982(2.3); 6.976(1.2); 6.963(2.1); 6.956(15.1); 6.952(16.0); 6.934(3.7); 6.933(3.5); 6.904(2.7); 6.899(3.4); 6.893(2.1); 6.880(2.7); 6.875(3.3); 6.870(2.1); 6.727(5.1); 6.726(5.0); 6.724(5.1); 6.722(4.8); 6.708(9.2); 6.707(9.3); 6.704 (9.4); 4.202(6.9); 4.187(7.2); 4.043(3.7); 4.026(4.0); 3.800(1.8); 3.787(3.8); 3.774(3.8); 3.761(4.9); 3.748(2.4); 3.733(1.0); 3.724(1.2); 3.719(1.2); 3.707(1.7); 3.697(1.5); 3.692(1.4); 3.682(1.2); 3.614(2.4); 3.603(2.7); 3.593(3.6); 3.587(2.5); 3.581 (4.9); 3.576(3.3); 3.566(6.3); 3.554(4.4); 3.543(3.5); 3.528(1.7); 3.508(1.3); 3.496(1.5); 3.484(10.9); 3.472(1.6); 3.469(1.4); 3.457(1.2); 3.445(1.1); 2.956(9.3); 2.879(7.8); 2.878(7.6); 2.281(0.6); 2.272(0.6); 2.266(0.6); 2.258(1.2); 2.247(0.9); 2.243 (0.7); 2.238(0.8); 2.232(0.9); 2.223(1.5); 2.214(0.8); 2.208(0.7); 2.199(0.7); 2.187(0.7); 2.174(1.3); 2.166(0.7); 2.161(0.9); 2.152(2.7); 2.139(3.7); 2.131(2.0); 2.125(1.8); 2.118(3.2); 2.111(1.8); 2.104(1.8); 2.099(3.4); 2.087(3.0); 2.075(3.4); 2.063 (2.5); 2.052(1.2); 2.039(1.8); 2.028(1.6); 2.017(0.7); 2.010(0.7); 2.004(07); 2.000(1.0); 1.993(0.9); 1.989(0.8); 1.982(0.5); 1.976(0.6); 1.965(0.7); 1.954(0.5); 1.449(4.9); 0.008(0.6); 0.000(19.6); −0.009(0.5)

Compound 1677a: 1H-NMR (400.0 MHz. CDCl3): δ =

8.001(1.8); 7.334(1.9); 7.327(3.8); 7.319(2.2); 7.312(5.7); 7.306(6.6); 7.300(4.3); 7.292(6.9); 7.286(5.1); 7.279(2.8); 7.272 (5.1); 7.262(65.8); 7.043(1.6); 7.040(4.0); 7.037(4.2); 7.034(4.5); 7.031(3.7); 7.019(9.5); 7.016(8.0); 7.013(7.7); 7.010(6.5); 7.007(2.8); 7.006(2.9); 7.005(3.1); 7.003(3.7); 7.001(4.5); 6.999(4.0); 6.998(4.2); 6.995(4.0); 6.992(3.7); 6.989(3.0); 6.978 (4.9); 6.977(5.7); 6.974(9.2); 6.971(6.4); 6.964(2.2); 6.958(4.9); 6.957(5.7); 6.955(6.4); 6.954(6.1); 6.953(5.9); 6.952(6.1); 6.946(3.0); 6.940(1.8); 6.915(4.5); 6.910(5.5); 6.905(3.5); 6.892(4.5); 6.886(5.5); 6.881(3.5); 6.394(3.5); 6.393(3.5); 6.385 (7.2); 6.383(5.0); 6.380(7.1); 6.378(7.3); 6.376(5.3); 6.375(5.0); 6.370(13.2); 6.362(7.7); 6.360(7.3); 6.266(12.9); 6.261(13.1); 6.256(11.0) 6.251(12.0); 6.250(8.3); 6.245(6.7); 6.240(5.47); 6.236(5.6); 4.150(11.5); 4.136(12.0); 3.992(6.1); 3.974(6.5); 3.803(3.0); 3.790(6.3); 3.776(6.6); 3.763(8.5); 3.750(5.6); 3.741(1.9); 3.736(3.5); 3.724(2.7); 3.714(2.4); 3.709(2.3); 3.699 (2.1); 3.641(4.2); 3.629(4.7); 3.620(4.9); 3.614(3.6); 3.608(4.43.602(3.5); 3.593(3.6); 3.581(3.3); 3.549(2.2); 3.537(2.5); 3.526(2.6); 3.522(2.1); 3.514(2.6); 3.510(2.2); 3.499(2.0); 3.487(1.9); 3.481(6.3); 3.467(1.9); 3.461(2.6); 3.452(4.1); 3.446 (4.0); 3.443(3.6); 3.437(3.2); 3.433(3.2); 3.428(3.5); 3.422(3.7); 3.414(1.8); 3.408(1.5); 2.956(16.0); 2.878(14.1); 2.877(14.0); 2.276(0.9); 2.267(0.9); 2.261(1.0); 2.252(1.8); 2.243(1.2); 2.241(1.4); 2.238(1.1); 2.232(1.3); 2.229(1.2); 2.226(1.4); 2.218 (2.42.209(1.2); 2.203(1.1); 2.194(1.0); 2.142(1.1); 2.129(2.3); 2.121(1.2); 2.116(1.4); 2.107(4.5); 2.094(6.2); 2.086(3.3); 2.080(2.9); 2.072(5.4); 2.064(3.1); 2.059(2.9); 2.052(5.8); 2.040(5.3); 2.028(5.7); 2.016(3.7); 2.004(2.2); 1.992(2.3); 1.980 (1.1); 1 972(1.1); 1 960(1.6); 1.950(1.2); 1 943(1.1); 1 937(1.1); 1.932(1.6); 1 925(1.4); 1.921(1.2); 1.915(0.9); 1.908(0.9); 1.898 (1.2); 1.886(0.8); 1.498(12.3); 0.008(0.7); 0.000(25.4); −0.009(0.7)

Compound 1153a: 1H-NMR (400.0 MHz. CDCl3): δ =

8.095(2.9); 8.090(5.8); 8.087(3.3); 8.082(5.6); 7.264(29.0); 7.127(1.4); 7.119(0.9); 7.113(3.1); 7.105(1.7); 7.097 (3.0); 7.089(1.6); 7.083(1.6); 7.075(0.7); 7.065(0.7); 7.061(0.7); 7.053(0.8); 7.048(1.1); 7.043(0.8); 7.035(0.7); 7.031(0.7); 7.013(1.5); 7.010(1.6); 7.001(1.7); 6.997(2.3); 6.992(1.7); 6.984(1.5); 6.980(1.5); 6.914(1.0); 6.907(0.8); 6.900(0.9); 6.886 (2.2); 6.879(1.7); 6.871(1.9); 6.666(2.1); 6.664(2.4); 6.658(5.6); 6.652(4.2); 6.650(3.9); 6.499(3.5); 6.476(7.7); 4.192(5.3); 4.181(5.3); 4.031(0.4); 3.987(2.4); 3.974(2.5); 3.912(50.0); 3.724(1.4); 3.715(2.9); 3.706(3.0); 3.698(3.43.689(1.6); 3.659 (0.6); 3.652(0.8); 3.649(0.8); 3.642(1.3); 3.634(0.9); 3.631(0.9); 3.624(1.8); 3.494(1.7); 3.488(3.2); 3.480(1.9); 3.476(1.7); 3.471(1.9); 3.468(1.7); 3.462(1.5); 3.454(1.4); 3.381(0.43.373(0.7); 3.365(1.0); 3.357(1.0); 3.348(0.7); 3.340(0.6); 3.278 (0.7); 3.268(1.6); 3.259(3.3); 3.253(2.3); 3.248(2.2); 3.242(2.8); 3.232(1.3); 2.272(0.3); 2.266(0.4); 2.262(0.4); 2.256(0.7); 2.249(0.7); 2.240(0.7); 2.233(0.8); 2.227(0.5); 2.223(0.4); 2.217(0.4); 2.110(0.6); 2.101(1.1); 2.096(0.8); 2.091(1.1); 2.087 (2.4); 2.077(3.6); 2.070(3.8); 2.063(6.4); 2.054(6.4); 2.046(6.1); 2.038(4.2); 2.031(2.1); 2.022(2.0); 2.014(1.1); 0.000(8.3)

Compound 532a threo: 1H-NMR (400.0 MHz. CDCl3): δ =

8.341(15.5); 8.339(15.4); 8.328(16.0); 8.326(15.5); 8.308(0.8); 7.519(4.8); 7.379(0.6); 7.310(1.0); 7.293(1.7); 7.260(903.9); 7.229(0.7); 7.210(1.3); 7.163(5.1); 7.142(8.1); 7.138(6.3); 7.121(7.6); 7.116(20.9); 7.112(19.5); 7.102(5.3); 7.097(10.7); 7.084(5.1); 7.078(5.8); 7.070(5.1); 7.058(4.8); 7.052(4.9); 7.032(12.4); 7.028(11.3); 7.018(11.4); 7.015(10.7); 6.996(5.2); 6.975(0.8); 6.918(3.2); 6.913(4.0); 6.909(5.6); 6.904(4.3); 6.898(4.3); 6.892(3.7); 6.887(4.7); 6.883(3.3); 6.877(2.4); 5.299 (4.5); 4.032(13.8); 4.014(14.6); 3.709(2.1); 3.696(3.1); 3.683(4.1); 3.672(3.6); 3.658(2.6); 3.384(4.7); 3.374(5.3); 3.366(5.1); 3.356(10.5); 3.346(7.1); 3.338(5.6); 3.328(5.2); 2.288(2.0); 2.278(2.2); 2.273(2.4); 2.263(4.3); 2.252(4.3); 2.242(3.4); 2.238 (4.3); 2.228(5.8); 2.218(3.2); 2.214(3.0); 2.204(2.6); 2.170(0.6); 2.088(2.8); 2.077(5.2); 2.067(3.0); 2.061(2.7); 2.050(5.2); 2.042(4.5); 2.031(2.0); 2.025(2.2); 2.014(3.4); 2.004(1.9); 1.541(60.1); 1.333(3.2); 1.284(6.3); 1.256(5.0); 0.880(0.8); 0.146 (1.0); 0.008(9.2); 0.000(342.5); −0.006(4.9); −0.009(11.0); −0.051(0.6); −0.150(1.1)

Compound 1288a: 1H-NMR (400.0 MHz. CDCl3): δ =

8.620(14.8); 8.617(14.8); 8.565(12.7); 8.562(12.6); 8.189(16.0); 8.185(15.7); 8.010(0.7); 7.963(13.47.960 (13.4); 7.520(1.1); 7.261(212.1); 7.215(2.8); 7.211(0.6); 7.195(5.3); 7.191(3.5); 7.180(3.4); 7.174(7.3); 7.170(5.7); 7.162 (3.3); 7.154(4.1); 7.149(5.2); 7.135(3.0); 7.129(3.1); 7.077(2.7); 7.056(4.8); 7.053(3.7); 7.046(3.1); 7.041(4.3); 7.036(6.4); 7.032(6.8); 7.023(4.7); 7.017(4.5); 7.011(4.5); 7.005(2.9); 6.997(4.1); 6.991(2.8); 6.978(2.5); 6.973(2.6); 6.860(1.8); 6.856 (2.2); 6.851(3.2); 6.846(2.3); 6.840(2.2); 6.835(2.0); 6.829(2.5); 6.825(1.8); 6.820(1.3); 4.292(9.2); 4.285(8.4); 4.270(9.6); 4.260 (8.7); 3.728(2.0); 3.717(2.8); 3.701(2.9); 3.690(3.2); 3.676(2.3); 3.645(2.3); 3.633(4.5); 3.619(4.6); 3.605(6.3); 3.594(6.0); 3.583(3.3); 3.577(4.0); 3.570(6.1); 3.561(3.6); 3.552(2.9); 3.548(3.1); 3.543(2.5); 3.536(2.5); 3.346(2.43.335(3.0); 3.323 (5.3); 3.319(3.3); 3.312(5.8); 3.308(3.2); 3.297(5.0); 3.286(4.9); 3.272(2.3); 3.261(2.1); 2.958(5.6); 2.882(4.8); 2.489(1.1); 2.480(1.2); 2.475(1.2); 2.466(1.8); 2.454(2.0); 2.441(1.8); 2.431(2.2); 2.422(1.4); 2.417(1.3); 2.408(1.1); 2.236(1.3); 2.225

(2.7); 2.215(1.5); 2.209(1.4); 2.198(2.9); 2.191(2.4); 2.180(1.1); 2.174(1.1); 2.163(2.0); 2.153(0.9); 2.063(1.0); 2.052(1.9); 2.040(1.5); 2.028(3.0); 2.017(3.8); 2.004(2.8); 1.992(3.3); 1.980(1.6); 1.960(1.7); 1.948(2.9); 1.935(2.4); 1.925(3.6); 1.913 (3.1); 1.902(1.3); 1.890(1.5); 1.878(0.9); 1.485(1.6); 0.008(2.6); 0.000(79.4); −0.009(2.3)

Compound 1477a: 1H-NMR (400.0 MHz. CDCl3): δ =

8.003(1.47.262(60.8); 7.166(1.4); 7.152(2.8); 7.145(2.5); 7.142(1.8); 7.131(4.7); 7.127(3.4); 7.121(2.6); 7.111(3.5); 7.106 (4.6); 7.100(2.0); 7.097(1.6); 7.091(1.6); 7.086(3.2); 7.079(1.4); 7.073(1.6); 7.071(1.5); 7.065(1.4); 7.052(1.3); 7.046(1.4); 7.016(2.3); 7.010(2.5); 6.997(3.0); 6.994(7.3); 6.991(9.2); 6.983(2.8); 6.971(2.9); 6.966(15.2); 6.962(14.1); 6.958(2.2); 6.954(1.4); 6.947(1.2); 6.941(1.0); 6.936(1.3); 6.931(1.0); 6.927(0.7); 6.903(1.7); 6.899(2.1); 6.894(2.9); 6.889(2.2); 6.883 (2.2); 6.878(1.8); 6.873(2.3); 6.868(1.7); 6.863(1.2); 6.722(10.6); 6.721(11.5); 6.719(11.3); 6.718(11.0); 6.715(6.8); 6.714(6.4); 6.711(6.2); 6.710(5.8); 4.199(7.1); 4.185(7.4); 4.010(3.9); 3.993(4.2); 3.813(2.0); 3.800(4.4); 3.787(4.0); 3.773(5.7); 3.761 (2.7); 3.749(1.1); 3.740(1.3); 3.735(1.3); 3.723(1.7); 3.713(1.6); 3.708(1.6); 3.698(1.2); 3.622(2.7); 3.610(3.0); 3.601(3.1); 3.595(2.4); 3.589(3.1); 3.583(2.4); 3.574(3.0); 3.567(1.4); 3.562(2.5); 3.559(1.3); 3.549(3.4); 3.536(4.0); 3.526(2.6); 3.521 (3.1); 3.515(2.3); 3.512(4.1); 3.504(1.9); 3.498(2.0); 3.492(2.0); 3.489(1.7); 3.485(7.5); 3.480(1.9); 3.478(1.6); 3.465(1.4); 3.454(1.3); 2.958(15.6); 2.957(16.0); 2.880(13.7); 2.878(14.0); 2.288(0.6); 2.279(0.7); 2.273(0.7); 2.264(1.3); 2.253(1.1); 2.249 (0.8); 2.244(0.9); 2.239(1.1); 2.229(1.6); 2.220(0.9); 2.214(0.8); 2.205(0.7); 2.192(0.7); 2.178(1.2); 2.171(0.7); 2.165(0.9); 2.156(2.9); 2.143(3.8); 2.135(2.1); 2.130(2.1); 2.121(3.4); 2.107(4.4); 2.095(3.4); 2.083(3.8); 2.071(2.9); 2.060(1.3); 2.048 (1.3); 2.036(0.7); 2.019(0.8); 2.008(1.2); 1.998(0.8); 1.991(0.8); 1.984(0.8); 1.980(1.3); 1.974(1.1); 1.970(0.9); 1.963(0.6); 1.956(0.6); 1.946(0.9); 1.935(0.6); 1.508(3.9); 0.008(0.7); 0.000(24.0); −0.009(0.7)

Compound 1542a: 1H-NMR (400.0 MHz. CDCl3): δ =

7.996(2.0); 7.368(1.2); 7.353(1.7); 7.347(4.4); 7.332(5.0); 7.327(5.9); 7.313(5.9); 7.307(3.6); 7.292(3.2); 7.266(32.8); 7.259 (11.9); 7.087(20.3); 7.078(1.6); 7.076(1.6); 7.072(1.6); 7.070(1.7); 7.056(4.1); 7.050(4.7); 7.036(8.0); 7.032(6.2); 7.015 (6.6); 7.010(4.4); 6.991(2.6); 6.980(6.2); 6.960(4.9); 6.941(3.4); 6.936(4.3); 6.931(4.4); 6.918(3.3); 6.913(4.3); 6.908(2.6); 4.294(8.1); 4.280(8.5); 4.068(4.7); 4.052(5.1); 3.853(2.1); 3.840(4.3); 3.826(4.1); 3.813(5.5); 3.800(2.7); 3.761(1.2); 3.751 (1.5); 3.747(1.6); 3.734(3.2); 3.724(3.1); 3.719(2.7); 3.709(5.0); 3.695(4.8); 3.686(3.2); 3.681(3.8); 3.672(4.3); 3.658(22); 3.647 (2.7); 3.636(3.1); 3.625(3.1); 3.620(2.7); 3.614(3.2); 3.609(2.6); 3.598(2.4); 3.587(2.2); 3.506(1.5); 3.495(1.7); 3.480(8.0); 3.470(2.1); 3.454(1.4); 3.443(1.3); 2.959(16.0); 2.877(13.6); 2.280(0.42.278(0.7); 2.273(0.8); 2.264(1.3); 2.253(1.4); 2.249(1.0); 2.239(2.3); 2.228(2.1); 2.218(1.8); 2.212(1.6); 2.203(3.3); 2.190(3.3); 2.182(2.1); 2.176(1.9); 2.168(2.3); 2.155 (1.5); 2.116(1.6); 2.104(2.4); 2.092(3.0); 2.080(3.2); 2.069(2.9); 2.057(1.7); 2.046(1.3); 2.033(0.9); 1.949(0.8); 1.939(1.5); 1.992 (0.9); 1.922(0.9); 1.911(1.7); 1.904(1.5); 1.894(0.7); 1.887(0.7); 1.876(1.2); 1.866(0.7); 1.729(4.4); 0.008(0.5); 0.000(12.4)

Compound 1565a: 1H-NMR (400.0 MHz. CDCl3): δ =

8.005(1.3); 7.351(2.1); 7.345(2.2); 7.334(2.0); 7.328(2.0); 7.2724(9.5); 7.2715(9.3); 7.264(57.7); 7.258(4.0); 7.252(3.7); 7.163(1.3); 7.142(4.7); 7.117(17.9); 7.109(2.4); 7.103(2.1); 7.097(5.7); 7.088(0.6); 7.082(0.5); 7.060(2.4); 7.054(2.3); 7.050 (2.6); 7.044(2.4); 7.039(1.5); 7.033(1.5); 7.028(1.4); 7.022(1.3); 4.269(5.0); 4.255(5.2); 4.046(3.2); 4.029(3.5); 3.866(1.4); 3.854(2.9); 3.840(2.7); 3.827(3.7); 3.814(1.8); 3.783(0.8); 3.773(1.0); 3.769(1.0); 3.759(1.1); 3.756(1.2); 3.746(1.2); 3.742 (1.2); 3.732(1.0); 3.713(0.8); 3.704(0.9); 3.697(0.8); 3.686(1.6); 3.676(2.2); 3.669(1.1); 3.661(3.4); 3.658(2.8); 3.653(2.1); 3.647(3.6); 3.638(3.1); 3.636(3.0); 3.630(2.0); 3.625(3.6); 3.620(1.9); 3.609(1.7); 3.598(1.5); 3.521(1.1); 3.510(1.2); 3.496 (1.5); 3.487(16.0); 3.469(1.0); 3.459(0.9); 2.960(11.7); 2.881(9.8); 2.880(9.9); 2.263(0.5); 2.259(0.5); 2.249(0.8); 2.238(1.0); 2.232(0.9); 2.228(0.8); 2.224(1.1); 2.219(1.0); 2.217(1.0); 2.213(1.2); 2.210(0.9); 2.204(1.3); 2.196(0.9); 2.190(0.8); 2.183 (2.0); 2.174(1.4); 2.169(1.3); 2.162(1.3); 2.160(1.4); 2.147(1.0); 2.112(1.1); 2.101(1.5); 2.100(1.5); 2.089(2.0); 2.077(2.0); 2.066(1.9); 2.054(1.1); 2.043(0.8); 2.041(0.8); 2.030(0.6); 1.939(0.5); 1.929(1.1); 1.918(0.6); 1.911(0.6); 1.901(1.2); 1.893 (1.0); 1.866(0.9); 1.564(3.9); 0.008(0.7); 0.000(21.5); −0.009(0.6)

Compound 1516a: 1H-NMR (400.0 MHz. CDCl3): δ =

7.262(50.0); 7.256(5.1); 7.222(1.7); 7.214(1.9); 7.208(2.1); 7.200(1.9); 7.150(2.6); 7.142(3.0); 7.136(3.5); 7.127 (3.2); 7.100(7.5); 7.085(0.5); 7.077(0.6); 7.071(2.2); 7.057(3.9); 7.051(3.9); 7.047(1.7); 7.043(2.4); 7.037(5.9); 7.022(2.6); 4.259(3.2); 4.250(3.3); 4.038(2.0); 4.027(2.1); 3.847(0.9); 3.839(1.9); 3.830(1.8); 3.821(2.2); 3.813(1.0); 3.787(0.4); 3.758 (0.6); 3.751(0.7); 3.748(0.7); 3.741(0.9); 3.730(1.3); 3.724(1.2); 3.719(0.6); 3.712(1.0); 3.706(0.6); 3.700(0.7); 3.694(1.4); 3.685(1.7); 3.678(1.2); 3.669(1.7); 3.660(0.9); 3.634(1.1); 3.627(1.2); 3.620(1.3); 3.616(1.2); 3.612(1.3); 3.609(1.1); 3.602 (1.0); 3.595(0.9); 3.499(0.6); 3.492(0.9); 3.490(0.8); 3.483(1.0); 3.476(1.0); 3.465(0.6); 3.458(0.5); 2.285(0.3); 2.279(0.3); 2.276(0.2); 2.269(0.6); 2.262(0.6); 2.253(0.6); 2.246(0.7); 2.239(0.4); 2.236(0.4); 2.230(0.4); 2.227(0.5); 2.218(0.7); 2.212 (0.6); 2.209(0.6); 2.203(1.3); 2.195(1.4); 2.189(0.8); 2.186(0.7); 2.180(1.0); 2.171(0.6); 2.099(0.6); 2.092(1.0); 2.084(1.2); 2.076(1.4); 2.068(1.3); 2.060(0.8); 2.052(0.7); 2.044(0.4); 1.927(0.3); 1.920(0.6); 1.913(0.4); 1.908(0.4); 1.901(0.7); 1.896 (0.7); 1.890(0.3); 1.885(0.3); 1.878(0.5); 1.541(6.6); 0.005(0.7); 0.000(13.6); −0.006(0.5)

Compound 208a: 1H-NMR (400.0 MHz. CDCl3): δ =

8.570(11.1); 8.567(11.4); 8.559(11.4); 8.555(11.2); 8.516(6.7); 8.512(6.9); 8.505(6.9); 8.501(6.8); 7.718(14.0); 7.715(13.8); 7.698(15.5); 7.694(17); 7.535(8.8); 7.531(8.5); 7.522(1.0); 7.515(9.8); 7.511(9.4); 7.263(118.6); 7.219(15.9); 7.214(5.0); 7.207(18.3); 7.199(16.3); 7.196(6.0); 7.190(6.5); 7.187(19.0); 7.181(8.5); 7.180(8.7); 7.176(4.9); 7.169(4.8); 7.164(5.4); 7.160(7.3); 7.155(7.5); 7.135(6.4); 7.110(12.6); 7.102(5.9); 7.098(13.8); 7.089(11.1); 7.078(10.7); 7.071(1.9); 7.024(2.6); 7.003(4.9); 6.999(3.1); 6.995(3.1); 6.989(3.4); 6.982(4.3); 6.977(6.2); 6.970(3.6); 6.968(3.3); 6.962(3.4); 6.958(4.1); 6.949 (2.8); 6.944(3.1); 6.906(2.2); 6.903(2.5); 6.901(2.3); 6.896(3.5); 6.893(2.6); 6.891(2.3); 6.887(2.3); 6.881(1.9); 6.875(2.3); 6.871(1.7); 6.866(1.3); 4.363(8.6); 4.356(12.9); 4.337(11.1); 4.333(16.0); 4.158(2.7); 4.141(8.1); 4.131(5.7); 4.123(3.5); 4.117 (9.3); 4.107(8.1); 4.098(2.7); 4.094(3.9); 4.083(3.6); 3.625(1.9); 3.611(3.9); 3.597(4.7); 3.583(5.5); 3.569(28.); 3.519(2.8); 3.505(5.6); 3.491(6.7); 3.483(11.2); 3.478(9.2); 3.464(6.9); 3.455(2.4); 3.449(3.2); 3.437(3.0); 3.421(2.2); 3.408(4.6); 3.394 (5.3); 3.388(5.5); 3.380(3.5); 3.374(5.2); 3.367(3.4); 3.360(3.5); 3.347(3.8); 3.341(3.1); 2.955(4.5); 2.880(3.8); 2.878(3.7); 2.405(5.2); 2.390(7.5); 2.388(7.6); 2.374(6.6); 2.372(7.7); 2.356(4.7); 2.103(2.0); 2.089(1.9); 2.079(2.2); 2.075(2.3); 2.068(3.3); 2.065 (4.4); 2.055(5.6); 2.052(2.8); 2.045(3.0); 2.041(2.8); 2.031(5.3); 2.017(2.5); 1.883(2.5); 1.872(2.8); 1.868(3.0); 1.863(3.0); 1.857(3.0); 1.853(3.3); 1.848(4.5); 1.838(4.5); 1.834(2.5); 1.829(2.4); 1.823(2.2); 1.818(2.3); 1.814(2.0); 1.803(1.8); 1.624 (2.7); 0.008(1.4); 0.000(44.8); −0.009(1.2)

| Compound 208a threo: 1H-NMR (400.0 MHz. CDCl3): δ = |
|---|
| 8.574(1.9); 8.570(2.0); 8.563(2.0); 8.559(2.0); 8.519(10.6); 8.515(11.0); 8.508(10.9); 8.504(10.9); 7.723(2.4); 7.720(2.4); 7.703(2.6); 7.699(2.5); 7.538(13.3); 7.534(13.7); 7.517(15.0); 7.513(14.7); 7.261(206.1); 7.223(2.7); 7.217(0.9); 7.211(3.7); 7.202(3.2); 7.199(1.0); 7.191(3.4); 7.182(1.6); 7.178(1.0); 7.172(1.4); 7.167(1.1); 7.162(1.4); 7.157(1.5); 7.138(1.2); 7.112 (16.2); 7.100(15.5); 7.091(14.3); 7.080(14.1); 7.024(4.2); 7.003(7.8); 7.000(5.1); 6.995(4.9); 6.989(5.3); 6.983(6.); 6.978 (9.3); 6.971(5.7); 6.968(5.2); 6.962(5.5); 6.958(6.5); 6.950(4.2); 6.944(4.8); 6.909(3.6); 6.905(3.9); 6.903(3.7); 6.899(5.6); 6.895(4.2); 6.893(3.7); 6.889(3.7); 6.884(2.9); 6.877(3.7); 6.874(2.7); 6.868(2.1); 4.366(12.7); 4.360(2.8); 4.341(16.0); 4.160 (4.3); 4.143(7.2); 4.134(4.0); 4.126(4.6); 4.117(5.6); 4.109(1.8); 4.100(3.6); 4.085(0.7); 3.631(3.3); 3.617(6.8); 3.603(8.4); 3.589(9.6); 3.575(4.9); 3.523(0.6); 3.509(1.1); 3.495(1.5); 3.488(5.1); 3.481(2.1); 3.472(7.5); 3.461(3.9); 3.454(5.6); 3.443 (5.1); 3.427(3.7); 3.412(1.0); 3.398(1.1); 3.392(1.1); 3.384(0.7); 3.378(1.1); 3.371(0.7); 3.364(0.7); 3.351(0.6); 2.409(8.5); 2.393(12.7); 2.377(12.6); 2.361(7.8); 2.093(0.7); 2.069(0.8); 2.058(1.5); 2.048(0.5); 2.045(0.5); 2.034(0.9); 1.873(0.5); 1.868 (0.6); 1.864(0.6); 1.858(0.6); 1.853(0.6); 1.849(0.8); 1.838(0.8); 1.607(3.5); 0.008(2.1); 0.000(77.2); −0.009(2.2) |

| Compound 1531a: 1H-NMR (400.0 MHz. CDCl3): δ = |
|---|
| 7.288(3.5); 7.262(50.0); 7.188(0.4); 7.174(1.0); 7.168(1.6); 7.155(3.2); 7.139(3.2); 7.131(12.3); 7.125(1.8); 7.117 (0.8); 7.112(0.6); 7.109(0.5); 7.104(0.5); 7.100(0.4); 7.085(0.3); 7.051(1.5); 7.047(1.6); 7.039(1.7); 7.034(2.4); 7.029(1.6); 7.021(1.5); 7.017(1.4); 6.980(0.6); 6.973(0.5); 6.966(0.6); 6.922(2.2); 6.915(1.7); 6.907(1.9); 4.268(5.1); 4.260(5.2); 4.040 (1.4); 4.029(1.5); 3.857(1.4); 3.849(2.9); 3.840(2.7); 3.831(3.3); 3.823(1.6); 3.772(0.4); 3.765(0.6); 3.763(0.5); 3.756(0.6); 3.747(0.7); 3.745(0.7); 3.738(0.7); 3.731(0.5); 3.724(0.8); 3.718(0.5); 3.710(1.6); 3.701(2.7); 3.694(1.9); 3.692(1.7); 3.685 (2.7); 3.676(1.4); 3.642(1.7); 3.635(1.9); 3.628(2.1); 3.624(1.9); 3.621(2.1); 3.618(1.7); 3.610(1.5); 3.603(1.4); 3.504(0.5); 3.497(0.6); 3.490(2.3); 3.481(0.8); 3.470(0.4); 3.463(0.4); 2.252(0.5); 2.245(0.5); 2.236(0.5); 2.228(0.5); 2.222(0.9); 2.214 (1.2); 2.208(0.9); 2.204(0.9); 2.199(1.9); 2.190(2.2); 2.184(1.3); 2.181(1.2); 2.175(1.5); 2.166(0.9); 2.107(1.0); 2.100(1.6); 2.092(1.9); 2.084(2.0); 2.076(1.9); 2.068(1.3); 2.061(1.0); 2.052(0.6); 1.925(0.5); 1.907(0.6); 1.901(0.6); 1.883(0.4); 1.566 (5.3); 0.000(14.6); −0.006(0.5) |

| Compound 1272a: 1H-NMR (400.0 MHz. CDCl3): δ = |
|---|
| 8.623(13.3); 8.620(13.8); 8.565(11.5); 8.561(11.5); 8.162(16.0); 8.159(15.6); 7.926(13.9); 7.922(13.8); 7.519 (6.5); 7.383(2.4); 7.369(2.7); 7.364(5.2); 7.349(5.1); 7.344(3.4); 7.329(3.5); 7.310(1.5); 7.308(0.7); 7.291(1.3); 7.286(1.7); 7.277(2.8); 7.271(5.2); 7.270(5.8); 7.269(7.2); 7.260(1202.0); 7.247(4.0); 7.231(2.5); 7.226(5.9); 7.212(4.5); 7.206(3.8); 7.198(1.2); 7.192(2.8); 7.169(1.0); 7.081(8.0); 7.078(6.4); 7.075(4.7); 7.060(7.4); 7.058(7.4); 7.054(6.3); 7.052(4.4); 7.043 (4.2); 7.038(5.1); 7.033(4.7); 7.020(3.9); 7.016(4.1); 7.010(2.3); 6.996(6.6); 6.969(2.1); 6.963(2.2); 6.960(2.4); 6.948(3.4); 6.946(3.8); 6.942(3.6); 6.939(4.2); 6.927(1.8); 6.925(1.9); 6.921(1.9); 6.918(2.0); 6.888(5.0); 6.886(4.5); 6.881 (3.7); 6.876(4.2); 6.870(6.5); 6.858(3.5); 6.852(3.5); 6.847(2.1); 4.302(8.8); 4.280(14.4); 4.254(8.3); 3.725(2.1); 3.711(2.6); 3.698(3.0); 3.687(2.9); 3.684(3.0); 3.673(2.5); 3.639(2.2); 3.626(4.1); 3.613(6.3); 3.599(5.5); 3.590(5.8); 3.586(5.1); 3.581(5.0); 3.566(3.9); 3.556(3.7); 3.348(2.6); 3.337(4.0); 3.326(4.5); 3.321(2.9); 3.314(5.9); 3.310(4.4); 3.303(3.3); 3.299(4.3); 3.287 (4.6); 3.276(2.4); 2.502(1.0); 2.493(1.2); 2.488(1.4); 2.479(2.1); 2.467(1.8); 2.453(1.9); 2.444(2.7); 2.435(1.6); 2.429(1.4); 2.421(1.3); 2.276(1.5); 2.265(3.0); 2.254(1.4); 2.249(1.5); 2.238(3.0); 2.230(2.5); 2.220(1.2); 2.214(1.2); 2.203(2.1); 2.192 (1.0); 2.089(1.0); 2.078(2.0); 2.065(1.6); 2.053(2.7); 2.043(4.0); 2.030(2.7); 2.017(3.6); 2.006(2.1); 1.977(1.8); 1.964(2.6); 1.954(2.2); 1.952(2.4); 1.942(3.3); 1.929(3.0); 1.919(1.2); 1.908(1.3); 1.894(0.9); 1.529(6.9); 1.255(1.0); 0.331(1.0); 0.238 (0.8); 0.157(1.8); 0.146(1.2); 0.008(12.9); 0.000(468.1); −0.009(13.6); −0.150(1.4) |

| Compound 1700a: 1H-NMR (400.0 MHz. CDCl3): δ = |
|---|
| 8.005(1.8); 7.291(3.2); 7.285(3.4); 7.274(3.2); 7.269(3.7); 7.262(60.2); 7.230(6.1); 7.224(6.4); 7.213(6.3); 7.207(6.3); 7.123 (1.7); 7.116(5.3); 7.102(6.4); 7.094(14.3); 7.086(3.5); 7.081(7.6); 7.073(11.9); 7.069(3.7); 7.065(1.2); 7.059(1.0); 7.053 (0.8); 7.044(4.5); 7.038(4.3); 7.032(4.8); 7.027(4.4); 7.022(2.8); 7.016(2.5); 7.011(2.4); 7.005(2.2); 6.998(0.5); 6.378(3.1); 6.377(3.1); 6.373(5.8); 6.372(5.8); 6.369(6.4); 6.364(10.8); 6.355(6.5); 6.282(10.0); 6.278(10.1); 6.272(8.2); 6.268(8.1); 6.261 (5.1); 6.256(5.1); 6.251(4.3); 6.247(4.2); 4.138(9.2); 4.124(9.5); 3.950(5.1); 3.931(5.5); 3.819(2.4); 3.806(5.3); 3.792(5.1); 3.779(7.2); 3.770(1.8); 3.766(3.6); 3.761(1.7); 3.756(1.6); 3.744(2.1); 3.734(3.7); 3.729(1.9); 3.719(1.7); 3.653(3.3); 3.641 (3.7); 3.632(3.8); 3.626(2.9); 3.620(3.8); 3.614(2.9); 3.605(2.8); 3.593(2.6); 3.562(1.7); 3.550(1.9); 3.538(2.1); 3.535(1.7); 3.526(2.1); 3.523(1.8); 3.511(1.6); 3.499(1.4); 3.485(6.8); 3.458(0.7); 3.450(1.0); 3.441(1.0); 3.433(2.1); 3.429(2.2); 3.420 (3.2); 3.413(3.5); 3.404(3.2); 3.396(3.3); 3.390(2.6); 3.381(1.3); 3.375(1.2); 2.958(16.0); 2.880(13.4); 2.879(12.9); 2.281(0.7); 2.272(0.7); 2.267(0.8); 2.258(1.5); 2.247(1.2); 2.243(0.9); 2.237(1.0); 2.232(1.2); 2.223(1.8); 2.214(0.9); 2.208(0.9); 2.199 (0.8); 2.146(0.8); 42.133(1.7); 2.125(0.9); 2.120(1.1); 2.111(3.5); 2.098(4.8); 2.090(2.8); 2.085(2.4); 2.077(4.2); 2.071(2.5); 2.063(2.5); 2.059(4.6); 2.047(4.3); 2.035(4.6); 2.023(3.4); 2.012(1.7); 2.000(1.7); 1.988(0.8); 1.952(0.9); 1.941(1.4); 1.930 (0.9); 1.923(0.9); 1.917(1.); 1.913(1.5); 1.906(1.3); 1.902(1.0); 1.896(0.8); 1.888(0.8); 1.878(1.1); 1.867(0.7); 1.489(10.1); 0.008(0.7); 0.000(22.5); −0.009(0.7) |

| Compound 1538a: 1H-NMR (400.0 MHz. CDCl3): δ = |
|---|
| 7.345(0.7); 7.341(0.7); 7.334(0.7); 7.330(0.7); 7.300(2.5); 7.262(50.0); 7.253(2.3); 7.250(2.1); 7.154(0.6); 7.142 (8.3); 7.130(2.0); 7.126(1.2); 7.116(4.3); 7.107(0.7); 7.102(2.8); 7.093(0.3); 7.085(0.4); 7.045(1.3); 7.041(1.4); 7.038(1.5); 7.034(1.4); 7.032(1.1); 7.027(1.0); 7.024(1.0); 7.020(0.8); 4.258(3.3); 4.249(3.4); 4.039(1.1); 4.028(1.1); 3.858(0.9); 3.850 (1.9); 3.841(1.8); 3.832(2.2); 3.824(1.1); 3.773(0.3); 3.766(0.4); 3.764(0.4); 3.755(0.5); 3.748(0.4); 3.746(0.5); 3.740(0.5); 3.735(0.4); 3.730(0.3); 3.723(0.6); 3.716(0.4); 3.711(0.4); 3.706(1.2); 3.697(1.8); 3.690(1.4); 3.687(1.1); 3.681(1.8); 3.672 (0.9); 3.644(1.1); 3.638(1.2); 3.630(1.3); 3.627(1.2); 3.623(1.3); 3.620(1.2); 3.612(1.0); 3.605(0.9); 3.505(1.4); 3.498(1.4); 3.491(2.3); 3.481(0.5); 3.471(0.3); 2.243(0.3); 2.236(0.4); 2.227(0.4); 2.220(0.7); 2.211(0.9); 2.206(0.6); 2.203(0.7); 2.197 (1.3); 2.188(1.4); 2.182(0.8); 2.179(0.8); 2.173(1.0); 2.164(0.6); 2.103(0.6); 2.095(1.0); 2.088(1.2); 2.080(1.4); 2.072(1.3); 2.064(0.8); 2.056(0.6); 2.049(0.4); 1.925(0.3); 1.906(0.4); 1.901(0.4); 1.556(3.1); 0.005(0.7); 0.000(14.1); −0.006(0.5) |

| Compound 532a erythro: 1H-NMR (400.0 MHz. CDCl3): δ = |
|---|
| 8.341(1.2); 8.321(12.7); 8.320(12.5); 8.309(12.9); 8.307(12.9); 7.519(43); 7.360(0.9); 7.309(0.9); 7.292(1.8); 7.286(1.4); 7.283(1.6); 7.271(3.9); 7.269(5.3); 7.260(812.3); 7.210(2.6); 7.163(0.5); 7.156(4.4); 7.135(7.0); 7.132(5.1); 7.115(6.6); 7.111 (7.8); 7.097(1.1); 7.090(4.7); 7.036(13.8); 7.033(14.0); 7.032(16.0); 7.019(4.5); 7.013(4.3); 7.001(4.1); 6.996(8.9); 6.992 (14.5); 6.988(11.4); 6.979(10.3); 6.975(11.6); 6.969(4.0); 6.866(2.4); 6.861(3.4); 6.856(4.5); 6.852(3.3); 6.845(3.5); 6.840 |

(2.9); 6.834(3.8); 6.830(2.7); 6.825(1.9); 5.299(12.0); 4.260(11.2); 4.244(11.5); 4.032(1.0); 4.014(1.0); 3.783(2.3); 3.770(2.5); 3.757(2.8); 3.748(2.8); 3.735(1.3); 3.531(1.3); 3.520(2.3); 3.509(2.5); 3.498(2.9); 3.472(1.9); 3.461(1.1); 3.351(3.1); 3.336 (5.6); 3.328(3.8); 3.320(3.4); 3.313(5.7); 3.297(2.9); 2.194(1.1); 2.180(1.7); 2.173(1.4); 2.167(1.5); 2.159(4.4); 2.146(5.1); 2.137(3.7); 2.135(2.9); 2.131(3.1); 2.123(3.9); 2.115(3.0); 2.110(3.0); 2.103(4.9); 2.092(4.3); 2.080(5.2); 2.068(4.3); 2.056 (1.7); 2.044(3.6); 2.032(1.2); 1.541(142.4); 1.491(0.8); 1.440(1.0); 1.425(1.0); 1.362(5.0); 1.333(2.7); 1.284(3.9); 1.256(5.8); 0.880(1.2); 0.146(1.0); 0.032(0.8); 0.008(9.6); 0.000(325.0); −0.009(9.2); −0.050(1.0); −0.150(0.9)

Compound 647a: 1H-NMR (600.1 MHz. CDCl3): δ =

8.185(0.3); 8.181(0.3); 8.041(0.3); 8.031(0.4); 8.027(0.4); 8.018(0.3); 7.449(0.3); 7.446(0.3); 7.438(0.3); 7.433 (0.4); 7.261(50.0); 7.211(0.4); 7.197(0.7); 7.058(0.3); 7.054(0.3); 7.051(0.3); 7.047(0.5); 7.037(0.4); 7.032(0.4); 7.025(0.7); 7.011(0.8); 6.842(0.4); 6.833(0.4); 6.828(0.4); 6.819(0.3); 4.211(0.4); 4.194(0.4); 4.144(0.7); 4.126(0.7); 3.758(0.4); 3.749 (0.4); 3.740(0.4); 1.557(3.5); 0.000(13.9); −0.006(0.5)

Compound 1137a: 1H-NMR (600.1 MHz. CDCl3): δ =

8.095(3.2); 8.086(8.3); 8.076(5.9); 7.303(1.9); 7.290(4.4); 7.279(4.1); 7.277(4.2); 7.263(42.9); 7.024(1.7); 7.021 (1.8); 7.010(4.0); 7.007(3.4); 6.996(3.2); 6.983(3.0); 6.970(2.1); 6.952(2.0); 6.946(4.5); 6.933(4.6); 6.900(3.2); 6.884 (3.2); 6.700(2.4); 6.691(2.4); 6.671(4.7); 6.663(4.6); 6.528(4.4); 6.487(8.6); 4.193(5.8); 4.181(5.9); 4.027(0.4); 4.012(3.0); 4.000 (3.0); 3.908(50.0); 3.708(1.5); 3.699(3.0); 3.690(3.2); 3.681(3.4); 3.672(1.7); 3.645(0.8); 3.638(1.0); 3.635(1.0); 3.628(1.6); 3.620(1.1); 3.617(1.0); 3.610(0.9); 3.488(3.6); 3.485(2.0); 3.476(2.0); 3.471(2.0); 3.467(1.8); 3.462(2.1); 3.458(1.8); 3.453 (1.6); 3.445(1.5); 3.378(0.9); 3.370(1.0); 3.362(1.3); 3.354(1.2); 3.345(0.9); 3.298(1.9); 3.288(2.3); 3.282(3.3); 3.277(2.4); 3.272(2.9); 3.262(1.9); 2.265(0.4); 2.259(0.5); 2.255(0.5); 2.249(0.8); 2.242(0.9); 2.232(0.9); 2.226(1.0); 2.220 (0.6); 2.216(0.6); 2.210(0.5); 2.107(0.8); 2.097(1.5); 2.095(1.4); 2.083(2.9); 2.074(4.4); 2.066(4.7); 2.060(6.6); 2.050(6.6); 2.043(6.4); 2.034(4.8); 2.027(2.9); 2.019(2.3); 2.011(1.4); 0.000(11.5)

Compound 1558a: 1H-NMR (400.0 MHz. CDCl3): δ =

7.997(2.2); 7.266(38.5); 7.258(12.2); 7.199(1.5); 7.179(3.9); 7.159(6.1); 7.136(6.6); 7.125(2.3); 7.115(4.9); 7.105(20.5); 7.093 (1.9); 7.067(2.6); 7.061(2.8); 7.049(2.8); 7.042(3.8); 7.035(3.0); 7.022(3.8); 7.017(2.8); 6.987(2.2); 6.983(1.9); 6.977(1.8); 6.971(1.5); 6.966(1.8); 6.961(1.5); 6.939(2.9); 6.934(3.6); 6.929(3.0); 6.923(2.8); 6.918(2.6); 6.913(3.0); 6.908(2.4); 4.283(7.9); 4.269(8.2); 4.050(4.7); 4.033(5.2); 3.861(2.1); 3.849(4.3); 3.835(4.2); 3.822(5.4); 3.809(2.7); 3.779(1.3); 3.769(1.6); 3.765(1.7); 3.752(2.0); 3.742(2.0); 3.738(2.0); 3.728(1.6); 3.716(1.4); 3.707(1.6); 3.699(1.4); 3.689 (2.8); 3.680(3.7); 3.666(4.8); 3.657(3.6); 3.652(5.4); 3.642(5.9); 3.630(5.3); 3.625(3.3); 3.619(3.5); 3.614(2.8); 3.603(2.4); 3.592(2.2); 3.517(1.5); 3.506(1.8); 3.491(2.6); 3.483(7.9); 3.466(1.5); 3.455(1.4); 2.961(16.0); 2.878(13.9); 2.280(0.7); 2.270 (0.8); 2.266(0.9); 2.256(1.3); 2.245(1.6); 2.232(2.5); 2.220(2.5); 2.210(2.1); 2.205(1.9); 2.196(3.5); 2.183(3.2); 2.174(2.2); 2.169(2.1); 2.160(2.4); 2.148(1.5); 2.113(1.7); 2.101(2.5); 2.090(3.1); 2.078(3.3); 2.067(2.9); 2.055(1.7); 2.043(1.4); 2.031 (0.9); 1.937(0.9); 1.927(1.6); 1.917(1.0); 1.910(0.9); 1.900(1.9); 1.892(1.); 1.882(0.8); 1.875(0.8); 1.864(1.4); 1.854(0.7) 1.706(4.1); 0.008(0.7); 0.000(14.6); −0.008(0.6)

Compound 1295a: 1H-NMR (400.0 MHz. CDCl3): δ =

8.623(14.4); 8.620(15.2); 8.570(12.8); 8.566(13.8); 8.199(15.6); 8.196(16.0); 7.971(13.3); 7.968(14.3); 7.519 (4.0); 7.385(7.9); 7.367(6.7); 7.260(668.8); 7.237(14.3); 7.231(13.7); 7.220(11.5); 7.214(10.7); 7.171(18.4); 7.168(19.9); 7.157(11.6); 7.153(17.4); 7.038(5.1); 7.017(11.7); 6.996(12.9); 6.981(5.7); 6.976(6.1); 6.970(6.5); 6.965(6.1); 4.281(15.1); 4.260(12.8); 4.256(11.9); 3.733(2.4); 3.721(4.4); 3.706(4.1); 3.693(4.5); 3.681(3.3); 3.645(3.3); 3.632(5.5); 3.619(5.8); 3.605 (8.3); 3.593(7.4); 3.579(7.2); 3.569(8.6); 3.556(6.1); 3.545(5.8); 3.533(3.5); 3.335(4.2); 3.320(6.5); 3.307(6.8); 3.297(6.7); 3.285(4.0); 3.280(3.4); 3.269(2.7); 2.464(2.3); 2.452(2.9); 2.442(2.9); 2.430(2.8); 2.420(2.0); 2.229(3.2); 2.202 (3.7); 2.194(3.2); 2.167(2.6); 2.058(1.4); 2.047(2.2); 2.035(2.1); 2.023(3.6); 2.012(4.8); 1.999(3.6); 1.987(4.2); 1.952(2.1); 1.940(3.6); 1.930(3.5); 1.918(4.4); 1.905(3.8); 1.883(2.0); 1.509(8.9); 0.146(1.3); 0.000(252.0); −0.150(1.8)

Compound 289a erythro: 1H-NMR (400.0 MHz. CDCl3): δ =

8.401(3.2); 8.395(3.4); 7.975(2.5); 7.380(0.9); 7.375(1.1); 7.369(0.8); 7.358(1.0); 7.352(1.2); 7.347(0.8); 7.269(0.5); 7.268 (0.6); 7.267(0.7); 7.261(42.5); 7.170(0.8); 7.149(1.4); 7.146(0.9); 7.129(1.1); 7.125(1.3); 7.104(0.8); 7.037(0.7); 7.031(0.7); 7.019(0.7); 7.012(0.9); 7.005(0.7); 6.993(0.6); 6.987(0.7); 6.890(0.5); 6.887(0.7); 6.881(0.9); 6.877(0.7); 6.871(0.6); 6.865 (0.6); 6.860(0.7); 6.856(0.5); 5.299(16.0); 4.487(2.1); 4.472(2.1); 3.633(0.9); 3.616(0.9); 3.092(0.9); 3.072(0.9); 3.049(1.4); 3.029(1.3); 2.907(1.4); 2.891(1.4); 2.864(1.0); 2.848(0.9); 0.000(15.4)

Compound 107a: 1H-NMR (400.0 MHz. CDCl3): δ =

8.492(0.7); 8.489(1.4); 8.485(0.8); 8.481(0.8); 8.477(1.4); 8.474(0.8); 8.419(0.7); 8.416(1.3); 8.412(0.8); 8.408(0.8); 8.405 (1.3 8.401(0.7); 7.434(0.8); 7.430(0.8); 7.416(1.4); 7.413(1.4); 7.410(2.6); 7.407(1.1); 7.399(1.3); 7.393(1.4); 7.390(1.4); 7.386(1.1); 7.295(1.3); 7.2843(1.6); 7.2835(1.5); 7.273(1.7); 7.271(0.5); 7.270(0.5); 7.269(0.5); 7.268(0.6); 7.2674(0.7); 7.2666 (0.8); 7.266(1.0); 7.261(77.3); 7.2543(1.0); 7.2536(1.0); 7.252(1.2); 7.248(0.6); 7.243(0.8); 7.241(0.8); 7.237(1.2); 7.233 (1.0); 7.227(0.9); 7.221(1.1); 7.220(1.5); 7.216(2.1); 7.197(1.3); 7.193(1.2); 7.177(1.4); 7.172(2.5); 7.166(3.3); 7.155(2.4); 7.151(3.2); 7.145(1.2); 7.134(0.7); 7.130(1.2); 7.009(1.0); 7.004(1.0); 6.997(1.2); 6.992(1.0); 6.986(1.8); 6.965(2.4); 6.944 (0.8); 4.345(1.8); 4.337(1.7); 4.321(2.0); 4.311(1.9); 4.148(1.1); 4.135(4.4); 4.094(1.1); 3.906(0.7); 3.896(0.6); 3.892(0.8); 3.889(0.6); 3.881(0.8); 3.661(0.8); 3.648(1.0); 3.634(1.0); 3.620(0.6); 3.535(0.7); 3.522(1.0); 3.508(1.1); 3.500(0.6); 3.494(0.7); 3.486(0.5); 3.480(0.6); 3.466(0.7); 3.410(0.6); 3.397(0.7); 3.390(0.7); 3.377(0.7); 2.410(0.9); 2.406(0.6); 2.401 (0.6); 2.396(1.0); 2.387(0.9); 2.374(0.9); 2.043(16.0); 2.036(0.5); 2.024(0.5); 1.841(0.5); 1.830(0.5); 1.625(0.8); 1.286(0.7); 1.284(0.7); 1.276(4.9); 1.258(10.4); 1.241(4.8); 0.008(0.8); 0.000(27.6); −0.009(0.8)

Compound 597a: 1H-NMR (400.0 MHz. CDCl3): δ =

8.373(13.1); 8.185(16.0); 7.421(0.7); 7.419(0.7); 7.406(1.0); 7.402(1.7); 7.400(1.4); 7.388(1.5); 7.384(1.6); 7.381(1.2); 7.370 (0.7); 7.366(1.0); 7.293(0.6); 7.261(45.8); 7.239(1.0); 7.224(1.7); 7.219(1.4); 7.215(1.6); 7.211(0.9); 7.205(1.4 7.202(1.7); 7.198(1.6); 7.194(1.0); 7.183(1.7); 7.174(1.8); 7.171(2.9); 7.168(2.0); 7.151(2.1); 7.117(3.6); 7.114(3.5); 7.095(4.4); 7.092 (4.2); 7.076(1.2); 7.074(1.2); 7.070(0.7); 6.997(0.5); 6.969(3.1); 6.954(4.2); 6.949(5.1); 6.941(2.5); 6.936(3.2); 6.933(3.4);

-continued 6.928(2.4); 6.923(1.5); 6.920(1.7); 6.914(0.7); 5.298(2.5); 4.274(3.2); 4.249(3.7); 4.205(3.6); 4.178(4.6); 3.996(1.0); 3.987 (1.0); 3.968(1.7); 3.959(1.7); 3.941(0.8); 3.931(0.8); 3.909(0.8); 3.897(0.8); 3.883(1.3); 3.871(1.3); 3.857(0.7); 3.845(0.7); 3.768(1.1); 3.755(1.8); 3.741(2.2); 3.728(2.0); 3.715(1.3); 3.607(0.9); 3.594(1.5); 3.581(2.0); 3.567(1.8); 3.554(1.1); 3.480 (1.2); 3.468(1.4); 3.457(1.5); 3.453(1.3); 3.446(1.5); 3.441(1.3); 3.430(1.2); 3.419(1.1); 3.395(1.0); 3.383(1.1); 3.372(1.2); 3.368(1.0); 3.360(1.2); 3.356(1.0); 3.346(0.9); 3.334(0.8); 2.955(2.8); 2.879(2.4); 2.564(0.6); 2.554(0.7); 2.550(0.7); 2.541 (1.0); 2.529(1.2); 2.518(1.2); 2.506(1.3); 2.497(0.8); 2.493(0.7); 2.483(0.7); 2.317(1.0); 2.306(1.0); 2.293(0.7); 2.290(0.7); 2.286(0.6); 2.278(1.1); 2.274(1.0); 2.271(1.0); 2.267(0.8); 2.259(0.6); 2.255(0.5); 2.243(0.7); 2.073(0.6); 2.061(0.5); 2.050 (0.8); 2.047(0.8); 2.042(0.7); 2.038(1.0); 2.035(0.8); 2.024(0.7); 2.012(0.8); 1.932(0.6); 1.919(0.9); 1.906(0.8); 1.897(1.2); 1.884(1.1); 1.874(0.5); 1.862(0.6); 1.516(1.5); 0.008(0.8); 0.000(18.0); −0.009(0.7)

Compound 599a: 1H-NMR (400.0 MHz. CDCl3): δ =

8.379(14.7); 8.197(16.0); 7.519(0.8); 7.392(0.8); 7.387(1.2); 7.375(14.4); 7.370(10.1); 7.358(5.7); 7.352(1.3); 7.341(1.0); 7.336(1.7); 7.295(0.5); 7.280(2.3); 7.275(3.5); 7.270(2.3); 7.269(2.3); 7.267(1.9); 7.260(141.7); 7.254(2.3); 7.236(1.1); 7.233 (1.6); 7.231(1.9); 7.228(2.2); 7.212(9.1); 7.209(9.1); 7.193(3.1); 7.190(2.0); 7.174(4.3); 7.172(3.5); 7.156(1.7); 7.153(1.8) 7.075(1.9); 7.071(2.9); 7.056(1.4); 7.053(2.37); 6.996(0.9); 4.249(3.8); 4.224(4.4); 4.180(3.9); 4.152(5.1); 3.989(0.9); 3.979; (0.9); 3.961(1.6); 3.952(1.5); 3.934(0.8); 3.924(0.7); 3.898(0.8); 3.886(0.43.872(1.4); 3.860(1.4); 3.845(0.43.834(0.7); 3.773(1.0); 3.760(1.6); 3.746(2.0); 3.733(1.9); 3.720(1.2); 3.610(0.9); 3.597(1.5); 3.583(2.1); 3.570(1.8); 3.557(1.2); 3.481 (1.1); 3.470(1.2); 3.458(1.3); 3.454(1.2); 3.447(1.3); 3.442(1.2); 3.431(1.1); 3.420(1.0); 3.396(1.1); 3.384(1.1); 3.374(1.2); 3.369(1.0); 3.362(1.2); 3.357(1.0); 3.347(0.9); 3.335(0.9); 2.560(0.5); 2.550(0.6); 2.546(0.6); 2.537(1.0); 2.525(1.1); 2.514(1.1); 2.502(1.3); 2.492(0.8); 2.489(0.8); 2.479(0.7); 2.308(0.9); 2.296(0.6); 2.292(0.7); 2.284(0.8); 2.280(1.0); 2.277(0.9); 2.273 (0.9); 2.269(0.8); 2.261(0.5); 2.257(0.5); 2.245(0.7); 2.068(0.6); 2.045(0.8); 2.041(0.9); 2.037(0.8); 2.033(1.1); 2.029(0.9); 2.018(0.7); 2.006(0.9); 1.922(0.7); 1.908(0.9); 1.896(0.8); 1.887(1.1); 1.873(1.2); 1.864(0.6); 1.852(0.6); 0.008(1.6); 0.000 (53.0); −0.009(1.6)

Compound 100a: 1H-NMR (400.0 MHz. CDCl3): δ =

8.503(1.6); 8.500(2.5); 8.497(1.6); 8.491(1.7); 8.488(2.5); 8.418(2.2); 8.414(1.4); 8.409(1.4); 8.406(2.2); 7.519(0.9); 7.469 (1.1); 7.465(1.2); 7.447(1.8); 7.445(2.4); 7.424(1.5); 7.421(1.5); 7.325(1.6); 7.313(2.5); 7.303(2.3); 7.292(1.9); 7.282(1.7); 7.260(161.3); 7.242(2.3); 7.239(2.3); 7.224(1.4); 7.219(2.8); 7.216(3.0); 7.206(1.4); 7.202(1.4); 7.198(3.4); 7.191(2.6); 7.187(3.3); 7.176 (3.5); 7.166(1.9); 7.155(0.9); 7.150(1.5); 7.115(1.1); 7.110(1.4); 7.095(0.47.089(0.9); 7.025(0.9); 7.004(1.47.001(1.2); 6.996(1.1); 6.984(1.5); 6.980(2.5); 6.974(1.1); 6.959(1.6); 6.956(1.3); 6.947(1.1); 6.934(0.9); 6.929(1.0); 6.881(0.9); 6.876 (1.2); 6.871(1.0); 6.865(0.9); 6.854(0.9); 4.351(3.0); 4.337(2.6); 4.326(3.3); 4.311(2.9); 4.150(1.2); 4.132(3.5); 4.115(3.5); 4.097(1.2); 3.950(0.6); 3.939(0.6); 3.928(1.4); 3.918(1.4); 3.904(1.6); 3.880(0.7); 3.875(0.8); 3.848(1.4); 3.871(0.6); 3.696(0.7); 3.682(1.3); 3.668(1.5); 3.654(1.8); 3.641(1.0); 3.557(0.8); 3.543(1.5); 3.529(2.1); 3.515(2.7); 3.501(1.7); 3.491(0.7); 3.485(0.8); 3.472 (0.7); 3.423(1.1); 3.410(1.2); 3.402(1.3); 3.395(0.9); 3.389(1.2); 3.382(0.9); 3.375(0.9); 3.362(0.8); 2.427(0.8); 2.417(1.5); 2.403(1.9); 2.394(1.8); 2.381(1.9); 2.368(0.8); 2.233(7.8); 2.107(1.2); 2.091(0.8); 2.079(0.8); 2.067(1.0); 2.056(1.3); 2.046 (16.0); 2.032(1.1); 2.019(0.5); 1.882(0.6); 1.867(0.7); 1.862(0.7); 1.857(0.7); 1.847(1.0); 1.837(1.0); 1.827(0.6); 1.277(4.2); 1.260(8.4); 1.242(4.1); 0.069(5.8); 0.008(2.6); 0.000(57.3); −0.009(2.1)

Compound 620a: 1H-NMR (400.0 MHz. CDCl3): δ =

8.381(16.0); 8.369(1.1); 8.243(1.1); 8.214(15.4); 7.519(5.4); 7.293(0.6); 7.289(0.8); 7.260(956.7); 7.250(5.0); 7.244(2.3); 7.229(3.0); 7.226(3.7); 7.218(2.0); 7.209(3.2); 7.205(3.4); 7.200(1.8); 7.185(2.0); 7.147(0.6); 7.128(1.3); 7.122 (1.8); 7.118(1.4); 7.112(1.2); 7.101(1.3); 7.093(1.8); 7.087(1.4); 7.071(2.0); 7.061(1.4); 7.050(3.1); 7.043(1.5); 7.030(1.9); 7.026(2.2); 7.006(1.7); 6.996(5.4); 6.921(1.6); 5.299(2.1); 4.265(3.9); 4.240(4.4); 4.184(3.4); 4.157(4.4); 3.974(0.8); 3.965(0.8); 3.946(1.4); 3.936(1.4); 3.917(0.7); 3.908(0.6); 3.887(0.8); 3.875(0.8); 3.862(1.4); 3.848(1.4); 3.836(0.9); 3.823(0.7); 3.779(0.9); 3.766(1.4); 3.753(1.8); 3.740(1.7); 3.726(1.1); 3.636(1.0); 3.623(1.6); 3.610(2.0); 3.597(1.9); 3.583(1.2); 3.478(0.9); 3.467(1.1); 3.456(1.1); 3.444(1.2); 3.428(1.0); 3.411(1.0); 3.399(1.1); 3.388(1.2); 3.377(1.2); 3.362(0.9); 3.350(0.9); 2.544 (0.6); 2.535(0.9); 2.522(1.0); 2.510(1.0); 2.499(1.3); 2.490(0.7); 2.476(0.6); 2.294(0.8); 2.266(0.9); 2.231(0.7); 2.040(1.1); 2.013(0.9); 2.005(0.7); 1.936(0.7); 1.923(1.); 1.912(0.9); 1.901(1.4); 1.888(1.2); 1.878(0.7); 1.865(0.7); 1.543(11.9); 1.371 (0.9); 1.333(1.7); 1.284(2.4); 1.256(2.2); 0.146(1.0); 0.008(9.1); 0.000(336.9); −0.009(9.9); −0.150(1.0)

Compound 84a: 1H-NMR (400.0 MHz. CDCl3): δ =

8.385(4.0); 8.377(5.5); 8.374(7.4); 8.368(6.9); 8.201(3.7); 7.959(6.9); 7.351(2.4); 7.345(3.2); 7.340(2.5); 7.328(3.5); 7.322 (3.5); 7.316(2.8); 7.307(3.5); 7.291(4.2); 7.286(4.9); 7.278(2.6); 7.272(6.6); 7.262(66.2); 7.251(4.4); 7.244(1.5); 7.041(1.1); 7.034(1.4); 7.029(1.9); 7.022(3.0); 7.013(2.3); 7.010(3.1); 7.008(3.1); 7.003(3.4); 7.001(3.5); 6.995(1.3); 6.989(1.6); 6.987 (1.6); 6.982(1.7); 6.966(2.4); 6.956(1.5); 6.950(3.1); 6.947(3.6); 6.937(1.8); 6.932(1.7); 6.927(1.6); 6.887(4.0); 6.868(3.8); 6.858(2.8); 6.853(3.1); 6.848(1.8); 6.835(2.4); 6.830(3.0); 6.825(1.8); 5.299(16.0); 4.307(5.9); 4.292(6.1); 4.057(3.2); 4.040 (3.4); 3.835(1.2); 3.798(1.6); 3.785(3.4); 3.772(3.5); 3.758(4.1); 3.745(2.43.690(0.9); 3.679(1.1); 3.675(1.1); 3.664(1.6); 3.653(1.3); 3.648(1.2); 3.638(1.0); 3.547(1.9); 3.535(2.2); 3.526(2.3); 3.520(2.0); 3.514(2.4); 3.509(2.1); 3.499(2.4); 3.487 (2.3); 3.474(2.4); 3.460(2.7); 3.446(2.8); 3.437(2.3); 3.422(1.1); 3.385(1.0); 3.373(1.2); 3.361(1.4); 3.349(1.4); 3.341(1.2); 3.335(1.0); 3.323(0.9); 3.320(0.9); 2.315(0.5); 2.305(0.9); 2.295(0.8); 2.284(0.9); 2.280(1.0); 2.270(1.2); 2.259(1.1); 2.245(1.5); 2.237(0.8); 2.231(0.9); 2.223(2.2); 2.209(2.6); 2.202(1.6); 2.195(1.5); 2.188(2.0); 2.174(1.3); 2.170(1.1); 2.162(1.3); 2.150 (2.3); 2.138(2.2); 2.127(2.8); 2.114(2.5); 2.102(1.8); 2.091(1.6); 2.084(0.8); 2.078(1.0); 2.073(1.2); 2.065(1.0); 2.054(0.6); 2.048(0.6); 2.043(0.8); 2.038(0.8); 2.005(0.9); 1.752(1.5); 1.371(0.6); 1.286(0.9); 1.258(1.4); 0.008(1.0); 0.000(25.2); −0.009(1.2)

Compound 295a: 1H-NMR (400.0 MHz. CDCl3): δ =

8.492(0.8); 8.488(1.6); 8.485(0.9); 8.480(0.9); 8.477(1.6); 8.473(0.9); 8.421(0.8); 8.417(1.5); 8.414(0.9); 8.410(0.8); 8.406 (1.5); 8.403(0.8); 7.557(1.4); 7.551(1.5); 7.541(1.4); 7.535(1.5); 7.431(0.9); 7.428(1.5); 7.410(1.3); 7.407(1.5); 7.404(1.5); 7.387(1.2); 7.383(1.1); 7.308(1.4); 7.302(1.5); 7.299(0.9); 7.293(3.2); 7.287(1.8); 7.282(2.5); 7.278(1.2); 7.272(2.5); 7.266 (1.7); 7.261(74.3); 7.250(1.0); 7.239(0.7); 7.236(0.8); 7.218(1.4); 7.216(0.9); 7.215(1.4); 7.213(0.9); 7.195(1.4); 7.192(1.3); 7.177(1.4); 7.166(2.4); 7.155(1.6); 7.148(2.0); 7.145(1.3); 7.134(0.7); 7.127(2.8); 7.107(1.5); 7.079(0.6); 7.073(0.6); 7.067 (0.7); 7.062(0.6); 7.057(0.9); 7.051(0.9); 7.046(0.9); 7.040(0.8); 6.965(1.9); 6.944(2.7); 6.923(1.3); 4.342(2.0); 4.332(1.8); 4.318(2.2); 4.306(2.0); 4.148(1.1); 4.130(3.3); 4.112(3.3); 4.094(1.1); 3.903(0.9); 3.892(0.7); 3.889(0.9); 3.878(0.9); 3.662(0.9); 3.648(1.0); 3.634(1.0); 3.621(07); 43.535(0.8); 3.522(1.1); 3.508(1.2); 3.501(0.7); 3.494(0.7); 3.486(0.6); 3.481(0.7); 3.467

(0.7); 3.453(0.5); 3.411(0.6); 3.398(0.7); 3.390(0.7); 3.383(0.5); 3.377(0.7); 2.419(0.5); 2.409(0.8); 2.405(0.6); 2.396(1.0); 2.387(1.1); 2.374(1.2); 2.095(0.9); 2.057(0.5); 2.043(16.0); 2.035(0.6); 2.023(0.6); 1.842(0.6); 1.831(0.6); 1.588(0.7); 1.333 (0.7); 1.284(1.1); 1.276(4.9); 1.258(10.4); 1.240(4.8); 0.008(0.8); 0.000(27.5); −0.009(0.7)

Compound 619a: 1H-NMR (400.0 MHz. CDCl3): δ =

8.384(14.1); 8.219(16.0); 7.588(2.5); 7.582(2.7); 7.572(2.6); 7.566(2.7); 7.519(1.1); 7.431(2.4); 7.425(2.6); 7.415(2.5); 7.410 (2.6); 7.325(1.3); 7.319(1.3); 7.314(1.5); 7.308(1.4); 7.304(1.9); 7.298(1.9); 7.293(2.0); 7.287(1.7); 7.260(176.1); 7.191 (3.4); 7.170(4.9); 7.150(2.8); 7.122(1.3); 7.116(1.2); 7.111(1.3); 7.105(1.3); 7.101(1.7); 7.095(1.7); 7.089(1.7); 7.084(1.6); 7.010(3.9); 6.996(1.3); 6.990(5.2); 6.969(2.6); 4.258(3.5); 4.233(4.0); 4.176(3.8); 4.148(4.9); 3.972(0.9); 3.962(0.9); 3.944 (1.5); 3.935(1.5); 3.917(0.7); 3.907(0.7); 3.879(0.8); 3.867(0.8); 3.853(1.4); 3.841(1.4); 3.828(0.8); 3.816(0.7); 3.780(1.1); 3.767(1.7); 3.753(2.0); 3.740(2.0); 3.727(1.3); 3.632(1.0); 3.619(1.6); 3.606(2.1); 3.593(2.0); 3.580(1.3); 3.477(1.2); 3.466(1.3); 3.454(1.4); 3.450(1.3); 3.443(1.4); 3.439(1.3); 3.427(1.2); 3.415(1.1); 3.409(1.2); 3.397(1.2); 3.386(1.3); 3.382(1.1); 3.375 (1.3); 3.371(1.1); 3.360(1.0); 3.348(1.0); 2.553(0.6); 2.543(0.6); 2.539(0.6); 2.530(1.3); 2.518(1.1); 2.507(1.1); 2.495(1.2); 2.485(0.8); 2.482(0.8); 2.472(0.6); 2.297(0.9); 2.282(0.6); 2.270(1.0); 2.266(0.9); 2.262(0.9); 2.258(0.8); 2.234(0.7); 2.071 (0.7); 2.059(0.5); 2.047(0.8); 2.044(0.9); 2.036(1.1); 2.021(0.8); 2.009(0.9); 1.997(0.5); 1.928(0.7); 1.915(1.0); 1.904(0.9); 1.893(1.3); 1.880(1.2); 1.870(0.7); 1.858(0.7); 1.845(0.5); 1.672(0.8); 1.621(0.6); 0.008(2.0); 0.000(66.8); −0.009(2.0)

Compound 289a: 1H-NMR (400.0 MHz. CDCl3): δ =

7.518(15.3); 7.294(5.1); 7.260(2831.6); 7.227(5.7); 7.209(4.0); 6.996(16.0); 1.537(809.6); 1.256(2.7); 0.146(3.8); 0.069 (19.1); 0.008(40.2); 0.000(960.5); −0.008(36.7); −0.150(3.9)

Compound 296a: 1H-NMR (400.0 MHz. CDCl3): δ =

8.410(3.1); 8.403(7.8); 8.396(5.2); 8.205(2.5); 7.969(4.4); 7.519(3.1); 7.373(2.2); 7.365(1.3); 7.359(1.9); 7.353(1.7); 7.342 (1.5); 7.336(1.9); 7.331(1.5); 7.289(1.9); 7.283(2.1); 7.278(1.7); 7.272(4.2); 7.260(579.5); 7.244(1.7); 7.227(0.9); 7.209(0.9); 7.197(2.7); 7.191(2.8); 7.181(2.6); 7.175(2.6); 7.121(1.2); 7.100(3.7); 7.093(2.9); 7.079(2.5); 7.072(6.5); 7.050(4.8); 7.044 (1.2); 7.039(1.3); 7.033(1.1); 7.029(0.7); 7.023(0.6); 7.018(0.6); 7.011(0.6); 6.996(3.3); 6.955(1.6); 6.949(1.6); 6.945(1.8); 6.939(1.5); 6.934(1.3); 6.928(1.3); 6.923(1.2); 6.917(1.1); 5.299(16.0); 4.286(3.44.271(3.9); 4.039(2.3); 4.022(2.5); 3.83 5(0.9); 3.814(1.0); 3.802(2.3); 3.788(2.2); 3.775(2.9); 3.762(1.3); 3.713(0.8); 3.703(0.8); 3.687(1.0); 3.676(0.9); 3.672(0.8); 3.662(0.7); 3.561(1.2); 3.550(1.5); 3.540(1.4); 3.535(1.3); 3.529(1.5); 3.523(1.2); 3.513(1.2); 3.502(1.1); 3.440(1.1); 3.426 (1.5); 3.404(1.4); 3.387(1.2); 3.374(0.9); 3.360(0.9); 3.347(0.7); 3.336(0.7); 2.615(1.1); 2.289(0.42.278(0.6); 2.264(0.7); 2.254(0.9); 2.235(0.7); 2.229(0.8); 2.221(0.6); 2.213(1.5); 2.200(1.5); 2.192(1.1); 2.186(1.0); 2.178(1.2); 2.170(0.9); 2.164 (0.8); 2.155(0.9); 2.143(1.4); 2.131(1.3); 2.120(1.7); 2.107(1.5); 2.098(0.7); 2.087(0.9); 2.071(0.8); 2.060(0.8); 2.053(0.6); 2.044(0.6); 2.025(0.6); 2.005(0.6); 1.552(6.2); 1.333(0.9); 1.284(1.0); 1.259(0.9); 0.146(0.6); 0.113(0.8); 0.008(6.2); 0.000 (194.3); −0.009(5.5); −0.150(0.6)

Compound 613a: 1H-NMR (400.0 MHz. CDCl3): δ =

8.381(16.0); 8.369(1.42); 8.243(1.1); 8.214(15.4); 7.519(5.4); 7.293(0.7); 7.289(0.8); 7.260(956.7); 7.250(5.0); 7.244(2.3); 7.229(3.0); 7.226(3.7); 7.218(2.0); 7.209(3.2); 7.205(3.4); 7.200(1.9); 7.185(2.0); 7.147(0.6); 7.128(1.3); 7.122(1.8); 7.118 (1.4); 7.112(1.2); 7.101(1.3); 7.093(1.8); 7.087(1.4); 7.071(2.0); 7.061(1.4); 7.050(3.1); 7.043(1.5); 7.030(1.9); 7.026(2.); 7.006(1.7); 6.996(5.4); 6.921(1.6); 5.299(2.1); 4.265(4.0); 4.240(4.4); 4.184(3.4); 4.157(4.4); 3.974(0.8); 3.965(0.8); 3.946(1.4); 3.936(1.4); 3.917(0.7); 3.908(0.6); 3.887(0.8); 3.875(0.8); 3.861(1.4); 3.848(1.4); 3.836(0.9); 3.823(0.7); 3.779(0.9); 3.766 (1.4); 3.753(1.8); 3.740(1.8); 3.726(1.1); 3.636(1.0); 3.623(1.6); 3.610(2.0); 3.597(2.0); 3.583(1.2); 3.478(0.9); 3.467(1.1); 3.456(1.2); 3.444(1.2); 3.428(1.0); 3.411(1.0); 3.399(1.1); 3.388(1.2); 3.377(1.2); 3.362(0.9); 3.350(0.9); 2.544(0.6); 2.535 (0.9); 2.522(1.0); 2.510(1.0); 2.499(1.3); 2.490(0.7); 2.476(0.6); 2.294(0.8); 2.266(0.9); 2.231(0.7); 2.040(1.1); 2.013(0.9); 2.005(0.7); 1.936(0.7); 1.923(1.0); 1.912(0.9); 1.901(1.4); 1.888(1.2); 1.878(0.7); 1.865(0.7); 1.543(11.9); 1.371(0.9); 1.33 3(1.7); 1.284(2.4); 1.256(2.2); 0.146(1.0); 0.008(9.1); 0.000(336.9); −0.009(9.9); −0.150(1.0)

Compound 86a: 1H-NMR (400.0 MHz. CDCl3): δ =

8.399(5.2); 8.392(5.9); 8.388(7.3); 8.381(7.3); 8.213(3.8); 7.967(6.9); 7.519(1.3); 7.347(2.5); 7.342(3.2); 7.336(2.6); 7.324 (2.9); 7.319(4.3); 7.313(4.2); 7.305(3.8); 7.295(5.5); 7.290(4.5); 7.285(7.2); 7.280(10.6); 7.277(8.4); 7.260(230.5); 7.250 (9.2); 7.242(3.1); 7.231(7.3); 7.226(3.4); 7.221(4.7); 7.216(2.8); 7.211(3.4); 7.175(1.0); 7.137(4.4); 7.133(7.2); 7.128(3.9); 7.061(2.7); 7.042(2.0); 6.996(1.8); 6.959(3.8); 6.940(3.4); 5.299(16.0); 4.491(0.6); 4.477(0.6); 4.278(5.6); 4.263(5.8); 4.038 (3.3); 4.021(3.5); 3.835(1.0); 3.802(1.5); 3.789(3.1); 3.776(3.2); 3.762(3.8); 3.749(1.9); 3.695(0.9); 3.684(1.4); 3.669(1.6); 3.658(1.3); 3.654(1.2); 3.643(1.2); 3.553(1.7); 3.542(2.0); 3.532(2.1); 3.526(1.8); 3.520(2.1); 3.515(1.7); 3.505(1.6); 3.493(2.0); 3.473(0.9); 3.463(2.2); 3.447(2.7); 3.437(2.1); 3.425(2.2); 3.408(1.1); 3.389(1.0); 3.377(1.0); 3.365(1.3); 3.353(1.3); 3.339 (0.9); 3.327(0.8); 2.964(0.8); 2.945(0.8); 2.911(0.6); 2.315(0.5); 2.300(0.5); 2.291(0.9); 2.281(1.0); 2.266(1.0); 2.255(1.4); 2.240(1.4); 2.232(1.3); 2.225(0.9); 2.218(2.1); 2.204(2.5); 2.196(1.5); 2.190(1.5); 2.183(1.9); 2.168(1.2); 2.158(1.3); 2.145 (2.3); 2.134(2.0); 2.122(2.7); 2.110(2.5); 2.099(1.8); 2.087(1.4); 2.074(1.4); 2.065(0.9); 2.048(0.6); 2.037(0.8); 1.570(1.7); 1.371(1.1); 1.333(0.9); 1.286(1.7); 1.257(2.5); 0.880(0.5); 0.008(3.5); 0.000(88.5); −0.009(3.7)

Compound 619 bab: 1H-NMR (400.0 MHz. CDCl3): δ =

8.421(9.4); 8.250(10.9); 7.595(1.5); 7.590(1.6); 7.580(1.5); 7.574(1.5); 7.417(1.6); 7.411(1.7); 7.401(1.6); 7.396(1.6); 7.328 (0.7); 7.322(0.7); 7.317(0.8); 7.311(0.7); 7.307(1.1); 7.301(1.1); 7.296(1.1); 7.290(1.0); 7.261(61.7); 7.217(1.9); 7.196(2.6); 7.176(1.3); 7.113(0.7); 7.107(0.7); 7.102(0.8); 7.096(0.8); 7.092(1.1); 7.086(1.1); 7.081(1.1); 7.075(0.9); 7.019(2.2); 6.999 (3.0); 6.978(1.4); 4.267(0.6); 4.254(1.3); 4.239(1.2); 4.225(1.7); 4.216(2.4); 4.190(2.5); 4.164(2.5); 4.136(3.1); 4.117(1.3); 4.102(1.2); 4.088(1.5); 4.075(0.9); 4.046(0.9); 4.034(1.0); 4.024(1.2); 4.017(0.9); 4.012(1.0); 4.006(0.8); 3.995(0.7); 3.983 (0.7); 3.961(16.0); 3.926(14.2); 3.908(0.8); 3.901(0.7); 3.896(0.8); 3.890(0.6); 3.879(0.43.868(0.6); 3.845(0.6); 3.836(0.6); 3.817(1.0); 3.807(1.0); 3.789(0.5); 3.779(0.5); 3.769(0.5); 3.741(0.8); 3.731(0.8); 2.682(0.6); 2.669(0.8); 2.659(0.8); 2.646 (0.8); 2.637(0.5); 2.464(0.5); 2.437(0.6); 2.183(0.6); 2.015(0.6); 2.004(0.6); 1.992(0.7); 1.980(0.7); 1.586(0.6); 1.255(0.7); 0.008(0.8); 0.000(23.4); −0.008(0.8)

| Compound 599 bae: 1H-NMR (400.0 MHz. CDCl3): δ = |
|---|
| 8.409(5.4); 8.215(5.9); 7.400(1.0); 7.396(2.3); 7.394(2.0); 7.392(1.5); 7.378(3.0); 7.274(0.8); 7.269(1.2); 7.261(39.2); 7.252 (1.0); 7.247(0.6); 7.242(0.5); 7.240(0.5); 7.237(0.6); 7.226(0.7); 7.222(1.0); 7.221(1.3); 7.217(1.1); 7.196(2.7); 7.177(1.7); 7.157(0.7); 7.052(0.9); 7.033(0.7); 4.214(1.4); 4.206(0.7); 4.188(1.8); 4.177(0.9); 4.163(1.7); 4.135(1.7); 4.058(0.6); 4.043 (0.6); 4.029(1.2); 4.016(0.7); 3.922(8.4); 3.889(0.5); 3.882(4.2); 3.878(4.3); 3.849(0.5); 3.822(0.5); 3.812(0.5); 3.407(16.0); 3.387(14.7); 0.000(14.8) |

| Compound 289a threo-1: 1H-NMR (400.0 MHz. CDCl3): δ = |
|---|
| 8.395(14.8); 8.389(14.9); 8.193(14.6); 7.521(1.2); 7.295(0.8); 7.285(0.6); 7.284(0.6); 7.283(0.6); 7.2823(0.5); 7.2815(0.5); 7.281(0.6); 7.2783(0.9); 7.2775(0.9); 7.277(1.0); 7.276(1.2); 7.272(6.5); 7.2663(10.5); 7.2655(11.5); 7.262 (205.0); 7.256(2.0); 7.255(1.7); 7.254(1.5); 7.253(1.4); 7.252(1.4); 7.244(7.3); 7.238(5.5); 7.155(5.5); 7.134(9.2); 7.131(6.3); 7.114(7.2); 7.110(9.2); 7.089(6.6); 7.083(5.1); 7.077(5.3); 7.065(5.2); 7.059(6.1); 7.057(6.0); 7.050(5.4); 7.038 (4.9); 7.032(5.1); 6.998(1.2); 6.923(3.3); 6.918(4.3); 6.913(6.2); 6.908(4.4); 6.902(4.4); 6.897(3.7); 6.892(5.0); 6.887(3.5); 6.882(2.5); 5.299(8.7); 4.045(15.0); 4.027(16.0); 3.708(4.0); 3.698(4.8); 3.694(4.9); 3.682(6.6); 3.671(5.8); 3.667(5.6); 3.657 (4.8); 3.482(2.7); 3.472(2.9); 3.464(2.8); 3.454(5.3); 3.445(3.1); 3.437(2.9); 3.427(2.6); 3.391(4.8); 3.380(5.6); 3.367(6.2); 3.365(5.4); 3.356(6.1); 3.353(5.8); 3.341(4.8); 3.329(4.4); 2.323(2.1); 2.313(2.3); 2.309(2.5); 2.299(4.3); 2.288(4.4); 2.285 (2.9); 2.278(3.4); 2.274(4.4); 2.264(5.6); 2.254(3.1); 2.250(2.9); 2.240(2.6); 2.096(2.7); 2.085(5.0); 2.074(2.9); 2.068(2.8); 2.058(5.3); 2.050(4.3); 2.047(3.4); 2.039(2.1); 2.033(2.2); 2.022(3.7); 2.011(1.9); 1.592(5.5); 1.333(1.0); 1.284(1.4); 1.255 (1.6); 0.008(2.0); 0.000(66.6); −0.009(2.0) |

| Compound 512a: 1H-NMR (400.0 MHz. CDCl3): δ = |
|---|
| 8.564(1.2); 8.544(11.3); 8.529(3.7); 8.495(16.0); 8.471(1.0); 8.440(0.7); 8.425(1.0); 8.412(7.1); 8.400(7.1); 8.393(2.6); 8.381(2.6); 8.372(10.3); 8.360(10.3); 7.521(0.9); 7.500(4.9); 7.495(5.3); 7.484(5.1); 7.478(5.3); 7.453(3.8); 7.447(4.1); 7.436 (3.9); 7.430(4.1); 7.373(0.8); 7.333(3.3); .327(3.3); 7.322(3.5); 7.316(3.6); 7.311(4.6); 7.305(4.5); 7.300(4.5); 7.294(4.6); 7.286(3.0); 7.281(3.3); 7.275(3.5); 7.270(5.2); 7.262(109.3); 7.254(4.7); 7.242(1.5); 7.219(6.0); 7.202(11.1); 7.198(12.8); 7.187(8.0); 7.181(12.3); 7.176(4.7); 7.160(5.4); 7.127(0.7); 7.105(8.9); 7.092(8.6); 6.998(0.8); 5.299(5.0); 4.417(7.0); 4.402 (7.1); 4.052(5.4); 4.034(5.5); 3.868(0.5); 3.851(0.5); 3.811(3.1); 3.801(3.4); 3.784(5.4); 3.773(3.4); 3.727(0.5); 3.690(13.9); 3.564(3.2); 3.546(3.4); 3.537(5.8); 3.519(6.0); 3.501(3.9); 3.489(4.1); 3.481(6.1); 3.472(8.7); 3.462(3.5); 3.454(3.5); 3.445 (3.1); 3.090(1.7); 3.071(3.2); 3.051(2.1); 3.021(3.2); 3.011(3.4); 2.987(4.8); 2.977(4.8); 2.885(1.8); 2.866(5.4); 2.852(4.7); 2.838(5.9); 2.827(7.5); 2.811(5.2); 2.804(4.4); 2.792(1.7); 2.777(1.4); 2.702(2.3); 2.683(3.6); 2.664(1.9); 2.494(0.9); 2.483 (1.5); 2.470(2.0); 2.465(1.9); 2.460(2.2); 2.451(2.2); 2.446(1.9); 2.441(2.4); 2.430(2.3); 2.422(2.0); 2.413(2.7); 2.404(2.5); 2.397(2.6); 2.387(2.4); 2.379(1.5); 2.370(1.3); 2.360(0.7); 1.840(1.0); 1.255(0.5); 0.008(1.6); 0.000(40.9); −0.009(1.7) |

| Example 1808(Iba): $^1$H-NMR (400.0 MHz. CDCl$_3$): δ = |
|---|
| 7.835(12.2); 7.822(15.8); 7.520(1.4); 7.301(3.3); 7.295(3.3); 7.290(0.7); 7.284(3.4); 7.278(3.9); 7.261(251.6); 7.254(6.1); 7.248(5.0); 7.237(4.5); 7.231(4.6); 7.128(5.3); 7.107(14.7); 7.086(1.0); 7.078(2.8); 7.072(2.5); 7.066(2.8); 7.061(2.6); 7.056 (1.4); 7.050(1.3); 7.044(3.7); 7.039(3.6); 7.033(3.1); 7.027(2.8); 7.023(1.9); 7.016(1.8); 7.012(1.7); 7.006(1.6); 6.997(1.5); 6.923(0.5); 6.852(16.0); 6.835(11.7); 4.225(6.0); 4.210(6.2); 4.133(4.8); 4.114(5.1); 3.813(1.7); 3.801(3.9); 3.787(3.6); 3.774 (4.8); 3.761(2.4); 3.757(1.6); 3.746(1.8); 3.743(1.7); 3.730(2.1); 3.719(2.1); 3.716(2.0); 3.705(1.6); 3.621(1.6); 3.601(3.4); 3.595(2.6); 3.589(4.9); 3.582(3.9); 3.573(4.2); 3.571(3.5); 3.563(3.3); 3.557(2.9); 3.547(2.4); 3.544(1.7); 3.530(1.9); 3.491 (1.7); 3.480(1.9); 3.467(2.0); 3.464(1.7); 3.456(2.0); 3.453(1.8); 3.440(1.6); 3.429(1.5); 2.232(0.6); 2.222(0.6); 2.218(0.7); 2.208(1.3); 2.197(1.5); 2.187(1.3); 2.183(1.4); 2.173(2.2); 2.163(1.2); 2.159(1.2); 2.149(1.0); 2.119(3.8); 2.112(1.6); 2.105 (6.0); 2.100(7.1); 2.091(3.3); 2.087(7.1); 2.074(2.8); 2.070(3.5); 2.067(1.9); 2.064(1.6); 2.056(0.7); 2.050(0.8); 2.039(1.3); 2.028(0.6); 1.528(1.8); 0.008(3.1); 0.000(98.2); −0.009(3.0) |

| Example 1774(Iba): $^1$H-NMR (400.0 MHz. CDCl$_3$): δ = |
|---|
| 8.741(9.4); 8.726(15.0); 8.004(1.0); 7.586(9.7); 7.467(16.0); 7.265(66.6); 7.160(1.7); 7.142(3.3); 7.139(3.3); 7.135(2.1); 7.121(5.3); 7.118(5.3); 7.115(3.4); 7.101(3.9); 7.097(5.3); 7.094(4.0); 7.087(2.0); 7.076(4.2); 7.069(2.1); 7.061(1.8); 7.048 (1.6); 7.043(1.6); 7.010(2.5); 7.004(2.7); 6.992(2.6); 6.986(3.3); 6.977(2.8); 6.965(2.6); 6.960(3.7); 6.950(2.1); 6.946(1.5); 6.940(1.5); 6.934(1.2); 6.929(1.6); 6.925(1.2); 6.920(0.8); 6.893(1.5); 6.889(2.4); 6.884(3.1); 6.879(2.4); 6.873(2.4); 6.868 (2.1); 6.863(2.6); 6.858(1.9); 6.853(1.3); 4.293(7.5); 4.279(7.8); 4.041(4.7); 4.024(5.4); 3.834(2.2); 3.822(5.2); 3.816(1.8); 3.808(5.2); 3.795(7.2); 3.786(5.0); 3.782(4.4); 3.777(3.1); 3.771(3.1); 3.763(3.9); 3.749(3.1); 3.739(1.7); 3.735(1.7); 3.725 (1.8); 3.722(2.0); 3.712(1.9); 3.708(1.9); 3.698(1.6); 3.603(2.7); 3.592(3.1); 3.581(3.1); 3.576(2.6); 3.570(3.2); 3.565(2.6); 3.554(2.4); 3.543(2.3); 3.483(3.6); 3.469(1.6); 3.458(1.8); 3.445(2.1); 3.443(1.9); 3.434(2.1); 3.432(1.9); 3.418(1.6); 3.407 (1.4); 2.958(8.7); 2.880(7.4); 2.879(7.4); 2.352(0.7); 2.343(0.8); 2.338(0.8); 2.328(1.5); 2.318(1.5); 2.314(1.0); 2.308(1.1); 2.304(1.5); 2.293(1.8); 2.284(1.0); 2.279(1.0); 2.274(1.1); 2.270(1.0); 2.261(1.4); 2.252(1.1); 2.247(1.2); 2.238(3.0); 2.225 (3.4); 2.217(2.1); 2.212(1.9); 2.203(2.5); 2.190(1.6); 2.158(1.7); 2.147(2.5); 2.135(3.1); 2.123(3.3); 2.111(2.9); 2.099(1.8); 2.088(1.3); 2.076(0.9); 2.013(0.9); 2.003(1.6); 1.993(0.9); 1.985(1.0); 1.975(1.7); 1.968(1.5); 1.965(1.2); 1.958(0.8); 1.951 (0.8); 1.940(1.3); 1.930(0.7); 1.816(4.8); 0.008(0.9); 0.000(25.3); −0.009(0.8) |

| Example 192(Iba): $^1$H-NMR (400.0 MHz. CDCl$_3$): δ = |
|---|
| 8.579(6.2(1b8.575(6.5); 8.568(6.5); 8.564(6.4); 8.524(6.7); 8.520(6.8); 8.512(6.9); 8.508(6.8); 7.734(7.2); 7.730(7.3); 7.714 (7.9); 7.710(7.7); 7.525(8.3); 7.521(8.4); 7.519(2.9); 7.505(9.2); 7.501(8.9); 7.383(2.3); 7.368(2.5); 7.363(4.5); 7.349(4.6); 7.343(3.3); 7.329(3.1); 7.293(0.6); 7.260(329.1); 7.225(8.3); 7.214(8.2); 7.205(10.0); 7.194(7.9); 7.190(3.1); 7.185(5.3); 7.170(9.4); 7.165(4.2); 7.155(3.4); 7.150(6.8); 7.107(3.1); 7.104(12.0); 7.097(3.5); 7.092(9.6); 7.084(10.9); 7.079(4.5); 7.072 (12.1); 7.068(2.3); 7.066(2.0); 7.053(4.5); 7.051(4.4); 7.047(3.4); 7.045(3.0); 7.033(2.3); 7.030(2.2); 7.026(1.7); 7.024 (1.6); 6.996(1.9); 6.971(3.9); 6.968(5.1); 6.965(4.7); 6.952(4.0); 6.948(4.5); .946(3.8); 6.926(2.1); 6.924(2.1); 6.920(2.7); 6.918(2.5); 6.905(3.4); 6.903(3.5); 6.899(4.7); 6.897(4.3); 6.884(4.3); 6.880(4.7); 6.875(6.2); 6.869(2.5); 6.856(3.7); 6.852 (4.1); 6.846(2.4); 4.395(7.9); 4.370(16.0); 4.346(8.9); 4.181(2.7); 4.170(5.1); 4.157(5.1); 4.146(8.8); 4.135(5.1); 4.121(4.4); 4.111(2.1); 3.630(2.1); 3.615(3.1); 3.602(5.5); 3.588(4.9); 3.574(3.2); 3.499(4.6); 3.485(6.0); 3.480(3.8); 3.471(5.8); 3.466 (4.2); 3.457(6.9); 3.452(2.9); 3.442(3.3); 3.438(2.7); 3.399(3.3); 3.385(3.7); 3.379(3.8); 3.371(2.2); 3.366(3.6); 3.358(2.2); 3.352(2.3); 3.338(2.0); 2.467(0.6); 2.454(1.42); .440(0.8); 2.433(2.5); 2.419(4.4); 2.413(2.8); 2.410(3.2); 2.406(2.9); 2.402 (3.3); 2.396(5.1); 2.387(3.1); 2.383(4.7); 2.378(2.8); 2.368(2.6); 2.359(0.8); 2.348(0.5); 2.344(0.7); 2.105(1.2); 2.091(2.3); |

-continued 2.081(1.3); 2.078(1.4); 2.071(1.8); 2.067(2.4); 2.057(3.2); 2.047(1.7); 2.043(1.6); 2.033(3.0); 2.019(1.4); 2.005(0.6); 1.873 (1.5); 1.858(1.7); 1.854(1.7); 1.848(1.8); 1.843(1.9); 1.839(2.6); 1.828(2.6); 1.824(1.5); 1.819(1.5); 1.813(1.3); 1.809(1.4); 1.804(1.2); 1.793(1.2); 1.622(4.0); 0.008(3.8); 0.000(122.5); −0.009(3.6)

Example 215(Iba): $^1$H-NMR (400.0 MHz. CDCl$_3$): δ =

8.577(10.7); 8.573(11.0); 8.565(11.1); 8.562(10.9); 8.524(6.5); 8.520(6.7); 8.512(6.8); 8.509(6.5); 7.729(11.1); 7.725(11.2); 7.708(12.4); 7.705(11.8); 7.539(8.0); 7.535(7.9); 7.518(15.9); 7.515(8.7); 7.414(8.9); 7.409(9.8); 7.398(9.1); 7.392(9.5); 7.359(1.4); 7.292(2.8); 7.260(1373.1); 7.251(10.7); 7.245(7.0); 7.239(5.8); 7.235(7.8); 7.227(15.1); 7.224(8.3); 7.216(14.9); 7.210(5.7); 7.207(12.2); 7.196(13.8); 7.192(6.9); 7.181(6.4); 7.175(6.8); 7.166(13.1); 7.158(1.8); 7.145(21.2); 7.124(8.8) 7.115(9.4); 7.103(9.0); 7.094(8.5); 7.083(8.6); 7.046(2.6); 7.040(2.5); 7.035(2.9); 7.029(2.6); 7.025(4.6); 7.019(4.5); 7.013 (4.6); 7.008(4.4); 6.996(8.2); 6.984(8.8); 6.963(12.5); 6.942(4.6); 6.914(1.0); 4.362(13.3); 4.357(9.1); 4.338(16.0); 4.332 (10.9); 4.163(2.9); 4.144(7.3); 4.133(5.4); 4.128(3.7); 4.120(10.4); 4.109(8.1); 4.103(2.9); 4.096(3.7); 4.085(3.6); 3.637(2.4); 3.623(4.6); 3.609(5.6); 3.596(6.3); 3.581(3.2); 3.524(3.3); 3.510(6.7); 3.496(7.6); 3.492(4.3); 3.482(10.3); 3.476(5.7); 3.468 (5.7); 3.458(3.7); 3.448(3.5); 3.430(2.6); 3.415(5.5); 3.401(6.5); 3.395(6.4); 3.387(3.9); 3.382(6.1); 3.374(3.9); 3.367 (4.42); .354(3.6); 2.413(4.9); 2.398(7.4); 2.382(6.8); 2.379(8.4); 2.365(4.9); 2.110(1.9); 2.097(3.6); 2.087(2.2); 2.073(4.2); 2.062(5.0); 2.052(2.8); 2.038(4.6); 2.025(2.2); 2.005(2.4); 1.882(2.8); 1.870(3.1); 1.866(3.3); 1.862(3.3); 1.855(3.1); 1.851 (3.6); 1.847(4.9); 1.836(4.7); 1.832(2.8); 1.827(2.8); 1.821(2.6); 1.816(2.5); 1.801(2.0); 1.587(6.3); 0.157(2.0); 0.146(1.6); 0.008(16.7); 0.000(516.3); −0.009(15.4); −0.050(1.6); −0.149(1.6)

Example 1484(Iba): $^1$H-NMR (400.0 MHz. CDCl$_3$): δ =

8.003(1.8); 7.301(2.2); 7.295(2.4); 7.284(2.4); 7.279(2.3); 7.263(50.3); 7.220(4.5); 7.214(4.8); 7.203(4.6); 7.197(4.6); 7.131 (1.3); 7.110(6.2); 7.089(14.8); 7.083(2.2); 7.077(2.4); 7.068(7.4); 7.062(0.8); 7.056(0.6); 7.050(0.6); 7.019(3.1); 7.014 (3.1); 7.009(3.5); 7.000(6.4); 6.997(6.9); 6.992(2.2); 6.987(2.1); 6.981(2.0); 6.973(11.3); 6.969(11.7); 6.718(14.0); 6.717 (14.2); 6.715(14.3); 6.190(6.7); 4.176(7.0); 4.010(3.4); 3.993(3.7); 3.813(1.8); 3.801(4.0); 3.787(3.7); 3.774(5.2); 3.761(2.5); 3.750(0.9); 3.741(1.1); 3.736(1.1); 3.724(1.4); 3.714(1.3); 3.709(1.3); 3.699(1.1); 3.623(2.4); 3.612(2.7); 3.602(2.8); 3.596 (2.2); 3.590(2.8); 3.585(2.2); 3.575(2.6); 3.564(2.9); 3.556(1.0); 3.546(3.2); 3.532(3.6); 3.522(2.5); 3.517(3.5); 3.508(3.8); 3.493(3.1); 3.484(15.8); 3.479(1.4); 3.466(1.1); 3.454(1.0); 2.958(16.0); 2.880(13.6); 2.879(13.4); 2.279(0.5); 2.270(0.6); 2.264(0.6); 2.255(1.1); 2.244(0.9); 2.240(0.6); 2.235(0.8); 2.211(0.9); 2.205(0.6); 2.196(0.6); 2.189 (0.7); 2.176(1.2); 2.168(0.7); 2.163(0.9); 2.154(2.6); 2.141(3.5); 2.133(2.0); 2.127(1.8); 2.119(2.9); 2.114(1.8); 2.106(1.9); 2.102(3.3); 2.090(3.1); 2.078(3.4); 2.066(2.6); 2.054(1.2); 2.042(1.2); 2.030(0.6); 2.018(0.6); 2.007(1.0); 1.996(0.7); 1.989 (0.6); 1.983(0.7); 1.979(1.1); 1.972(0.9); 1.968(0.7); 1.954(0.5); 1.944(0.8); 1.496(6.6); 0.008(0.6); 0.000(19.0)

Example 127 threo: $^1$H-NMR (600.1 MHz. CDCl$_3$): δ =

7.660(1.8); 7.648(3.2); 7.635(2.0); 7.444(0.5); 7.432(0.4); 7.282(3.0); 7.269(3.4); 7.261(50.0); 7.211(3.3); 7.205(1.1); 7.199(3.4); 7.194(1.7); 7.189(1.4); 7.183(1.9); 7.180(1.6); 7.175(0.9); 7.172(0.9); 7.166(1.2); 7.152(0.4); 7.088(1.1); 7.084(1.2); 7.074(0.9); 7.017(0.3); 7.001(0.4); 6.819(0.4); 6.806(0.4); 4.362(0.4); 4.345(0.4); 4.270(2.7); 4.254(2.8); 3.555(0.); 3.548(1.0); 3.538(1.4); 3.529(1.2); 3.520(0.8); 3.456(0.7); 3.449(0.8); 3.439(1.4); 3.432(1.3); 3.422(0.9); 3.415(0.7); 3.304(0.8); 3.296(0.9); 3.288 (1.1); 3.286(0.9); 3.280(1.0); 3.278(0.9); 3.270(0.8); 3.262(0.7); 2.003(0.4); 1.995(0.7); 1.987(0.5); 1.978(0.8); 1.972(1.0); 1.964(0.6); 1.955(0.8); 1.947(0.4); 1.771(0.4); 1.764(0.5); 1.761(0.5); 1.755(0.8); 1.748(0.8); 1.739(0.8); 1.732(0.6); 1.725 (0.5); 1.723(0.4); 1.716(0.3); 1.528(4.5); 0.005(0.8); 0.000(14.4); −0.006(0.5)

Example 127 erythro: $^1$H-NMR (600.1 MHz. CDCl$_3$): δ =

7.457(1.2); 7.444(2.2); 7.431(1.4); 7.261(50.0); 7.166(2.0); 7.152(1.8); 7.032(0.5); 7.017(1.5); 7.004(1.4); 7.01(1.7); 6.995 (0.6); 6.987(1.0); 6.983(0.5); 6.864(0.8); 6.857(0.6); 6.850(0.6); 6.819(1.9); 6.807(1.8); 4.362(1.8); 4.346(1.9); 3.701(0.5); 3.694(0.7); 3.691(0.6); 3.684(0.8); 3.675(0.7); 3.673(0.7); 3.666(0.5); 3.445(0.5); 3.440(0.5); 3.428(0.9); 3.423(0.9); 3.410 (0.5); 3.405(0.5); 3.351(0.5); 3.343(0.6); 3.335(0.8); 3.327(0.8); 3.317(0.5); 3.309(0.5); 2.404(0.5); 2.397(0.5); 2.388(0.5); 2.381(0.6); 2.375(0.4); 2.371(0.3); 2.271(0.3); 2.263(0.6); 2.256(0.7); 2.252(0.4); 2.245(0.7); 2.240(0.6); 2.222(0.4); 1.546 (10.9); 0.005(0.7); 0.000(14.2)

Example 1758(Iba): $^1$H-NMR (400.0 MHz. CDCl$_3$): δ =

8.730(9.1); 8.710(15.1); 8.004(0.7); 7.588(9.6); 7.449(16.0); 7.334(1.6); 7.319(1.8); 7.312(3.8); 7.297(4.1); 7.291(5.1); 7.277(5.2); 7.271(4.2); 7.265(70.6); 7.257(3.8); 7.049(1.2); 7.047(1.4); 7.043(1.4); 7.041(1.6); 7.032(2.2); 7.030(2.6); 7.026 (4.7); 7.022(3.0); 7.020(3.3); 7.011(6.1); 7.009(7.3); 7.005(6.1); 6.999(2.0); 6.991(4.6); 6.984(2.2); 6.982(2.1); 6.975(2.3); 6.970(2.5); 6.964(1.5); 6.952(2.2); 6.946(2.7); 6.941(4.6); 6.940(4.7); 6.937(5.2); 6.935(4.8); 6.919(3.6); 6.918 (4.6); 6.916(4.4); 6.892(3.3); 6.887(4.1); 6.881(2.5); 6.869(3.2); 6.863(4.1); 6.858(2.5); 4.300(8.2); 4.286(8.6); 4.063(4.9); 4.046(5.7); 3.842(1.2); 3.833(1.5); 3.826(2.9); 3.823(3.2); 3.813(5.7); 3.810(6.6); 3.804(3.6); 3.797(6.5); 3.789(5.0); 3.783 (6.5); 3.775(2.2); 3.770(3.0); 3.730(1.3); 3.720(1.6); 3.716(1.6); 3.704(2.0); 3.693(1.9); 3.689(1.8); 3.679(1.6); 3.596(2.7); 3.585(3.1); 3.575(3.1); 3.569(2.6); 3.563(3.2); 3.558(2.6); 3.548(2.5); 3.536(3.3); 3.481(4.2); 3.458(1.6); 3.447(1.8); 3.434 (2.1); 3.432(1.7); 3.423(2.0); 3.420(1.8); 3.407(1.6); 3.396(1.4); 2.9563(6.8); 2.9558(6.7); 2.879(5.8); 2.878(5.8); 2.354(0.7); 2.345(0.8); 2.339(0.8); 2.330(1.6); 2.319(1.3); 2.315(0.9); 2.310(1.1); 2.305(1.3); 2.295(1.9); 2.286(1.0); 2.280(1.1); 2.277 (1.2); 2.271(1.0); 2.263(1.7); 2.255(1.1); 2.250(1.2); 2.242(3.3); 2.228(3.8); 2.220(2.1); 2.215(1.9); 2.206(2.8); 2.193(1.6); 2.157(1.7); 2.146(2.7); 2.134(3.2); 2.122(3.6); 2.110(3.1); 2.098(1.8); 2.086(1.5); 2.074(0.9); 2.027(0.9); 2.017(1.4); 2.006 (1.0); 1.999(0.9); 1.992(1.0); 1.989(1.5); 1.982(1.3); 1.978(1.1); 1.971(0.8); 1.964(0.8); 1.954(1.2); 1.943(0.7); 1.808(3.8); 0.008(0.8); 0.000(27.4); −0.009(0.8)

Example 181(Iba): $^1$H-NMR (400.0 MHz. CDCl$_3$): δ =

8.523(3.7); 8.520(1.5); 8.517(1.6); 8.513(3.7); 8.481(5.3); 8.472(5.3); 7.263(50.0); 7.259(12.4); 7.200(1.1); 7.186(2.3); 7.180(1.4); 7.176(1.); 7.170(2.8); 7.166(4.8); 7.162(5.3); 7.157(5.1); 7.154(4.); 7.147(1.2); 7.086(0.3); 7.063(1.6); 7.061 (1.3); 7.057(1.2); 7.046(2.2); 7.032(2.7); 7.016(2.6); 7.002(1.5); 6.990(1.4); 6.987(1.5); 6.978(1.5); 6.974(2.0); 6.969(1.5); 6.960 (1.4); 6.957(1.4); 6.930(6.1); 6.927(5.8); 6.866(1.9); 6.863(1.6); 6.859(1.5); 6.852(1.6); 4.381(4.8); 4.364(5.0); 4.317(3.8); 4.301(3.9); 3.684(1.3); 3.677(1.8); 3.675(1.8); 3.667(2.2); 3.658(2.1); 3.657(2.0); 3.649(1.5); 3.563(1.0); 3.554(1.7); 3.545 (2.1); 3.536(2.0); 3.527(1.2); 3.488(4.1); 3.458(1.0); 3.451(1.1); 3.42(2.0); 3.435(2.4); 3.426(1.3); 3.420(2.9); 3.415(2.5);

3.404(1.4); 3.398(1.3); 3.377(1.5); 3.370(1.7); 3.361(2.0); 3.359(1.8); 3.354(2.0); 3.352(1.8); 3.343(1.5); 3.336(1.4); 3.330 (1.2); 3.322(1.3); 3.315(1.4); 3.312(1.3); 3.307(1.4); 3.304(1.3); 3.297(1.2); 3.289(1.0); 2.403(0.6); 2.397(0.7); 2.393(0.7); 2.387(1.2); 2.380(1.3); 2.371(1.3); 2.364(1.6); 2.358(1.0); 2.354(0.9); 2.349(0.8); 2.261(0.9); 2.254(1.7); 2.246(1.0); 2.243 (1.0); 2.236(1.9); 2.230(1.6); 2.223(0.7); 2.220(0.7); 2.213(1.2); 2.205(0.6); 2.001(0.7); 1.994(1.2); 1.985(1.2); 1.977(1.7); 1.970(2.0); 1.962(1.7); 1.953(2.1); 1.945(1.7); 1.915(2.2); 1.833(0.9); 1.825(1.1); 1.817(1.2); 1.810(1.4); 1.801(1.4); 1.794 (0.9); 1.787(0.8); 1.778(0.6); 0.005(0.6); 0.000(12.8); −0.006(0.5)

Example 1515(Iba): $^1$H-NMR (400.0 MHz, CDCl$_3$): δ =

7.361(0.5); 7.351(0.7); 7.348(1.0); 7.338(2.5); 7.328(2.1); 7.324(3.6); 7.315(3.2); 7.311(2.1); 7.301(1.9); 7.291(4.1); 7.262 (50.0); 7.114(12.4); 7.092(0.4); 7.085(0.3); 7.072(0.5); 7.068(0.6); 7.058(1.0); 7.052(1.8); 7.047(1.8); 7.036(3.3); 7.033(4.1); 7.019(2.6); 7.010(0.8); 7.007(1.0); 6.995(0.48); 6.992(1.0); 6.969(3.8); 6.956(3.5); 6.930(2.2); 6.927(3.0); 6.914(2.2); 6.911 (2.9); 4.280(5.6); 4.271(5.7); 4.061(1.8); 4.050(1.9); 3.851(1.5); 3.843(3.0); 3.834(2.9); 3.825(3.5); 3.816(1.7); 3.761(0.6); 3.755(1.0); 3.749(1.1); 3.739(2.5); 3.730(3.8); 3.723(2.5); 3.714(2.9); 3.705(1.4); 3.640(1.7); 3.633(1.9); 3.625(2.1); 3.622 (1.9); 3.618(2.1); 3.615(1.8); 3.607(1.6); 3.600(1.5); 3.495(0.6); 3.490(2.8); 3.478(0.9); 3.471(0.9); 3.460(0.5); 3.453(0.5); 2.259(0.5); 2.252(0.6); 2.243(0.6); 2.236(0.6); 2.230(1.0); 2.221(1.4); 2.215(0.9); 2.212(0.9); 2.207(2.1); 2.198(2.3); 2.192 (1.3); 2.189(1.2); 2.183(1.7); 2.174(0.9); 2.110(1.0); 2.103(1.7); 2.095(1.9); 2.087(2.3); 2.079(2.1); 2.071(1.3); 2.064(1.1); 2.055(0.6); 1.939(0.5); 1.932(0.3); 1.928(0.3); 1.921(0.6); 1.916(0.6); 1.897(0.5); 1.556(7.6); 0.000(14.4); −0.006(0.5)

Example 1461(Iba): $^1$H-NMR (400.0 MHz, CDCl$_3$): δ =

8.004(1.0); 7.343(1.1); 7.328(1.4); 7.324(3.8); 7.309(4.0); 7.304(5.0); 7.289(4.9); 7.284(3.1); 7.269(3.2); 7.261(50.1); 7.054 (0.9); 7.052(1.1); 7.047(1.1); 7.045(1.5); 7.043(1.9); 7.041(2.0); 7.036(2.1); 7.034(2.6); 7.031(2.5); 7.027(3.6); 7.024(4.7); 7.022(5.5); 7.020(4.4); 7.016(3.6); 7.013(3.8); 7.009(2.2); 7.004(3.9); 7.001(2.8); 6.999(2.0); 6.995(1.9); 6.992(2.1); 6.988 (6.3); 6.985(7.2); 6.982(2.3); 6.976(1.2); 6.963(2.1); 6.956(15.1); 6.952(16.0); 6.934(3.7); 6.933(3.5); 6.904(2.7); 6.899 (3.4); 6.893(2.1); 6.880(2.7); 6.875(3.3); 6.870(2.1); 6.727(5.1); 6.726(5.0); 6.724(4.8); 6.708(9.2); 6.707(9.3); 6.704(9.4); 4.202(6.9); 4.187(7.2); 4.043(3.7); 4.026(4.0); 3.800(1.8); 3.787(3.4;3.774(3.8); 3.761(4.9); 3.748(2.4); 3.733 (1.0); 3.724(1.2); 3.719(1.2); 3.707(1.7); 3.697(1.5); 3.692(1.4); 3.682(1.2); 3.614(2.4); 3.603(2.7); 3.593(3.6); 3.587(2.5); 3.581(4.9); 43.576(3.3); 3.566(6.3); 3.554(4.4); 3.543(3.5); 3.528(1.7); 3.508(1.7); 3.496(1.5); 3.484(10.9); 3.472(1.6); 3.469 (1.4); 3.457(1.2); 3.445(1.1); 2.956(9.3); 2.879(7.4;2.878(7.6); 2.281(0.6); 2.272(0.5); 2.266(0.6); 2.258(1.2); 2.247(0.9); 2.243(0.7); 2.238(0.8); 2.232(0.9); 2.223(1.5); 2.214(0.8); 2.208(0.7); 2.199(0.7); 2.187(0.7); 2.174(1.3); 2.166(0.7); 2.161 (0.9); 2.152(2.7); 2.139(3.7); 2.131(2.0); 2.125(1.8); 2.118(3.4;2.111(1.8); 2.104(1.8); 2.099(3.4); 2.087(3.0); 2.075(3.4); 2.063(2.5); 2.052(1.2); 2.039(1.8); 2.028(1.6); 2.017(0.8); 2.010(0.7); 2.004(0.7); 2.000(1.0); 1.993(0.9); 1.989(0.8); 1.982 (0.5); 1.976(0.6); 1.965(0.7); 1.954(0.5); 1.449(4.9); 0.008(0.6); 0.000(19.6); −0.009(0.5)

Example 1677(Iba): $^1$H-NMR (400.0 MHz, CDCl$_3$): δ =

8.001(1.8); 7.334(1.9); 7.327(3.8); 7.319(2.2); 7.312(5.7); 7.306(6.6); 7.300(4.3); 7.292(6.9); 7.286(5.1); 7.279(2.8); 7.272 (5.1); 7.262(65.8); 7.043(1.6); 7.040(4.0); 7.037(4.2); 7.034(4.5); 7.031(3.7); 7.019(9.5); 7.016(8.0); 7.013(7.7); 7.010(6.5); 7.007(2.8); 7.006(2.9); 7.005(3.1); 7.003(3.7); 7.001(4.5); 6.999(4.0); 6.998(4.2); 6.995(4.0); 6.992(3.7); 6.989(3.0); 6.978 (4.9); 6.977(5.7); 6.974(9.2); 6.971(6.4); 6.964(2.2); 6.958(4.9); 6.957(5.1); 6.955(6.4); 6.954(6.1); 6.953(5.9); 6.952(6.1); 6.946(3.0); 6.940(1.8); 6.915(4.5); 6.910(5.5); 6.905(3.5); 6.892(4.5); 6.886(5.5); 6.881(3.5); 6.394(3.5); 6.393(3.5); 6.385 (7.2); 6.383(5.0); 6.380(7.1); 6.378(7.3); 6.376(5.3); 6.375(5.0); 6.370(13.2); 6.362(7.7); 6.360(7.3); 6.266(12.4;6.261 (13.1); 6.256(11.0); 6.251(12.0); 6.250(8.3); 6.245(6.7); 6.240(5.7); 6.236(5.6); 4.150(11.5); 4.136(12.0); 3.992(6.1); 3.974 (6.5); 3.803(3.0); 3.790(6.3); 3.776(6.6); 3.763(8.5); 3.750(5.6); 3.741(1.9); 3.736(1.9); 3.724(2.7); 3.714(2.4); 3.709(2.3); 3.699(2.1); 3.641(4.2); 3.629(4.7); 3.620(4.9); 3.614(3.6); 3.608(4.8); 3.602(3.5); 3.593(3.6); 3.581(3.3); 3.549(2.2); 3.537 (2.5); 3.526(2.6); 3.522(2.1); 3.514(2.6); 3.510(2.2); 3.499(2.0); 3.487(1.9); 3.481(6.3); 3.467(1.9); 3.461(2.6); 3.452(4.1); 3.446(4.0); 3.443(3.4;6); .437(3.2); 3.433(3.2); 3.428(3.5); 3.422(3.7); 3.414(1.8); 3.408(1.5); 2.956(16.0); 2.878(14.1); 2.877 (14.0); 2.276(0.9); 2.267(0.9); 2.261(1.0); 2.252(1.8); 2.243(1.2); 2.241(1.4); 2.238(1.1); 2.232(1.3); 2.229(1.2); 2.226 (1.4); 2.218(2.2); 2.209(1.2); 2.203(1.1); 2.194(1.0); 2.142(1.1); 2.129(2.3); 2.121(1.2); 2.116(1.4); 2.107(4.5); 2.094(6.2); 2.086 (3.3); 2.080(2.9); 2.072(5.4); 2.064(3.1); 2.059(2.9); 2.052(5.8); 2.040(5.3); 2.028(5.7); 2.016(3.7); 2.004(2.2); 1.992 (2.3); 1.980(1.1); 1.972(1.1); 1.960(1.6); 1.950(1.2); 1.943(1.1); 1.937(0.9); 1.932(1.6); 1.925(1.4); 1.921(1.2); 1.915(0.9); 1.908(0.9); 1.898(1.2); 1.886(0.8); 1.498(12.3); 0.008(0.7); 0.000(25.4); −0.009(0.7)

Example 1153(Iba): $^1$H-NMR (400.0 MHz, CDCl$_3$): δ =

8.095(2.9); 8.090(5.8); 8.087(3.3); 8.082(5.6); 7.264(29.0); 7.127(1.4); 7.119(0.9); 7.113(3.1); 7.105(1.7); 7.097(3.0); 7.089 (1.6); 7.083(1.6); 7.075(0.7); 7.065(0.7); 7.061(0.7); 7.053(0.8); 7.048(1.1); 7.043(0.8); 7.035(0.7); 7.031(0.7); 7.013(1.5); 7.010(1.6); 7.001(1.7); 6.997(2.3); 6.992(1.7); 6.984(1.5); 6.980(1.5); 6.914(1.7); 6.907(0.8); 6.900(0.9); 6.886(2.2); 6.879 (1.7); 6.871(1.9); 6.666(2.1); 6.664(2.4); 6.658(5.6); 6.652(4.2); 6.650(3.9); 6.499(3.5); 6.476(7.7); 4.192(5.3); 4.181(5.3); 4.031(0.4); 3.987(2.4); 3.974(2.5); 3.912(50.0); 3.724(1.4); 3.715(2.9); 3.706(3.0); 3.698(3.3); 3.689(1.6); 3.659(0.6); 3.652 (0.8); 3.649(0.8); 3.642(1.3); 3.634(0.9); 3.631(0.9); 3.624(0.7); 3.494(1.7); 3.488(3.2); 3.480(1.9); 3.476(1.7); 3.471(1.9); 3.468(1.7); 3.462(1.5); 3.454(1.4); 3.381(0.7); 3.373(0.8); 3.365(1.0); 3.357(1.0); 3.348(0.7); 3.340(0.6); 3.278(0.7); 3.268 (1.6); 3.259(3.3); 3.253(2.3); 3.248(2.2); 3.242(2.8); 3.232(1.3); 2.272(0.5); 2.266(0.4); 2.262(0.4); 2.256(0.7); 2.249 (0.7); 2.240(0.7); 2.233(0.8); 2.227(0.5); 2.223(0.4); 2.217(0.4); 2.110(0.6); 2.101(1.1); 2.096(0.8); 2.091(1.1); 2.087(2.4); 2.077(3.6); 2.070(3.8); 2.063(6.4); 2.054(6.4); 2.046(6.1); 2.038(4.2); 2.031(2.1); 2.022(2.4;2.014(1.1); 0.000(8.3)

Example 532 threo(Iba): $^1$H-NMR (400.0 MHz, CDCl$_3$): δ =

8.341(15.5); 8.339(15.4); 8.328(16.0); 8.326(15.5); 8.308(0.8); 7.519(4.8); 7.379(0.6); 7.310(1.0); 7.293(1.7); 7.260(903.9); 7.229(0.7); 7.210(1.3); 7.163(5.1); 7.142(8.1); 7.138(6.3); 7.121(7.6); 7.116(20.9); 7.112(19.5); 7.102(5.3); 7.097(10.7); 7.084(5.1); 7.078(5.8); 7.070(5.1); 7.058(4.8); 7.052(4.9); 7.032(12.4); 7.028(11.3); 7.018(11.4); 7.015(10.7); 6.996(5.2); 6.975(0.8); 6.918(3.2); 6.913(4.0); 6.909(5.6); 6.904(4.3); 6.898(4.3); 6.894(4.1); 6.892(3.7); 6.887(4.7); 6.883(3.3); 6.877(2.4); 5.299 (4.5); 4.032(13.8); 4.014(14.6); 3.709(2.1); 3.696(3.1); 3.683(4.1); 3.672(3.6); 3.658(2.6); 3.384(4.7); 3.374(5.3); 3.366 (5.1); 3.356(10.5); 3.346(7.1); 3.338(5.6); 3.328(5.2); 2.288(2.0); 2.278(2.2); 2.273(2.4); 2.263(4.3); 2.252(4.3); 2.242(3.4); 2.238(4.3); 2.228(5.8); 2.218(3.2); 2.214(3.0); 2.204(2.6); 2.170(0.6); 2.088(2.8); 2.077(5.2); 2.067(3.0); 2.061(2.7); 2.050 (5.2); 2.042(4.5); 2.031(2.0); 2.025(2.2); 2.014(3.4); 2.004(1.9); 1.541(60.1); 1.333(3.2); 1.284(6.3); 1.256(5.0); 0.880(0.8); 0.146(1.0); 0.008(9.2); 0.000(342.5); −0.006(4.9); −0.009(11.0); −0.051(0.6); −0.150(1.1)

| -continued |
|---|
| Example 1288(Iba): ¹H-NMR (400.0 MHz. CDCl₃): δ = |
| 8.620(14.8); 8.617(14.8); 8.565(12.7); 8.562(12.6); 8.189(16.0); 8.185(15.7); 8.010(0.7); 7.963(13.7); 7.960(13.4); 7.520 (1.1); 7.261(212.1); 7.215(2.8); 7.211(0.6); 7.195(5.3); 7.191(3.5); 7.180(3.4); 7.174(7.3); 7.170(5.7); 7.162(3.3); 7.154(4.1); 7.149(5.2); 7.135(3.0); 7.129(3.1); 7.077(2.7); 7.056(4.8); 7.045(3.7); 7.046(4.3); 7.036(6.4); 7.032(6.8); 7.023 (4.7); 7.017(4.5); 7.011(4.5); 7.005(2.9); 6.997(4.1); 6.991(2.8); 6.978(2.5); 6.973(2.6); 6.860(1.8); 6.856(2.2); 6.851(3.2) 6.846(2.3); 6.840(2.2); 6.835(2.0); 6.829(2.5); 6.825(1.8); 6.820(1.3); 4.292(9.2); 4.285(8.4); 4.270(9.6); 4.260(8.7); 3.728 (2.0); 3.717(2.8); 3.701(2.9); 3.690(3.2); 3.676(2.3); 3.645(2.3); 3.633(4.5); 3.619(4.6); 3.605(6.3); 3.594(6.0); 3.583(3.3); 3.577(4.0); 3.570(6.1); 3.561(3.6); 3.552(2.9); 3.548(3.1); 3.543(2.5); 3.536(2.5); 3.346(2.7); 3.335(3.0); 3.323(5.3); 3.319 (3.3); 3.312(5.8); 3.308(3.2); 3.297(5.0); 3.286(4.9); 3.272(2.3); 3.261(2.1); 2.958(5.6); 2.882(4.8); 2.489(1.1); 2.480(1.2); 2.475(1.2); 2.466(1.8); 2.454(2.0); 2.441(1.8); 2.431(2.2); 2.422(1.4); 2.417(1.3); 2.408(1.1); 2.236(1.3); 2.225(2.7); 2.215 (1.5); 2.209(1.4); 2.198(2.9); 2.191(2.4); 2.180(1.1); 2.174(1.1); 2.163(2.0); 2.153(0.9); 2.063(1.0); 2.052(1.9); 2.040(1.5); 2.028(3.0); 2.017(3.8); 2.004(2.8); 1.992(3.3); 1.980(1.6); 1.960(1.7); 1.948(2.9); 1.935(2.4); 1.925(3.6); 1.913(3.1); 1.902 (1.3); 1.890(1.5); 1.878(0.9); 1.485(1.6); 0.008(2.6); 0.000(79.4); −0.009(2.3) |
| Example 1785(Iba): ¹H-NMR (400.0 MHz. CDCl₃): δ = |
| 7.832(12.1); 7.818(16.0); 7.519(2.3); 7.351(0.5); 7.338(3.8); 7.323(4.4); 7.317(6.8); 7.303(6.9); 7.297(5.3); 7.283(5.7); 7.260 (409.8); 7.228(0.5); 7.053(1.9); 7.051(2.7); 7.047(3.2); 7.044(3.0); 7.041(2.0); 7.032(3.6); 7.030(4.9); 7.026(5.9); 7.023 (5.4); 7.020(3.4); 7.005(5.2); 7.002(5.8); 6.996(2.9); 6.983(3.3); 6.974(2.8); 6.968(6.0); 6.951(4.6); 6.947(6.4); 6.926(3.0); 6.920(3.6); 6.915(2.2); 6.902(2.8); 6.897(3.6); 6.892(2.1); 6.827(15.9); 6.821(11.6); 4.240(7.1); 4.225(7.5); 4.163(5.3); 4.144 (5.6); 3.802(2.0); 3.789(4.4); 3.775(4.2); 3.762(5.4); 3.749(2.6); 3.742(4.1); 3.731(1.8); 3.728(1.8); 3.716(2.4); 3.704(2.2); 3.701(2.2); 3.690(1.8); 3.648(1.7); 3.632(3.2); 3.628(2.9); 3.611(3.5); 3.596(3.4); 3.589(1.7); 3.580(3.9); 3.565(3.2); 3.563 (2.6); 3.553(2.3); 3.547(3.0); 3.538(2.5); 3.536(1.9); 3.533(1.8); 3.520(2.2); 3.487(2.0); 3.475(2.2); 3.463(2.4); 3.460(1.9); 3.452(2.3); 3.448(1.9); 3.436(1.8); 3.425(1.7); 2.241(0.7); 2.231(0.8); 2.227(0.7); 2.217(1.3); 2.206(1.5); 2.196(1.4); 2.19 2(1.6); 2.183(2.3); 2.173(1.3); 2.169(1.3); 2.159(1.3); 2.130(1.4); 2.120(3.9); 2.109(5.7); 2.102(7.1); 2.096(3.5); 2.090(7.4); 2.085(4.3); 2.074(2.9); 2.072(3.3); 2.056(1.3); 2.045(0.6); 1.540(5.3); 0.157(0.6); ); 0.146(0.5); 0.008(5.3); 0.000(153.6); −0.009(4.4) |
| Example 1801(Iba): ¹H-NMR (400.0 MHz. CDCl₃): δ = |
| 7.832(12.4); 7.820(16.0); 7.265(65.4); 7.167(2.3); 7.163(1.8); 7.146(4.0); 7.142(5.1); 7.138(2.2); 7.126(3.1); 7.122(5.9); 7.117(3.1); 7.101(2.7); 7.097(2.2); 7.091(1.6); 7.085(1.7); 7.073(1.6); 7.067(1.9); 7.065(1.9); 7.059(1.7); 7.045(2.8); 7.040 (3.0); 7.027(2.0); 7.021(2.4); 7.012(2.2); 7.000(2.1); 6.994(2.1); 6.953(1.1); 6.949(1.4); 6.944(1.9); 6.939(1.5); 6.933(1.4); 6.926(2.2); 6.922(3.0); 6.919(2.5); 6.916(3.2); 6.912(2.3); 6.905(1.5); 6.900(1.5); 6.894(2.0); 6.890(1.5); 6.885(1.0); 6.839 (15.3); 6.821(11.4); 4.238(5.9); 4.223(6.2); 4.139(4.7); 4.120(5.0); 3.805(1.7); 3.792(3.8); 3.778(3.4); 3.765(4.8); 3.752(2.3); 3.748(1.5); 3.737(1.7); 3.734(1.7); 3.721(2.0); 3.710(2.0); 3.707(1.9); 3.696(1.6); 3.625(1.6); 3.609(2.8); 3.605(3.1); 3.598 (1.7); 3.591(3.5); 3.585(3.0); 3.580(3.0); 3.572(2.3); 3.564(4.3); 3.561(2.3); 3.553(2.4); 3.547(2.5); 3.537(2.5); 3.534(1.6); 3.520(1.9); 3.484(0.7); 3.481(1.7); 3.470(1.9); 3.457(2.0); 3.454(1.7); 3.446(2.0); 3.443(1.8); 3.430(1.6); 3.419(1.5); 2.959 (2.7); 2.881(2.3); 2.880(2.3); 2.232(0.6); 2.222(0.7); 2.218(0.7); 2.209(1.3); 2.197(1.4); 2.187(1.2); 2.184(1.4); 2.174(2.1); 2.164(1.1); 2.160(1.1); 2.150(1.0); 2.115(3.9); 2.108(1.6); 2.102(5.6); 2.097(8.1); 2.088(2.8); 2.084(6.7); 2.080(5.3); 2.067 (3.9); 2.062(1.7); 2.059(1.3); 2.051(0.7); 2.045(0.7); 2.035(1.2); 2.024(0.6); 1.685(2.4); 0.008(0.8); 0.000(24.1); −0.009(0.7) |
| Example 215(Iba): ¹H-NMR (400.0 MHz. CDCl₃): δ = |
| 8.574(6.6); 8.570(6.9); 8.562(6.8); 8.558(6.8); 8.521(6.7); 8.518(7.0); 8.510(6.9); 8.506(6.9); 8.012(0.9); 7.724(7.7); 7.720 (7.8); 7.704(8.5); 7.700(8.3); 7.537(8.5); 7.533(8.6); 7.521(1.0); 7.516(9.5); 7.512(9.3); 7.412(5.5); 7.406(6.0); 7.395(5.7); 7.389(5.9); 7.262(113.0); 7.253(2.8); 7.247(2.4); 7.242(2.7); 7.236(2.7); 7.232(4.1); 7.224(9.9); 7.221(4.6); 7.215(4.4); 7.212(9.3); 7.203(8.4); 7.198(6.0); 7.192(14.0); 7.181(6.0); 7.175(6.3); 7.164(8.0); 7.143(12.5); 7.121(5.1); 7.113(9.6); 7.101 (9.4); 7.092(8.8); 7.081(8.6); 7.047(2.3); 7.039(2.0); 7.033(2.5); 7.027(4.2); 7.017(4.5); 7.012(4.4); 7.006(4.1); 6.998(0.8); 6.984(8.6); 6.962(12.5); 6.941(4.5); 4.359(8.7); 4.355(9.2); 4.335(10.5); 4.329(11.3); 4.161(2.7); 4.143(5.5); 4.136 (2.6); 4.131(3.3); 4.127(3.2); 4.118(7.4); 4.108(5.1); 4.102(2.6); 4.095(2.4); 4.084(2.3); 3.632(2.1); 3.618(4.4); 3.604(5.3); 3.590(6.2); 3.576(3.1); 3.522(1.9); 3.507(3.7); 3.494(4.5); 3.485(16.0); 3.480(6.3); 3.470(5.4); 3.468(3.6); 3.465(3.7); 3.459(2.6); 3.453(3.6); 3.443(3.6); 3.425(2.4); 3.412(3.2); 3.398(3.7); 3.392(3.8); 3.384(2.3); 3.379(3.6); 3.371(2.4); 3.365 (2.4); 3.351(2.1); 2.955(9.0); 2.881(7.6); 2.880(7.7); 2.410(4.9); 2.395(7.7); 2.379(6.9); 2.376(8.4); 2.362(5.0); 2.108(1.1); 2.094(2.3); 2.084(1.2); 2.081(1.3); 2.073(1.9); 2.071(2.5); 2.060(2.3); 2.050(1.8); 2.046(1.6); 2.036(3.0); 2.022(1.4); 1.882 (1.5); 1.871(1.7); 1.867(1.8); 1.862(1.8); 1.856(1.8); 1.852(2.0); 1.847(2.8); 1.837(2.7); 1.833(1.5); 1.828(1.5); 1.822(1.); 1.817(1.4); 1.813(1.); 1.802(1.1); 1.629(2.8); 0.008(1.3); 0.000(42.2); −0.009(1.3) |
| Example 1477(Iba): ¹H-NMR (400.0 MHz. CDCl₃): δ = |
| 8.003(1.7); 7.262(60.8); 7.166(1.4); 7.152(2.8); 7.145(2.5); 7.142(1.8); 7.131(4.7); 7.127(3.4); 7.121(2.6); 7.111(3.5); 7.106 (4.6); 7.100(2.0); 7.097(1.6); 7.091(1.6); 7.086(3.2); 7.079(1.4); 7.073(1.6); 7.071(1.5); 7.065(1.4); 7.052(1.3); 7.046(1.4); 7.016(2.3); 7.010(2.5); 6.997(3.0); 6.994(7.3); 6.991(9.2); 6.983(2.8); 6.971(2.9); 6.966(15.2); 6.962(14.1); 6.958(2.2); 6.954(1.4); 6.947(1.2); 6.941(1.0); 6.936(1.3); 6.931(1.0); 6.927(0.7); 6.899(2.1); 6.894(2.0); 6.890(2.9); 6.889(2.2); 6.883 (2.2); 6.878(1.8); 6.873(2.3); 6.868(1.7); 6.863(1.2); 6.722(10.6); 6.721(11.5); 6.719(11.3); 6.718(11.0); 6.715(6.8); 6.714 (6.4); 6.711(6.2); 6.710(5.8); 4.199(7.1); 4.185(7.4); 4.010(3.9); 3.993(4.2); 3.813(2.0); 3.800(4.4); 3.787(4.0); 3.773(5.7); 3.761 (2.7); 3.749(1.1); 3.740(1.3); 3.735(1.3); 3.723(1.7); 3.713(1.6); 3.708(1.6); 3.698(1.4); 3.622(2.7); 3.610(3.0); 3.601(3.1); 13.595(2.4); 3.589(3.1); 3.583(2.4); 3.574(3.0); 3.567(1.4); 3.562(2.5); 3.559(1.3); 3.549(3.4); 3.536(4.0); 3.526(2.6); 3.521 (3.1); 3.515(2.3); 3.512(4.1); 3.504(1.9); 3.498(2.0); 3.492(2.0); 3.489(1.7); 3.485(7.5); 3.480(1.9); 3.478(1.6); 3.465 (1.4); 3.454(1.3); 2.957(16.0); 2.880(13.0); 2.878(14.0); 2.288(0.6); 2.279(0.7); 2.273(0.7); 2.264(1.3); 2.253 (1.1); 2.249(0.8); 2.244(0.9); 2.239(1.1); 2.229(1.6); 2.220(0.9); 2.214(0.8); 2.205(0.7); 2.192(0.7); 2.178(1.2); 2.171(0.7); 2.165 (0.9); 2.156(2.9); 2.143(3.8); 2.135(2.3); 2.130(2.1); 2.121(3.4); 2.107(4.4); 2.095(3.4); 2.083(3.8); 2.071(2.9); 2.060 (1.3); 2.048(1.3); 2.036(0.7); 2.019(0.8); 2.008(1.2); 1.998(0.8); 1.991(0.8); 1.984(0.8); 1.980(1.3); 1.974(1.1); 1.970(0.9); 1.963 (0.6); 1.956(0.6); 1.946(0.9); 1.935(0.6); 1.508(3.9); 0.008(0.7); 0.000(24.0); −0.009(0.7) |

Example 1542(Iba): ¹H-NMR (400.0 MHz, CDCl₃): δ =

7.996(2.0); 7.368(1.2); 7.353(1.7); 7.347(4.4); 7.332(5.0); 7.327(5.9); 7.313(5.9); 7.307(3.6); 7.292(3.2); 7.266(32.8); 7.259 (11.9); 7.087(20.3); 7.078(1.6); 7.076(1.6); 7.072(1.6); 7.070(1.7); 7.056(4.1); 7.050(4.7); 7.036(8.47.032(6.2); 7.015(6.6); 7.010(4.4); 6.991(2.6); 6.980(6.2); 6.960(4.9); 6.941(3.4); 6.936(4.3); 6.931(2.6); 6.918(3.3); 6.913(4.3); 6.908(2.6); 4.294(8.1); 4.280(8.5); 4.068(4.7); 4.052(5.1); 3.853(2.1); 3.840(4.3); 3.826(4.1); 3.813(5.5); 3.800(2.7); 3.761(1.2); 3.751 (1.5); 3.747(1.6); 3.734(3.2); 3.724(3.1); 3.719(2.7); 3.709(5.0); 3.695(4.8); 3.686(3.2); 3.681(3.8); 3.672(4.3); 3.658(2.2); 3.647(2.7); 3.636(3.1); 3.625(3.1); 3.620(2.7); 3.614(3.2); 3.609(2.6); 3.598(2.4); 3.587(2.2); 3.506(1.5); 3.495(1.7); 3.480 (8.0); 3.470(2.1); 3.454(1.4); 3.443(1.3); 2.959(16.0); 2.877(13.6); 2.288(0.7); 2.278(0.8); 2.273(0.8); 2.264(1.3); 2.253(1.4); 2.249(1.0); 2.239(2.3); 2.228(2.1); 2.218(1.8); 2.212(1.6); 2.203(3.3); 2.190(3.2); 2.182(2.1); 2.176(1.9); 2.168(2.3); 2.155 (1.5); 2.116(1.6); 2.104(2.4); 2.092(3.0); 2.080(3.2); 2.069(2.9); 2.057(1.7); 2.046(1.3); 2.033(0.9); 1.949(0.8); 1.939(1.5); 1.929(0.9); 1.922(0.9); 1.911(1.7); 1.904(1.5); 1.894(0.7); 1.887(0.7); 1.876(1.2); 1.866(0.7); 1.729(4.4); 0.008(0.5); 0.000 (12.4)

Example 1565(Iba): ¹H-NMR (400.0 MHz, CDCl₃): δ =

8.005(1.3); 7.351(2.1); 7.345(2.2); 7.334(2.0); 7.328(2.0); 7.2724(9.5); 7.2715(9.3); 7.264(57.7); 7.258(4.0); 7.252(3.7); 7.163(1.3); 7.142(4.7); 7.117(17.9); 7.109(2.4); 7.103(2.1); 7.097(5.7); 7.088(0.6); 7.082(0.5); 7.060(2.4); 7.054(2.3); 7.050 (2.6); 7.044(2.4); 7.039(1.5); 7.033(1.5); 7.028(1.4); 7.022(1.3); 4.269(5.0); 4.255(5.2); 4.046(3.2); 4.029(3.5); 3.866(1.4); 3.854(2.9); 3.840(2.7); 3.827(3.7); 3.814(1.8); 3.783(0.8); 3.773(1.0); 3.769(1.0); 3.759(1.1); 3.756(1.2); 3.746(1.2); 3.742 (1.2); 3.732(1.0); 3.713(0.8); 3.704(0.9); 3.697(0.8); 3.686(1.6); 3.676(2.2); 3.669(1.1); 3.661(3.4); 3.658(2.8); 3.653(2.1); 3.647(3.6); 3.638(3.1); 3.636(3.0); 3.630(2.0); 3.625(3.6); 3.620(1.5); 3.609(1.1); 3.598(1.5); 3.521(1.1); 3.510(1.2); 3.496 (1.5); 3.487(16.0); 3.469(1.0); 3.459(0.9); 2.960(11.7); 2.881(9.8); 2.880(9.9); 2.263(0.5); 2.259(0.5); 2.249(0.8); 2.238(1.0); 2.232(0.9); 2.228(0.8); 2.224(1.1); 2.219(1.0); 2.217(1.0); 2.213(1.2); 2.210(0.9); 2.204(1.3); 2.196(2.0); 2.190(0.8); 2.183 (2.0); 2.174(1.4); 2.169(1.3); 2.162(1.3); 2.160(1.4); 2.147(1.0); 2.112(1.1); 2.101(1.5); 2.100(1.5); 2.089(2.0); 2.077(2.0); 2.066(1.9); 2.054(1.1); 2.043(0.8); 2.041(0.8); 2.030(0.6); 1.939(0.5); 1.929(1.1); 1.918(0.6); 1.911(0.6); 1.901(1.2); 1.893 (1.0); 1.866(0.9); 1.564(3.9); 0.008(0.7); 0.000(21.5); −0.009(0.6)

Example 1516(Iba): ¹H-NMR (400.0 MHz, CDCl₃): δ =

7.262(50.0); 7.256(5.1); 7.222(1.7); 7.214(1.9); 7.208(2.1); 7.200(1.9); 7.150(2.6); 7.142(3.0); 7.136(3.5); 7.127(3.2); 7.100 (7.5); 7.085(0.5); 7.077(0.6); 7.071(2.2); 7.057(3.9); 7.051(3.9); 7.047(1.7); 7.043(2.4); 7.037(5.9); 7.022(2.6); 4.259(3.2); 4.250(3.3); 4.038(2.0); 4.027(2.1); 3.847(0.9); 3.839(1.9); 3.830(1.8); 3.821(2.2); 3.813(1.0); 3.787(0.4); 3.758(0.6); 3.751 (0.7); 3.748(0.7); 3.741(0.9); 3.731(1.3); 3.724(1.2); 3.719(0.6); 3.712(1.0); 3.706(0.6); 3.700(0.7); 3.694(1.4); 3.685(1.7); 3.678(1.2); 3.669(1.7); 3.660(0.9); 3.634(1.1); 3.627(1.2); 3.620(1.3); 3.616(1.2); 3.612(1.3); 3.609(1.1); 3.602(1.0); 3.595 (0.9); 3.499(0.6); 3.492(0.9); 3.490(0.8); 3.483(1.0); 3.476(1.0); 3.465(0.6); 3.458(0.5); 2.285(0.3); 2.279(0.3); 2.276(0.4); 2.269(0.6); 2.262(0.6); 2.253(0.6); 2.246(0.7); 2.239(0.4); 2.236(0.4); 2.230(0.4); 2.227(0.5); 2.218(0.7); 2.212(0.6); 2.209 (0.6); 2.203(1.3); 2.195(1.4); 2.189(0.8); 2.186(0.7); 2.180(1.0); 2.171(0.6); 2.099(0.6); 2.092(1.0); 2.084(1.2); 2.076(1.4); 2.068(13); 2.060(0.8); 2.052(0.7); 2.044(0.4); 1.927(0.3); 1.920(0.6); 1.913(0.4); 1.908(0.4); 1.901(0.7); 1.896(0.7); 1.890 (0.3); 1.885(0.3); 1.878(0.5); 1.541(6.6); 0.005(0.7); 0.000(13.6); −0.006(0.5)

Example 208(Iba): ¹H-NMR (400.0 MHz, CDCl₃): δ =

8.570(11.1); 8.567(11.4); 8.559(11.4); 8.555(11.2); 8.516(6.7); 8.512(6.9); 8.505(6.9); 8.501(6.8); 7.718(14.0); 7.715(13.8); 7.698(15.5); 7.694(17); 7.535(8.8); 7.531(8.5); 7.522(1.0); 7.515(9.8); 7.511(9.4); 7.263(118.6); 7.219(15.9); 7.214(5.0); 7.207(18.3); 7.199(16.3); 7.196(6.0); 7.190(6.5); 7.187(19.0); 7.181(8.5); 7.180(8.7); 7.176(4.9); 7.169(4.8); 7.164(5.4); 7.160(7.3); 7.155(7.5); 7.135(6.4); 7.110(12.6); 7.102(5.9); 7.098(13.8); 7.089(11.1); 7.078(10.7); 7.071(1.9); 7.024(2.6); 7.003(4.9); 6.999(3.7); 6.995(3.1); 6.989(3.4); 6.982(4.3); 6.977(6.2); 6.970(3.6); 6.968(3.3); 6.962(3.4); 6.958(4.1); 6.949 (2.8); 6.944(3.1); 6.906(2.2); 6.903(2.5); 6.901(2.3); 6.896(3.5); 6.893(2.6); 6.891(2.3); 6.887(2.3); 6.881(1.9); 6.875(2.3); 6.871(1.7); 6.866(1.3); 4.363(8.6); 4.356(12.9); 4.337(11.1); 4.333(16.0); 4.158(2.7); 4.141(8.1); 4.131(5.7); 4.123(3.5); 4.117 (9.3); 4.107(8.1); 4.098(2.7); 4.094(3.9); 4.083(3.6); 3.625(1.9); 3.611(3.9); 3.597(4.7); 3.583(5.5); 3.569(28.); 3.519(2.8); 3.505(5.6); 3.491(6.7); 3.483(11.2); 3.478(9.2); 3.464(6.9); 3.455(2.4); 3.449(3.2); 3.437(3.0); 3.421(2.2); 3.408(4.6); 3.394 (5.3); 3.388(5.5); 3.380(3.5); 3.374(5.2); 3.367(3.4); 3.360(3.5); 3.347(3.1); 2.955(4.5); 2.880(3.8); 2.878(3.7); 2.405(5.2); 2.390(7.5); 2.388(7.6); 2.374(6.6); 2.372(7.7); 2.356(4.7); 2.103(2.0); 2.089(4.0); 2.079(2.2); 2.075(2.3); 2.068(3.3); 2.065 (4.4); 2.055(5.6); 2.052(2.8); 2.045(3.0); 2.041(2.8); 2.031(5.3); 2.017(2.5); 1.883(2.5); 1.872(2.8); 1.868(3.0); 1.863(3.0); 1.857(3.0); 1.853(3.3); 1.848(4.5); 1.838(4.5); 1.834(2.5); 1.829(2.4); 1.823(2.2); 1.818(2.3); 1.814(2.0); 1.803(1.8); 1.624 (2.7); 0.008(1.4); 0.000(44.8); −0.009(1.2)

Example 208 threo(Iba): ¹H-NMR (400.0 MHz, CDCl₃): δ =

8.574(1.9); 8.570(2.0); 8.563(2.0); 8.559(2.0); 8.519(10.6); 8.515(11.0); 8.508(10.9); 8.504(10.9); 7.723(2.4); 7.720(2.4); 7.703(2.6); 7.699(2.5); 7.538(13.3); 7.534(13.7); 7.517(15.0); 7.513(14.7); 7.261(206.1); 7.223(2.7); 7.217(0.9); 7.211(3.7); 7.202(3.2); 7.199(2.9); 7.191(3.4); 7.182(1.6); 7.178(1.0); 7.172(0.9); 7.167(1.1); 7.162(1.4); 7.157(1.5); 7.138(1.2); 7.112 (16.2); 7.100(15.5); 7.091(14.3); 7.080(14.1); 7.024(4.2); 7.003(7.8); 7.000(5.1); 6.995(4.9); 6.989(5.3); 6.983(6.2); 6.978 (9.3); 6.971(5.7); 6.968(5.2); 6.962(5.5); 6.958(6.5); 6.950(4.2); 6.944(4.8); 6.909(3.6); 6.905(3.9); 6.903(3.7); 6.899(5.6); 6.895(4.2); 6.893(3.7); 6.889(3.7); 6.884(2.9); 6.877(3.7); 6.874(2.7); 6.868(2.1); 4.366(12.7); 4.360(2.8); 4.341(16.0); 4.160 (4.3); 4.143(7.2); 4.134(4.0); 4.126(4.6); 4.117(5.6); 4.109(1.8); 4.100(3.6); 4.085(0.7); 3.631(3.3); 3.617(6.8); 3.603(8.4); 3.589(9.6); 3.575(4.9); 3.523(0.6); 3.509(1.1); 3.495(1.5); 3.488(5.1); 3.481(2.1); 3.472(7.5); 3.461(3.9); 3.454(5.6); 3.443 (5.1); 3.427(3.7); 3.412(1.0); 3.398(1.1); 3.392(1.1); 3.384(0.7); 3.378(1.1); 3.371(0.9); 3.364(0.7); 3.351(0.6); 2.409(8.5); 2.393(12.7); 2.377(12.6); 2.361(7.8); 2.093(0.7); 2.069(0.8); 2.058(1.5); 2.048(0.5); 2.045(0.5); 2.034(0.9); 1.873(0.5); 1.868 (0.6); 1.864(0.6); 1.858(0.6); 1.853(0.6); 1.849(0.8); 1.838(0.8); 1.607(3.5); 0.008(2.1); 0.000(77.2); −0.009(2.2)

Example 1531(Iba): ¹H-NMR (400.0 MHz, CDCl₃): δ =

7.288(3.5); 7.262(50.0); 7.188(0.4); 7.174(1.0); 7.168(1.6); 7.155(3.2); 7.139(3.2); 7.131(12.3); 7.125(1.8); 7.117 (0.8); 7.112(0.6); 7.109(0.5); 7.104(0.5); 7.100(0.4); 7.085(0.3); 7.051(1.5); 7.047(1.6); 7.039(1.7); 7.034(2.4); 7.029(1.6); 7.021(1.5); 7.017(1.4); 6.980(0.6); 6.973(0.5); 6.966(0.6); 6.922(2.2); 6.915(1.7); 6.907(1.9); 4.268(5.1); 4.260(5.2); 4.040 (1.4); 4.029(1.5); 3.857(1.4); 3.849(2.9); 3.840(2.7); 3.831(3.3); 3.823(1.6); 3.772(0.4); 3.765(0.6); 3.763(0.5); 3.756(0.6); 3.747(0.7); 3.745(0.7); 3.738(0.7); 3.731(0.5); 3.724(0.8); 3.718(0.5); 3.710(1.6); 3.701(2.7); 3.694(1.9); 3.692(1.7); 3.685

(2.7); 3.676(1.4); 3.642(1.7); 3.635(1.9); 3.628(2.1); 3.624(1.9); 3.621(2.1); 3.618(1.7); 3.610(1.5); 3.603(1.4); 3.504(0.5); 3.497(0.6); 3.490(2.3); 3.481(0.8); 3.470(0.4); 3.463(0.4); 2.252(0.4); 2.245(0.5); 2.236(0.5); 2.228(0.5); 2.222(0.9); 2.214 (1.2); 2.208(0.9); 2.204(0.9); 2.199(1.9); 2.190(2.2); 2.184(1.3); 2.181(1.2); 2.175(1.5); 2.166(0.9); 2.107(1.0); 2.100(1.6); 2.092(1.9); 2.084(2.0); 2.076(1.9); 2.068(1.3); 2.061(1.0); 2.052(0.6); 1.925(0.5); 1.907(0.6); 1.901(0.6); 1.883(0.4); 1.566 (5.3); 0.000(14.6); −0.006(0.5)

Example 1272(Iba): $^1$H-NMR (400.0 MHz, CDCl$_3$): δ =

8.623(13.3); 8.620(13.8); 8.565(11.5); 8.561(11.5); 8.162(16.0); 8.159(15.6); 7.926(13.9); 7.922(13.8); 7.519 (6.5); 7.383(2.4); 7.369(2.7); 7.364(5.2); 7.349(5.1); 7.344(3.4); 7.329(3.5); 7.310(1.5); 7.308(0.7); 7.291(1.3); 7.286(1.7); 7.277(2.8); 7.271(5.2); 7.270(5.8); 7.269(7.2); 7.260(1202.0); 7.247(4.0); 7.231(2.5); 7.226(5.9); 7.212(4.5); 7.206(3.8); 7.198(1.2); 7.192(2.8); 7.169(1.0); 7.081(8.0); 7.078(6.4); 7.075(4.7); 7.060(7.4); 7.058(7.4); 7.054(6.3); 7.052(4.4); 7.043 (4.2); 7.038(5.1); 7.033(4.7); 7.020(3.9); 7.016(4.1); 7.010(2.3); 6.996(3.9); 6.969(2.1); 6.967(2.1); 6.963(2.2); 6.960(2.4); 6.948(3.4); 6.946(3.8); 6.942(3.6); 6.939(4.2); 6.927(1.8); 6.925(1.9); 6.921(1.9); 6.918(2.0); 6.888(5.0); 6.886(4.5); 6.881 (3.7); 6.876(4.2); 6.870(6.5); 6.858(3.5); 6.852(3.5); 6.847(2.1); 4.302(8.8); 4.280(14.4); 4.254(8.3); 3.725(2.1); 3.711(2.6); 3.698(3.0); 3.687(2.9); 3.684(3.0); 3.673(2.5); 3.639(2.2); 3.626(4.1); 3.613(6.3); 3.599(5.5); 3.590(5.8); 3.586(5.1); 3.581 (5.0); 3.566(3.9); 3.556(3.7); 3.348(2.6); 3.337(4.0); 3.326(4.5); 3.321(2.9); 3.314(5.9); 3.310(4.4); 3.303(3.3); 3.299(4.3); 3.287 (4.6); 3.276(2.4); 2.502(1.0); 2.493(1.2); 2.488(1.4); 2.479(2.1); 2.467(1.8); 2.453(1.5); 2.444(2.7); 2.435(1.6); 2.429(1.4); 2.421(1.3); 2.276(1.5); 2.265(3.0); 2.254(1.4); 2.249(1.5); 2.238(3.0); 2.230(2.5); 2.220(1.2); 2.214(1.2); 2.203(2.1); 2.192 (1.0); 2.089(1.0); 2.078(2.0); 2.065(1.6); 2.053(2.7); 2.043(4.0); 2.030(2.7); 2.017(3.6); 2.006(2.1); 1.977(1.8); 1.964(2.6); 1.954(2.2); 1.952(2.4); 1.942(3.3); 1.929(3.0); 1.919(1.2); 1.908(1.3); 1.894(0.9); 1.529(6.9); 1.255(1.0); 0.331(1.0); 0.238 (0.8); 0.157(1.8); 0.146(1.2); 0.008(12.9); 0.000(468.1); −0.009(13.6); −0.150(1.4)

Example 1781(Iba): $^1$H-NMR (400.0 MHz, CDCl$_3$): δ =

8.749(7.1); 8.735(14.0); 7.600(7.8); 7.480(16.0); 7.301(2.8); 7.296(2.9); 7.285(2.9); 7.279(3.0); 7.263(83.3); 7.224(5.4); 7.218(5.7); 7.207(5.5); 7.201(5.6); 7.125(1.6); 7.104(5.9); 7.101(5.9); 7.083(7.3); 7.079(14.8); 7.072(3.1); 7.067(2.7); 7.058 (8.6); 7.051(0.8); 7.046(0.7); 7.007(3.7); 7.001(3.7); 6.996(4.1); 6.990(3.7); 6.986(2.6); 6.980(2.4); 6.975(2.4); 6.969(2.1); 4.283(8.0); 4.269(8.4); 4.038(4.1); 4.020(4.7); 3.839(2.3); 3.826(5.3); 3.813(5.2); 3.806(1.6); 3.799(7.5); 3.787(4.7); 3.783 (4.5); 3.773(2.9); 3.769(3.2); 3.759(4.1); 3.753(1.6); 3.744(2.8); 3.739(1.5); 3.727(1.7); 3.717(1.6); 3.712(1.6); 3.702(1.3); 3.609(2.8); 3.598(3.2); 3.587(3.2); 3.582(2.7); 3.576(3.2); 3.571(2.7); 3.560(2.5); 3.549(2.3); 3.486(3.4); 3.474(1.3); 3.463 (1.5); 3.449(1.8); 3.438(1.6); 3.436(1.6); 3.423(1.2); 3.412(1.2); 2.958(3.8); 2.881(3.2); 2.880(3.1); 2.347(0.6); 2.338(0.7); 2.333(0.7); 2.323(1.2); 2.313(1.2); 2.309(0.8); 2.303(1.0); 2.298(1.2); 2.288(1.5); 2.278(1.0); 2.274(1.6); 2.262(1.7); 2.253 (1.1); 2.248(1.2); 2.239(3.1); 2.226(3.6); 2.217(2.2); 2.212(2.0); 2.204(2.3); 2.191(1.6); 2.158(1.7); 2.146(2.7); 2.135(3.2); 2.123(3.5); 2.111(3.0); 2.099(1.8); 2.088(1.4); 2.076(0.9); 2.015(0.47); .005(1.3); 1.994(0.8); 1.987(0.8); 1.977(1.4); 1.970 (1.2); 1.959(0.6); 1.952(0.7); 1.942(1.0); 1.932(0.6); 1.753(6.0); 0.008(1.1); 0.000(31.9); −0.009(0.9)

Example 1700(Iba): $^1$H-NMR (400.0 MHz, CDCl$_3$): δ =

8.005(1.8); 7.291(3.2); 7.285(3.4); 7.274(3.2); 7.269(3.7); 7.262(60.2); 7.230(6.1); 7.224(6.4); 7.213(6.3); 7.207(6.3); 7.123 (1.7); 7.116(5.3); 7.102(6.4); 7.094(14.3); 7.086(3.5); 7.081(7.6); 7.073(11.9); 7.069(3.7); 7.065(1.2); 7.059(1.0); 7.053 (0.8); 7.044(4.5); 7.038(4.3); 7.032(4.8); 7.027(4.4); 7.022(2.8); 7.016(2.5); 7.011(2.4); 7.005(2.2); 6.998(0.5); 6.378(3.1); 6.377(3.1); 6.373(5.8); 6.372(5.8); 6.369(6.4); 6.364(10.8); 6.355(6.5); 6.282(10.0); 6.278(10.1); 6.272(8.2); 6.268(8.1); 6.261 (5.1); 6.256(5.1); 6.251(4.3); 6.247(4.2); 4.138(9.2); 4.124(9.5); 3.950(5.1); 3.931(5.5); 3.819(2.4); 3.806(5.3); 3.792(5.1); 3.779(7.2); 3.770(1.8); 3.766(3.6); 3.761(1.7); 3.756(1.6); 3.744(2.1); 3.734(1.9); 3.729(1.9); 3.719(1.7); 3.653(3.3); 3.641 (3.7); 3.632(3.8); 3.626(2.9); 3.620(3.8); 3.614(2.9); 3.605(2.8); 3.593(2.6); 3.562(1.7); 3.550(1.9); 3.538(2.1); 3.535(1.7); 3.526(2.1); 3.523(1.8); 3.511(1.6); 3.499(1.4); 3.485(6.8); 3.458(0.7); 3.450(1.0); 3.441(1.6); 3.433(2.1); 3.429(2.2); 3.420 (3.2); 3.413(3.5); 3.404(3.2); 3.396(3.3); 3.390(2.6); 3.381(1.3); 3.375(1.2); 2.958(16.0); 2.880(13.4); 2.879(12.9); 2.281(0.7); 2.272(0.7); 2.267(0.8); 2.258(1.5); 2.247(1.2); 2.243(0.9); 2.237(1.0); 2.232(1.2); 2.223(1.8); 2.214(0.9); 2.208(0.9); 2.199 (0.8); 2.146(0.8); 42.133(1.7); 2.125(0.9); 2.120(1.1); 2.111(3.5); 2.098(4.8); 2.090(2.8); 2.085(2.4); 2.077(4.2); 2.071(2.5); 2.063(2.5); 2.059(4.6); 2.047(4.3); 2.035(4.6); 2.023(3.4); 2.012(1.7); 2.000(1.7); 1.988(0.8); 1.952(0.9); 1.941(1.4); 1.930 (0.9); 1.923(0.9); 1.917(1.); 1.913(1.5); 1.906(1.3); 1.902(1.0); 1.896(0.8); 1.888(0.8); 1.878(1.1); 1.867(0.7); 1.489(10.1); 0.008(0.7); 0.000(22.5); −0.009(0.7)

Example 1538(Iba): $^1$H-NMR (400.0 MHz, CDCl$_3$): δ =

7.345(0.7); 7.341(0.7); 7.334(0.7); 7.330(0.7); 7.300(2.5); 7.262(50.0); 7.253(2.3); 7.250(2.1); 7.154(0.6); 7.142 (8.3); 7.130(2.0); 7.126(1.2); 7.116(4.3); 7.107(0.7); 7.102(2.8); 7.093(0.3); 7.085(0.4); 7.045(1.3); 7.041(1.4); 7.038(1.5); 7.034(1.4); 7.032(1.1); 7.027(1.0); 7.024(1.0); 7.020(0.8); 4.258(3.3); 4.249(3.4); 4.039(1.1); 4.028(1.1); 3.858(0.9); 3.850 (1.9); 3.841(1.8); 3.832(2.2); 3.824(1.1); 3.773(0.3); 3.766(0.4); 3.764(0.4); 3.755(0.5); 3.748(0.4); 3.746(0.5); 3.740(0.5); 3.735(0.4); 3.730(0.3); 3.723(0.6); 3.716(0.4); 3.711(0.4); 3.706(1.2); 3.697(1.8); 3.690(1.2); 3.687(1.1); 3.681(1.8); 3.672 (0.9); 3.644(1.1); 3.638(1.2); 3.630(1.3); 3.627(1.2); 3.623(1.3); 3.620(1.2); 3.612(1.0); 3.605(0.9); 3.505(0.4); 3.498(0.4); 3.491(2.3); 3.481(0.5); 3.471(0.3); 2.243(0.3); 2.236(0.4); 2.227(0.4); 2.220(0.7); 2.211(0.9); 2.206(0.6); 2.203(0.7); 2.197 (1.3); 2.188(1.4); 2.182(0.8); 2.179(0.8); 2.173(1.0); 2.164(0.6); 2.103(0.6); 2.095(1.0); 2.088(1.2); 2.080(1.4); 2.072(1.3); 2.064(0.8); 2.056(0.6); 2.049(0.4); 1.925(0.3); 1.906(0.4); 1.901(0.4); 1.556(3.1); 0.005(0.7); 0.000(14.1); −0.006(0.5)

Example 532 erythro(Iba): $^1$H-NMR (400.0 MHz, CDCl$_3$): δ =

8.341(15.5); 8.339(15.4); 8.328(16.0); 8.326(15.5); 8.308(0.8); 7.519(4.8); 7.379(0.6); 7.310(1.0); 7.293(1.7); 7.260(903.9); 7.229(0.7); 7.210(1.3); 7.163(5.1); 7.142(8.1); 7.138(6.3); 7.121(7.6); 7.116(20.9); 7.112(19.5); 7.102(5.3); 7.097(10.7); 7.084(5.1); 7.078(5.8); 7.070(5.1); 7.058(4.8); 7.052(4.9); 7.032(12.4); 7.028(11.3); 7.018(11.4); 7.015(10.7); 6.996(5.2); 6.975(0.8); 6.918(3.2); 6.913(4.0); 6.909(5.6); 6.904(4.3); 6.898(4.3); 6.892(3.7); 6.887(4.7); 6.883(3.3); 6.877(2.4); 5.299 (4.5); 4.032(13.8); 4.014(14.6); 3.709(2.1); 3.696(3.1); 3.683(4.1); 3.672(3.6); 3.658(2.6); 3.384(4.7); 3.374(5.3); 3.366 (5.1); 3.356(10.5); 3.346(7.1); 3.338(5.6); 3.328(5.2); 2.288(2.0); 2.278(2.4); 2.273(4.7); 2.263(4.3); 2.252(4.3); 2.242(3.4); 2.238(4.3); 2.228(5.8); 2.218(3.2); 2.214(3.0); 2.204(2.6); 2.170(0.6); 2.088(2.8); 2.077(5.2); 2.067(3.0); 2.061(2.7); 2.050 (5.2); 2.042(4.5); 2.031(2.0); 2.025(2.2); 2.014(3.4); 2.004(1.9); 1.541(60.1); 1.333(3.2); 1.284(6.3); 1.256(5.0); 0.880(0.8); 0.146(1.0); 0.008(9.2); 0.000(342.5); −0.006(4.9); −0.009(11.0); −0.051(0.6); −0.150(1.1) (5.40.880(1.40.146(1.40.032(0.40.008(9.6); 0.000(325.4-0.009(9.2); −0.050(1.0); −0.150(0.9)

-continued

| Example 647(Iba): $^1$H-NMR (600.1 MHz. CDCl$_3$): δ = |
|---|
| 8.185(0.3); 8.181(0.3); 8.041(0.3); 8.031(0.4); 8.027(0.4); 8.018(0.3); 7.449(0.3); 7.446(0.3); 7.438(0.3); 7.433 (0.4); 7.261(50.0); 7.211(0.4); 7.197(0.7); 7.058(0.3); 7.054(0.3); 7.051(0.3); 7.047(0.5); 7.037(0.4); 7.032(0.4); 7.025(0.7); 7.011(0.8); 6.842(0.4); 6.833(0.4); 6.828(0.4); 6.819(0.3); 4.211(0.4); 4.194(0.4); 4.144(0.7); 4.126(0.7); 3.758(0.4); 3.749 (0.4); 3.740(0.4); 1.557(3.5); 0.000(13.9); −0.006(0.5) |

| Example 1137(Iba): $^1$H-NMR (600.1 MHz. CDCl$_3$): δ = |
|---|
| 8.095(3.2); 8.086(8.3); 8.076(5.9); 7.303(1.9); 7.290(4.4); 7.279(4.1); 7.277(4.2); 7.263(42.9); 7.024(1.7); 7.021 (1.8); 7.010(4.0); 7.007(3.4); 6.996(3.2); 6.983(3.0); 6.970(2.1); 6.952(2.0); 6.946(4.5); 6.933(4.6); 6.900(3.2); 6.884 (3.2); 6.700(2.4); 6.691(2.4); 6.671(4.7); 6.663(4.6); 6.528(4.4); 6.487(8.6); 4.193(5.8); 4.181(5.9); 4.027(0.4); 4.012(3.0); 4.000 (3.0); 3.908(50.0); 3.708(1.5); 3.699(3.0); 3.690(3.2); 3.681(3.4); 3.672(1.7); 3.645(0.8); 3.638(1.0); 3.635(1.0); 3.628(1.6); 3.620(1.1); 3.617(1.0); 3.610(0.9); 3.488(3.6); 3.485(2.0); 3.476(2.0); 3.471(2.0); 3.467(1.8); 3.462(2.1); 3.458(1.8); 3.453 (1.6); 3.445(1.5); 3.378(0.9); 3.370(1.0); 3.362(1.3); 3.354(1.2); 3.345(0.9); 3.337(0.8); 3.298(1.9); 3.288(3.2); 3.282(3.3); 3.277(2.4); 3.272(2.9); 3.262(1.9); 2.265(0.4); 2.259(0.5); 2.255(0.5); 2.249(0.8); 2.242(0.9); 2.232(0.9); 2.226(1.0); 2.220 (0.6); 2.216(0.6); 2.210(0.5); 2.107(0.8); 2.097(1.5); 2.095(1.4); 2.083(2.9); 2.074(4.4); 2.066(4.7); 2.060(6.6); 2.050(6.6); 2.043(6.4); 2.034(4.8); 2.027(2.9); 2.019(2.3); 2.011(1.4); 0.000(11.5) |

| Example 1558(Iba): $^1$H-NMR (400.0 MHz. CDCl$_3$): δ = |
|---|
| 7.997(2.2); 7.266(38.5); 7.258(12.2); 7.199(1.5); 7.179(3.9); 7.159(6.1); 7.136(6.6); 7.125(2.3); 7.115(4.9); 7.105(20.5); 7.093 (1.9); 7.067(2.6); 7.061(2.8); 7.049(2.8); 7.042(3.8); 7.035(3.0); 7.022(2.6); 7.017(2.7); 6.997(1.3); 6.992(1.7); 6.987(2.2); 6.983(1.9); 6.977(1.8); 6.971(1.5); 6.966(1.8); 6.961(1.5); 6.939(2.9); 6.934(3.6); 6.929(3.0); 6.923(2.8); 6.918(2.6); 6.913(3.0); 6.908(2.4); 4.283(7.9); 4.269(8.2); 4.050(4.7); 4.033(5.2); 3.861(2.1); 3.849(4.3); 3.835(4.2); 3.822(5.4); 3.809(2.7); 3.779(1.3); 3.769(1.6); 3.765(1.7); 3.752(2.0); 3.742(2.0); 3.738(2.0); 3.728(1.6); 3.716(1.4); 3.707(1.6); 3.699(1.4); 3.689 (2.8); 3.680(3.7); 3.666(4.8); 3.657(3.6); 3.652(5.4); 3.642(5.9); 3.630(5.3); 3.625(3.3); 3.619(3.5); 3.614(2.8); 3.603(2.4); 3.592(2.2); 3.517(1.5); 3.506(1.8); 3.491(2.6); 3.483(7.9); 3.466(1.5); 3.455(1.4); 2.961(16.0); 2.878(13.9); 2.280(0.7); 2.270 (0.8); 2.266(0.9); 2.256(1.3); 2.245(1.6); 2.232(2.5); 2.220(2.5); 2.210(2.1); 2.205(1.9); 2.196(3.5); 2.183(3.2); 2.174(2.2); 2.169(2.1); 2.160(2.4); 2.148(1.5); 2.113(1.7); 2.101(2.5); 2.090(3.1); 2.078(3.3); 2.067(2.9); 2.055(1.7); 2.043(1.4); 2.031 (0.9); 1.937(0.9); 1.927(1.6); 1.917(1.0); 1.910(0.9); 1.900(1.9); 1.892(1.); 1.882(0.8); 1.875(0.8); 1.864(1.4); 1.854(0.7) 1.706(4.1); 0.008(0.7); 0.000(14.6); −0.008(0.6) |

| Example 1295(Iba): $^1$H-NMR (400.0 MHz. CDCl$_3$): δ = |
|---|
| 8.623(14.4); 8.620(15.2); 8.570(12.8); 8.566(13.8); 8.199(15.6); 8.196(16.0); 7.971(13.3); 7.968(14.3); 7.519 (4.0); 7.385(7.9); 7.367(6.7); 7.260(668.3); 7.237(14.3); 7.231(13.7); 7.220(11.5); 7.214(10.7); 7.171(18.4); 7.168(19.9); 7.157(11.6); 7.153(17.4); 7.038(5.1); 7.017(11.7); 6.996(12.9); 6.981(5.7); 6.976(6.1); 6.970(6.5); 6.965(6.1); 4.281(15.1); 4.260(12.8); 4.256(11.9); 3.733(2.4); 3.721(4.4); 3.706(4.1); 3.693(4.5); 3.681(3.3); 3.645(3.3); 3.632(5.5); 3.619(5.8); 3.605 (8.3); 3.593(7.4); 3.579(7.2); 3.569(8.6); 3.556(6.1); 3.545(5.8); 3.533(3.5); 3.346(3.1); 3.335(4.2); 3.320(6.5); 3.307(6.8); 3.297(6.7); 3.285(4.0); 3.280(3.4); 3.269(2.7); 2.464(2.3); 2.452(2.9); 2.442(2.9); 2.430(2.8); 2.420(2.0); 2.229(3.2); 2.202 (3.7); 2.194(3.2); 2.167(2.6); 2.058(1.4); 2.047(2.2); 2.035(2.1); 2.023(3.6); 2.012(4.8); 1.999(3.6); 1.987(4.2); 1.952(2.1); 1.940(3.6); 1.930(3.5); 1.918(4.4); 1.905(3.8); 1.883(2.0); 1.509(8.9); 0.146(1.3); 0.000(252.0); −0.150(1.8) |

| Example 289 erythro1(Iba): $^1$H-NMR (400.0 MHz. CDCl$_3$): δ = |
|---|
| 8.401(3.2); 8.395(3.4); 7.975(2.5); 7.380(0.9); 7.375(1.1); 7.369(0.8); 7.358(1.0); 7.352(1.2); 7.347(0.8); 7.269(0.5); 7.268 (0.6); 7.267(0.7); 7.261(42.5); 7.170(0.8); 7.149(1.4); 7.146(0.9); 7.129(1.1); 7.125(1.3); 7.104(0.8); 7.037(0.7); 7.031(0.7); 7.019(0.7); 7.012(0.9); 7.005(0.7); 6.993(0.6); 6.987(0.7); 6.890(0.5); 6.887(0.7); 6.881(0.9); 6.877(0.7); 6.871(0.6); 6.865 (0.6); 6.860(0.7); 6.856(0.5); 5.299(16.0); 4.487(2.1); 4.472(2.1); 3.633(0.9); 3.616(0.9); 3.092(0.9); 3.072(0.9); 3.049(1.4); 3.029(1.3); 2.907(1.4); 2.891(1.4); 2.864(1.0); 2.848(0.9); 0.000(15.4) |

| Example 107(Iba): $^1$H-NMR (400.0 MHz. CDCl$_3$): δ = |
|---|
| 8.492(0.7); 8.489(1.4); 8.485(0.8); 8.481(0.8); 8.477(1.4); 8.474(0.8); 8.419(0.7); 8.416(1.3); 8.412(0.8); 8.408(0.8); 8.405 (1.38.401(0.7); 7.434(0.8); 7.430(0.8); 7.416(1.4); 7.413(1.4); 7.410(2.6); 7.407(1.1); 7.399(1.3); 7.393(1.4); 7.390(1.2); 7.386(1.1); 7.295(1.3); 7.2843(1.6); 7.2835(1.5); 7.273(1.7); 7.271(0.5); 7.270(0.5); 7.269(0.5); 7.268(0.6); 7.2674(0.7); 7.2666 (0.8); 7.266(1.0); 7.261(77.3); 7.2543(1.0); 7.2536(1.0); 7.252(1.2); 7.248(0.6); 7.243(0.8); 7.241(0.8); 7.237(1.2); 7.233 (1.0); 7.227(0.9); 7.221(1.1); 7.220(1.5); 7.216(2.1); 7.197(1.3); 7.193(1.2); 7.177(1.4); 7.172(2.5); 7.163(3.3); 7.155(2.4); 7.151(3.2); 7.145(1.2); 7.134(0.7); 7.130(1.2); 7.009(1.0); 7.004(1.0); 6.997(1.2); 6.992(1.0); 6.986(1.8); 6.965(2.4); 6.944 (0.8); 4.345(1.8); 4.337(1.7); 4.321(2.0); 4.311(1.9); 4.148(1.1); 4.130(3.3); 4.112(3.4); 4.094(1.1); 3.906(0.7); 3.896(0.6); 3.892(0.8); 3.889(0.6); 3.881(0.8); 3.661(0.8); 3.648(1.0); 3.634(1.0); 3.620(0.6); 3.535(0.7); 3.522(1.0); 3.508(1.1); 3.500(0.6); 3.494(0.7); 3.486(0.5); 3.480(0.6); 3.466(0.7); 3.410(0.6); 3.397(0.7); 3.390(0.7); 3.377(0.7); 2.410(0.9); 2.406(0.6); 2.401 (0.6); 2.396(1.0); 2.387(0.9); 2.374(0.9); 2.043(16.0); 2.036(0.5); 2.024(0.5); 1.841(0.5); 1.830(0.5); 1.625(0.8); 1.286(0.7); 1.284(0.7); 1.276(4.9); 1.258(10.4); 1.241(4.8); 0.008(0.8); 0.000(27.6); −0.009(0.8) |

| Example 597(Iba): $^1$H-NMR (400.0 MHz. CDCl$_3$): δ = |
|---|
| 8.373(13.1); 8.185(16.0); 7.421(0.7); 7.419(0.7); 7.406(1.0); 7.402(1.7); 7.400(1.4); 7.388(1.5); 7.384(1.6); 7.381(1.2); 7.370 (0.7); 7.366(1.0); 7.293(0.6); 7.261(45.8); 7.239(1.0); 7.224(1.7); 7.219(1.4); 7.215(1.6); 7.211(0.9); 7.205(1.47.202(1.7); 7.198(1.6); 7.194(1.0); 7.183(1.7); 7.174(1.8); 7.171(2.9); 7.168(2.0); 7.151(2.1); 7.117(3.6); 7.114(3.5); 7.095(4.4); 7.092 (4.2); 7.076(1.2); 7.074(1.2); 7.070(0.7); 6.997(0.5); 6.969(3.1); 6.954(4.2); 6.949(5.1); 6.941(2.5); 6.936(3.2); 6.933(3.4); 6.928(2.4); 6.923(1.5); 6.920(1.7); 6.914(0.7); 5.298(2.5); 4.274(3.2); 4.249(3.7); 4.205(3.4); 4.178(4.6); 3.996(1.0); 3.987 (1.0); 3.968(1.7); 3.959(1.7); 3.941(0.8); 3.931(0.8); 3.909(0.8); 3.897(0.8); 3.883(1.3); 3.871(1.3); 3.857(0.7); 3.845(0.7); 3.768(1.1); 3.755(1.8); 3.741(2.2); 3.728(2.0); 3.715(1.3); 3.607(0.9); 3.594(1.5); 3.581(2.0); 3.567(1.8); 3.554(1.1); 3.480 (1.2); 3.468(1.4); 3.457(1.5); 3.453(1.3); 3.446(1.5); 3.441(1.3); 3.430(1.2); 3.419(1.1); 3.395(1.0); 3.383(1.1); 3.372(1.2); 3.368(1.0); 3.360(1.2); 3.356(1.0); 3.346(0.9); 3.334(0.8); 2.955(2.8); 2.879(2.4); 2.564(0.6); 2.554(0.7); 2.550(0.7); 2.541 (1.0); 2.529(1.2); 2.518(1.2); 2.506(1.3); 2.497(0.8); 2.493(0.7); 2.483(0.7); 2.317(0.5); 2.306(1.0); 2.293(0.7); 2.290(0.7); 2.286(0.6); 2.278(1.1); 2.274(1.0); 2.271(1.0); 2.267(0.8); 2.259(0.6); 2.255(0.5); 2.243(0.7); 2.073(0.6); 2.061(0.5); 2.050 |

(0.8); 2.047(0.8); 2.042(0.7); 2.038(1.0); 2.035(0.8); 2.024(0.7); 2.012(0.8); 1.932(0.6); 1.919(0.9); 1.906(0.8); 1.897(1.2); 1.884(1.1); 1.874(0.5); 1.862(0.6); 1.516(1.5); 0.008(0.8); 0.000(18.0); −0.009(0.7)

Example 491(Iba): $^1$H-NMR (400.0 MHz. CDCl$_3$): δ =

8.608(13.1); 8.526(7.1); 8.514(16.0); 8.501(13.0); 8.495(15.1); 7.521(1.3); 7.422(11.2); 7.410(11.2); 7.397(11.9); 7.396 (12.0); 7.392(8.0); 7.351(6.5); 7.345(5.1); 7.340(7.1); 7.331(16.3); 7.328(18.1); 7.325(11.9); 7.321(10.0); 7.314(14.3); 7.306 (4.9); 7.303(5.8); 7.301(5.7); 7.299(5.6); 7.295(4.8); 7.286(8.0); 7.283(9.7); 7.281(10.0); 7.278(9.6); 7.271(8.9); 7.262 (219.4); 7.249(3.3); 7.231(6.7); 7.212(10.2); 7.192(5.0); 7.154(8.4); 6.998(3.2); 6.990(4.3); 6.972(3.7); 5.298(3.5); 4.333(6.1); 4.317(7.1); 4.157(7.3); 4.142(8.4); 4.044(2.1); 3.944(2.3); 3.934(2.7); 3.916(2.9); 3.906(2.8); 3.892(2.1); 3.717(1.8); 3.703 (3.5); 3.690(4.1); 3.676(4.5); 3.663(2.3); 3.613(2.8); 3.602(3.2); 3.597(3.4); 3.586(6.4); 3.575(4.1); 3.570(4.1); 3.559 (3.5); 3.514(1.8); 3.486(2.6); 3.455(1.4); 3.380(3.7); 3.367(4.1); 3.358(4.5); 3.353(3.5); 3.345(4.3); 3.340(3.6); 3.331(3.5); 3.318 (3.2); 2.285(1.1); 2.273(1.8); 2.260(1.4); 2.250(2.2); 2.245(2.2); 2.238(3.1); 2.225(2.4); 2.222(2.6); 2.209(3.5); 2.197(2.6); 2.168(2.3); 2.153(3.2); 2.144(3.2); 2.137(3.0); 2.130(3.2); 2.120(3.9); 2.106(5.4); 2.095(4.5); 2.084(4.8); 2.071(4.0); 2.060 (1.8); 2.048(1.8); 2.035(1.0); 1.605(1.9); 1.255(0.7); 0.008(2.4); 0.000(79.2); −0.009(2.3)

Example 511(Ibs): $^1$H-NMR (400.0 MHz. CDCl$_3$): δ =

8.609(12.9); 8.530(15.0); 8.517(15.4); 8.502(14.8); 7.598(4.4); 7.592(4.6); 7.582(4.5); 7.577(4.5); 7.521(1.1); 7.435 (8.8); 7.422(8.7); 7.348(3.6); 7.331(6.6); 7.318(4.1); 7.302(2.3); 7.296(2.3); 7.291(2.5); 7.285(2.4); 7.281(3.1); 7.274(3.2); 7.269(3.9); 7.262(187.8); 7.254(0.9); 7.2533(0.7); 7.2525(0.6); 7.252(0.5); 7.141(5.9); 7.120(8.7); 7.100(4.6); 7.046(1.3); 7.025(6.5); 7.006(7.9); 6.998(3.6); 5.299(16.0); 4.354(4.8); 4.338(5.6); 4.140(3.9); 4.124(4.5); 4.030(1.5); 3.927(1.4); 3.918 (1.7); 3.913(1.5); 3.900(2.0); 3.889(1.7); 3.884(1.6); 3.874(1.3); 3.740(1.3); 3.727(2.6); 3.714(2.9); 3.700(3.3); 3.688(1.9); 3.632(1.8); 3.620(2.2); 3.616(2.3); 3.605(4.1); 3.594(2.6); 3.589(2.8); 3.578(2.3); 3.497(1.9); 3.387(2.4); 3.374(2.7); 3.365 (3.0); 3.360(2.4); 3.352(2.9); 3.347(2.5); 3.338(2.3); 3.325(2.1); 2.278(0.7); 2.266(1.2); 2.250(0.9); 2.242(1.6); 2.238(1.6); 2.231(2.3); 2.215(2.0); 2.203(2.7); 2.191(2.1); 2.161(2.2); 2.151(2.1); 2.146(2.0); 2.137(2.2); 2.125(2.8); 2.113(3.9); 2.101 (3.2); 2.090(3.6); 2.078(2.9); 2.067(1.4); 2.054(1.4); 2.042(0.41.600(0.9); 0.008(2.1); 0.000(69.7); −0.009(2.1)

Example 599(Iba): $^1$H-NMR (400.0 MHz. CDCl$_3$): δ =

8.379(14.7); 8.197(16.0); 7.519(0.8); 7.392(0.8); 7.387(1.2); 7.375(14.4); 7.370(10.1); 7.358(5.7); 7.352(1.3); 7.341(1.0); 7.336(1.7); 7.295(0.5); 7.280(2.3); 7.275(3.5); 7.270(2.3); 7.269(2.3); 7.267(1.9); 7.260(141.7); 7.254(2.3); 7.236(1.1); 7.233 (1.6); 7.231(1.9); 7.228(2.2); 7.212(9.1); 7.209(9.1); 7.193(3.1); 7.190(2.0); 7.174(4.3); 7.172(3.5); 7.156(1.7); 7.153 (1.8); 7.075(1.9); 7.071(2.9); 7.056(1.4); 7.053(2.3); 6.996(0.9); 4.249(3.8); 4.224(4.4); 4.180(3.9); 4.152(5.1); 3.989(0.9); 3.979(0.9); 3.961(1.6); 3.952(1.5); 3.934(0.8); 3.924(0.7); 3.898(0.8); 3.886(0.8); 3.872(1.4); 3.860(1.4); 3.845(0.7); 3.834. (0.7); 3.773(1.0); 3.760(1.6); 3.746(2.0); 3.733(1.9); 3.720(1.2); 3.610(0.9); 3.597(1.5); 3.583(2.1); 3.570(1.8); 3.557(1.2); 3.481(1.1); 3.470(1.2); 3.458(1.3); 3.454(1.2); 3.447(1.3); 3.442(1.2); 3.431(1.1); 3.420(1.0); 3.396(1.1); 3.384(1.1); 3.374 (1.4); 3.369(1.0); 3.362(1.2); 3.357(1.0); 3.347(0.9); 3.335(0.9); 3.260(0.5); 2.550(0.6); 2.546(0.6); 2.537(1.0); 2.525(1.1); 2.514 (1.1); 2.502(1.3); 2.492(0.8); 2.489(0.8); 2.479(0.7); 2.308(0.9); 2.296(0.6); 2.292(0.7); 2.284(0.8); 2.280(1.0); 2.277 (0.9); 2.273(0.9); 2.269(0.8); 2.261(0.5); 2.257(0.5); 2.245(0.7); 2.068(0.6); 2.045(0.8); 2.041(0.9); 2.037(0.8); 2.033(1.1); 2.029 (0.9); 2.018(0.7); 2.006(0.9); 1.922(0.7); 1.908(0.9); 1.896(0.8); 1.887(1.3); 1.873(1.2); 1.864(0.6); 1.852(0.6); 0.008 (1.6); 0.000(53.0); −0.009(1.6)

Example 100(Iba): $^1$H-NMR (400.0 MHz. CDCl$_3$): δ =

8.503(1.6); 8.500(2.5); 8.497(1.6); 8.491(1.7); 8.488(2.5); 8.418(2.2); 8.414(1.4); 8.409(1.4); 8.406(2.2); 7.519(0.9); 7.469 (1.1); 7.465(1.2); 7.447(1.8); 7.445(2.4); 7.424(1.5); 7.421(1.5); 7.413(2.5); 7.303(2.3); 7.292(1.9); 7.282(1.7); 7.260(161.3); 7.242(2.3); 7.239(2.3); 7.224(1.4); 7.219(2.8); 7.216(3.0); 7.206(1.4); 7.198(3.4); 7.191(2.6); 7.187(3.3); 7.176 (3.5); 7.166(1.9); 7.155(0.9); 7.150(1.5); 7.115(1.1); 7.110(1.4); 7.095(0.47.089(0.9); 7.025(0.9); 7.004(1.47.001(1.2); 6.996(1.1); 6.984(1.5); 6.980(2.5); 6.974(1.1); 6.959(1.6); 6.956(1.3); 6.947(1.1); 6.934(0.9); 6.929(1.0); 6.881(0.9); 6.876 (1.2); 6.871(1.0); 6.865(0.9); 6.854(0.9); 4.351(3.0); 4.337(2.6); 4.154(2.9); 4.150(1.2); 4.132(3.5); 4.115(3.5); 4.097(1.2); 3.950(0.6); 3.939(0.6); 3.928(1.4); 3.918(1.4); 3.904(1.6); 3.893(1.5); 3.880(0.7); 3.871(0.6); 3.696(1.3); 3.682(1.3); 3.668(1.5); 3.654(1.8); 3.641(1.0); 3.557(0.8); 3.543(1.5); 3.529(2.1); 3.515(2.7); 3.501(1.7); 3.491(0.7); 3.485(0.8); 3.472 (0.7); 3.423(1.1); 3.410(1.2); 3.402(1.3); 3.395(0.9); 3.389(1.2); 3.382(0.9); 3.375(0.9); 3.362(0.8); 2.427(0.8); 2.417(1.5); 2.403(1.9); 2.394(1.8); 2.381(1.9); 2.368(0.8); 2.233(7.8); 2.107(1.2); 2.091(0.8); 2.079(0.8); 2.067(1.0); 2.056(1.3); 2.046 (16.0); 2.032(1.1); 2.019(0.5); 1.882(0.6); 1.867(0.6); 1.862(0.7); 1.857(0.7); 1.847(1.0); 1.837(1.0); 1.827(0.6); 1.277(4.2); 1.260(8.4); 1.242(4.1); 0.069(5.8); 0.008(2.6); 0.000(57.3); −0.009(2.1)

Example 289 erythro1(Iba): $^1$H-NMR (400.0 MHz. CDCl$_3$): δ =

8.393(7.4); 8.195(7.2); 7.521(1.0); 7.295(0.6); 7.262(185.3); 7.246(6.1); 7.155(4.0); 7.134(7.9); 7.131(5.5); 7.114(6.1); 7.110 (7.9); 7.090(5.1); 7.083(4.2); 7.078(4.3); 7.065(4.4); 7.059(5.5); 7.051(4.4); 7.039(4.0); 7.033(4.0); 6.998(1.1); 6.918 (4.2); 6.914(5.2); 6.909(4.4); 6.903(3.9); 6.897(3.7); 6.892(4.3); 6.888(3.4); 5.299(16.0); 4.046(10.1); 4.028(10.6); 3.708(2.7); 3.697(3.8); 3.694(3.8); 3.682(5.1); 3.671(4.4); 3.667(4.2); 3.657(3.7); 3.483(2.2); 3.474(2.0); 3.466(2.7); 3.456(4.3); 3.447 (2.9); 3.439(2.6); 3.429(2.1); 3.391(3.0); 3.380(3.4); 3.367(4.6); 3.356(4.6); 3.341(2.9); 3.330(2.7); 2.324(1.3); 2.310(1.7); 2.300(2.6); 2.289(3.2); 2.276(3.3); 2.265(3.4); 2.255(2.2); 2.241(1.5); 2.096(1.7); 2.086(3.2); 2.075(2.1); 2.069(2.1); 2.058 (3.9); 2.050(3.4); 2.040(1.6); 2.033(1.6); 2.023(2.3); 2.012(1.2); 1.622(3.8); 1.333(0.8); 1.284(1.1); 1.256(1.6); 0.008(2.0); 0.000(64.2); −0.006(0.6); −0.007(0.5); −0.009(1.8)

Example 620(Iba): $^1$H-NMR (400.0 MHz. CDCl$_3$): δ =

8.381(16.0); 8.369(1.1); 8.243(1.1); 8.214(15.4); 7.519(5.4); 7.293(0.6); 7.289(0.8); 7.260(956.7); 7.250(5.0); 7.244 (2.3); 7.229(3.0); 7.226(3.7); 7.218(2.0); 7.209(3.2); 7.205(3.4); 7.200(1.8); 7.185(2.0); 7.147(0.6); 7.128(1.3); 7.122(1.8); 7.118(1.4); 7.112(1.2); 7.101(1.3); 7.093(1.8); 7.087(1.4); 7.071(2.0); 7.061(1.4); 7.050(3.1); 7.043(1.5); 7.030(1.9); 7.026 (2.2); 7.006(1.7); 6.996(5.4); 6.921(1.6); 5.299(2.1); 4.265(3.9); 4.240(4.4); 4.184(3.4); 4.157(4.4); 3.974(0.8); 3.965(0.8); 3.946(1.4); 3.936(1.4); 3.917(0.7); 3.908(0.6); 3.887(0.8); 3.875(0.8); 3.861(1.4); 3.848(1.4); 3.836(0.9); 3.823(0.7); 3.779 (0.9); 3.766(1.4); 3.753(1.8); 3.740(1.7); 3.726(1.1); 3.636(1.0); 3.623(1.6); 3.610(2.0); 3.597(1.9); 3.583(1.2); 3.478(0.9); 3.467(1.1); 3.456(1.1); 3.444(1.2); 3.428(1.0); 3.411(1.0); 3.399(1.1); 3.388(1.2); 3.377(1.2); 3.362(0.9); 3.350(0.9); 2.544 (0.6); 2.535(0.9); 2.522(1.0); 2.510(1.0); 2.499(1.3); 2.490(0.7); 2.476(0.6); 2.294(0.8); 2.266(0.9); 2.231(0.7); 2.040(1.1);

-continued 2.013(0.9); 2.005(0.7); 1.936(0.7); 1.923(1.0); 1.912(0.9); 1.901(1.4); 1.888(1.2); 1.878(0.7); 1.865(0.7); 1.543(11.9); 1.371 (0.9); 1.333(1.7); 1.284(2.4); 1.256(2.2); 0.146(1.0); 0.008(9.1); 0.000(336.9); −0.009(9.9); −0.150(1.0)

Example 84(Iba): $^1$H-NMR (400.0 MHz. CDCl$_3$): δ =

8.385(4.0); 8.377(5.5); 8.374(7.4); 8.368(6.9); 8.201(3.7); 7.959(69); 47.351(2.4); 7.345(3.2); 7.340(2.5); 7.328(3.5); 7.322 (3.5); 7.316(2.8); 7.307(3.5); 7.291(4.2); 7.286(4.9); 7.278(2.6); 7.272(6.6); 7.262(66.2); 7.251(4.4); 7.244(1.5); 7.041(1.1); 7.034(1.4); 7.029(1.9); 7.022(3.0); 7.013(2.3); 7.010(3.1); 7.008(3.1); 7.003(3.4); 7.001(3.5); 6.995(1.3); 6.989(1.6); 6.987 (1.6); 6.982(1.7); 6.966(2.4); 6.956(1.5); 6.950(3.1); 6.947(3.6); 6.932(1.6); 6.927(1.8); 6.922(1.0); 6.887(4.0); 6.868(3.8); 6.858(2.8); 6.853(3.1); 6.848(1.8); 6.835(2.4); 6.830(3.0); 6.825(1.8); 5.299(16.0); 4.307(5.9); 4.292(6.1); 4.057(3.2); 4.040 (3.4); 3.835(1.2); 3.798(1.6); 3.785(3.4); 3.772(3.5); 3.758(4.1); 3.745(2.0); 3.690(0.9); 3.679(1.1); 3.675(1.1); 3.664 (1.6); 3.653(1.3); 3.648(1.2); 3.638(1.0); 3.547(1.9); 3.535(2.2); 3.526(2.3); 3.520(2.0); 3.514(2.4); 3.509(2.1); 3.499(2.4); 3.487 (2.3); 3.474(2.4); 3.460(2.7); 3.446(2.0); 3.437(2.3); 3.422(1.1); 3.385(1.0); 3.373(1.2); 3.361(1.4); 3.349(1.4); 3.346 (1.2); 3.335(1.0); 3.323(0.9); 2.320(0.5); 2.315(0.5); 2.305(0.9); 2.295(1.0); 2.284(0.9); 2.280(1.0); 2.270(1.2); 2.259(1.1); 2.245 (1.5); 2.237(0.8); 2.231(0.9); 2.223(2.2); 2.209(2.6); 2.202(1.6); 2.195(1.5); 2.188(2.0); 2.174(1.3); 2.170(1.1); 2.162(1.3); 2.150(2.3); 2.138(2.2); 2.127(2.8); 2.114(2.5); 2.102(1.8); 2.091(1.6); 2.084(0.8); 2.078(1.0); 2.073(1.2); 2.065(1.0); 2.054 (0.6); 2.048(0.6); 2.043(0.8); 2.038(0.8); 2.005(0.9); 1.752(1.5); 1.371(0.6); 1.286(0.9); 1.258(1.4); 0.008(1.0); 0.000 (25.2); −0.009(1.2)

Example 295(Iba): $^1$H-NMR (400.0 MHz. CDCl$_3$): δ =

8.492(0.8); 8.488(1.6); 8.485(0.9); 8.480(0.9); 8.477(1.6); 8.473(0.9); 8.421(0.8); 8.417(1.5); 8.414(0.9); 8.410(0.8); 8.406 (1.5); 8.403(0.8); 7.557(1.4); 7.551(1.5); 7.541(1.4); 7.535(1.5); 7.431(0.9); 7.428(0.9); 7.410(1.3); 7.407(1.5); 7.404(1.0); 7.387(1.2); 7.383(1.1); 7.308(1.4); 7.302(1.5); 7.299(0.9); 7.293(3.2); 7.287(1.8); 7.282(2.5); 7.278(1.2); 7.272(2.5); 7.266 (1.7); 7.261(74.3); 7.250(1.0); 7.239(0.7); 7.236(0.8); 7.218(1.4); 7.216(0.9); 7.215(1.4); 7.213(0.9); 7.195(1.4); 7.192(1.3); 7.177(1.4); 7.166(2.4); 7.155(1.6); 7.148(2.0); 7.145(1.3); 7.134(0.7); 7.127(2.4); 7.107(1.5); 7.079(0.6); 7.073(0.6); 7.067 (0.7); 7.062(0.6); 7.057(0.9); 7.051(0.9); 7.046(0.9); 7.040(0.8); 6.965(1.9); 6.944(2.7); 6.923(1.3); 4.342(2.0); 4.332(1.8); 4.318(2.2); 4.306(2.0); 4.148(1.1); 4.130(3.3); 4.112(3.3); 4.094(1.1); 3.903(0.9); 3.892(0.7); 3.889(0.9); 3.878(0.9); 3.662(0.9); 3.648(1.0); 3.634(1.0); 3.621(07); 43.535(0.8); 3.522(1.1); 3.508(1.2); 3.501(0.7); 3.494(0.7); 3.486(0.6); 3.481(0.7); 3.467 (0.7); 3.453(0.5); 3.411(0.6); 3.398(0.7); 3.390(0.7); 3.383(0.5); 3.377(0.7); 2.419(0.5); 2.409(0.8); 2.405(0.6); 2.396(1.0); 2.387(1.1); 2.374(1.2); 2.095(0.9); 2.057(0.5); 2.043(16.0); 2.035(0.6); 2.023(0.6); 1.842(0.6); 1.831(0.6); 1.588(0.7); 1.333 (0.7); 1.284(1.1); 1.276(4.9); 1.258(10.4); 1.240(4.8); 0.008(0.8); 0.000(27.5); −0.009(0.7)

Example 619(Iba): $^1$H-NMR (400.0 MHz. CDCl$_3$): δ =

8.384(14.1); 8.219(16.0); 7.588(2.5); 7.582(2.7); 7.572(2.6); 7.566(2.7); 7.519(1.1); 7.431(2.4); 7.425(2.6); 7.415(2.5); 7.410 (2.6); 7.325(1.3); 7.319(1.3); 7.314(1.5); 7.308(1.4); 7.304(1.9); 7.298(1.9); 7.293(2.0); 7.287(1.7); 7.260(176.1); 7.191 (3.4); 7.170(4.9); 7.150(2.8); 7.122(1.3); 7.116(1.2); 7.111(1.3); 7.105(1.3); 7.101(1.7); 7.095(1.7); 7.089(1.7); 7.084(1.6); 7.010(3.9); 6.996(1.3); 6.990(5.2); 6.969(2.6); 4.258(3.5); 4.233(4.0); 4.176(3.8); 4.148(4.9); 3.972(0.9); 3.962(0.9); 3.944 (1.5); 3.935(1.5); 3.917(0.7); 3.907(0.7); 3.879(0.8); 3.867(0.8); 3.853(1.4); 3.841(1.4); 3.828(0.8); 3.816(0.7); 3.780(1.1); 3.767(1.7); 3.753(2.0); 3.740(2.0); 3.727(1.3); 3.632(1.0); 3.619(1.6); 3.606(2.1); 3.593(2.0); 3.580(1.3); 3.477(1.2); 3.466(1.3); 3.454(1.4); 3.450(1.3); 3.443(1.4); 3.439(1.3); 3.427(1.2); 3.415(1.1); 3.409(1.2); 3.397(1.2); 3.386(1.3); 3.382(1.1); 3.375 (1.3); 3.371(1.1); 3.360(1.0); 3.348(1.0); 2.553(0.6); 2.543(0.6); 2.539(0.6); 2.530(1.0); 2.518(1.1); 2.507(1.1); 2.495(1.2); 2.485(0.8); 2.482(0.8); 2.472(0.6); 2.297(0.9); 2.282(0.6); 2.270(1.0); 2.266(0.9); 2.262(0.9); 2.258(0.8); 2.234(0.7); 2.071 (0.7); 2.059(0.5); 2.047(0.8); 2.044(0.9); 2.036(1.1); 2.021(0.8); 2.009(0.9); 1.997(0.5); 1.928(0.7); 1.915(1.0); 1.904(0.9); 1.893(1.3); 1.880(1.2); 1.870(0.7); 1.858(0.7); 1.845(0.5); 1.672(0.8); 1.621(0.6); 0.008(2.0); 0.000(66.8); −0.009(2.0)

Example 489(Iba): $^1$H-NMR (400.0 MHz. CDCl$_3$): δ =

8.597(1.1); 8.576(1.6); 8.561(1.5); 8.526(1.7); 8.494(2.3); 8.485(2.3); 8.469(1.4); 8.444(4.3); 8.371(2.7); 8.358(2.7); 8.305 (4.3); 8.255(0.6); 7.844(2.4); 7.831(2.4); 7.714(2.8); 7.701(2.7); 7.519(1.6); 7.311(2.9); 7.286(4.4); 7.260(284.4); 7.211 (2.8); 7.191(1.7); 7.054(1.7); 7.042(1.8); 7.015(1.5); 6.996(2.3); 6.961(1.6); 6.941(1.4); 6.878(1.7); 6.826(0.9); 6.805(1.2); 6.700(0.6); 5.298(1.2); 4.469(0.7); 4.444(1.3); 4.429(1.2); 4.419(1.1); 4.404(0.8); 4.380(0.6); 4.365(0.8); 4.348(0.7); 4.335 (0.7); 4.254(1.1); 4.084(1.0); 4.063(1.0); 3.947(0.6); 3.795(0.9); 3.782(0.7); 3.690(0.9); 3.609(0.9); 3.540(1.5); 3.531(1.6); 3.513 (1.6); 3.495(2.2); 3.471(16.0); 3.440(1.7); 3.105(0.6); 3.082(0.6); 2.924(0.5); 2.473(2.5); 2.457(2.3); 2.449(2.4); 2.423 (1.2); 2.186(1.7); 2.163(1.7); 1.253(0.9); 0.007(4.2); 0.000(100.3); −0.001(97.6); −0.008(5.1); −0.150(0.5)

Example 511(Iba): $^1$H-NMR (400.0 MHz. CDCl$_3$): δ =

8.620(14.0); 8.556(12.5); 8.543(12.3); 8.521(13.4); 7.920(7.6); 7.906(8.6); 7.898(8.8); 7.884(7.8); 7.843(1.2); 7.836(9.9); 7.831(3.8); 7.823(10.5); 7.819(5.1); 7.817(5.0); 7.814(11.0); 7.806(3.8); 7.800(10.4); 7.793(1.1); 7.603(5.1); 7.597(5.3); 7.588(5.2); 7.582(5.1); 7.525(5.9); 7.519(4.6); 7.512(5.8); 7.495(4.0); 7.483(3.7); 7.342(3.4); 7.309(3.1); 7.303(3.0); 7.298 (3.2); 7.292(3.4); 7.288(3.9); 7.282(4.0); 7.277(4.2); 7.270(4.7); 7.260(243.0); 7.151(6.7); 7.130(10.9); 7.127(16.0); 7.121 (5.0); 7.110(11.4); 7.104(25.6); 7.098(5.6); 7.089(6.2); 7.083(22.9); 7.077(5.3); 7.065(3.9); 7.060(11.9); 7.037(6.2); 7.017 (5.3); 6.996(4.1); 5.298(10.2); 4.412(1.9); 4.401(2.1); 4.386(2.2); 4.300(3.2); 4.286(3.6); 4.275(3.1); 4.260(4.2); 4.246(4.4); 4.232(5.2); 4.217(2.5); 4.179(1.8); 4.164(3.1); 4.150(3.0); 4.135(2.9); 4.119(2.0); 4.104(5.1); 4.088(6.8); 4.073(3.5); 4.067 (3.7); 4.058(2.9); 4.053(3.4); 4.045(3.0); 4.039(3.2); 4.025(3.1); 3.910(1.6); 3.901(1.9); 3.881(2.0); 3.873(1.9); 3.782(1.5); 2.541(0.7); 2.526(1.3); 2.512(1.4); 2.497(1.6); 2.490(2.2); 2.476(1.9); 2.461(2.1); 2.448(1.4); 2.392(3.5); 2.367(3.7); 2.359 (3.1); 2.347(3.5); 2.332(2.4); 2.323(2.1); 2.311(1.4); 2.286(1.5); 1.256(1.5); 0.994(0.6); 0.974(1.6); 0.950(6.5); 0.930(16.0); 0.922(0.6); 0.910(7.9); 0.611(0.7); 0.591(0.7); 0.547(2.5); 0.528(7.3); 0.508(6.7); 0.488(1.8); 0.008(3.2); 0.000(91.7); −0.009(2.6)

Example 289(Iba): $^1$H-NMR (400.0 MHz. CDCl$_3$): δ =

7.518(15.3); 7.294(5.1); 7.260(2831.6); 7.227(5.7); 7.209(4.0); 6.996(16.0); 1.537(809.6); 1.256(2.7); 0.146(3.8); 0.069 (19.1); 0.008(40.2); 0.000(960.5); −0.008(36.7); −0.150(3.9)

| Example 505(Iba): $^1$H-NMR (400.0 MHz. CDCl$_3$): δ = |
|---|
| 8.607(13.2); 8.526(13.9); 8.513(14.5); 8.499(16.0); 7.520(1.2); 7.439(7.7); 7.426(7.6); 7.327(2.9); 7.314(2.9); 7.295(0.9); 7.261(218.8); 7.251(2.0); 7.239(1.9); 7.232(2.5); 7.224(1.9); 7.212(2.1); 7.207(3.3); 7.185(3.2); 7.166(3.1); 7.161(3.1); 7.148(1.0); 7.142(2.9); 7.112(3.7); 7.091(4.5); 7.066(3.7); 7.045(2.2); 6.997(2.6); 6.978(2.2); 6.955(1.4); 6.849(2.0); 5.299 (12.2); 4.358(4.3); 4.342(4.9); 4.148(3.0); 4.132(3.5); 4.038(1.4); 3.928(1.1); 3.918(1.4); 3.902(1.7); 3.890(1.4); 3.876(1.0); 3.726(1.6); 3.712(1.8); 3.699(2.0); 3.614(1.4); 3.602(1.7); 3.587(1.6); 3.498(1.7); 3.353(1.4); 2.280(0.6); 2.267(1.0); 2.244 (1.3); 2.232(1.8); 2.216(1.6); 2.204(2.2); 2.192(1.7); 2.158(1.9); 2.149(1.8); 2.143(1.6); 2.134(1.9); 2.127(2.4); 2.114(3.1); 2.102(2.4); 2.091(3.3); 2.079(2.4); 2.067(1.2); 2.056(1.3); 2.043(0.7); 2.005(0.7); 1.586(1.7); 1.492(2.0); 1.318(1.6); 1.255 (0.9); 0.008(2.6); 0.0064(1.0); 0.0056(1.0); 0.005(1.1); 0.000(80.3); −0.006(0.8); −−0.007(0.7); −0.009(2.3) |

| Example 296(Iba): $^1$H-NMR (400.0 MHz. CDCl$_3$): δ = |
|---|
| 8.410(3.1); 8.403(7.8); 8.396(5.2); 8.205(2.5); 7.969(4.4); 7.519(3.1); 7.373(2.2); 7.365(1.3); 7.359(1.9); 7.353(1.7); 7.342 (1.5); 7.336(1.9); 7.331(1.5); 7.289(1.9); 7.283(2.1); 7.278(1.7); 7.272(4.2); 7.260(579.5); 7.244(1.7); 7.227(0.9); 7.209(0.9); 7.197(2.7); 7.191(2.8); 7.181(2.6); 7.175(2.6); 7.121(1.2); 7.100(3.7); 7.093(2.9); 7.079(2.5); 7.072(6.5); 7.050(4.8); 7.044 (1.2); 7.039(1.3); 7.033(1.1); 7.029(0.7); 7.023(0.6); 7.018(0.6); 7.011(0.6); 6.996(3.3); 6.955(1.6); 6.949(1.6); 6.945(1.8); 6.939(1.6); 6.934(1.3); 6.928(1.3); 6.923(1.2); 6.917(1.1); 5.299(1.6); 4.286(3.44.271(3.9); 4.039(2.3); 4.022(2.5); 3.835 (0.9); 3.814(1.0); 3.802(2.3); 3.788(2.2); 3.775(2.9); 3.762(1.3); 3.713(0.6); 3.703(0.8); 3.687(1.0); 3.676(0.9); 3.672(0.8); 3.662(0.7); 3.561(1.2); 3.550(1.5); 3.540(1.4); 3.535(1.3); 3.529(1.5); 3.523(1.2); 3.513(1.2); 3.502(1.1); 3.440(1.1); 3.426 (1.5); 3.404(1.4); 3.387(1.2); 3.374(0.9); 3.360(0.9); 3.347(0.7); 3.336(0.7); 2.615(1.1); 2.289(0.42.278(0.6); 2.264(0.7); 2.254(0.9); 2.235(0.7); 2.229(0.8); 2.221(0.6); 2.213(1.5); 2.200(1.5); 2.192(1.1); 2.186(1.0); 2.178(1.2); 2.170(0.9); 2.164 (0.8); 2.155(0.9); 2.143(1.4); 2.131(1.3); 2.120(1.7); 2.107(1.5); 2.098(0.7); 2.087(0.9); 2.071(0.8); 2.060(0.8); 2.053(0.6); 2.044(0.6); 2.025(0.6); 2.005(0.6); 1.552(6.2); 1.333(0.9); 1.284(1.0); 1.259(0.9); 0.146(0.6); 0.113(0.8); 0.008(6.2); 0.000 (194.3); −0.009(5.5); −0.150(0.6) |

| Example 613(Iba): $^1$H-NMR (400.0 MHz. CDCl$_3$): δ = |
|---|
| 8.381(16.0); 8.369(1.42); 8.243(1.1); 8.214(15.4); 7.519(5.4); 7.293(0.7); 7.289(0.8); 7.260(956.7); 7.250(5.0); 7.244(2.3); 7.229(3.0); 7.226(3.7); 7.218(2.0); 7.209(3.2); 7.205(3.4); 7.200(1.9); 7.185(2.0); 7.147(0.6); 7.128(1.3); 7.122(1.8); 7.118 (1.4); 7.112(1.2); 7.101(1.3); 7.093(1.8); 7.087(1.4); 7.071(2.0); 7.061(1.4); 7.050(3.1); 7.043(1.5); 7.030(1.9); 7.026(2.); 7.006(1.7); 6.996(5.4); 6.921(1.6); 5.299(2.1); 4.265(4.0); 4.240(4.4); 4.184(3.4); 4.157(4.4); 3.974(0.8); 3.965(0.8); 3.946(1.4); 3.936(1.4); 3.917(0.7); 3.908(0.6); 3.887(0.8); 3.875(0.8); 3.861(1.4); 3.848(1.4); 3.836(0.9); 3.823(0.7); 3.779(0.9); 3.766 (1.4); 3.753(1.8); 3.740(1.8); 3.726(1.1); 3.636(1.0); 3.623(1.6); 3.610(2.0); 3.597(2.0); 3.583(1.2); 3.478(0.9); 3.467(1.1); 3.456(1.2); 3.444(1.2); 3.428(1.0); 3.411(1.0); 3.399(1.1); 3.388(1.2); 3.377(1.2); 3.362(0.9); 3.350(0.9); 2.544(0.6); 2.535 (0.9); 2.522(1.0); 2.510(1.0); 2.499(1.3); 2.490(0.7); 2.476(0.6); 2.294(0.8); 2.266(0.9); 2.231(0.7); 2.040(1.1); 2.013(0.9); 2.005(0.7); 1.936(0.7); 1.923(1.0); 1.912(0.9); 1.901(1.4); 1.888(1.2); 1.878(0.7); 1.865(0.7); 1.543(11.9); 1.371(0.9); 1.333 (1.7); 1.284(2.4); 1.256(2.2); 0.146(1.0); 0.008(9.1); 0.000(336.9); −0.009(9.9); −0.150(1.0) |

| Example 289 threo2(Iba): $^1$H-NMR (400.0 MHz. CDCl$_3$): δ = |
|---|
| 8.393(7.4); 8.195(7.2); 7.521(1.0); 7.295(0.6); 7.262(185.3); 7.246(6.1); 7.155(4.0); 7.134(7.9); 7.131(5.5); 7.114(6.1); 7.110 (7.9); 7.090(5.1); 7.083(4.2); 7.078(4.3); 7.065(4.4); 7.059(5.5); 7.051(4.4); 7.039(4.0); 7.033(4.0); 6.998(1.1); 6.918 (4.2); 6.914(5.2); 6.909(4.4); 6.903(3.9); 6.897(3.7); 6.892(4.3); 6.888(3.4); 5.299(16.0); 4.046(10.1); 4.028(10.6); 3.708(2.7); 3.697(3.8); 3.694(3.8); 3.682(5.1); 3.671(4.4); 3.667(4.2); 3.657(3.2); 3.483(2.2); 3.474(2.2); 3.466(2.7); 3.456(4.3); 3.447 (2.9); 3.439(2.6); 3.429(2.1); 3.391(3.0); 3.380(3.4); 3.367(4.6); 3.356(4.6); 3.341(2.9); 3.330(2.7); 2.324(1.3); 2.310(1.7); 2.300(2.6); 2.289(3.2); 2.276(3.3); 2.265(3.4); 2.255(2.2); 2.241(1.5); 2.096(1.7); 2.086(3.2); 2.075(2.1); 2.069(2.1); 2.058 (3.9); 2.050(3.4); 2.040(1.6); 2.033(1.6); 2.023(2.3); 2.012(1.2); 1.622(3.8); 1.333(0.8); 1.284(1.1); 1.256(1.6); 0.008(2.0); 0.000(64.2); −0.006(0.6); −0.007(0.5); −0.009(1.8) |

| Example 86(Iba): $^1$H-NMR (400.0 MHz. CDCl$_3$): δ = |
|---|
| 8.399(5.2); 8.392(5.9); 8.388(7.3); 8.381(7.0); 8.213(3.8); 7.967(6.9); 7.519(1.3); 7.347(2.5); 7.342(3.2); 7.336(2.6); 7.324 (2.9); 7.319(4.3); 7.313(4.2); 7.305(3.8); 7.295(5.5); 7.290(4.5); 7.285(7.2); 7.280(10.6); 7.277(8.4); 7.260(230.5); 7.250 (9.2); 7.242(3.1); 7.231(7.3); 7.226(3.4); 7.221(4.7); 7.216(2.8); 7.175(0.7); 7.137(4.4); 7.133(7.2); 7.128(3.9); 7.061(2.7); 7.042(2.0); 6.996(1.8); 6.959(3.8); 6.940(3.4); 5.299(16.0); 4.491(0.6); 4.477(0.6); 4.278(5.6); 4.263(5.8); 4.038 (3.3); 4.021(3.5); 3.835(1.0); 3.802(1.5); 3.789(3.1); 3.776(3.2); 3.762(3.8); 3.749(1.9); 3.695(0.9); 3.684(1.4); 3.669(1.6); 3.658(1.3); 3.654(1.2); 3.643(1.2); 3.553(1.7); 3.542(2.0); 3.532(2.1); 3.526(1.8); 3.520(2.1); 3.515(1.7); 3.505(1.6); 3.493 (2.0); 3.473(0.9); 3.463(2.2); 3.447(2.7); 3.437(2.1); 3.425(2.2); 3.408(1.1); 3.389(1.0); 3.377(1.0); 3.365(1.3); 3.353(1.3); 3.339(0.9); 3.327(0.8); 2.964(0.8); 2.945(0.8); 2.911(0.5); 2.315(0.5); 2.300(0.9); 2.291(0.9); 2.281(1.0); 2.266(1.0); 2.25 (1.4); 2.240(1.4); 2.232(1.3); 2.225(0.9); 2.218(2.1); 2.204(2.5); 2.196(1.5); 2.190(1.5); 2.183(1.9); 2.168(1.2); 2.158(1.3); 2.145(2.3); 2.134(2.0); 2.122(2.7); 2.110(2.5); 2.099(1.8); 2.087(1.4); 2.074(1.4); 2.065(0.9); 2.048(0.6); 2.037(0.8); 1.570 (1.7); 1.371(1.1); 1.333(0.9); 1.286(1.7); 1.257(2.5); 0.880(0.5); 0.008(3.5); 0.000(88.5); −0.009(3.7) |

| Example 619(Ibab): $^1$H-NMR (400.0 MHz. CDCl$_3$): δ = |
|---|
| 8.421(9.4); 8.250(10.9); 7.595(1.5); 7.590(1.6); 7.580(1.5); 7.574(1.5); 7.417(1.6); 7.411(1.7); 7.401(1.6); 7.396(1.6); 7.328 (0.7); 7.322(0.7); 7.317(0.8); 7.311(0.7); 7.307(1.1); 7.301(1.1); 7.296(1.1); 7.290(1.0); 7.261(61.7); 7.217(1.9); 7.196(2.6); 7.176(1.3); 7.113(0.7); 7.107(0.7); 7.102(0.8); 7.096(0.8); 7.092(1.1); 7.086(1.1); 7.081(1.1); 7.075(0.9); 7.019(2.2); 6.999 (3.0); 6.978(1.4); 4.267(0.6); 4.254(1.3); 4.239(1.2); 4.225(1.7); 4.216(2.4); 4.190(2.5); 4.164(2.5); 4.136(3.1); 4.117(1.3); 4.102(1.5); 4.088(1.5); 4.075(0.9); 4.046(0.9); 4.034(1.0); 4.024(1.1); 4.017(0.9); 4.012(1.0); 4.006(0.8); 3.995(0.7); 3.983 (0.7); 3.961(16.0); 3.926(14.2); 3.908(0.8); 3.901(0.7); 3.896(0.8); 3.890(0.6); 3.879(0.43.868(0.6); 3.845(0.6); 3.836(0.6); 3.817(1.0); 3.807(1.0); 3.789(0.5); 3.779(0.5); 3.769(0.5); 3.741(0.8); 3.731(0.8); 2.682(0.6); 2.669(0.8); 2.659(0.8); 2.646 (0.8); 2.637(0.5); 2.464(0.5); 2.437(0.6); 2.183(0.6); 2.015(0.6); 2.004(0.6); 1.992(0.7); 1.980(0.7); 1.586(0.6); 1.255(0.7); 0.008(0.8); 0.000(23.4); −0.008(0.8) |

-continued

| Example 599(Ibae): $^1$H-NMR (400.0 MHz. CDCl$_3$): δ = |
|---|
| 8.409(5.4); 8.215(5.9); 7.400(1.0); 7.396(2.3); 7.394(2.0); 7.392(1.5); 7.378(3.0); 7.274(0.8); 7.269(1.2); 7.261(39.2); 7.252 (1.0); 7.247(0.6); 7.242(0.5); 7.240(0.5); 7.237(0.6); 7.226(0.7); 7.222(1.0); 7.221(1.3); 7.217(1.1); 7.196(2.7); 7.177(1.7); 7.157(0.7); 7.052(0.9); 7.033(0.7); 4.214(1.4); 4.206(0.7); 4.188(1.8); 4.177(0.9); 4.163(1.7); 4.135(1.7); 4.058(0.6); 4.043 (0.6); 4.029(1.2); 4.016(0.7); 3.922(8.4); 3.889(0.5); 3.882(4.2); 3.878(4.3); 3.849(0.5); 3.822(0.5); 3.812(0.5); 3.407(16.0); 3.387(14.7); 0.000(14.8) |

| Example 289 threo 1(Iba): $^1$H-NMR (400.0 MHz. CDCl$_3$): δ = |
|---|
| 8.395(14.8); 8.389(14.9); 8.193(14.6); 7.521(1.2); 7.295(0.8); 7.285(0.6); 7.284(0.6); 7.283(0.6); 7.2823(0.5); 7.2815(0.5); 7.281(0.6); 7.2783(0.9); 7.2775(0.9); 7.277(1.0); 7.276(1.2); 7.272(6.5); 7.2663(10.5); 7.2655(11.5); 7.262 (205.0); 7.256(2.0); 7.255(1.7); 7.254(1.5); 7.253(1.4); 7.252(1.4); 7.249(5.9); 7.244(7.3); 7.238(5.5); 7.155(5.5); 7.134(9.2); 7.131(6.3); 7.114(7.2); 7.110(9.2); 7.089(6.6); 7.083(5.1); 7.077(5.3); 7.065(5.2); 7.059(6.1); 7.057(6.0); 7.050(5.4); 7.038 (4.9); 7.032(5.1); 6.998(1.2); 6.923(3.3); 6.918(4.3); 6.913(6.2); 6.908(4.4); 6.902(4.4); 6.897(3.7); 6.892(5.0); 6.887(3.5); 6.882(2.5); 5.299(8.7); 4.045(15.0); 4.027(16.0); 3.708(4.0); 3.698(4.8); 3.694(4.9); 3.682(6.6); 3.671(5.8); 3.667(5.6); 3.657 (4.8); 3.482(2.7); 3.472(2.9); 3.464(2.8); 3.454(5.3); 3.445(3.1); 3.437(2.9); 3.427(2.6); 3.391(4.8); 3.380(5.6); 3.367(6.2); 3.365(5.4); 3.356(6.1); 3.353(5.8); 3.341(4.8); 3.329(4.4); 2.323(2.1); 2.313(2.3); 2.309(2.5); 2.299(4.3); 2.288(4.4); 2.285 (2.9); 2.278(3.4); 2.274(4.4); 2.264(5.6); 2.254(3.1); 2.250(2.9); 2.240(2.6); 2.096(1.7); 2.085(5.0); 2.074(2.9); 2.068(2.8); 2.058(5.3); 2.050(4.3); 2.047(3.4); 2.039(2.1); 2.033(2.2); 2.022(3.7); 2.011(1.9); 1.592(5.5); 1.333(1.0); 1.284(1.4); 1.255 (1.6); 0.008(2.0); 0.000(66.6); −0.009(2.0) |

| Example 512(Iba): $^1$H-NMR (400.0 MHz. CDCl$_3$): δ = |
|---|
| 8.564(1.2); 8.544(11.3); 8.529(3.7); 8.495(16.0); 8.471(1.0); 8.440(0.7); 8.425(1.0); 8.412(7.1); 8.400(7.1); 8.393(2.6); 8.381(2.6); 8.372(10.3); 8.360(10.3); 7.521(0.9); 7.500(4.9); 7.495(5.3); 7.484(5.1); 7.478(5.3); 7.453(3.8); 7.447(4.1); 7.436 (3.9); 7.430(4.1); 7.373(0.8); 7.333(3.3); .327(3.3); 7.322(3.5); 7.316(3.6); 7.311(4.6); 7.305(4.5); 7.300(4.5); 7.294(4.6); 7.286(3.0); 7.281(3.3); 7.275(3.5); 7.270(5.2); 7.262(109.3); 7.254(4.7); 7.242(1.5); 7.219(6.0); 7.202(11.1); 7.198(12.8); 7.187(8.0); 7.181(12.3); 7.176(4.7); 7.160(5.4); 7.127(0.7); 7.105(8.9); 7.092(8.6); 6.998(0.8); 5.299(5.0); 4.417(7.0); 4.402 (7.1); 4.052(5.4); 4.034(5.5); 3.868(0.5); 3.851(0.5); 3.811(3.1); 3.801(3.1); 3.784(3.4); 3.773(3.4); 3.727(0.5); 3.690(13.9); 3.564(3.2); 3.546(3.4); 3.537(5.8); 3.519(6.0); 3.501(3.9); 3.489(4.1); 3.481(6.1); 3.472(8.7); 3.462(3.5); 3.454(3.5); 3.445 (3.1); 3.090(1.7); 3.071(3.2); 3.051(2.1); 3.021(3.2); 3.011(3.4); 2.987(4.8); 2.977(4.8); 2.885(1.8); 2.866(5.4); 2.852(4.7); 2.838(5.9); 2.827(7.5); 2.811(5.2); 2.804(4.4); 2.792(1.7); 2.777(1.4); 2.702(2.3); 2.683(3.6); 2.664(1.9); 2.494(0.9); 2.483 (1.5); 2.470(2.0); 2.465(1.9); 2.460(2.2); 2.451(2.2); 2.446(1.9); 2.441(2.4); 2.430(2.3); 2.422(2.0); 2.413(2.7); 2.404(2.5); 2.397(2.6); 2.387(2.4); 2.379(1.5); 2.370(1.3); 2.360(0.7); 1.840(1.0); 1.255(0.5); 0.008(1.6); 0.000(40.9); −0.009(1.7) |

| Example 619(Ibab): $^1$H-NMR (400.0 MHz. CDCl$_3$): δ = |
|---|
| 8.421(9.4); 8.250(10.9); 7.595(1.5); 7.590(1.6); 7.580(1.5); 7.574(1.5); 7.417(1.6); 7.411(1.7); 7.401(1.6); 7.396(1.6); 7.328 (0.7); 7.322(0.7); 7.317(0.8); 7.311(0.7); 7.307(1.1); 7.301(1.1); 7.296(1.1); 7.290(1.0); 7.261(61.7); 7.217(1.9); 7.196(2.6); 7.176(1.3); 7.113(0.7); 7.107(0.7); 7.102(0.8); 7.096(0.8); 7.092(1.1); 7.086(1.1); 7.081(1.1); 7.075(0.9); 7.019(2.2); 6.999 (3.0); 6.978(1.4); 4.267(0.6); 4.254(1.3); 4.239(1.2); 4.225(1.7); 4.216(2.4); 4.190(2.5); 4.164(2.5); 4.136(3.1); 4.117(1.3); 4.102(1.2); 4.088(1.5); 4.075(0.9); 4.046(0.9); 4.034(1.0); 4.024(1.1); 4.017(0.9); 4.012(1.0); 4.006(0.8); 3.995(0.7); 3.983 (0.7); 3.961(16.0); 3.926(14.2); 3.908(0.8); 3.901(0.7); 3.896(0.8); 3.890(0.6); 3.879(0.43.868(0.6); 3.845(0.6); 3.836(0.6); 3.817(1.0); 3.807(1.0); 3.789(0.5); 3.779(0.5); 3.769(0.5); 3.741(0.8); 3.731(0.8); 2.682(0.6); 2.669(0.8); 2.659(0.8); 2.646 (0.8); 2.637(0.5); 2.464(0.5); 2.437(0.6); 2.183(0.6); 2.015(0.6); 2.004(0.6); 1.992(0.7); 1.980(0.7); 1.586(0.6); 1.255(0.7); 0.008(0.8); 0.000(23.4); −0.008(0.8) |

| Example 6198(Iba): $^1$H-NMR (400.0 MHz. CDCl$_3$): δ = |
|---|
| 8.384(14.1); 8.219(16.0); 7.588(2.5); 7.582(2.7); 7.572(2.6); 7.566(2.7); 7.519(1.1); 7.431(2.4); 7.425(2.6); 7.415(2.47.); 7.410(2.6); 7.325(1.3); 7.319(1.3); 7.314(1.5); 7.308(1.4); 7.304(1.9); 7.298(1.9); 7.293(2.0); 7.287(1.7); 7.260(176.1); 7.191 (3.4); 7.170(4.9); 7.150(2.8); 7.122(1.3); 7.116(1.2); 7.111(1.3); 7.105(1.3); 7.101(1.7); 7.095(1.7); 7.089(1.7); 7.084(1.6); 7.010(3.9); 6.996(1.3); 6.990(5.2); 6.969(2.6); 4.258(3.45); .233(4.0); 4.176(3.8); 4.148(4.9); 3.972(0.9); 3.962(0.9); 3.944 (1.5); 3.935(1.5); 3.917(0.7); 3.879(0.8); 3.867(0.8); 3.853(1.4); 3.841(1.4); 3.828(0.8); 3.816(0.7); 3.780(1.1); 3.767(1.7); 3.753(2.0); 3.740(2.0); 3.727(1.3); 3.632(1.0); 3.619(1.6); 3.606(2.1); 3.593(2.0); 3.580(1.3); 3.477(1.2); 3.466 (1.3); 3.454(1.4); 3.450(1.3); 3.443(1.4); 3.439(1.3); 3.427(1.2); 3.415(1.1); 3.409(1.2); 3.397(1.2); 3.386(1.3); 3.382(1.1); 3.375(1.3); 3.371(1.1); 3.360(1.0); 3.348(1.0); 2.553(0.6); 2.543(0.6); 2.539(0.6); 2.530(1.0); 2.518(1.1); 2.507(1.1); 2.495 (1.2); 2.485(0.8); 2.482(0.8); 2.472(0.6); 2.297(0.9); 2.282(0.6); 2.270(1.0); 2.266(0.9); 2.262(0.9); 2.258(0.8); 2.234(0.7); 2.071(0.7); 2.059(0.5); 2.047(0.8); 2.044(0.9); 2.036(1.1); 2.021(0.8); 2.009(0.9); 1.997(0.5); 1.928(0.7); 1.915(1.0); 1.904 (0.9); 1.893(1.3); 1.880(1.2); 1.870(0.7); 1.858(0.7); 1.845(0.5); 1.672(0.8); 1.621(0.6); 0.008(2.0); 0.000(66.8); −0.009(2.0) |

| Example 208 threo(Iba): $^1$H-NMR (400.0 MHz. CDCl$_3$): δ = |
|---|
| 8.574(1.9); 8.570(2.0); 8.563(2.0); 8.559(2.0); 8.519(10.6); 8.515(11.0); 8.508(10.9); 8.504(10.9); 7.723(2.4); 7.720(2.4); 7.703(2.6); 7.699(2.5); 7.538(13.3); 7.534(13.7); 7.517(15.0); 7.513(14.7); 7.261(206.1); 7.223(2.7); 7.217(0.9); 7.211(3.7); 7.202(3.2); 7.199(1.0); 7.191(3.4); 7.182(1.6); 7.178(1.0); 7.172(0.9); 7.167(1.1); 7.162(1.4); 7.157(1.5); 7.138(1.2); 7.112 (16.2); 7.100(15.5); 7.091(14.3); 7.080(14.1); 7.024(4.2); 7.003(7.8); 7.000(5.1); 6.995(4.9); 6.989(5.3); 6.983(6.); 6.978 (9.3); 6.971(5.7); 6.968(5.2); 6.962(5.5); 6.958(6.5); 6.950(4.2); 6.944(4.8); 6.909(3.6); 6.905(3.9); 6.903(3.7); 6.899(5.6); 6.895(4.2); 6.893(3.7); 6.889(3.7); 6.884(2.9); 6.877(3.7); 6.874(2.7); 6.868(2.1); 4.366(12.7); 4.360(2.8); 4.341(16.0); 4.160 (4.3); 4.143(7.2); 4.134(4.0); 4.126(4.6); 4.117(5.6); 4.109(1.8); 4.100(3.6); 4.085(0.7); 3.631(3.3); 3.617(6.8); 3.603(8.4); 3.589(9.6); 3.575(4.9); 3.523(0.6); 3.509(1.1); 3.495(1.5); 3.488(5.1); 3.481(3.7); 3.472(7.5); 3.461(3.9); 3.454(5.6); 3.443 (5.1); 3.427(3.7); 3.412(1.0); 3.398(1.1); 3.392(1.1); 3.384(0.7); 3.378(1.1); 3.371(0.7); 3.364(0.7); 3.351(0.6); 2.409(8.5); 2.393(12.7); 2.377(12.6); 2.361(7.8); 2.093(0.7); 2.069(0.8); 2.058(1.5); 2.048(0.5); 2.045(0.5); 2.034(0.9); 1.873(0.5); 1.868 (0.6); 1.864(0.6); 1.858(0.6); 1.853(0.6); 1.849(0.8); 1.838(0.8); 1.607(3.5); 0.008(2.1); 0.000(77.2); −0.009(2.2) |

-continued

Example 1693(Iba): $^1$H-NMR (400.0 MHz. CDCl$_3$): δ =

8.012(0.8); 7.261(52.9); 7.160(0.8); 7.156(1.4); 7.139(1.4); 7.135(3.0); 7.131(1.6); 7.118(1.47.115(2.8); 7.110(2.3); 7.094 (1.0); 7.090(1.6); 7.086(0.7); 7.080(0.7); 7.068(0.6); 7.062(0.8); 7.059(0.7); 7.053(0.7); 7.041(0.6); 7.035(0.7); 7.025(1.1); 7.019(1.3); 7.007(1.2); 7.001(1.4); 6.998(1.4); 6.992(1.3); 6.980(1.1); 6.974(1.2); 6.963(0.6); 6.958(0.8); 6.954(0.6); 6.948 (0.6); 6.937(0.6); 6.926(0.9); 6.921(1.1); 6.915(1.4); 6.911(1.1); 6.905(1.1); 6.899(0.6); 6.894(1.2); 6.889(0.8); 6.885(0.6); 6.377(3.2); 6.368(5.6); 6.359(3.7); 6.279(4.2); 6.275(4.3); 6.269(3.5); 6.265(3.5); 6.257(2.2); 6.252(2.2); 6.247(1.9); 6.242 (1.48); .144(3.5); 4.130(3.6); 3.951(1.9); 3.933(2.0); 3.821(1.0); 3.808(2.2); 3.795(2.1); 3.781(2.9); 3.769(1.5); 3.762(0.7) 3.757(0.6); 3.745(0.8); 3.735(0.8); 3.730(0.8); 3.720(0.7); 3.655(1.4); 3.643(1.5); 3.633(1.6); 3.628(1.2); 3.622(1.6); 3.616 (1.2); 3.606(1.2); 3.595(1.1); 3.563(0.7); 3.551(0.8); 3.539(0.9); 3.536(0.7); 3.528(0.9); 3.525(0.8); 3.512(0.7); 3.501(0.6); 3.488(1.2); 3.437(0.7); 3.432(1.1); 3.424(1.4); 3.418(1.3); 3.408(1.2); 3.404(1.0); 3.400(1.2); 3.394(1.0); 3.386(0.5); 2.957 (7.8); 2.956(7.8); 2.882(6.7); 2.881(6.7); 2.264(0.6); 2.229(0.7); 2.137(0.7); 2.115(1.4); 2.102(2.0); 2.094(1.1); 2.088(1.0); 2.080(1.8); 2.078(1.3); 2.066(2.2); 2.053(1.8); 2.042(1.9); 2.030(1.4); 2.018(0.7); 2.005(16.0); 1.943(0.6); 1.915(0.6); 1.908 (0.5); 1.462(2.5); 0.008(0.6); 0.000(19.5); −0.009(0.6)

Example 1700(Iba): $^1$H-NMR (400.0 MHz. CDCl$_3$): δ =

8.005(1.8); 7.291(3.2); 7.285(3.4); 7.274(3.2); 7.269(3.7); 7.262(60.2); 7.230(6.1); 7.224(6.4); 7.213(6.3); 7.207(6.3); 7.123 (1.7); 7.116(5.3); 7.102(6.4); 7.094(14.3); 7.086(3.5); 7.081(7.6); 7.073(11.9); 7.069(3.7); 7.065(1.2); 7.059(1.0); 7.053 (0.8); 7.044(4.5); 7.038(4.3); 7.032(4.8); 7.027(4.4); 7.022(2.8); 7.016(2.5); 7.011(2.4); 7.005(2.2); 6.998(0.5); 6.378(3.1); 6.377(3.1); 6.373(5.8); 6.372(5.8); 6.369(6.4); 6.364(10.8); 6.355(6.5); 6.282(10.0); 6.278(10.1); 6.272(8.2); 6.268(8.1); 6.261 (5.1); 6.256(5.1); 6.251(4.3); 6.247(4.2); 4.138(9.2); 4.124(9.5); 3.950(5.1); 3.931(5.5); 3.819(2.4); 3.806(5.3); 3.792(5.1); 3.779(7.2); 3.770(1.8); 3.766(3.6); 3.761(1.7); 3.756(1.6); 3.744(2.1); 3.734(1.9); 3.729(1.9); 3.719(1.7); 3.653(3.3); 3.641 (3.7); 3.632(3.8); 3.626(2.9); 3.620(3.8); 3.614(2.9); 3.605(2.8); 3.593(2.6); 3.562(1.7); 3.550(1.9); 3.538(2.1); 3.535(1.7); 3.526(2.1); 3.523(1.8); 3.511(1.6); 3.499(1.4); 3.485(6.8); 3.458(0.7); 3.450(1.0); 3.441(1.0); 3.433(2.1); 3.429(2.2); 3.420 (3.2); 3.413(3.5); 3.404(3.2); 3.396(3.3); 3.390(2.6); 3.381(1.3); 3.375(1.2); 2.958(16.0); 2.880(13.4); 2.879(12.9); 2.281(0.7); 2.272(0.7); 2.267(0.8); 2.258(1.5); 2.247(1.2); 2.243(0.9); 2.237(1.0); 2.232(1.2); 2.223(1.8); 2.214(0.9); 2.208(0.9); 2.199 (0.8); 2.146(0.8); 42.133(1.7); 2.125(0.9); 2.120(1.1); 2.111(3.5); 2.098(4.8); 2.090(2.8); 2.085(2.4); 2.077(4.2); 2.071(2.5); 2.063(2.5); 2.059(4.6); 2.047(4.3); 2.035(4.6); 2.023(3.4); 2.012(1.7); 2.000(1.7); 1.988(0.8); 1.952(0.9); 1.941(1.4); 1.930 (0.9); 1.923(0.9); 1.917(1.); 1.913(1.5); 1.906(1.3); 1.902(1.0); 1.896(0.8); 1.888(0.8); 1.878(1.1); 1.867(0.7); 1.489(10.1); 0.008(0.7); 0.000(22.5); −0.009(0.7)

The retention time (Rt) given in the Rt table below for the enantiomer of the formula (Ia) in question is given in minutes (min), where the letter a, b, c or d given after the forward slash after the retention time refers to the conditions stated above for HPLC on a chiral column and the respective mobile phase stated above, i.e. mobile phase a, mobile phase b, mobile phase c or mobile phase d.

Rt Table: Rt in min.

| No. | Q(R$^2$)$_n$ | (R$^3$)$_m$ | erythro-1 | erythro-2 | threo-1 | threo-2 |
|---|---|---|---|---|---|---|
| 289a | 3,4-F$_2$ | 5-fluoropyridin-3-yl | 7.070/c | 7.385/c | 11.894/c | 14.023/c |

Formulation Examples a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A readily water-dispersible dispersion concentrate is obtained by mixing 20 parts by weight of a compound of the formula (I) with 6 parts by weight of alkylphenol poly glycol ether (®Triton X 207), 3 parts by weight of isotridecanol polyglycol ether (8 EO) and 71 parts by weight of paraffinic mineral oil (boiling range for example about 255 to about 277° C.) and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxyethylated nonylphenol as emulsifier.

e) Water-dispersible granules are obtained by mixing

| | | |
|---|---|---|
| 75 | parts by weight | of a compound of the formula (I), |
| 10 | parts by weight | of calcium lignosulfonate, |
| 5 | parts by weight | of sodium lauryl sulfate, |
| 3 | parts by weight | of polyvinyl alcohol and |
| 7 | parts by weight | of kaolin, | grinding the mixture in a pinned-disk mill, and granulating the powder in a fluidized bed by spray application of water as a granulating liquid.

f) Water-dispersible granules are also obtained by homogenizing and precomminuting, in a colloid mill,

| | | |
|---|---|---|
| 25 | parts by weight | of a compound of the formula (I), |
| 5 | parts by weight | of sodium 2,2'-dinaphthylmethane-6,6'-disulfonate, |
| 2 | parts by weight | of sodium oleoylmethyltaurinate, |
| 1 | part by weight | of polyvinyl alcohol, |
| 17 | parts by weight | of calcium carbonate and |
| 50 | parts by weight | of water, | then grinding the mixture in a bead mill and atomizing and drying the resulting suspension in a spray tower by means of a one-phase nozzle.

BIOLOGICAL EXAMPLES

Example PE

Herbicidal Pre-Emergence Action

Seeds of monocotyledonous and dicotyledonous weed plants and crop plants were placed in wood-fiber pots in sandy loam and covered with soil. The compounds (I) according to the invention, formulated in the form of wettable powders (WP), were then applied as aqueous suspension or emulsion at a water application rate of 600 l/ha (converted) with the addition of 0.2% of wetting agent to the surface of the covering soil.

After the treatment, the pots were placed in a greenhouse and kept under good growth conditions for the test plants. After about 3 weeks, the effect was scored visually in comparison with untreated controls as percentages. For example, 100% activity=the plants have died, 50% herbicidal activity or damage=the plants have been reduced by 50% or the plant mass has been reduced by 50%, 0% activity=like control plants.

The results obtained show that compounds (I) according to the invention and their salts, in particular the compounds according to the invention characterized as preferred, have good to very good pre-emergence herbicidal activity against harmful plants at an application rate of 320 g or less per hectare, generally also even at a respective application rate of 80 g/ha.

The biological tests were carried out in each case separately with the compounds according to the invention below which, by virtue of the good to very good herbicidal activity thereof, are particularly preferred according to the invention:

Compound No. 532a threo, 532a erythro, 1288a, 1272a, 1295a, 208 threo, 208a, 208a threo, 215a, 1477a, 1461a, 1484a, 1542a, 1558a, 1565a, 1677a, 1531a, 1515a, 1538a, 181a, 647a, 1153a, 1137a, 1516a, 289a, 289 threo-1, 289 erythro-1, 100a, 107a, 296a, 613a, 620a, 86a, 597a, 512a, 599a and 599bae.

Here, these compounds according to the invention were in each case employed in the biological tests as a component of a wettable powder (WP formulation).

At an application rate of 320 g/ha, all the compounds according to the invention mentioned showed 80% to 100% herbicidal activity in the biological tests, against one, more than one or all of the harmful plants below:

ALOMY=*Alopecurus myosuroides*
AVEFA=*Avena fatua*
CYPES=*Cyperus esculentus*
ECHCG=*Echinochloa crus-galli*
LOLMU=*Lolium multiflorum*
SETVI=*Setaria viridis*
ABUTH=*Abutilon theophrasti*
AMARE=*Amaranthus retroflexus*
POLCO=*Polygonum convolvulus* (=*Fallopia convolvulus*)
STEME=*Stellaria media*
VIOTR=*Viola tricolor*
VERPE=*Veronica persica*

What was determined was the respective herbicidal activity, in each case at the same point in time after application of the formulation in question, i.e. the damage to the respective harmful plant in %.

Furthermore, the compounds according to the invention mentioned above were applied to the following useful plants, in each case at the application rates mentioned.

ORYSA=*Oryza sativa* (common rice)
TRZAS=*triticum aestivum* (spring) (summer wheat)
ZEAMX=*Zea mays* (maize)
BRSNW=*Brassica napus* subsp. *napus* (winter) (winter oilseed rape)

Here, the observed damage to said useful plants was in each case within the acceptable range and was generally assessed as low (generally in the range from 0 to 20%, mostly in the range from 0 to 10%).

Example PO

Herbicidal Post-Emergence Action

Seeds of monocotyledonous and dicotyledonous weeds and crop plants were placed in sandy loam in wood-fiber pots, covered with soil and cultivated in a greenhouse under good growth conditions. 2 to 3 weeks after sowing, the test plants were treated at the one-leaf stage, where the compounds according to the invention, formulated in the form of wettable powders (WP), were applied by spraying as aqueous suspension or emulsion at a water application rate of 600 l/ha (converted) with the addition of 0.2% of wetting agent to the green parts of the plants. After the test plants had been kept in the greenhouse under optimum growth conditions for about 3 weeks, the activity of the preparations was rated visually in comparison to untreated controls in percent (%). For example, 100% activity=the plants have died, 50% herbicidal activity or damage=the plants have been reduced by 50% or the plant mass has been reduced by 50%, 0% activity=like control plants.

The biological tests were in each case carried out separately using the compounds according to the invention below which are particularly preferred according to the invention by virtue of their good to very good herbicidal activity:

Compound No. 532a threo, 1288a, 1542a, 1558a, 1700, 1700a, 1531a, 151a, 1538a, 181a, 647a, 1516a, 289a, 289 erythro-1, 289 threo-2, 100a, 107a, 296a, 613a, 620a, 86a, 84a, 295a, 599a, 599bae, 619, 6191bab, 619a and 619bab.

The results obtained show that compounds (I) according to the invention and their salts, in particular the compounds according to the invention mentioned as being preferred, have good to very good post-emergence herbicidal activity against harmful plants at an application rate of 320 g or less per hectare, frequently even at a respective application rate of 80 g/ha.

At an application rate of 320 g/ha, all of the compounds according to the invention mentioned show, in the biological tests, 80% to 100% herbicidal activity against one, more than one or all of the harmful plants mentioned in the above biological example PE. In each case, as in the above biological example PE, the observed damage of the crop plants ORYSA, TRZAS, ZEAMX and BRSNW was likewise in the acceptable range.

The invention claimed is:

1. A compound of the formula (I) or salt thereof,

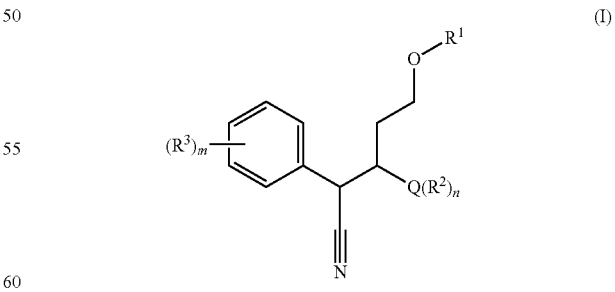

in which

Q represents a mono- or bicyclic heteroaromatic radical with in total 1 to 9 carbon ring atoms, where the heteroatom or heteroatoms in the heteroaromatic ring are selected from the group consisting of N, O, S, P, B, Si, and Se, R¹ represents hydrogen or a hydrolyzable radical, (R²)$_n$ represent n substituents R², where R² (if n=1) or each of the substituents R² (if n is greater than 1) independently of one another represents halogen, cyano, nitro, $(C_1-C_8)$alkyl, $(C_1-C_8)$alkoxy, $(C_1-C_8)$alkylthio, $(C_1-C_8)$alkylsulfinyl, $(C_1-C_8)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri-[$(C_1-C_4)$alkyl]silyl or tri-[$(C_1-C_4)$alkyl]silyl-$(C_1-C_4)$alkyl, or in each case two R² directly adjacent on the heteroaromatic radical Q are together a group of the formula —Z¹-A*¹—Z²—, in which A* represents an alkylene group having 1 to 4 carbon atoms which is optionally substituted by one or more radicals selected from the group consisting of halogen, $(C_1-C_4)$alkyl, $(C_1-C_4)$haloalkyl, $(C_1-C_4)$alkoxy and $(C_1-C_4)$haloalkoxy, Z¹ represents a direct bond, O or S and Z² represents a direct bond, O or S, where the group —Z¹-A*-Z²— together with the atoms of the heteroaromatic radical Q bonded to this group Q form a 5- or 6-membered ring, and (R³)$_m$ represents m substituents R³, where R³ (if m=1) or each of the substituents R³ (if m is greater than 1) independently of one another represents halogen, cyano, nitro, $(C_1-C_8)$alkyl, $(C_1-C_8)$alkoxy, $(C_1-C_8)$alkylthio, $(C_1-C_8)$alkylsulfinyl, $(C_1-C_8)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri-[$(C_1-C_4)$alkyl]silyl, tri-[$(C_1-C_4)$alkyl]silyl-$(C_1-C_4)$alkyl or —NR*R**, where R* and R**, independently of one another and independently of any other radicals —NR*R** present, are in each case selected from the group consisting of H, $(C_1-C_8)$alkyl, $(C_2-C_8)$alkenyl, $(C_2-C_8)$alkynyl, $(C_1-C_4)$alkoxy-$(C_1-C_4)$alkyl, $(C_1-C_6)$alkanoyl, [$(C_1-C_4)$haloalkyl]carbonyl, [$(C_1-C_4)$alkoxy]carbonyl, [$(C_1-C_4)$haloalkoxy]carbonyl, $(C_3-C_6)$cycloalkyl, $(C_3-C_6)$cycloalkyl-$(C_1-C_4)$alkyl, $(C_3-C_6)$cycloalkenyl, $(C_3-C_6)$cycloalkenyl-$(C_1-C_4)$alkyl, phenyl and phenyl-$(C_1-C_4)$alkyl, where each of the specified radicals $(C_3-C_6)$cycloalkyl, $(C_3-C_6)$cycloalkyl-$(C_1-C_4)$alkyl, $(C_3-C_6)$cycloalkenyl, $(C_3-C_6)$cycloalkenyl-$(C_1-C_4)$alkyl, phenyl and phenyl-$(C_1-C_4)$alkyl is substituted in the cycle optionally by one or more identical or different radicals R$^{bb}$, where R$^{bb}$ in each case represents halogen, $(C_1-C_4)$alkyl, $(C_1-C_4)$haloalkyl, $(C_1-C_4)$alkoxy or $(C_1-C_4)$haloalkoxy and, in the case of $(C_3-C_6)$cycloalkyl, $(C_3-C_6)$cycloalkyl-$(C_1-C_4)$alkyl, $(C_3-C_6)$cycloalkenyl, $(C_3-C_6)$cycloalkenyl-$(C_1-C_4)$alkyl, R$^{bb}$ may additionally represent oxo, or NR*R represents a 3- to 8-membered heterocycle which, in addition to this nitrogen atom, optionally contains one or two further ring heteroatoms selected from the group consisting of N, O and S and which is unsubstituted or substituted by one or more radicals selected from the group consisting of $(C_1-C_4)$alkyl, $(C_1-C_4)$haloalkyl and oxo, or where in each case two groups R³ directly adjacent on the ring together represent a group of the formula —Z³-A-Z⁴—, in which A represents an alkylene group having 1 to 4 carbon atoms which is optionally substituted by one or more radicals selected from the group consisting of halogen, $(C_1-C_4)$alkyl, $(C_1-C_4)$haloalkyl, $(C_1-C_4)$alkoxy and $(C_1-C_4)$haloalkoxy, Z³ represents a direct bond, O or S and Z⁴ represents a direct bond, 0 or S, where the group —Z³-A-Z⁴ together with the carbon atoms, bonded to this group, of the phenyl ring form a 5- or 6-membered ring, n represents 0, or an integer in the range from 1 to 5, and m represents 0, 1, 2, 3, 4 or 5.

2. The compound of the formula (I) or salt thereof according to claim 1, wherein Q represents a mono- or bicyclic heteroaromatic radical having in total 2 to 9 carbon ring atoms, where the heteroaromatic radical Q contains 1, 2, 3 or 4 heteroatoms in the heteroaromatic ring and the heteroatom or the heteroatoms are selected from the group consisting of N, O, and S.

3. The compound of the formula (I) or salt thereof as claimed in claim 1, wherein Q represents a mono- or bicyclic heteroaromatic radical selected from the group consisting of pyrimidinyl, pyridinyl, pyridazinyl, pyrazinyl, thienyl, furyl, oxazolyl, thiazolyl, imidazolyl, pyrazolyl, triazinyl, quinolyl, isoquinolyl, cinnolinyl-, quinazolinyl, quinoxalinyl, pteridinyl, indolyl and phthalazinyl.

4. The compound of the formula (I) or salt thereof as claimed in claim 1, wherein the compound of the formula (I) corresponds to the formula (I-1), (I-2) or (I-3) defined below

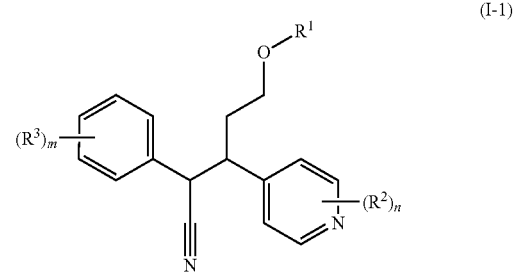

(I-1)

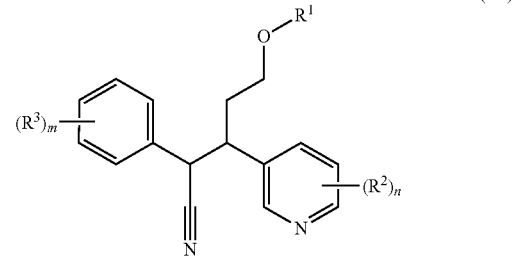

(I-2)

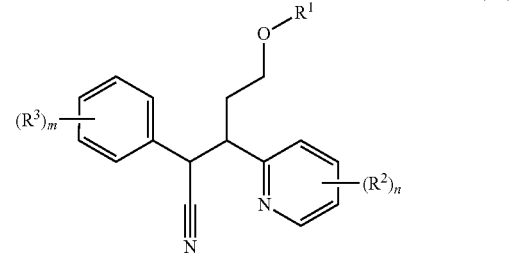

(I-3)

where
$R^1$, $R^2$, $R^3$, m and n have the meaning defined in claim 1.

5. The compound of the formula (I) or salt thereof as claimed in claim 1, wherein
$R^1$ represents hydrogen or a hydrolyzable radical having in total up to 30 carbon atoms.

6. The compound of the formula (I) or salt thereof as claimed in claim 1, wherein
$R^1$ represents hydrogen or a hydrolyzable radical having in total 1 to 24 carbon atoms, where $R^1$
represents an optionally substituted hydrocarbon radical or an optionally substituted heterocyclyl radical, or
represents a radical of the formula $SiR^aR^bR^c$, or $-NR^aR^b$,
where each of the radicals $R^a$ and $R^b$ independently of the other represents hydrogen or an optionally substituted hydrocarbon radical and $R^c$ independently represents an optionally substituted hydrocarbon radical, or
$-NR^aR^b$ represents a 3- to 9-membered heterocycle which, in addition to this nitrogen atom, may contain one or two further ring heteroatoms from the group consisting of N, O and S and which is substituted or unsubstituted, or
represents a radical of the formula $-C(=O)-R^e$ or $-P(=O)(R^f)_2$, where $R^e$ and both radicals $R^f$ in each case independently of one another are selected from the group consisting of hydrogen, OH, unsubstituted or substituted $(C_1-C_8)$alkyl, unsubstituted or substituted $(C_1-C_4)$haloalkyl, unsubstituted or substituted $(C_2-C_8)$alkenyl, unsubstituted or substituted $(C_2-C_8)$alkynyl, unsubstituted or substituted $(C_1-C_6)$alkoxy, unsubstituted or substituted $(C_1-C_6)$alkoxy-$(C_1-C_8)$alkyl, unsubstituted or substituted $(C_1-C_4)$haloalkoxy, unsubstituted or substituted $(C_1-C_4)$haloalkoxy-$(C_1-C_8)$alkyl, unsubstituted or substituted $(C_3-C_8)$alkenyloxy, unsubstituted or substituted $(C_3-C_8)$alkenyloxy-$(C_1-C_8)$alkyl, unsubstituted or substituted $(C_3-C_8)$alkynyloxy, unsubstituted or substituted $(C_3-C_8)$alkynyloxy-$(C_1-C_8)$alkyl, unsubstituted or substituted $-NR^*R^{**}$, where $R^*$ and $R^{**}$ are as defined above, unsubstituted or substituted tri-$[(C_1-C_4)$alkyl]silyl, unsubstituted or substituted tri-$[(C_1-C_4)$alkyl]silyl-$(C_1-C_8)$alkyl, unsubstituted or substituted $(C_3-C_6)$cycloalkyl, unsubstituted or substituted $(C_3-C_6)$cycloalkyl-$(C_1-C_8)$alkyl, unsubstituted or substituted $(C_5-C_6)$cycloalkenyl, unsubstituted or substituted $(C_5-C_6)$cycloalkenyl-$(C_1-C_8)$alkyl, unsubstituted or substituted $(C_5-C_6)$cycloalkynyl, unsubstituted or substituted $(C_5-C_6)$cycloalkynyl-$(C_1-C_8)$alkyl, unsubstituted or substituted phenyl, unsubstituted or substituted phenyl-$(C_1-C_8)$alkyl, unsubstituted or substituted phenoxy, unsubstituted or substituted phenoxy-$(C_1-C_8)$alkyl, unsubstituted or substituted phenylamino, unsubstituted or substituted phenylamino$(C_1-C_8)$alkyl, unsubstituted or substituted Het, unsubstituted or substituted Het-$(C_1-C_6)$alkyl and unsubstituted or substituted Het-O—$(C_1-C_6)$alkyl, where
Het in each case represents a saturated, partially unsaturated or heteroaromatic monocyclic heterocyclyl radical having 3 to 9 ring atoms or a 9- or 10-membered bicyclic heterocycle in each case containing 1, 2, 3 or 4 heteroatoms selected from the group consisting of O, N and S, where each of the specified substituted radicals is substituted in the acyclic moiety by one or more identical or different radicals $R^A$ and/or where each of the specified substituted radicals is substituted in the cyclic moiety by one or more identical or different radicals $R^B$, where
$R^A$ represents halogen, cyano, hydroxy or $(C_1-C_6)$alkoxy, and
$R^B$ independently of any further radicals $R^B$ present is selected from the group consisting of halogen, cyano, hydroxy, oxo, nitro, $(C_1-C_8)$alkyl, $(C_1-C_6)$haloalkyl, cyano-$(C_1-C_6)$alkyl, hydroxy-$(C_1-C_6)$alkyl, nitro-$(C_1-C_6)$alkyl, $(C_2-C_8)$alkenyl, $(C_2-C_8)$haloalkenyl, $(C_2-C_8)$alkynyl, $(C_2-C_8)$haloalkynyl, $(C_1-C_8)$alkoxy, $(C_2-C_8)$alkenyloxy, $(C_2-C_8)$alkinyloxy, $(C_1-C_8)$haloalkoxy, $(C_1-C_6)$alkoxy-$(C_1-C_6)$alkyl, $(C_1-C_6)$alkoxy-$(C_1-C_4)$alkoxy, $(C_1-C_6)$haloalkoxy-$(C_1-C_4)$alkyl, $(C_1-C_6)$haloalkoxy-$(C_1-C_4)$alkoxy, $(C_1-C_8)$alkylthio, $(C_2-C_6)$alkenylthio, $(C_2-C_6)$alkynylthio, $(C_1-C_8)$alkylsulfinyl, $(C_1-C_6)$haloalkylsulfinyl, $(C_1-C_8)$alkylsulfonyl, $(C_1-C_6)$haloalkylsulfonyl, $R^{aa}-C(=O)-$, $R^{aa}-C(=O)-(C_1-C_6)$alkyl, $-NR^*R^{**}$, tri-$[(C_1-C_4)$alkyl]silyl, tri-$[(C_1-C_4)$alkyl]silyl-$(C_1-C_6)$alkyl, $(C_3-C_8)$cycloalkyl, $(C_3-C_8)$cycloalkoxy, $(C_3-C_8)$cycloalkyl-$(C_1-C_8)$alkyl, $(C_3-C_8)$cycloalkyl-$(C_1-C_8)$alkoxy, phenyl, phenyl-$(C_1-C_8)$alkyl, phenoxy, phenoxy-$(C_1-C_8)$alkyl, phenylamino, phenylamino-$(C_1-C_8)$alkyl or a 5- or 6-membered monocyclic or 9- or 10-membered bicyclic heterocycle containing 1, 2, 3 or 4 heteroatoms selected from the group consiting of O, N and S, where each of these specified radicals can be substituted in the cyclic moiety by one or more identical or different $R^{bb}$, where
$R^{aa}$ in each case independently of one another represent hydrogen, OH, $(C_1-C_8)$alkyl, $(C_1-C_6)$haloalkyl, $(C_2-C_8)$alkenyl, $(C_2-C_8)$alkynyl, $(C_1-C_8)$alkoxy, $(C_1-C_6)$alkoxy-$(C_1-C_6)$alkyl, $(C_1-C_6)$alkoxy-$(C_1-C_6)$alkyloxy, $(C_1-C_6)$haloalkoxy, $(C_1-C_6)$haloalkoxy-$(C_1-C_6)$alkyl, $(C_1-C_6)$haloalkoxy-$(C_1-C_6)$alkoxy, $(C_3-C_8)$alkenyloxy, $(C_3-C_8)$alkenyloxy-$(C_1-C_6)$alkyl, $(C_3-C_8)$alkenyloxy-$(C_1-C_6)$alkoxy, $(C_3-C_8)$alkynyloxy, $(C_3-C_8)$alkynyloxy-$(C_1-C_6)$alkyl, $(C_3-C_8)$alkynyloxy-$(C_1-C_6)$alkoxy, $-NR^*R^{**}$, tri-$[(C_1-C_4)$alkyl]silyl, tri-$[(C_1-C_4)$alkyl]silyl-$(C_1-C_6)$alkyl, tri-$[(C_1-C_4)$alkyl]silyl-$(C_1-C_6)$alkoxy, $(C_3-C_8)$cycloalkyl, $(C_3-C_8)$cycloalkoxy, $(C_3-C_8)$cycloalkyl-$(C_1-C_8)$alkyl, $(C_3-C_8)$cycloalkyl-$(C_1-C_8)$alkoxy, $(C_5-C_8)$cycloalkenyl, $(C_5-C_8)$cycloalkenyl-$(C_1-C_6)$alkyl, $(C_5-C_8)$cycloalkenyloxy, $(C_5-C_8)$cycloalkynyl, $(C_5-C_8)$cycloalkynyl-$(C_1-C_6)$alkyl, $(C_5-C_8)$cycloalkynyl-$(C_1-C_6)$alkoxy, phenyl, phenyl-$(C_1-C_8)$alkyl, phenyl-$(C_1-C_8)$alkoxy, phenoxy, phenoxy-$(C_1-C_8)$alkyl, phenoxy-$(C_1-C_8)$alkoxy, phenylamino, phenylamino-$(C_1-C_8)$alkyl, phenylamino-$(C_1-C_8)$alkoxy or a 5- or 6-membered monocyclic or 9- or 10-membered bicyclic heterocycle containing 1, 2, 3 or 4 heteroatoms and optionally bonded via an alkylene group or an alkoxy group is selected from the group consisting of O, N and S, where each of the radicals $R^{aa}$ encompassing a cycle is optionally substituted in the cyclic moiety by one or more identical or different radicals $R^{bb}$, and where
$R^*$, $R^{**}$, $-NR^*R^{**}$ and $R^{bb}$ have the meaning given above.

7. The compound of the formula (I) or salt thereof as claimed in claim 1, wherein
$R^1$ represents hydrogen, unsubstituted $(C_1-C_{18})$alkyl, unsubstituted $(C_2-C_{18})$alkenyl, unsubstituted $(C_2-C_{18})$alkynyl, substituted $(C_1-C_{18})$alkyl, substituted $(C_2-C_{18})$alkenyl or substituted $(C_2-C_{18})$alkynyl, where in the case of substituted $(C_1-C_{18})$alkyl, substituted $(C_2-C_{18})$ alkenyl and substituted $(C_2-C_{18})$alkynyl the substituent(s) is/are each independently of one another selected from groups (a)-(e) below:

(a) halogen, cyano, thio, nitro, hydroxy, carboxy, $(C_1-C_8)$alkoxy, $(C_2-C_8)$alkenyloxy, $(C_2-C_8)$alkynyloxy, $(C_1-C_8)$haloalkoxy, $(C_1-C_4)$alkoxy-$(C_1-C_4)$alkoxy, $(C_1-C_8)$alkylthio, $(C_2-C_8)$alkenylthio, $(C_2-C_8)$alkyinylthio, $(C_1-C_8)$haloalkylthio, $(C_2-C_8)$haloalkenylthio, $(C_2-C_8)$haloalkinylthio, $(C_1-C_8)$alkylsulfinyl, $(C_2-C_8)$alkenylsulfinyl, $(C_2-C_8)$alkynylsulfinyl, $(C_1-C_8)$haloalkylsulfinyl, $(C_2-C_8)$haloalkenylsulfinyl, $(C_2-C_8)$haloalkinylsulfinyl, $(C_1-C_8)$alkylsulfonyl, $(C_2-C_8)$alkenylsulfonyl, $(C_2-C_8)$alkynylsulfonyl, $(C_1-C_8)$haloalkylsulfonyl, $(C_2-C_8)$haloalkenylsulfonyl, $(C_2-C_8)$haloalkynylsulfonyl, —NR*R**,
where R*, R** and —NR*R** in each case have the meaning given above, (b) $(C_3-C_8)$cycloalkyl, $(C_5-C_8)$cycloalkenyl, $(C_5-C_8)$cycloalkinyl, $(C_3-C_8)$cycloalkyl-$(C_1-C_6)$alkoxy, $(C_3-C_8)$cycloalkyl-$(C_1-C_6)$alkyl-$S(O)_p$—, $(C_5-C_8)$cycloalkenyl-$(C_1-C_6)$alkoxy, $(C_5-C_8)$cycloalkenyl-$(C_1-C_6)$alkyl-$S(O)_p$—, $(C_5-C_8)$cycloalkynyl-$(C_1-C_6)$alkoxy, $(C_5-C_8)$cycloalkynyl-$(C_1-C_6)$alkyl-$S(O)_p$—, $(C_3-C_8)$cycloalkoxy, $(C_3-C_8)$cycloalkyl-$S(O)_p$—, $(C_5-C_8)$cycloalkenyloxy, $(C_5-C_8)$cycloalkenyl-$S(O)_p$—, $(C_5-C_8)$cycloalkynyloxy, $(C_5-C_8)$cycloalkynyl-$S(O)_p$—, $(C_3-C_8)$cycloalkoxy-$(C_1-C_6)$alkoxy, $(C_3-C_8)$cycloalkoxy-$(C_1-C_6)$alkyl-$S(O)_p$—, phenyl, phenyl$(C_1-C_6)$alkoxy, phenoxy, phenyl-$S(O)_p$—, phenyl-$(C_1-C_6)$alkyl-$S(O)_p$—, phenoxy-$(C_1-C_6)$alkoxy, phenoxy-$(C_1-C_6)$alkyl-$S(O)_p$—, a radical $Het^1$, $Het^1$-$S(O)_p$—, $Het^1$-$(C_1-C_6)$alkoxy, $Het^1$-O—, $Het^1$-O—$(C_1-C_6)$alkoxy, where the radical $Het^1$ has the meaning given above, and where each of the last-mentioned radicals of the group (b) in the acyclic moiety is unsubstituted or substituted by one or more identical or different radicals selected from the group consisting of halogen, cyano, hydroxy and $(C_1-C_6)$alkoxy, and/or in the cyclic moiety is unsubstituted or substituted by one or more identical or different radicals $R^B$,
where $R^B$ independently of any further radicals $R^B$ present is selected from the group consisting of halogen, cyano, hydroxy, oxo, nitro, $(C_1-C_8)$alkyl, $(C_1-C_6)$haloalkyl, cyano-$(C_1-C_6)$alkyl, hydroxy-$(C_1-C_6)$alkyl, nitro-$(C_1-C_6)$alkyl, $(C_2-C_8)$alkenyl, $(C_2-C_8)$haloalkenyl, $(C_2-C_8)$alkynyl, $(C_2-C_8)$haloalkynyl, $(C_1-C_8)$alkoxy, $(C_2-C_8)$alkenyloxy, $(C_2-C_8)$alkinyloxy, $(C_1-C_8)$haloalkoxy, $(C_1-C_6)$alkoxy-$(C_1-C_6)$alkyl, $(C_1-C_6)$alkoxy-$(C_1-C_4)$alkoxy, $(C_1-C_6)$haloalkoxy-$(C_1-C_4)$alkyl, $(C_1-C_6)$haloalkoxy-$(C_1-C_4)$alkoxy, $(C_1-C_8)$alkylthio, $(C_2-C_6)$alkenylthio, $(C_2-C_6)$alkynylthio, $(C_1-C_8)$alkylsulfinyl, $(C_1-C_6)$haloalkylsulfinyl, $(C_1-C_8)$alkylsulfonyl, $(C_1-C_6)$haloalkylsulfonyl, $R^{aa}$—C(=O)—, $R^{aa}$—C(=O)—$(C_1-C_6)$alkyl, —NR*R**, tri-[$(C_1-C_4)$alkyl]silyl, tri-[$(C_1-C_4)$alkyl]silyl-$(C_1-C_6)$alkyl, $(C_3-C_8)$cycloalkyl, $(C_3-C_8)$cycloalkoxy, $(C_3-C_8)$cycloalkyl-$(C_1-C_8)$alkyl, $(C_3-C_8)$cycloalkyl-$(C_1-C_8)$alkoxy, phenyl, phenyl-$(C_1-C_8)$alkyl, phenoxy, phenoxy-$(C_1-C_8)$alkyl, phenylamino, phenylamino-$(C_1-C_8)$alkyl or a 5- or 6-membered monocyclic or 9- or 10-membered bicyclic heterocycle containing 1, 2, 3 or 4 heteroatoms selected from the group consisting of O, N and S, where each of these specified radicals can be substituted in the cyclic moiety by one or more identical or different $R^{bb}$,
and the index p is in each case 0, 1 or 2, (c) —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$),
where R*, R** and —NR*R** in each case have the meaning given above and $R^c$ and $R^D$ are as defined below, (d) —SiR'$_3$, —O—SiR'$_3$, (R')$_3$Si—$(C_1-C_6)$alkoxy, —CO—O—NR'$_2$, —O—N=CR'$_2$, —N=CR'$_2$, —O—NR'$_2$, —CH(OR')$_2$ and —O—(CH$_2$)$_q$—CH(OR')$_2$, in which each of the radicals R' is independently selected from the group consisting of H, $(C_1-C_4)$alkyl or phenyl which is unsubstituted or substituted by one or more radicals from the group consisting of halogen, $(C_1-C_4)$alkyl, $(C_1-C_4)$alkoxy, $(C_1-C_4)$haloalkyl, $(C_1-C_4)$haloalkoxy and nitro or substituted at two adjacent positions by a $(C_2-C_6)$ alkylene bridge, and the index q represents an integer from 0 to 6, and (e) R"O—CHR'"CH(OR")—$(C_1-C_6)$alkoxy,
in which each of the radicals R" independently of the others represents H or $(C_1-C_4)$-alkyl or together the radicals represent a $(C_1-C_6)$-alkylene group and R'" represents H or $(C_1-C_4)$-alkyl, or $R^1$ represents $(C_3-C_9)$cycloalkyl, $(C_5-C_9)$cycloalkenyl, $(C_5-C_9)$cycloalkynyl or phenyl,
where each of these radicals is unsubstituted or substituted by one or more radicals from the group consisting of the radicals of subgroups (a')-(e') below:

(a') halogen, cyano, thio, nitro, hydroxy, carboxy, $(C_1-C_8)$alkyl, $(C_1-C_8)$haloalkyl, $(C_1-C_4)$alkoxy-$(C_1-C_4)$alkyl, $(C_2-C_8)$alkenyl, $(C_2-C_8)$haloalkenyl, $(C_2-C_8)$alkynyl, $(C_2-C_8)$haloalkynyl, $(C_1-C_8)$alkoxy, $(C_2-C_8)$alkenyloxy, $(C_2-C_8)$alkynyloxy, $(C_1-C_8)$haloalkoxy, $(C_1-C_4)$alkoxy-$(C_1-C_4)$alkoxy, $(C_1-C_8)$alkylthio, $(C_2-C_8)$alkenylthio, $(C_2-C_8)$alkynylthio and —NR*R**, where R*, R**, —NR*R**, and $R^{bb}$ in each case have the meaning given above, (b') radicals of the formulae —C(=O)—$R^C$, —C(=O)—O—$R^C$, —O—C(=O)—$R^C$, —O—C(=O)—O—$R^C$, —C(=O)—S—$R^C$, —C(=S)—S—$R^C$, —C(=O)—NR*R**, —C(=O)—O—NR*R**, —O—C(=O)—NR*R**, —N(R*)—C(=O)—$R^C$, —N(R*)—C(=O)—NR*R**, —N(R*)—C(=O)—O—$R^C$, —P(=O)($R^C$)($R^D$), —P(=O)(O$R^C$)($R^D$), —P(=O)(O$R^C$)(O$R^D$) or —O—P(=O)(O$R^C$)(O$R^D$),
where R*, R**, —NR*R** and $R^{bb}$ in each case have the meaning given above and $R^C$ and $R^D$ have the meaning defined below, (c') radicals of the formulae —SiR'$_3$, —O—SiR'$_3$, (R')$_3$Si—$(C_1-C_6)$alkoxy, —CO—O—NR'2, —O—N=CR'$_2$, —N=CR'$_2$, —O—NR'$_2$, —CH(OR')$_2$ and —O—(CH$_2$)$_q$—CH(OR')$_2$, in which each of the radicals R' independently of the others represents H, $(C_1-C_4)$-alkyl or phenyl which is unsubstituted or substituted by one or more radicals from the group consisting of halogen, $(C_1-C_4)$-alkyl, $(C_1-C_4)$-alkoxy, $(C_1-C_4)$-haloalkyl, $(C_1-C_4)$-haloalkoxy and nitro or is substituted at two adjacent positions by a $(C_2-C_6)$-alkylene bridge, and q represents an integer from 0 to 6, and (d') radicals of the formula R"O—CHR'"CH(OR")—$(C_1-C_6)$alkoxy, in which each of the radicals R" independently of the others represents H or $(C_1-C_4)$-alkyl or together the radicals represent a $(C_1-C_6)$-alkylene group and R'" represents H or $(C_1-C_4)$-alkyl, and (e') a radical of the formula Het$^1$ which is unsubstituted or substituted by one or more identical or different radicals $R^B$, where $R^B$ has the meaning given above, or $R^1$ represents a polycyclic radical based on $(C_3-C_9)$cycloalkyl, $(C_5-C_9)$cycloalkenyl, $(C_5-C_9)$cycloalkynyl or phenyl, where the base ring is fused with a carbocyclic or heterocyclic ring, and where the base ring or the polycyclic system is unsubstituted or substituted by one or more identical or different radicals $R^B$, where $R^B$ has the meaning given above, or $R^1$ represents a heterocyclic radical Het$^1$ which is unsubstituted in the ring or in the polycyclic system or substituted by one or more identical or different radicals $R^B$, where $R^B$ has the meaning given above, where Het$^1$ in each case independently of the others is a saturated, partially unsaturated or heteroaromatic monocyclic heterocyclyl radical having 3 to 9 ring atoms, or a 9- or 10-membered bicyclic heterocycle containing 1, 2, 3 or 4 heteroatoms selected from the group consisting of O, N and S, $R^A$ represents halogen, cyano, hydroxy or $(C_1-C_6)$alkoxy, $R^B$ has the meaning given above, $R^C$ and $R^D$ each independently of one another (and also independently of radicals $R^C$, $R^D$ in other groups) represent a radical selected from the group consisting of:

(i) hydrogen, unsubstituted $(C_1-C_8)$alkyl, unsubstituted $(C_2-C_8)$alkenyl, unsubstituted $(C_2-C_8)$alkynyl, substituted $(C_1-C_8)$alkyl, substituted $(C_2-C_8)$alkenyl, or substituted $(C_2-C_8)$alkynyl, where each of these substituted radicals is substituted by one or more radicals from the group halogen, cyano, nitro, hydroxy, $(C_1-C_6)$alkoxy, $(C_2-C_6)$alkenyloxy, $(C_2-C_6)$alkynyloxy, $(C_1-C_8)$haloalkoxy, $(C_1-C_4)$alkoxy-$(C_1-C_4)$alkoxy, $(C_1-C_8)$alkylthio, $(C_1-C_8)$haloalkylthio, $(C_1-C_8)$alkylsulfinyl, $(C_1-C_8)$haloalkylsulfinyl, $(C_1-C_8)$alkylsulfonyl, $(C_1-C_8)$haloalkylsulfonyl and tri-$[(C_1-C_4)$alkyl]silyl, and (ii) $(C_3-C_8)$cycloalkyl, $(C_5-C_8)$cycloalkenyl, $(C_5-C_8)$cycloalkynyl, phenyl, $(C_3-C_8)$cycloalkyl-$(C_1-C_6)$alkyl, $(C_5-C_8)$cycloalkenyl-$(C_1-C_6)$alkyl, $(C_5-C_8)$cycloalkynyl-$(C_1-C_6)$alkyl, phenyl-$(C_1-C_6)$alkyl, $(C_3-C_8)$cycloalkyloxy-$(C_1-C_6)$alkyl, $(C_3-C_8)$cycloalkyl-S(O)$_p$—$(C_1-C_6)$alkyl, $(C_5-C_8)$cycloalkenyloxy-$(C_1-C_6)$alkyl, $(C_5-C_8)$cycloalkynyloxy-$(C_1-C_6)$alkyl, phenoxy-$(C_1-C_6)$alkyl, phenyl-S(O)$_p$—$(C_1-C_6)$alkyl, $(C_3-C_8)$cycloalkylamino-$(C_1-C_6)$alkyl, $(C_5-C_8)$cycloalkenylamino-$(C_1-C_6)$alkyl, $(C_5-C_8)$cycloalkynylamino-$(C_1-C_6)$alkyl, phenylamino-$(C_1-C_6)$alkyl, Het$^1$, Het$^1$-$(C_1-C_6)$alkyl, Het$^1$-O—$(C_1-C_6)$alkyl or Het$^1$-S(O)$_p$—$(C_1-C_6)$alkyl, where Het$^1$ has the meaning given above, and where each of these radicals is unsubstituted in the acyclic moiety or substituted by one or more identical or different radicals $R^A$ and in the cyclic moiety is unsubstituted or substituted by one or more identical or different radicals $R^B$ and p in each case represents 0, 1 or 2, where $R^A$ and $R^B$ in each case have the meaning given above, $R^{aa}$ has the meaning given above, and where $R^{aa}$ preferably independently is a radical selected from the group consisting of hydrogen, OH, $(C_1-C_6)$alkyl, $(C_1-C_4)$haloalkyl, $(C_2-C_6)$alkenyl, $(C_2-C_6)$alkynyl, $(C_1-C_6)$alkoxy, $(C_1-C_6)$alkoxy-$(C_1-C_6)$alkyl, $(C_1-C_6)$alkoxy-$(C_1-C_6)$alkyloxy, $(C_1-C_4)$haloalkoxy, $(C_1-C_4)$haloalkoxy-$(C_1-C_6)$alkyl, $(C_1-C_4)$haloalkoxy-$(C_1-C_6)$alkoxy, $(C_3-C_6)$alkenyloxy, $(C_3-C_6)$alkenyloxy-$(C_1-C_6)$alkyl, $(C_3-C_6)$alkenyloxy-$(C_1-C_6)$alkoxy, $(C_3-C_6)$alkynyloxy, $(C_3-C_6)$alkynyloxy-$(C_1-C_6)$alkyl, $(C_3-C_6)$alkynyloxy-$(C_1-C_6)$alkoxy, —NR*R**, where R* and R** are as defined above, tri$[(C_1-C_4)$alkyl]silyl, tri$[(C_1-C_4)$alkyl]silyl-$(C_1-C_6)$alkyl, tri$[(C_1-C_4)$alkyl]silyl-$(C_1-C_6)$alkoxy, $(C_3-C_6)$cycloalkyl, $(C_3-C_6)$cycloalkoxy, $(C_3-C_6)$cycloalkyl-$(C_1-C_8)$alkyl, $(C_3-C_6)$cycloalkyl-$(C_1-C_8)$alkoxy, $(C_5-C_6)$cycloalkenyl, $(C_5-C_6)$cycloalkenyl-$(C_1-C_6)$alkyl, $(C_5-C_6)$cycloalkenyloxy, $(C_5-C_6)$cycloalkynyl, $(C_5-C_6)$cycloalkynyl-$(C_1-C_6)$alkyl, $(C_5-C_6)$cycloalkynyl-$(C_1-C_6)$alkoxy, phenyl, phenyl-$(C_1-C_6)$alkyl, phenyl-$(C_1-C_6)$alkoxy, phenoxy, phenoxy-$(C_1-C_6)$alkyl, phenoxy-$(C_1-C_6)$alkoxy, phenylthio, phenyl-S(O)$_p$—$(C_1-C_6)$alkyl, phenyl-S(O)$_p$—$(C_1-C_6)$alkoxy, where p in each case independently of one another is 0, 1 or 2, phenylamino, phenylamino-$(C_1-C_6)$alkyl, phenylamino-$(C_1-C_6)$alkoxy or a 5- or 6-membered monocyclic or 9- or 10-membered bicyclic heterocycle optionally bonded via an alkylene group or an alkoxy group, containing 1, 2, 3 or 4 heteroatoms selected from the group consisting of O, N and S, where each of the specified cyclic radicals $R^{aa}$ in the cyclic moiety is optionally substituted by one or more identical or different radicals selected from the group consisting of halogen, $(C_1-C_4)$alkyl, $(C_1-C_4)$haloalkyl, $(C_1-C_4)$alkoxy and $(C_1-C_4)$haloalkoxy.

8. The compound of the formula (I) or salt thereof as claimed in claim 1, wherein $(R^2)_n$ represents n substituents $R^2$, where $R^2$ (if n=1) or each of the substituents $R^2$ (if n is greater than 1) independently of the others represents halogen, cyano, nitro, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$haloalkyl, $(C_2-C_6)$haloalkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, tri$[(C_1-C_4)$alkyl]silyl or tri$[(C_1-C_4)$alkyl]silyl-$(C_1-C_4)$alkyl, and/or $(R^3)_m$ represents m substituents $R^3$, where $R^3$ (if m=1) or each of the substituents $R^3$ (if m is greater than 1) independently of one another represents halogen, cyano, nitro, $(C_1-C_6)$alkyl, $(C_1-C_6)$alkoxy, $(C_1-C_6)$alkylthio, $(C_1-C_6)$alkylsulfinyl, $(C_1-C_6)$alkylsulfonyl, $(C_1-C_6)$halo alkyl, $(C_2-C_6)$halo alkenyl, $(C_1-C_6)$haloalkoxy, $(C_1-C_6)$haloalkylthio, $(C_1-C_6)$haloalkylsulfinyl, $(C_1-C_6)$haloalkylsulfonyl, $(C_2-C_6)$alkenyl, $(C_2-C_6)$alkynyl, NR*R, tri$[(C_1-C_4)$alkyl]silyl or tri$[(C_1-C_4)$alkyl]silyl$(C_1-C_4)$alkyl or where in each case two groups $R^3$ directly adjacent on the ring together represent a group of the formula —Z$^3$-A-Z$^4$—, in which A represents an alkylene group having 1 to 4 carbon atoms which is optionally substituted by one or more radicals from the group consisting of halogen, ($C_1$-$C_4$)alkyl, ($C_1$-$C_4$)haloalkyl, ($C_1$-$C_4$)alkoxy and ($C_1$-$C_4$)haloalkoxy, $Z^3$ represents a direct bond, O or S and $Z^4$ represents a direct bond, O or S, where the group —$Z^3$-A—$Z^4$ together with the carbon atoms, bonded to the group, of the phenyl ring form a fused-on 5- or 6-membered ring, R*, R** each independently of one another or together with the nitrogen atom have the meaning mentioned above and n, m in each case independently of one another represent 0, 1, 2, 3, 4 or 5.

9. The compound of the formula (I) or salt thereof as claimed in claim 1, wherein $(R^2)_n$ represents n substituents $R^2$, where, in the case that n=1, the substituent $R^2$ or, in the case that n is greater than 1, each of the substituents $R^2$ independently of the others represents halogen, cyano, nitro, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)haloalkyl, ($C_2$-$C_4$)haloalkenyl, ($C_1$-$C_4$)haloalkoxy, ($C_1$-$C_4$)haloalkylthio, ($C_1$-$C_4$)haloalkylsulfinyl, ($C_1$-$C_4$)haloalkylsulfonyl, ($C_2$-$C_4$)alkenyl, ($C_2$-$C_4$)alkynyl, tri[($C_1$-$C_4$)alkyl]silyl or tri[($C_1$-$C_4$)alkyl]silyl($C_1$-$C_4$)alkyl, and n represents 0, 1, 2, 3, or 4.

10. The compound of the formula (I) or salt thereof as claimed in claim 1, wherein $(R^3)_m$ represents m substituents $R^3$, where in the case that m=1, the substituent $R^3$ or, in the case that m is greater than 1, each of the substituents $R^3$ independently of one another represents halogen, cyano, nitro, ($C_1$-$C_4$)alkyl, ($C_1$-$C_4$)alkoxy, ($C_1$-$C_4$)alkylthio, ($C_1$-$C_4$)alkylsulfinyl, ($C_1$-$C_4$)alkylsulfonyl, ($C_1$-$C_4$)haloalkyl, ($C_2$-$C_4$)haloalkenyl, ($C_1$-$C_4$)haloalkoxy, ($C_1$-$C_4$)haloalkylthio, ($C_1$-$C_4$)haloalkylsulfinyl, ($C_1$-$C_4$)haloalkylsulfonyl, ($C_2$-$C_6$)alkenyl, ($C_2$-$C_6$)alkynyl or tri[($C_1$-$C_4$)alkyl]silyl-$Z^b$—, where $Z^b$=is a covalent bond or ($C_1$-$C_4$)alkylene, or in each case two groups $R^3$ directly adjacent to one another at the ring together represent a group of the formula —$Z^3$-A-$Z^4$—, where A represents an alkylene group which is optionally substituted by one or more radicals from the group halogen, ($C_1$-$C_4$)alkyl, ($C_1$-$C_4$)haloalkyl, ($C_1$-$C_4$)alkoxy and ($C_1$-$C_4$)haloalkoxy, $Z^3$ represents O or S and $Z^4$ represents O or S, where the group —$Z^3$-A**-$Z^4$— together with the carbon atoms, attached to the group, of the phenyl ring form a fused-on 5- or 6-membered ring, m represents 0, 1, 2, 3, 4 or 5.

11. The compound of the formula (I) or salt thereof as claimed in claim 1, wherein $(R^2)_n$ represents n substituents $R^2$, where, in the case that n=1, the substituent $R^2$ or, in the case that n is greater than 1, each of the substituents $R^2$ independently of one another represents fluorine, chlorine, bromine, iodine, cyano, nitro, methyl, ethyl, methoxy, methylthio, methylsulfinyl, methyl-sulfonyl, trifluoromethyl, trifluoromethoxy, trifluoroalkylthio, trifluoromethylsulfinyl or trifluoromethylsulfonyl, and $(R^3)_m$ represents m substituents $R^3$, where, in the case that m=1, the substituent $R^3$ or, in the case that m is greater than 1, each of the substituents $R^3$ independently of the others represents fluorine, chlorine, bromine, iodine, cyano, nitro, methyl, methoxy, methylthio, methylsulfinyl, methylsulfonyl, trifluoromethyl, trifluoromethoxy, trifluoroalkylthio, trifluoromethylsulfinyl or trifluoromethylsulfonyl, and m represents 0, 1, 2, 3 or 4, and n represents 0, 1, 2 or 3.

12. The compound of the formula (I) or salt thereof according to claim 1, wherein Q represents a heteroaromatic radical selected from the group consisting of pyridinyl, pyrazinyl, thienyl and thiazolyl; and $R^1$ is selected from the group consisting of hydrogen, acetyl, propanoyl, butanoyl, pentanoyl, hexanoyl, 2-methylpropanoyl, 2,2-difluoroacetyl, 2,2,2-trifluoroacetyl, C(=O)OMe, cyclopropanecarbonyl, 1-methylcyclopropanecarbonyl, acryl, prop-2-ynoyl, but-2-ynoyl, 2-methylacryl, benzoyl, 4-chlorobenzoyl, 3-chlorobenzoyl, 2-chlorobenzoyl, 4-fluorobenzoyl, 3-fluorobenzoyl, 2-fluorobenzoyl, 2,2-dimethylpropanoyl, 3,3-dimethylbutanoyl, 2-nitrobenzoyl, 2-fluoroacetyl, 2-chloroacetyl, 2-bromoacetyl, 2,2-dichloroacetyl, 2-methoxyacetyl, 2,6-difluorobenzoyl, C(O)C(=O)OMe and C(O)CH$_2$C(O)OMe.

13. The compound of the formula (I) or salt thereof according to claim 5, wherein R1 represents hydrogen or a hydrolyzable radical having in 1 to 20 carbon atoms.

14. A herbicidal or plant growth-regulating composition, wherein the composition comprises one or more compounds of the formula (I) or salts thereof as defined in claim 1, and one or more further substances selected from groups (i) and/or (ii):

(i) one or more further agrochemically active substances, (ii) one or more formulation auxiliaries customary in crop protection.

15. The composition according to claim 14, wherein the one or more further agrochemically active substances are selected from the group consisting of insecticides, acaricides, nematicides, further herbicides, fungicides, safeners, fertilizers and further growth regulators.

16. A method for controlling harmful plants or for regulating the growth of plants, comprising applying an effective amount of one or more compounds of the formula (I) or salts thereof, as defined in claim 1, or a composition thereof, to the plants, seeds of plants, the soil in which or on which the plants grow or an area under cultivation.

17. A process for preparing a compound of the formula (I) or a salt thereof as defined in claim 1, comprising converting a compound of the formula (E)

(E)
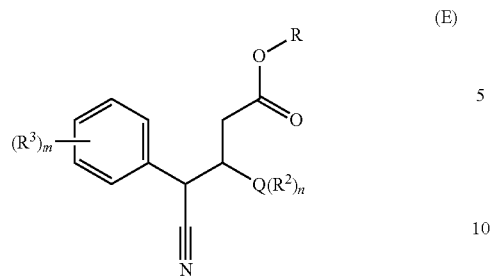
by reduction into a compound of the formula (Ia)
(Ia)
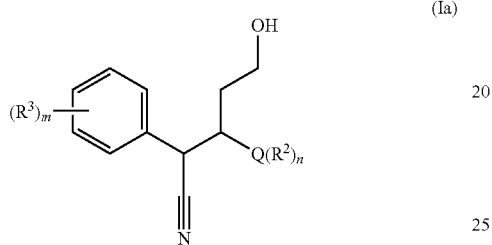
and the compound (Ia) is optionally reacted further to give a compound of the formula (I), wherein $R^1$ in formula (I) does not represent hydrogen, where R represents hydrogen or a hydrolysable radical.
* * * * *